(12) United States Patent
Blainey et al.

(10) Patent No.: US 11,702,649 B2
(45) Date of Patent: Jul. 18, 2023

(54) SINGLE CELL CELLULAR COMPONENT ENRICHMENT FROM BARCODED SEQUENCING LIBRARIES

(71) Applicants: THE BROAD INSTITUTE, INC., Cambridge, MA (US); MASSACHUSETTS INSTITUTE OF TECHNOLOGY, Cambridge, MA (US)

(72) Inventors: Paul Blainey, Cambridge, MA (US); Navpreet Ranu, Cambridge, MA (US); Todd Gierahn, Cambridge, MA (US); J. Christopher Love, Cambridge, MA (US)

(73) Assignees: The Broad Institute, Inc., Cambridge, MA (US); Massachusetts Institute of Technology, Cambridge, MA (US)

( * ) Notice: Subject to any disclaimer, the term of this patent is extended or adjusted under 35 U.S.C. 154(b) by 570 days.

(21) Appl. No.: 16/758,640

(22) PCT Filed: Oct. 23, 2018

(86) PCT No.: PCT/US2018/057161
§ 371 (c)(1),
(2) Date: Apr. 23, 2020

(87) PCT Pub. No.: WO2019/084046
PCT Pub. Date: May 2, 2019

(65) Prior Publication Data
US 2020/0392479 A1     Dec. 17, 2020

Related U.S. Application Data

(60) Provisional application No. 62/576,031, filed on Oct. 23, 2017, provisional application No. 62/736,863, filed on Sep. 26, 2018.

(51) Int. Cl.
*C12N 15/10*     (2006.01)
*C12Q 1/6806*     (2018.01)
(Continued)

(52) U.S. Cl.
CPC ......... *C12N 15/1006* (2013.01); *C12N 1/205* (2021.05); *C12Q 1/6806* (2013.01);
(Continued)

(58) Field of Classification Search
None
See application file for complete search history.

(56) References Cited

U.S. PATENT DOCUMENTS

| 9,469,874 | B2 | 10/2016 | Chen et al. |
| 2012/0220494 | A1* | 8/2012 | Samuels et al. ...... C12Q 1/6804 506/26 |

FOREIGN PATENT DOCUMENTS

| WO | 2016100977 A1 | 6/2016 | |
| WO | WO-2016100977 A1 * | 6/2016 | ............. A61K 35/17 |

OTHER PUBLICATIONS

Sun et al., "Ultra-deep profiling of alternatively spliced *Drosophila* Dscam isoforms by circularization-assisted multi-segment sequencing," EMBO J. 2013, 32:2029-2038. (Year: 2013).*

(Continued)

*Primary Examiner* — Kaijiang Zhang
(74) *Attorney, Agent, or Firm* — F. Brent Nix, Esq.; Johnson, Marcou, Isaacs & Nix, LLC

(57) ABSTRACT

The present invention relates to the analysis of complex single cell sequencing libraries. Disclosed are methods for enrichment of library members based on the presence of cell-of origin barcodes to identify and concentrate DNA that is relevant to interesting cells or components that would be expensive or difficult to study otherwise. Also, disclosed are methods of capturing cDNA library molecules by use of
(Continued)

CRISPR systems, hybridization or PCR. The present invention allows for identifying the properties of rare cells in single cell RNA-seq data and accurately profile them through clustering approaches. Further information on transcript abundances from subpopulations of single cells can be analyzed at a lower sequencing effort. The methods also allow for linking TCR alpha and beta chains at the single cell level.

18 Claims, 32 Drawing Sheets

Specification includes a Sequence Listing.

(51) Int. Cl.
| | |
|---|---|
| *C12Q 1/6869* | (2018.01) |
| *C40B 30/04* | (2006.01) |
| *C40B 50/06* | (2006.01) |
| *C12N 1/20* | (2006.01) |
| *C40B 40/06* | (2006.01) |
| *C40B 40/10* | (2006.01) |
| *C12R 1/465* | (2006.01) |

(52) U.S. Cl.
CPC .......... *C12Q 1/6869* (2013.01); *C40B 30/04* (2013.01); *C40B 40/06* (2013.01); *C40B 40/10* (2013.01); *C40B 50/06* (2013.01); *C12N 2310/20* (2017.05); *C12R 2001/465* (2021.05); *C12Y 301/11* (2013.01); *C12Y 302/02027* (2013.01)

(56) References Cited

OTHER PUBLICATIONS

Macosko et al., "Highly Parallel Genome-wide Expression Profiling of Individual Cells Using Nanoliter Droplets," Cell 2015, 161:1202-1214. (Year: 2015).*

International Search Report and Written Opinion of PCT/US2018/057161, 10 pages, dated Dec. 27, 2018, 10 pages.

International Preliminary Report on Patentability issued in International Application No. PCT/US2018/057161, dated May 7, 2020, 7 pages.

Benz et al., "Hematopoietic Stem Cell Subtypes Expand Differentially During Development and Display Distinct Lymphopoietic Programs", Cell Stem Cell, vol. 10, No. 3, Mar. 2, 2012, 273-283.

Grun et al., "Single-Cell Messenger RNA Sequencing Reveals Rare Intestinal Cell Types", Nature, vol. 525, No. 7568, Sep. 10, 2015, 251-255.

Heimberg et al., "Low Dimensionality in Gene Expression Data Enables the Accurate Extraction of Transcriptional Programs from Shallow Sequencing", Cell Systems, vol. 2, No. 4, Apr. 27, 2016, 239-250.

Howie et al., "High-throughput Pairing of T Cell Receptor $\alpha$ and $\beta$ Sequences", Science Translational Medicine, vol. 7, Issue. 301, Aug. 19, 2015, 11 pages.

Jaitin et al., "Massively Parallel Single-Cell RNA-Seq for Marker-Free Decomposition of Tissues into Cell Types", Science, vol. 343, Issue 6172, Feb. 2014, 776-779.

Kliebenstein, DanielJ. , "Exploring the Shallow End; Estimating Information Content in Transcriptomics Studies", Frontiers in Plant Science, vol. 3, No. 213, Sep. 10, 2012, 10 pages.

Mahata et al., "Single-cell RNA Sequencing Reveals T Helper Cells Synthesizing Steroids De Novo to Contribute to Immune Homeostasis", Cell Reports, vol. 7, No. 4, May 22, 2014, 1130-1142.

Pollen et al., "Low-Coverage Single-Cell mRNA Sequencing Reveals Cellular Heterogeneity and Activated Signaling Pathways in Developing Cerebral Cortex", Nature Biotechnology, vol. 32, Issue 10, Aug. 2014, 37 pages.

Spencer et al., "Massively Parallel Sequencing of Single Cells by epicPCR Links Functional Genes with Phylogenetic Markers", The ISME Journal, vol. 10, No. 2, Feb. 2016, 427-436.

Woodruff et al., "Registry in a Tube: Multiplexed Pools of Retrievable Parts for Genetic Design Space Exploration", Nucleic Acids Research, vol. 45, No. 3, Feb. 17, 2017, 1553-1565.

* cited by examiner

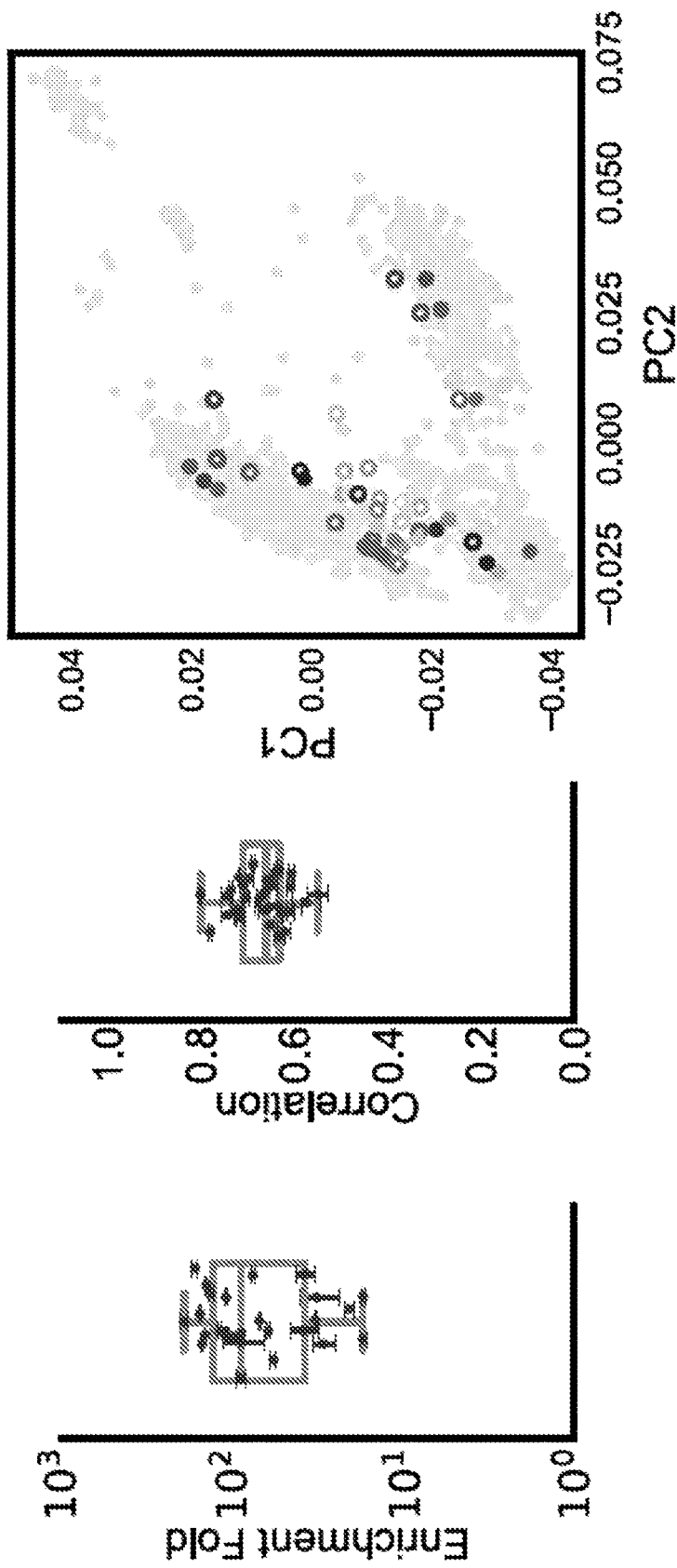

Bio

| Single cell Barcode | nUMIs in pre | nGenes in pre | nReads in Enrichment | PCR plex | Enrichment Fold | Correlation | Notes |
|---|---|---|---|---|---|---|---|
| AAATGCCTCATGGTCA | 7858 | 2315 | 824042 | 10 | 110.61 | 0.90 | |
| ACGATACTCCTATTCA | 8144 | 2324 | 91965 | 10 | 12.08 | 0.84 | |
| AGACGTTAGGAGTTGC | 6384 | 1868 | 171784 | 10 | 44.07 | 0.89 | |
| CATATTCAGCCAGTTT | 6178 | 1868 | 592900 | 10 | 143.34 | 0.88 | |
| CGCTATCGTCCAAGTT | 9518 | 2223 | 1043853 | 10 | 120.26 | 0.91 | |
| CTCACACGTAGGACAC | 7971 | 2010 | 501911 | 10 | 85.71 | 0.91 | |
| GATGCTACACTTAGGA | 10052 | 370 | 691070 | 10 | 246.92 | 0.52 | Low gene in pre |
| GGCCGATAGTGTCCCG | 9779 | 2236 | 853049 | 10 | 125.90 | 0.91 | |
| AGGGAGTAGAAACCGC | 5411 | 143 | 209971 | 10 | 109.18 | 0.67 | Low gene in pre |
| GATGCTACACTTAGGA | 10052 | 370 | 691070 | 10 | 244.77 | 0.52 | Low gene in pre |
| GCAAACTAGTGAAGGC | 7648 | 246 | 470000 | 10 | 216.89 | 0.63 | Low gene in pre |
| GTCAAGTCATGTTGAC | 6545 | 209 | 152900 | 10 | 69.03 | 0.63 | Low gene in pre |
| CTGTGCTAGGATGTGG | 6964 | 261 | 41053 | 10 | 10.88 | 0.78 | Low gene in pre |
| CTGAAGTCACTGGACG | 9971 | 388 | 413623 | 10 | 134.74 | 0.74 | Low gene in pre |
| AACTCAGCACCCATGG | 7094 | 1857 | 1217407 | 10 | 217.70 | 0.69 | |
| AAGACCTTCGGCGGTT | 7507 | 1966 | 893563 | 10 | 223.75 | 0.93 | |
| AGAGCTTAGATGAGAG | 7965 | 2007 | 24269 | 10 | 1.94 | 0.62 | |
| CGATGTACAGCGTTCG | 10077 | 2467 | 920177 | 10 | 153.58 | 0.90 | |
| CAGGTGCGTGTATGGG | 8540 | 2200 | 488395 | 10 | 86.81 | 0.90 | |
| CTGGTCTTCTTTATG | 6952 | 1748 | 53153 | 10 | 7.70 | 0.79 | |
| CTGATAGGTGGCTCCA | 9580 | 2177 | 198282 | 8 | 49.43 | 0.89 | |
| GTCTCGTCACCACGCA | 8218 | 2093 | 602383 | 8 | 149.45 | 0.88 | |
| TTGACTTAGAATCTCC | 5497 | 1524 | 224032 | 8 | 57.80 | 0.79 | |
| TACCTATTCTTTAAGT | 3552 | 1337 | 38167 | 8 | 12.97 | 0.79 | |
| TAAGAGAGTACCTACA | 3701 | 1446 | 2080 | 8 | | | Low reads in enriched |
| GAGCAGAGTTGAACTC | 6131 | 1926 | 134 | 8 | | | Low reads in enriched |
| GTCGGGTCACGCGAAA | 3233 | 1383 | 194051 | 8 | 89.16 | 0.84 | |
| ATAGACCAGTCCGGTC | 5906 | 1656 | 959804 | 8 | 297.35 | 0.77 | |

CD19+ cells

FIG. 27

| HLA-DR+ cells | | | | | | |
|---|---|---|---|---|---|---|
| Single cell Barcode | nUMIs in pre | nGenes in pre | nReads in Enrichment | PCR plex | Enrichment Fold | Correlation | Notes |
| GCACTCTGTGCCTGCA | 1650 | 38 | 127674 | 11 | | | Low genes and UMI in pre |
| CGTCAGGAGATGCCTT | 1650 | 96 | 125667 | 11 | | | Low genes and UMI in pre |
| GGCCGATGTCGTCTTC | 1534 | 99 | 139187 | 11 | | | Low genes and UMI in pre |
| TTAGGCAAGCACGCCT | 1339 | 491 | 142003 | 11 | | | Low genes and UMI in pre |
| GTTACAGGTACGACCC | 2522 | 992 | 223089 | 11 | 195.33 | 0.74 | |
| CAGCTAATCCAAAGTC | 2208 | 995 | 237749 | 11 | 165.57 | 0.71 | |
| TATCAGGCAGGGATTG | 4678 | 1495 | 330127 | 11 | 157.60 | 0.84 | |
| ATCACGAGTGACCAAG | 4602 | 1496 | 324238 | 11 | 150.10 | 0.82 | |
| GGGTCTGGTAGCTCCG | 7501 | 1991 | 275944 | 11 | 80.98 | 0.90 | |
| GCTCCTACAGACTCGC | 9079 | 1996 | 659647 | 11 | 169.20 | 0.80 | |
| AGTGGGAAGACACTAA | 10854 | 2463 | 13800 | 11 | | | Low reads in enriched |
| AACACGTTCCACGCAG | 3198 | 956 | 139292 | 10 | 97.28 | 0.78 | |
| TTCTCAAAGGGCACTA | 4543 | 1169 | 256944 | 10 | 109.12 | 0.64 | |
| ACGTCAAAGTACGATA | 6241 | 2133 | 55921 | 10 | 18.60 | 0.81 | |
| GAGTCCGCAATCACAC | 5667 | 1900 | 298236 | 10 | 119.37 | 0.78 | |
| ACAGCCGAGTGAACGC | 9969 | 2473 | 275116 | 10 | 78.10 | 0.90 | |
| GGTATTGCAATGTTGC | 5104 | 1306 | 403230 | 10 | 184.78 | 0.72 | |
| TTCTCCTCACGACGAA | 3607 | 1492 | 59057 | 10 | 38.54 | 0.84 | |
| TGCCAAATCGCACTCT | 4401 | 1460 | 147491 | 10 | 79.98 | 0.85 | |
| TCAGATGCAGACAGGT | 4208 | 1347 | 48426 | 10 | 21.05 | 0.82 | |
| TTCCCAGCACACAGAG | 3258 | 1321 | 276432 | 10 | 59.93 | 0.83 | |
| CCTAGCTTCGTTTGCC | 10532 | 2681 | 259572 | 10 | 55.61 | 0.92 | |
| ACGCCGATCTGGCGTG | 10288 | 2472 | 743352 | 10 | 111.44 | 0.72 | |
| GTGAAGGAGGTGATTA | 8163 | 2171 | 13816 | 10 | | | Low reads in enriched |
| CAGCCGAAGGACAGCT | 7648 | 2284 | 188554 | 10 | 51.81 | 0.90 | |
| GGTGTTAGTGCCTTGG | 7331 | 2114 | 151393 | 10 | 42.52 | 0.91 | |
| GATTCAGCACACCGCA | 3758 | 1309 | 73142 | 10 | 14.65 | 0.74 | |
| TCATTACGTCGGGTCT | 3382 | 1245 | 261260 | 10 | 103.57 | 0.71 | |
| ATCACGAGTCCTCTTG | 7875 | 2148 | 173557 | 10 | 38.32 | 0.88 | |
| GACCAATAGTTATCGC | 7392 | 2064 | 516990 | 10 | 121.41 | 0.76 | |
| CCACTACTCTCCAACC | 7343 | 2162 | 765042 | 10 | 164.26 | 0.72 | |
| AGCGTATTCATTGCCC | 10597 | 2306 | 1439195 | 10 | 148.75 | 0.82 | |
| GCTTGAAAGTGAAGAG | 10088 | 2367 | 334239 | 10 | 32.20 | 0.79 | |
| CGCGGTATCGGCATCG | 12141 | 2706 | 796027 | 10 | 79.35 | 0.94 | |
| AGAATAGGTCTAGGTT | 7664 | 2081 | 8679 | 10 | | | Low reads in enriched |
| CACAGTATCAATACCG | 4593 | 1302 | 32994 | 10 | 4.24 | 0.81 | |
| TCAACGATCGCACTCT | 9554 | 2323 | 613668 | 10 | 72.40 | 0.91 | |
| CCACTACTCTCTAGGA | 5895 | 1560 | 268203 | 10 | 37.30 | 0.76 | |
| TCTCATAGTGGTCCGT | 12695 | 2815 | 304674 | 10 | 26.21 | 0.90 | |
| CGATGGCAGTCCATAC | 3594 | 1364 | 273390 | 10 | 65.42 | 0.85 | |
| GTGAAGGCAATGGAGC | 6101 | 2018 | 572219 | 10 | 85.45 | 0.86 | |
| GTCTCGTAGCACAGGT | 5814 | 1874 | 639242 | 15 | 81.28 | 0.88 | |
| GCAGTTAAGGGTCGAT | 7257 | 2169 | 760696 | 15 | 93.80 | 0.86 | |
| GGGAGATCAAGCGCTC | 6405 | 1898 | 1422742 | 15 | 211.93 | 0.80 | |
| GGCGTGTAGATCGGGT | 1939 | 911 | 277 | 15 | | | Low reads in enriched |
| GCCAAATTCAGTCCCT | 5789 | 2052 | 1502496 | 15 | 224.65 | 0.87 | |
| CTACACCGTCAAGCGA | 9097 | 2361 | 199714 | 15 | 20.39 | 0.92 | |
| AACCGCGTCGAATGGG | 5026 | 1726 | 90286 | 15 | 19.87 | 0.91 | |
| TACGGATTCAATCTCT | 6191 | 2001 | 123374 | 15 | 11.32 | 0.80 | |
| TTCTTAGGTTACGTCA | 6729 | 2018 | 67294 | 15 | 5.44 | 0.81 | |
| TTGTAGGGTTAAAGTG | 6066 | 1910 | 54834 | 15 | 6.75 | 0.84 | |
| TTCTCCTCACATAACC | 5574 | 1776 | 208947 | 15 | 29.51 | 0.84 | |
| ACACCAATCTCCAACC | 6442 | 1884 | 1877930 | 15 | 233.53 | 0.75 | |
| AAAGTAGTCTGCAAGT | 8906 | 2395 | 4213 | 15 | | | Low reads in enriched |
| CCTAAAGAGTGTTAGA | 6217 | 2172 | 6661 | 15 | | | Low reads in enriched |
| CGATGGCCAAGTCTAC | 6385 | 1854 | 1327900 | 15 | 181.55 | 0.82 | |

FIG. 28

SEQUENCE LISTING

```
<160> NUMBER OF SEQ ID NOS: 127

<210> SEQ ID NO 1
<211> LENGTH: 16
<212> TYPE: DNA
<213> ORGANISM: Artificial Sequence
<220> FEATURE:
<223> OTHER INFORMATION: Synthetic

<400> SEQUENCE: 1
ccactactct ccaacc                                                    16

<210> SEQ ID NO 2
<211> LENGTH: 16
<212> TYPE: DNA
<213> ORGANISM: Artificial Sequence
<220> FEATURE:
<223> OTHER INFORMATION: Synthetic

<400> SEQUENCE: 2
gaccaatagt tatcgc                                                    16

<210> SEQ ID NO 3
<211> LENGTH: 16
<212> TYPE: DNA
<213> ORGANISM: Artificial Sequence
```

```
<220> FEATURE:
<223> OTHER INFORMATION: Synthetic

<400> SEQUENCE: 3
atcacgagtc ctcttg                                                   16

<210> SEQ ID NO 4
<211> LENGTH: 16
<212> TYPE: DNA
<213> ORGANISM: Artificial Sequence
<220> FEATURE:
<223> OTHER INFORMATION: Synthetic

<400> SEQUENCE: 4
tcattacgtc gggtct                                                   16

<210> SEQ ID NO 5
<211> LENGTH: 16
<212> TYPE: DNA
<213> ORGANISM: Artificial Sequence
<220> FEATURE:
<223> OTHER INFORMATION: Synthetic

<400> SEQUENCE: 5
gattcagcac accgca                                                   16

<210> SEQ ID NO 6
<211> LENGTH: 16
<212> TYPE: DNA
<213> ORGANISM: Artificial Sequence
<220> FEATURE:
<223> OTHER INFORMATION: Synthetic

<400> SEQUENCE: 6
ggtgttagtg ccttgg                                                   16

<210> SEQ ID NO 7
<211> LENGTH: 16
<212> TYPE: DNA
<213> ORGANISM: Artificial Sequence
<220> FEATURE:
<223> OTHER INFORMATION: Synthetic

<400> SEQUENCE: 7
cagccgaagg acagct                                                   16

<210> SEQ ID NO 8
<211> LENGTH: 16
<212> TYPE: DNA
<213> ORGANISM: Artificial Sequence
<220> FEATURE:
<223> OTHER INFORMATION: Synthetic

<400> SEQUENCE: 8
gtgaaggagg tgatta                                                   16

<210> SEQ ID NO 9
<211> LENGTH: 16
<212> TYPE: DNA
<213> ORGANISM: Artificial Sequence
<220> FEATURE:
<223> OTHER INFORMATION: Synthetic

<400> SEQUENCE: 9
acgccgatct ggcgtg                                                   16
```

```
<210> SEQ ID NO 10
<211> LENGTH: 16
<212> TYPE: DNA
<213> ORGANISM: Artificial Sequence
<220> FEATURE:
<223> OTHER INFORMATION: Synthetic

<400> SEQUENCE: 10
cctagcttcg tttgcc                                                       16

<210> SEQ ID NO 11
<211> LENGTH: 16
<212> TYPE: DNA
<213> ORGANISM: Artificial Sequence
<220> FEATURE:
<223> OTHER INFORMATION: Synthetic

<400> SEQUENCE: 11
aaatgcctca tggtca                                                       16

<210> SEQ ID NO 12
<211> LENGTH: 16
<212> TYPE: DNA
<213> ORGANISM: Artificial Sequence
<220> FEATURE:
<223> OTHER INFORMATION: Synthetic

<400> SEQUENCE: 12
acgatactcc tattca                                                       16

<210> SEQ ID NO 13
<211> LENGTH: 16
<212> TYPE: DNA
<213> ORGANISM: Artificial Sequence
<220> FEATURE:
<223> OTHER INFORMATION: Synthetic

<400> SEQUENCE: 13
agacgttagg agttgc                                                       16

<210> SEQ ID NO 14
<211> LENGTH: 16
<212> TYPE: DNA
<213> ORGANISM: Artificial Sequence
<220> FEATURE:
<223> OTHER INFORMATION: Synthetic

<400> SEQUENCE: 14
catattcagc cagttt                                                       16

<210> SEQ ID NO 15
<211> LENGTH: 16
<212> TYPE: DNA
<213> ORGANISM: Artificial Sequence
<220> FEATURE:
<223> OTHER INFORMATION: Synthetic

<400> SEQUENCE: 15
cgctatcgtc caagtt                                                       16

<210> SEQ ID NO 16
<211> LENGTH: 16
<212> TYPE: DNA
<213> ORGANISM: Artificial Sequence
<220> FEATURE:
<223> OTHER INFORMATION: Synthetic
```

```
<400> SEQUENCE: 16
ctcacacgta ggacac                                                    16

<210> SEQ ID NO 17
<211> LENGTH: 16
<212> TYPE: DNA
<213> ORGANISM: Artificial Sequence
<220> FEATURE:
<223> OTHER INFORMATION: Synthetic

<400> SEQUENCE: 17
gatgctacac ttacga                                                    16

<210> SEQ ID NO 18
<211> LENGTH: 16
<212> TYPE: DNA
<213> ORGANISM: Artificial Sequence
<220> FEATURE:
<223> OTHER INFORMATION: Synthetic

<400> SEQUENCE: 18
ggccgatagt gtcccg                                                    16

<210> SEQ ID NO 19
<211> LENGTH: 16
<212> TYPE: DNA
<213> ORGANISM: Artificial Sequence
<220> FEATURE:
<223> OTHER INFORMATION: Synthetic

<400> SEQUENCE: 19
agggagtaga aaccgc                                                    16

<210> SEQ ID NO 20
<211> LENGTH: 16
<212> TYPE: DNA
<213> ORGANISM: Artificial Sequence
<220> FEATURE:
<223> OTHER INFORMATION: Synthetic

<400> SEQUENCE: 20
gatgctacac ttacga                                                    16

<210> SEQ ID NO 21
<211> LENGTH: 16
<212> TYPE: DNA
<213> ORGANISM: Artificial Sequence
<220> FEATURE:
<223> OTHER INFORMATION: Synthetic

<400> SEQUENCE: 21
gcaaactagt caaggc                                                    16

<210> SEQ ID NO 22
<211> LENGTH: 16
<212> TYPE: DNA
<213> ORGANISM: Artificial Sequence
<220> FEATURE:
<223> OTHER INFORMATION: Synthetic

<400> SEQUENCE: 22
gtcaagtcat gttgac                                                    16

<210> SEQ ID NO 23
```

```
<211> LENGTH: 16
<212> TYPE: DNA
<213> ORGANISM: Artificial Sequence
<220> FEATURE:
<223> OTHER INFORMATION: Synthetic

<400> SEQUENCE: 23
ctgtgctaga tgtcgg                                                       16

<210> SEQ ID NO 24
<211> LENGTH: 16
<212> TYPE: DNA
<213> ORGANISM: Artificial Sequence
<220> FEATURE:
<223> OTHER INFORMATION: Synthetic

<400> SEQUENCE: 24
ctgaagtcac tcgacg                                                       16

<210> SEQ ID NO 25
<211> LENGTH: 16
<212> TYPE: DNA
<213> ORGANISM: Artificial Sequence
<220> FEATURE:
<223> OTHER INFORMATION: Synthetic

<400> SEQUENCE: 25
aactcagcac ccatgg                                                       16

<210> SEQ ID NO 26
<211> LENGTH: 16
<212> TYPE: DNA
<213> ORGANISM: Artificial Sequence
<220> FEATURE:
<223> OTHER INFORMATION: Synthetic

<400> SEQUENCE: 26
aagaccttcg gcggtt                                                       16

<210> SEQ ID NO 27
<211> LENGTH: 16
<212> TYPE: DNA
<213> ORGANISM: Artificial Sequence
<220> FEATURE:
<223> OTHER INFORMATION: Synthetic

<400> SEQUENCE: 27
agagcttaga tgagag                                                       16

<210> SEQ ID NO 28
<211> LENGTH: 16
<212> TYPE: DNA
<213> ORGANISM: Artificial Sequence
<220> FEATURE:
<223> OTHER INFORMATION: Synthetic

<400> SEQUENCE: 28
cgatgtacag cgttcg                                                       16

<210> SEQ ID NO 29
<211> LENGTH: 16
<212> TYPE: DNA
<213> ORGANISM: Artificial Sequence
<220> FEATURE:
<223> OTHER INFORMATION: Synthetic

<400> SEQUENCE: 29
```
caggtgcgtg tatggg                                                    16

<210> SEQ ID NO 30
<211> LENGTH: 16
<212> TYPE: DNA
<213> ORGANISM: Artificial Sequence
<220> FEATURE:
<223> OTHER INFORMATION: Synthetic

<400> SEQUENCE: 30
ctggtcttct cttatg                                                    16

<210> SEQ ID NO 31
<211> LENGTH: 16
<212> TYPE: DNA
<213> ORGANISM: Artificial Sequence
<220> FEATURE:
<223> OTHER INFORMATION: Synthetic

<400> SEQUENCE: 31
ctgataggtg gctcca                                                    16

<210> SEQ ID NO 32
<211> LENGTH: 16
<212> TYPE: DNA
<213> ORGANISM: Artificial Sequence
<220> FEATURE:
<223> OTHER INFORMATION: Synthetic

<400> SEQUENCE: 32
gtctcgtcac accgca                                                    16

<210> SEQ ID NO 33
<211> LENGTH: 16
<212> TYPE: DNA
<213> ORGANISM: Artificial Sequence
<220> FEATURE:
<223> OTHER INFORMATION: Synthetic

<400> SEQUENCE: 33
ttgacttaga atctcc                                                    16

<210> SEQ ID NO 34
<211> LENGTH: 16
<212> TYPE: DNA
<213> ORGANISM: Artificial Sequence
<220> FEATURE:
<223> OTHER INFORMATION: Synthetic

<400> SEQUENCE: 34
tacctattct ttacgt                                                    16

<210> SEQ ID NO 35
<211> LENGTH: 16
<212> TYPE: DNA
<213> ORGANISM: Artificial Sequence
<220> FEATURE:
<223> OTHER INFORMATION: Synthetic

<400> SEQUENCE: 35
taagagagta cctaca                                                    16

<210> SEQ ID NO 36
<211> LENGTH: 16
<212> TYPE: DNA

```
<213> ORGANISM: Artificial Sequence
<220> FEATURE:
<223> OTHER INFORMATION: Synthetic

<400> SEQUENCE: 36
gagcagagtt gaactc                                                     16

<210> SEQ ID NO 37
<211> LENGTH: 16
<212> TYPE: DNA
<213> ORGANISM: Artificial Sequence
<220> FEATURE:
<223> OTHER INFORMATION: Synthetic

<400> SEQUENCE: 37
gtcgggtcac gcgaaa                                                     16

<210> SEQ ID NO 38
<211> LENGTH: 16
<212> TYPE: DNA
<213> ORGANISM: Artificial Sequence
<220> FEATURE:
<223> OTHER INFORMATION: Synthetic

<400> SEQUENCE: 38
atagaccagt ccggtc                                                     16

<210> SEQ ID NO 39
<211> LENGTH: 16
<212> TYPE: DNA
<213> ORGANISM: Artificial Sequence
<220> FEATURE:
<223> OTHER INFORMATION: Synthetic

<400> SEQUENCE: 39
gcactctgtg cctgca                                                     16

<210> SEQ ID NO 40
<211> LENGTH: 16
<212> TYPE: DNA
<213> ORGANISM: Artificial Sequence
<220> FEATURE:
<223> OTHER INFORMATION: Synthetic

<400> SEQUENCE: 40
cgtcaggaga tgcctt                                                     16

<210> SEQ ID NO 41
<211> LENGTH: 16
<212> TYPE: DNA
<213> ORGANISM: Artificial Sequence
<220> FEATURE:
<223> OTHER INFORMATION: Synthetic

<400> SEQUENCE: 41
ggccgatgtc gtcttc                                                     16

<210> SEQ ID NO 42
<211> LENGTH: 16
<212> TYPE: DNA
<213> ORGANISM: Artificial Sequence
<220> FEATURE:
<223> OTHER INFORMATION: Synthetic

<400> SEQUENCE: 42
ttaggcaagc acgcct                                                     16
```

<210> SEQ ID NO 43
<211> LENGTH: 16
<212> TYPE: DNA
<213> ORGANISM: Artificial Sequence
<220> FEATURE:
<223> OTHER INFORMATION: Synthetic

<400> SEQUENCE: 43
gttacaggta cgaccc                                                       16

<210> SEQ ID NO 44
<211> LENGTH: 16
<212> TYPE: DNA
<213> ORGANISM: Artificial Sequence
<220> FEATURE:
<223> OTHER INFORMATION: Synthetic

<400> SEQUENCE: 44
cagctaatcc aaagtc                                                       16

<210> SEQ ID NO 45
<211> LENGTH: 16
<212> TYPE: DNA
<213> ORGANISM: Artificial Sequence
<220> FEATURE:
<223> OTHER INFORMATION: Synthetic

<400> SEQUENCE: 45
tatcaggcag ggattg                                                       16

<210> SEQ ID NO 46
<211> LENGTH: 16
<212> TYPE: DNA
<213> ORGANISM: Artificial Sequence
<220> FEATURE:
<223> OTHER INFORMATION: Synthetic

<400> SEQUENCE: 46
atcacaggtg accaag                                                       16

<210> SEQ ID NO 47
<211> LENGTH: 16
<212> TYPE: DNA
<213> ORGANISM: Artificial Sequence
<220> FEATURE:
<223> OTHER INFORMATION: Synthetic

<400> SEQUENCE: 47
gggtctggta gctccg                                                       16

<210> SEQ ID NO 48
<211> LENGTH: 16
<212> TYPE: DNA
<213> ORGANISM: Artificial Sequence
<220> FEATURE:
<223> OTHER INFORMATION: Synthetic

<400> SEQUENCE: 48
gctcctacag actcgc                                                       16

<210> SEQ ID NO 49
<211> LENGTH: 16
<212> TYPE: DNA
<213> ORGANISM: Artificial Sequence
<220> FEATURE:

<223> OTHER INFORMATION: Synthetic

<400> SEQUENCE: 49
agtgggaaga cactaa                                                          16

<210> SEQ ID NO 50
<211> LENGTH: 16
<212> TYPE: DNA
<213> ORGANISM: Artificial Sequence
<220> FEATURE:
<223> OTHER INFORMATION: Synthetic

<400> SEQUENCE: 50
aacacgttcc acgcag                                                          16

<210> SEQ ID NO 51
<211> LENGTH: 16
<212> TYPE: DNA
<213> ORGANISM: Artificial Sequence
<220> FEATURE:
<223> OTHER INFORMATION: Synthetic

<400> SEQUENCE: 51
ttctcaaagg gacact                                                          16

<210> SEQ ID NO 52
<211> LENGTH: 16
<212> TYPE: DNA
<213> ORGANISM: Artificial Sequence
<220> FEATURE:
<223> OTHER INFORMATION: Synthetic

<400> SEQUENCE: 52
acgtcaaagt acgata                                                          16

<210> SEQ ID NO 53
<211> LENGTH: 16
<212> TYPE: DNA
<213> ORGANISM: Artificial Sequence
<220> FEATURE:
<223> OTHER INFORMATION: Synthetic

<400> SEQUENCE: 53
gagtccgcaa tcacac                                                          16

<210> SEQ ID NO 54
<211> LENGTH: 16
<212> TYPE: DNA
<213> ORGANISM: Artificial Sequence
<220> FEATURE:
<223> OTHER INFORMATION: Synthetic

<400> SEQUENCE: 54
acagccgaga tacggc                                                          16

<210> SEQ ID NO 55
<211> LENGTH: 16
<212> TYPE: DNA
<213> ORGANISM: Artificial Sequence
<220> FEATURE:
<223> OTHER INFORMATION: Synthetic

<400> SEQUENCE: 55
ggtattgcaa tgttgc                                                          16

<210> SEQ ID NO 56
<211> LENGTH: 16
<212> TYPE: DNA
<213> ORGANISM: Artificial Sequence
<220> FEATURE:
<223> OTHER INFORMATION: Synthetic

<400> SEQUENCE: 56
ttctcctcac gacgaa                                                       16

<210> SEQ ID NO 57
<211> LENGTH: 16
<212> TYPE: DNA
<213> ORGANISM: Artificial Sequence
<220> FEATURE:
<223> OTHER INFORMATION: Synthetic

<400> SEQUENCE: 57
tgccaaatcg cactct                                                       16

<210> SEQ ID NO 58
<211> LENGTH: 16
<212> TYPE: DNA
<213> ORGANISM: Artificial Sequence
<220> FEATURE:
<223> OTHER INFORMATION: Synthetic

<400> SEQUENCE: 58
tcagatgcag acaggt                                                       16

<210> SEQ ID NO 59
<211> LENGTH: 16
<212> TYPE: DNA
<213> ORGANISM: Artificial Sequence
<220> FEATURE:
<223> OTHER INFORMATION: Synthetic

<400> SEQUENCE: 59
ttcccagcac acagag                                                       16

<210> SEQ ID NO 60
<211> LENGTH: 16
<212> TYPE: DNA
<213> ORGANISM: Artificial Sequence
<220> FEATURE:
<223> OTHER INFORMATION: Synthetic

<400> SEQUENCE: 60
cctagcttcg tttgcc                                                       16

<210> SEQ ID NO 61
<211> LENGTH: 16
<212> TYPE: DNA
<213> ORGANISM: Artificial Sequence
<220> FEATURE:
<223> OTHER INFORMATION: Synthetic

<400> SEQUENCE: 61
acgccgatct ggcgtg                                                       16

<210> SEQ ID NO 62
<211> LENGTH: 16
<212> TYPE: DNA
<213> ORGANISM: Artificial Sequence
<220> FEATURE:
<223> OTHER INFORMATION: Synthetic

```
<400> SEQUENCE: 62
gtgaaggagg tgatta                                                      16

<210> SEQ ID NO 63
<211> LENGTH: 16
<212> TYPE: DNA
<213> ORGANISM: Artificial Sequence
<220> FEATURE:
<223> OTHER INFORMATION: Synthetic

<400> SEQUENCE: 63
cagccgaagg acagct                                                      16

<210> SEQ ID NO 64
<211> LENGTH: 16
<212> TYPE: DNA
<213> ORGANISM: Artificial Sequence
<220> FEATURE:
<223> OTHER INFORMATION: Synthetic

<400> SEQUENCE: 64
ggtgttagtg ccttgg                                                      16

<210> SEQ ID NO 65
<211> LENGTH: 16
<212> TYPE: DNA
<213> ORGANISM: Artificial Sequence
<220> FEATURE:
<223> OTHER INFORMATION: Synthetic

<400> SEQUENCE: 65
gattcagcac accgca                                                      16

<210> SEQ ID NO 66
<211> LENGTH: 16
<212> TYPE: DNA
<213> ORGANISM: Artificial Sequence
<220> FEATURE:
<223> OTHER INFORMATION: Synthetic

<400> SEQUENCE: 66
tcattacgtc gggtct                                                      16

<210> SEQ ID NO 67
<211> LENGTH: 16
<212> TYPE: DNA
<213> ORGANISM: Artificial Sequence
<220> FEATURE:
<223> OTHER INFORMATION: Synthetic

<400> SEQUENCE: 67
atcacgagtc ctcttg                                                      16

<210> SEQ ID NO 68
<211> LENGTH: 16
<212> TYPE: DNA
<213> ORGANISM: Artificial Sequence
<220> FEATURE:
<223> OTHER INFORMATION: Synthetic

<400> SEQUENCE: 68
gaccaatagt tatcgc                                                      16

<210> SEQ ID NO 69
<211> LENGTH: 16
```

```
<212> TYPE: DNA
<213> ORGANISM: Artificial Sequence
<220> FEATURE:
<223> OTHER INFORMATION: Synthetic

<400> SEQUENCE: 69
ccacatctct ccaacc                                                    16

<210> SEQ ID NO 70
<211> LENGTH: 16
<212> TYPE: DNA
<213> ORGANISM: Artificial Sequence
<220> FEATURE:
<223> OTHER INFORMATION: Synthetic

<400> SEQUENCE: 70
agcgtattca ttgccc                                                    16

<210> SEQ ID NO 71
<211> LENGTH: 16
<212> TYPE: DNA
<213> ORGANISM: Artificial Sequence
<220> FEATURE:
<223> OTHER INFORMATION: Synthetic

<400> SEQUENCE: 71
gcttgaaagt gaagag                                                    16

<210> SEQ ID NO 72
<211> LENGTH: 16
<212> TYPE: DNA
<213> ORGANISM: Artificial Sequence
<220> FEATURE:
<223> OTHER INFORMATION: Synthetic

<400> SEQUENCE: 72
cgcggtatcg gcatcg                                                    16

<210> SEQ ID NO 73
<211> LENGTH: 16
<212> TYPE: DNA
<213> ORGANISM: Artificial Sequence
<220> FEATURE:
<223> OTHER INFORMATION: Synthetic

<400> SEQUENCE: 73
agaataggtc taggtt                                                    16

<210> SEQ ID NO 74
<211> LENGTH: 16
<212> TYPE: DNA
<213> ORGANISM: Artificial Sequence
<220> FEATURE:
<223> OTHER INFORMATION: Synthetic

<400> SEQUENCE: 74
cacagtatca ataccg                                                    16

<210> SEQ ID NO 75
<211> LENGTH: 16
<212> TYPE: DNA
<213> ORGANISM: Artificial Sequence
<220> FEATURE:
<223> OTHER INFORMATION: Synthetic

<400> SEQUENCE: 75
```
tcaacgatcg cactct                                                  16

<210> SEQ ID NO 76
<211> LENGTH: 16
<212> TYPE: DNA
<213> ORGANISM: Artificial Sequence
<220> FEATURE:
<223> OTHER INFORMATION: Synthetic

<400> SEQUENCE: 76
ccacatctct actgga                                                  16

<210> SEQ ID NO 77
<211> LENGTH: 16
<212> TYPE: DNA
<213> ORGANISM: Artificial Sequence
<220> FEATURE:
<223> OTHER INFORMATION: Synthetic

<400> SEQUENCE: 77
tctcatagtg gtccgt                                                  16

<210> SEQ ID NO 78
<211> LENGTH: 16
<212> TYPE: DNA
<213> ORGANISM: Artificial Sequence
<220> FEATURE:
<223> OTHER INFORMATION: Synthetic

<400> SEQUENCE: 78
cgatggcagt ccatac                                                  16

<210> SEQ ID NO 79
<211> LENGTH: 16
<212> TYPE: DNA
<213> ORGANISM: Artificial Sequence
<220> FEATURE:
<223> OTHER INFORMATION: Synthetic

<400> SEQUENCE: 79
gtgaaggcaa atggcg                                                  16

<210> SEQ ID NO 80
<211> LENGTH: 16
<212> TYPE: DNA
<213> ORGANISM: Artificial Sequence
<220> FEATURE:
<223> OTHER INFORMATION: Synthetic

<400> SEQUENCE: 80
gtctcgtagc acaggt                                                  16

<210> SEQ ID NO 81
<211> LENGTH: 16
<212> TYPE: DNA
<213> ORGANISM: Artificial Sequence
<220> FEATURE:
<223> OTHER INFORMATION: Synthetic

<400> SEQUENCE: 81
gcagttaagg gtcgat                                                  16

<210> SEQ ID NO 82
<211> LENGTH: 16
<212> TYPE: DNA
<213> ORGANISM: Artificial Sequence

```
<220> FEATURE:
<223> OTHER INFORMATION: Synthetic

<400> SEQUENCE: 82
gggagatcaa gcgctc                                                    16

<210> SEQ ID NO 83
<211> LENGTH: 16
<212> TYPE: DNA
<213> ORGANISM: Artificial Sequence
<220> FEATURE:
<223> OTHER INFORMATION: Synthetic

<400> SEQUENCE: 83
ggcgtgtaga tcgggt                                                    16

<210> SEQ ID NO 84
<211> LENGTH: 16
<212> TYPE: DNA
<213> ORGANISM: Artificial Sequence
<220> FEATURE:
<223> OTHER INFORMATION: Synthetic

<400> SEQUENCE: 84
gccaaattca gtccct                                                    16

<210> SEQ ID NO 85
<211> LENGTH: 16
<212> TYPE: DNA
<213> ORGANISM: Artificial Sequence
<220> FEATURE:
<223> OTHER INFORMATION: Synthetic

<400> SEQUENCE: 85
ctacaccgtc aagcga                                                    16

<210> SEQ ID NO 86
<211> LENGTH: 16
<212> TYPE: DNA
<213> ORGANISM: Artificial Sequence
<220> FEATURE:
<223> OTHER INFORMATION: Synthetic

<400> SEQUENCE: 86
aaccgcgtcg aatggg                                                    16

<210> SEQ ID NO 87
<211> LENGTH: 16
<212> TYPE: DNA
<213> ORGANISM: Artificial Sequence
<220> FEATURE:
<223> OTHER INFORMATION: Synthetic

<400> SEQUENCE: 87
tacggtatca atctct                                                    16

<210> SEQ ID NO 88
<211> LENGTH: 16
<212> TYPE: DNA
<213> ORGANISM: Artificial Sequence
<220> FEATURE:
<223> OTHER INFORMATION: Synthetic

<400> SEQUENCE: 88
ttcttaggat ctgtca                                                    16
```

-continued

```
<210> SEQ ID NO 89
<211> LENGTH: 16
<212> TYPE: DNA
<213> ORGANISM: Artificial Sequence
<220> FEATURE:
<223> OTHER INFORMATION: Synthetic

<400> SEQUENCE: 89
ttgtagggtt aaagtg                                                       16

<210> SEQ ID NO 90
<211> LENGTH: 16
<212> TYPE: DNA
<213> ORGANISM: Artificial Sequence
<220> FEATURE:
<223> OTHER INFORMATION: Synthetic

<400> SEQUENCE: 90
ttctcctcac ataacc                                                       16

<210> SEQ ID NO 91
<211> LENGTH: 16
<212> TYPE: DNA
<213> ORGANISM: Artificial Sequence
<220> FEATURE:
<223> OTHER INFORMATION: Synthetic

<400> SEQUENCE: 91
acaccaatct ccaacc                                                       16

<210> SEQ ID NO 92
<211> LENGTH: 16
<212> TYPE: DNA
<213> ORGANISM: Artificial Sequence
<220> FEATURE:
<223> OTHER INFORMATION: Synthetic

<400> SEQUENCE: 92
aaagtagtct gcaagt                                                       16

<210> SEQ ID NO 93
<211> LENGTH: 16
<212> TYPE: DNA
<213> ORGANISM: Artificial Sequence
<220> FEATURE:
<223> OTHER INFORMATION: Synthetic

<400> SEQUENCE: 93
cctaaagagt aggtat                                                       16

<210> SEQ ID NO 94
<211> LENGTH: 16
<212> TYPE: DNA
<213> ORGANISM: Artificial Sequence
<220> FEATURE:
<223> OTHER INFORMATION: Synthetic

<400> SEQUENCE: 94
cgatggccaa gtctac                                                       16

<210> SEQ ID NO 95
<211> LENGTH: 14
<212> TYPE: DNA
<213> ORGANISM: Artificial Sequence
<220> FEATURE:
<223> OTHER INFORMATION: Synthetic
```

<400> SEQUENCE: 95
ctattgtgat ggtc                                                        14

<210> SEQ ID NO 96
<211> LENGTH: 14
<212> TYPE: DNA
<213> ORGANISM: Artificial Sequence
<220> FEATURE:
<223> OTHER INFORMATION: Synthetic

<400> SEQUENCE: 96
gaggatcttg cttt                                                        14

<210> SEQ ID NO 97
<211> LENGTH: 14
<212> TYPE: DNA
<213> ORGANISM: Artificial Sequence
<220> FEATURE:
<223> OTHER INFORMATION: Synthetic

<400> SEQUENCE: 97
ggccgaactc gtag                                                        14

<210> SEQ ID NO 98
<211> LENGTH: 24
<212> TYPE: DNA
<213> ORGANISM: Artificial Sequence
<220> FEATURE:
<223> OTHER INFORMATION: Synthetic

<400> SEQUENCE: 98
caagcagaag acggcatacg agat                                             24

<210> SEQ ID NO 99
<211> LENGTH: 14
<212> TYPE: DNA
<213> ORGANISM: Artificial Sequence
<220> FEATURE:
<223> OTHER INFORMATION: Synthetic

<400> SEQUENCE: 99
agaatggacg acat                                                        14

<210> SEQ ID NO 100
<211> LENGTH: 24
<212> TYPE: DNA
<213> ORGANISM: Artificial Sequence
<220> FEATURE:
<223> OTHER INFORMATION: Synthetic

<400> SEQUENCE: 100
caagcagaag acggcatacg agat                                             24

<210> SEQ ID NO 101
<211> LENGTH: 14
<212> TYPE: DNA
<213> ORGANISM: Artificial Sequence
<220> FEATURE:
<223> OTHER INFORMATION: Synthetic

<400> SEQUENCE: 101
atgtcgtcca ttct                                                        14

<210> SEQ ID NO 102

```
<211> LENGTH: 14
<212> TYPE: DNA
<213> ORGANISM: Artificial Sequence
<220> FEATURE:
<223> OTHER INFORMATION: Synthetic

<400> SEQUENCE: 102
ggcgacacag agta                                                          14

<210> SEQ ID NO 103
<211> LENGTH: 24
<212> TYPE: DNA
<213> ORGANISM: Artificial Sequence
<220> FEATURE:
<223> OTHER INFORMATION: Synthetic

<400> SEQUENCE: 103
caagcagaag acggcatacg agat                                               24

<210> SEQ ID NO 104
<211> LENGTH: 14
<212> TYPE: DNA
<213> ORGANISM: Artificial Sequence
<220> FEATURE:
<223> OTHER INFORMATION: Synthetic

<400> SEQUENCE: 104
tactctgtgt cgcc                                                          14

<210> SEQ ID NO 105
<211> LENGTH: 14
<212> TYPE: DNA
<213> ORGANISM: Artificial Sequence
<220> FEATURE:
<223> OTHER INFORMATION: Synthetic

<400> SEQUENCE: 105
ggctaatgga tgaa                                                          14

<210> SEQ ID NO 106
<211> LENGTH: 24
<212> TYPE: DNA
<213> ORGANISM: Artificial Sequence
<220> FEATURE:
<223> OTHER INFORMATION: Synthetic

<400> SEQUENCE: 106
caagcagaag acggcatacg agat                                               24

<210> SEQ ID NO 107
<211> LENGTH: 14
<212> TYPE: DNA
<213> ORGANISM: Artificial Sequence
<220> FEATURE:
<223> OTHER INFORMATION: Synthetic

<400> SEQUENCE: 107
ttcatccatt agcc                                                          14

<210> SEQ ID NO 108
<211> LENGTH: 14
<212> TYPE: DNA
<213> ORGANISM: Artificial Sequence
<220> FEATURE:
<223> OTHER INFORMATION: Synthetic

<400> SEQUENCE: 108
```
gtacagtgtc gaca					14

<210> SEQ ID NO 109
<211> LENGTH: 24
<212> TYPE: DNA
<213> ORGANISM: Artificial Sequence
<220> FEATURE:
<223> OTHER INFORMATION: Synthetic

<400> SEQUENCE: 109
caagcagaag acggcatacg agat					24

<210> SEQ ID NO 110
<211> LENGTH: 14
<212> TYPE: DNA
<213> ORGANISM: Artificial Sequence
<220> FEATURE:
<223> OTHER INFORMATION: Synthetic

<400> SEQUENCE: 110
tgtcgacact gtac					14

<210> SEQ ID NO 111
<211> LENGTH: 14
<212> TYPE: DNA
<213> ORGANISM: Artificial Sequence
<220> FEATURE:
<223> OTHER INFORMATION: Synthetic

<400> SEQUENCE: 111
acggaggaac ctga					14

<210> SEQ ID NO 112
<211> LENGTH: 24
<212> TYPE: DNA
<213> ORGANISM: Artificial Sequence
<220> FEATURE:
<223> OTHER INFORMATION: Synthetic

<400> SEQUENCE: 112
caagcagaag acggcatacg agat					24

<210> SEQ ID NO 113
<211> LENGTH: 14
<212> TYPE: DNA
<213> ORGANISM: Artificial Sequence
<220> FEATURE:
<223> OTHER INFORMATION: Synthetic

<400> SEQUENCE: 113
tcaggttcct ccgt					14

<210> SEQ ID NO 114
<211> LENGTH: 14
<212> TYPE: DNA
<213> ORGANISM: Artificial Sequence
<220> FEATURE:
<223> OTHER INFORMATION: Synthetic

<400> SEQUENCE: 114
tgtaggtggt tacg					14

<210> SEQ ID NO 115
<211> LENGTH: 24
<212> TYPE: DNA

```
<213> ORGANISM: Artificial Sequence
<220> FEATURE:
<223> OTHER INFORMATION: Synthetic

<400> SEQUENCE: 115
caagcagaag acggcatacg agat                                               24

<210> SEQ ID NO 116
<211> LENGTH: 14
<212> TYPE: DNA
<213> ORGANISM: Artificial Sequence
<220> FEATURE:
<223> OTHER INFORMATION: Synthetic

<400> SEQUENCE: 116
cgtaaccacc taca                                                          14

<210> SEQ ID NO 117
<211> LENGTH: 14
<212> TYPE: DNA
<213> ORGANISM: Artificial Sequence
<220> FEATURE:
<223> OTHER INFORMATION: Synthetic

<400> SEQUENCE: 117
aagccatggc cttc                                                          14

<210> SEQ ID NO 118
<211> LENGTH: 24
<212> TYPE: DNA
<213> ORGANISM: Artificial Sequence
<220> FEATURE:
<223> OTHER INFORMATION: Synthetic

<400> SEQUENCE: 118
caagcagaag acggcatacg agat                                               24

<210> SEQ ID NO 119
<211> LENGTH: 14
<212> TYPE: DNA
<213> ORGANISM: Artificial Sequence
<220> FEATURE:
<223> OTHER INFORMATION: Synthetic

<400> SEQUENCE: 119
gaaggccatg gctt                                                          14

<210> SEQ ID NO 120
<211> LENGTH: 14
<212> TYPE: DNA
<213> ORGANISM: Artificial Sequence
<220> FEATURE:
<223> OTHER INFORMATION: Synthetic

<400> SEQUENCE: 120
gaaatactcc ctac                                                          14

<210> SEQ ID NO 121
<211> LENGTH: 24
<212> TYPE: DNA
<213> ORGANISM: Artificial Sequence
<220> FEATURE:
<223> OTHER INFORMATION: Synthetic

<400> SEQUENCE: 121
caagcagaag acggcatacg agat                                               24
```

<210> SEQ ID NO 122
<211> LENGTH: 14
<212> TYPE: DNA
<213> ORGANISM: Artificial Sequence
<220> FEATURE:
<223> OTHER INFORMATION: Synthetic

<400> SEQUENCE: 122
gtagggagta tttc                                                       14

<210> SEQ ID NO 123
<211> LENGTH: 14
<212> TYPE: DNA
<213> ORGANISM: Artificial Sequence
<220> FEATURE:
<223> OTHER INFORMATION: Synthetic

<400> SEQUENCE: 123
cgtagcctta gtcg                                                       14

<210> SEQ ID NO 124
<211> LENGTH: 24
<212> TYPE: DNA
<213> ORGANISM: Artificial Sequence
<220> FEATURE:
<223> OTHER INFORMATION: Synthetic

<400> SEQUENCE: 124
caagcagaag acggcatacg agat                                            24

<210> SEQ ID NO 125
<211> LENGTH: 14
<212> TYPE: DNA
<213> ORGANISM: Artificial Sequence
<220> FEATURE:
<223> OTHER INFORMATION: Synthetic

<400> SEQUENCE: 125
cgactaaggc tacg                                                       14

<210> SEQ ID NO 126
<211> LENGTH: 66
<212> TYPE: DNA
<213> ORGANISM: Artificial Sequence
<220> FEATURE:
<223> OTHER INFORMATION: Synthetic

<400> SEQUENCE: 126
aatgatacgg cgaccaccga gatctacacg cctgtccgcg gaagcagtgg tatcaacgca     60
gagtac                                                                66

<210> SEQ ID NO 127
<211> LENGTH: 61
<212> TYPE: DNA
<213> ORGANISM: Artificial Sequence
<220> FEATURE:
<223> OTHER INFORMATION: Synthetic

<400> SEQUENCE: 127
aatgatacgg cgaccaccga gatctacaca cactctttcc tacacgacgc tcttccgatc     60
t                                                                     61

SINGLE CELL CELLULAR COMPONENT ENRICHMENT FROM BARCODED SEQUENCING LIBRARIES

CROSS-REFERENCE TO RELATED APPLICATIONS

This application is a 35 U.S.C. § 371 national stage application of International Patent Application No. PCT/US2018/057161 filed Oct. 23, 2018, and entitled: "Single Cell Cellular Component Enrichment from Barcoded Sequencing Libraries," and claims the benefit of U.S. Provisional Application Nos. 62/576,031, filed Oct. 23, 2017 and 62/736,863, filed Sep. 26, 2018. The entire contents of the above-identified applications are hereby fully incorporated herein by reference.

STATEMENT REGARDING FEDERALLY SPONSORED RESEARCH

This invention was made with government support under grant numbers HG006193, AI118668 and DK097681 awarded by the National Institutes of Health. The government has certain rights in the invention.

REFERENCE TO AN ELECTRONIC SEQUENCE LISTING

The contents of the electronic sequence listing (BROD-0860WP.ST25.txt"; Size is 25 Kilobytes and it was created on Oct. 8, 2018) is herein incorporated by reference in its entirety.

TECHNICAL FIELD

The subject matter disclosed herein is generally directed to methods for detecting transcriptomes in single cells. Specifically, the subject matter is directed to enriching of cDNA constructs from a barcoded single cell sequencing library and sequencing the enriched cDNA constructs, thereby enabling high resolution gene expression analysis in rare cells.

BACKGROUND

Intensive interest exists in applying single-cell genomic analyses including gene expression, chromatin accessibility, and DNA copy number variation to resolve differences between cells in a population. Pooled analysis of thousands of single cells is now routinely practiced by introducing cell-specific DNA barcodes early in cell processing protocols to produce a pooled library that is sequenced as a single sample and deconvoluted in silico. While such pooled experimental workflows are now a mainstream approach in life science research including cell atlasing efforts (M. Enge, et al., Cell, 171(2):321-330, 2017; T M. Gierahn, et al., Nat Meth, 14(4):395-398, 2017; X. Han, et al., Cell, 172:1091-1107, 2018; A M. Klein, et al., Cell, 161(5):1187-1201, 2015; EZ. Macosko, et al., Cell, 161(5):1202-1211, 2015; GL. Manno, et al., Cell, 167(2):566-580, 2016; CC. Ooi, et al., PLoS ONE, 12(11), 2017; and MJT. Stubbington, et al., Bio Direct, 10, 2015), these workflows do not currently enable cell targeting, even in cases when only a few rare cells are of interest (SC. Bendall and GP. Nolan, Nat Biotech, 30(7):639-647, 2012; AK. Shalek, et al., Nature, 510:363-369, 2014; and AC. Villani, et al., Science, 356 (6335), 2017). Moreover, this approach is wasteful when not all cells present are of interest and in studies of rare cell subsets. Increasingly, to identify and study rare cell types, investigators are turning to enriching targets at the cellular level before library construction with methods such as flow cytometry, which requires painstaking protocol and reagent development for each new target.

As cell type and cell state discovery moves towards rare target populations (C. Benz, et al., Cell Stem Cell, 10:273-283, 2012; D. Grun, et al., Nature, 525:251-255, 2015; and B. Mahata, et al., Cell Rep, 7:1130-1142, 2014), the challenge of identifying and accessing rare cells in pooled sequence libraries becomes increasingly important. In instances where rare cells are of interest, investigators must cope with applying extremely high sequencing effort or the sample loss and perturbation associated with enrichment by fluorescence-activated cell sorting (FACS), which ultimately limits the types of samples that can be processed (AE. Saliba, et al., Nuc. Acids Res., 42(14), 2014). Additionally, the analysis of single cell sequencing data can be limited by sequencing cost/effort when trying to identify specific library members (cells or genes) within a complex sequencing library. The typical approach is to sequence deeper, however, this results in analyzing more noise than signal (where the signal represents the members of the sequencing library) especially when the signal is present at much lower abundance. Thus, there is a need for improved methods of sequencing rare cells or subsets of cells.

SUMMARY

In certain example embodiments, the present invention provides for an enrichment and sequencing scheme that relies on the presence of barcodes to identify and concentrate sequencing library molecules that are relevant to a biological question, such as gene expression in rare cells and identifying T cell receptor (TCR) or B cell receptor (BCR) pairs in single cells.

This disclosure provides methods for obtaining and optionally sequencing the transcriptome of a single cell. As an example, the methods may be used to identify the transcriptome of a cell having a particular T cell receptor or B cell receptor amongst a population of cells, e.g., a population of cells comprising T cells and/or B cells. In another example, the methods may be used to identify the transcriptome of a cancer cell amongst the transcripts of a population of cells, e.g., non-cancerous cells. The cancer cell may also include a rare cancer stem cell. The transcriptomes can be obtained or isolated from transcript libraries (e.g., single cell RNA sequencing libraries) generated from a population of cells where each cell, or cell type, or group of cells is labeled with a unique barcode. Thus, provided herein are methods for (i) identifying a barcode associated with transcripts from a single cell, (ii) counting the number of cells associated with a target gene by determining the number of unique barcodes, and/or (iii) obtaining or isolating the transcriptome of single cells based on their unique barcodes.

In one aspect, the present invention provides for a method of enriching barcoded DNA constructs from a single cell library (e.g., library of transcripts) generated from a plurality of cells comprising capturing DNA library molecules from the library by targeting one or more unique cell-identifying barcodes and/or target transcript. The method may be a method of identifying a transcriptome from at least one single cell or a subpopulation of single cells, said method comprising enriching library molecules from the at least one single cell or subpopulation of single cells based on the one or more unique cell-identifying barcodes, wherein the targeted barcodes identify transcripts of single cells represented within the sequencing library.

In certain embodiments, the method may comprise: capture of DNA library molecules from the library by targeting one or more target transcripts; sequencing the captured DNA library molecules; identifying cell-identifying barcodes associated with the captured DNA library molecules; and capturing DNA library molecules from the library by targeting the identified cell-identifying barcodes, whereby DNA constructs associated with single cells expressing one or more target transcripts are enriched.

In certain embodiments, the method may comprise PCR amplification of one or more DNA library molecules with primer pairs complementary to each of the one or more DNA library molecules, wherein the primer pairs comprise one primer comprising a complementary sequence to a cell-identifying barcode or target transcript sequence for each of the one or more DNA library molecules. The capture may comprise PCR amplification of one or more DNA library molecules specific for at least one single cell or subpopulation of single cells.

The PCR amplification may comprise contacting the library with a 5' primer and a 3' primer, wherein the 5' primer or the 3' primer comprises a nucleotide sequence that is complementary to the unique barcode of a single cell from the at least one single cell or subpopulation of single cells; and amplifying the library molecules comprising the unique barcode of the single cell; thereby obtaining a plurality of transcripts from the single cell. The method of PCR wherein, (a) the 5' primer may comprise a nucleotide sequence that is complementary to a 5' universal primer site contained in each library molecule and a nucleotide sequence that is complementary to the unique barcode and the 3' primer comprises a nucleotide sequence that is complementary to a 3' universal primer site contained in each library molecule; (b) the 5' primer may comprise a nucleotide sequence that is complementary to a 5' universal primer site contained in each library molecule and the 3' primer comprises a nucleotide sequence that is complementary to a 3' universal primer site contained in each library molecule and a nucleotide sequence that is complementary to the unique barcode; (c) the 5' primer may comprise a nucleotide sequence that is complementary to a 5' universal primer site different from the 5' universal primer site contained in each library molecule and a nucleotide sequence that is complementary to the unique barcode and the 3' primer comprises a nucleotide sequence that is complementary to a 3' universal primer site contained in each library molecule; or (d) the 5' primer may comprise a nucleotide sequence that is complementary to a 5' universal primer site contained in each library molecule and the 3' primer comprises a nucleotide sequence that is complementary to a 3' universal primer site different from the 3' universal primer site contained in each library molecule and a nucleotide sequence that is complementary to the unique barcode.

In certain embodiments, the library molecules are pair-end DNA constructs comprising a first priming site outside of a single cell barcode at one end of the construct and a second priming site at the other end of the construct, and wherein PCR amplification comprises a first primer specific for the first priming site and single cell barcode and a second primer specific for the second priming site.

In certain embodiments, at least one primer for amplification of DNA library molecules (or transcripts) comprises a label, wherein amplification products may be separated from the library by capturing amplification products comprising the label. The label may comprise biotin. The separating of the labeled amplification product from the library may comprise contacting the biotin-labeled amplification product with streptavidin. The streptavidin may be conjugated to a bead.

In certain embodiments, the library molecules comprise uracil. The method may further comprise: treating the amplified library molecules with uracil DNA glycosylase (UDG) and exonuclease; and amplifying the library molecules a second time. In certain embodiments, amplifying the library molecules from the single cell comprises: providing a single cell library from a plurality of cells, with library molecules from each cell comprising a unique barcode, and wherein the library comprises uracil; amplifying the transcripts having the unique barcode by contacting the library of transcripts with a 5' primer and a 3' primer, wherein the 5' primer or the 3' primer comprises a nucleotide sequence that is complementary to the unique barcode of the single cell and a polymerase that does not recognize uracil; treating the amplified transcripts with uracil DNA glycosylase (UDG) and exonuclease; and amplifying the transcripts treated with uracil DNA glycosylase (UDG) and exonuclease.

In certain embodiments, the method of amplifying library molecules by PCR according to any embodiment herein may further comprise sequencing the amplified library molecules.

In certain embodiments, the method may comprise capture of library molecules by hybridization of DNA library molecules to oligonucleotides specific for target cell-identifying barcodes or target transcript sequences; and separating the oligonucleotides hybridized to the target cell-identifying barcodes or target transcript sequences from the library. The hybridization may be performed in solution. The oligonucleotides may comprise a label, wherein DNA library molecules may be separated from the library by capturing hybridized DNA library molecules comprising the label. The label may comprise biotin. The separating of the labeled oligonucleotide hybridized to the target library molecules may comprise contacting the biotin-labeled oligonucleotide hybridized to the target library molecules with streptavidin. The streptavidin may be conjugated to a bead. The method may further comprise PCR amplification of hybridized library molecules.

In certain embodiments, the method of hybridizing according to any embodiment herein may further comprise sequencing the hybridized library molecules.

In certain embodiments, the method of capture may comprise contacting the library with a CRISPR system, wherein the CRISPR system comprises CRISPR guide RNAs complementary to target cell-identifying barcodes or target transcript sequences. Contacting the library with a CRISPR system may be performed in solution. The CRISPR system may comprise an enzymatically inactive CRISPR enzyme. The CRISPR system may comprise an RNA guided DNA targeting CRISPR enzyme. The CRISPR enzyme may be Cas9 or Cpf1. The method of capturing library molecules using CRISPR according to any embodiment herein may comprise isolating captured DNA library molecules are isolated on a solid support (e.g., beads), wherein the captured DNA library molecules isolated on a solid support may be released from the solid support by treatment with RNase, proteinase, or denaturing conditions. The method of capturing library molecules using CRISPR may further comprise sequencing the captured library molecules.

In another aspect, the present invention provides for a sequencing method for identifying a single cell transcriptome in at least one single cell or subpopulation of single cells within a population of cells comprising: enriching library molecules from a single cell RNA sequencing (scRNA-seq) library for at least one single cell or subpopulation of single cells, wherein the library molecules comprise cell-identifying barcodes; and sequencing the enriched library molecules, whereby gene expression may be determined for the at least one single cell or subpopulation of single cells.

In certain embodiments, the method may further comprise a first step before the enriching step, wherein the first step comprises performing single cell RNA sequencing on a population of cells thereby generating a library of barcoded library molecules, wherein barcodes are identified for at least one single cell or subpopulation of single cells of interest from the population of cells. The single cell RNA sequencing may comprise deep sequencing of the library. Not being bound by a theory, initial deep sequencing of the library may detect library molecules (e.g., transcripts) from rare cells that may be enriched in order to determine a transcriptome for the rare cells. The at least one single cell or subpopulation of single cells may comprise T cells or B cells and barcodes specific to T cells or B cells may be enriched. T cell receptor (TCR) or B cell receptor (BCR) pairs may be determined (i.e., from sequencing an enriched library). The single cell RNA sequencing library may be generated from a tumor sample comprising tumor infiltrating lymphocytes (TIL). Not being bound by a theory, TCRs or BCRs specific for tumor cells may be identified.

In another aspect, the present invention provides for a sequencing method for identifying a single cell transcriptome in at least one single cell or subpopulation of single cells within a population of cells, wherein the at least one single cell or subpopulation of cells express a subset of transcripts of interest comprising: determining expression of the transcripts of interest in a single cell library from the population of cells, wherein the library molecules comprise cell-identifying barcodes; identifying barcodes associated with expression of the transcripts of interest in the single cell library; enriching library molecules comprising the cell-identifying barcodes associated with expression of the transcripts of interest from the single cell library; and sequencing the enriched library molecules, whereby a single cell transcriptome is identified for at least one single cell or subpopulation of single cells expressing a subset of transcripts of interest.

In another aspect, the present invention provides for a method for identifying a barcode associated with transcripts from a single cell in a library of transcripts comprising: providing a library of transcripts from a plurality of cells, with transcripts from each cell comprising a unique barcode; contacting the library of transcripts with a labeled oligonucleotide that is complementary to a target transcript encoding a specific T cell receptor or a specific B cell receptor under conditions sufficient for the labeled oligonucleotide to hybridize with the target transcript; and separating the labeled oligonucleotide hybridized to the target transcript from the library of transcripts; thereby separating cell barcodes of cells expressing the T cell receptor or B cell receptor. The single cell may be a T cell or a B cell.

In another aspect, the present invention provides for a method for isolating a transcriptome of a single cell from a library of transcripts comprising: providing a library of transcripts from a plurality of cells, with transcripts from each cell comprising a unique barcode; detecting and separating the transcripts comprising the unique barcode of the single cell; and sequencing the transcripts; wherein: (i) the library of transcripts is generated from 50,000 cells or more; (ii) transcripts that occur at a frequency of less than $1:10^8$ to $1:10^9$ in the library of transcripts are identified; or (iii) the single cell is a cell type that occur at a frequency of less than 1%-0.001% in the plurality of cells. The detecting and separating of the transcripts comprising the unique barcode of the single cell may comprise: isolating a target transcript from the library of transcripts; sequencing the barcode in the target transcript(s); and amplifying the transcripts comprising the unique barcode of the single cell.

In certain embodiments, the method according to any of the preceding embodiments includes sequencing, wherein the captured library molecules are sequenced by pyrosequencing, single-molecule real-time sequencing, ion torrent sequencing, sequencing by synthesis, sequencing by ligation, or Sanger sequencing. The sequencing of the captured library molecules may comprise a sequencing depth greater than about 5000 reads per cell. The sequencing of the captured library molecules may comprise a sequencing depth less than about 5000 reads per cell.

In certain embodiments, the method according to any of the preceding embodiments may further comprise counting the unique barcodes that are identified from sequencing of a single cell library or enriched single cell library as a measure of the number of cells that express a target transcript or subset of transcripts, wherein each unique barcode identifies a single cell.

The method according to any of the preceding embodiments, wherein the library may be a single cell RNA sequencing (scRNA-seq) library. The library may comprise cDNA. The single cell RNA sequencing library may be generated by 3' digital gene expression (DGE), SMART-seq2, SeqWell, droplet microfluidic barcoding, split and pool barcoding, or combinatorial indexing.

The method according to any of the preceding embodiments, wherein the barcode may be 10-20 nucleotides in length.

In certain embodiments, the library may be generated from 50,000 cells or more. In certain embodiments, transcripts that occur at a frequency of less than $1:10^8$ to $1:10^9$ in the library may be identified. The single cell may be a cell type that is present at a frequency of less than 1%-0.001% (i.e., rare cell).

The method according to any of the preceding embodiments may comprise target transcripts (e.g., PCR, hybridization, CRISPR system), wherein the target transcript may encode a cytokine, a T cell receptor, a B cell receptor, a pathogen transcript, a chemokine, a circulating tumor cell marker, a cell activation marker, an oncogene, or a somatic variant (e.g., an indel, single-nucleotide variant (SNV), or fusion). The circulating tumor cell marker may be selected from EpCAM, EphB4, EGFR, CEA, HER2, or MUC-1. The cell activation marker may be selected from CD154, CD137, CD134, CD278, or CD69. The oncogene may be selected from tp53, MUC16, KRAS, EGFR, VEGF, CDKN2A or any mutation found in a database herein. In certain embodiments, transcripts are enriched by hybridization or PCR amplification, as described herein.

The at least one single cell or subpopulation of single cells according to any embodiment herein may comprise a tumor cell, a T cell, a B cell, an NK cell, a cytokine-secreting cell, a dendritic cell, or a pathogen-infected cell. The library according to any embodiment herein may be generated from a population of cells comprising cultured cells, some or all of a tumor, a tissue sample, a bone marrow sample, or a blood sample.

In certain embodiments, the method of enriching, isolating or separating library molecules according to any embodiment herein may comprise any method of PCR amplification, hybridization, or CRISPR capture as described herein.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

FIG. 1A-FIG. 1G—Targeted enrichment of single cells within a pooled RNA sequence library. FIG. 1A shows a workflow for enrichment based on single-cell barcodes on the 5' end of sequence library molecules. Target cells (barcodes) of interest are identified based on shallow sequencing of the original pooled library. PCR with barcode-specific primers is used to create a new sequence library enriched for reads from the target cells. FIG. 1B shows an example enrichment plot for a single target cell from a multiplex-enrichment reaction. The original library was deeply sequenced as a control to identify gene expression profiles in the target cell. Enrichment fold is the fold-difference in overall sequencing effort to detect 50% of the maximum detectable number of genes. FIG. 1C shows the distribution of enrichment-fold values for 65 targeted cells amplified in multiplex PCR enrichments. FIG. 1D shows the pairwise correlation of gene expression profiles before and after PCR enrichment for CD19$^+$ cells (top) and HLA-DR$^+$ cells (bottom) libraries. The upper dashed line and shaded region in each plot represent the mean +/− two standard deviations of Bootstrap replicates of the original gene expression profiles against themselves (which represents the best correlation achievable given the read sampling, UMI sampling, and distribution of expression levels across genes in these specific cells). Red points show the correlation for targeted cells (post-enrichment profiles versus pre-enrichment profiles for the same cell). Gray box plots show distribution of correlation coefficients for control (non-target) cells existing in the library (post-enrichment profiles of the subject control cell versus pre-enrichment profiles of all cells). The dotted line shows the mean correlation for the cell barcodes that had at least 6 mismatches at the 3' end. Control comparisons are shown as a function of the number of mismatches (Hamming distance) between the six most 3' base pairs of the 16-base pair subject control cell barcode and the six most 3' base pairs of the 16-base pair barcode of compared targeted cells. FIG. 1E shows 10-plex PCR enrichment and FIG. 1F shows the correlation of gene expression profiles for 25 single cells with a minimum threshold of at least 1 UMI per gene in the pre-enriched cell. Error bars represent the standard deviation of technical replicates. FIG. 1G shows Principal Component Analysis (PCA) with the pre (closed circles) and post (open circles) enrichment positions of single cells where each color represents one cell barcode.

FIG. 2A shows the cutoff. The dashed red line (threshold of approximately 1000 UMIs) represents the cutoff used when calling whether a given barcode represented a cell or was noise. The cutoff was determined through 10X's CellRanger pipeline. FIG. 2B shows targeting barcodes for enrichment. The number of UMI pre and post enrichment is shown for all barcodes in the cell libraries. The barcodes in red were targeted for enrichment in the multiplex amplification. The sequencing effort for the control and enriched samples were normalized in the calculation of the fold change of number of UMIs.

FIG. 3A shows an example plot of UMI counts for three replicates against the expression profile in the original deeply sequenced library. FIG. 3B shows the pearson correlation coefficient of all barcodes enriched for (left) 2000 single-cell library across replicates. The color bar shows the number of UMI's identified in the control library (right). Computational filtering of replicates to reduce noise in gene expression profiles. Filtering was performed by looking at whether each replicate contained the same barcode-UMI-mapped gene information. 1 refers to the barcode-UMI-gene being present in only one replicate whereas 3 means that the combination existed in all replicates (left).

FIG. 15A shows reduced dimensionality representation of 19 cells from CD19+ cells (a) and FIG. 15B shows 46 cells from HLA-DR$^+$ cells (b) showing the position of targeted cells based on the expression profiles from the original deep sequenced library (closed circles) and the enriched library (open circles), where each color represents one cell/barcode. The gray data points show all cells within the two original deeply sequenced libraries and make visible the major clusters of cells with related expression profiles. Principal components analysis (PCA) and t-SNE, a nonlinear dimensionality reduction approach, are used to represent the high-dimensional datasets with corresponding color schemes. FIG. 15C shows AS dendritic cell signature analysis. Bar plots at top show the fraction of cells with at least one UMI count for the corresponding gene (number of cells above the dashed gray line in bottom panel, with black for all non-target cells, and red for target cells in the original library, middle bar, and red for target cells in the enriched library, right bar). Bottom panel: the expression of the classifier genes for all non-target cells in the original library (black points, left group for each gene), target cells in the original library (colored points, middle group), and enriched target cells (colored points, right). The same color is used for each targeted cell across the different classifier genes to facilitate comparison. The total number of cells in the HLA-DR$^+$ cells library was 2397 cells and nine putative AS DC cells were targeted for enrichment.

Figure 1A:
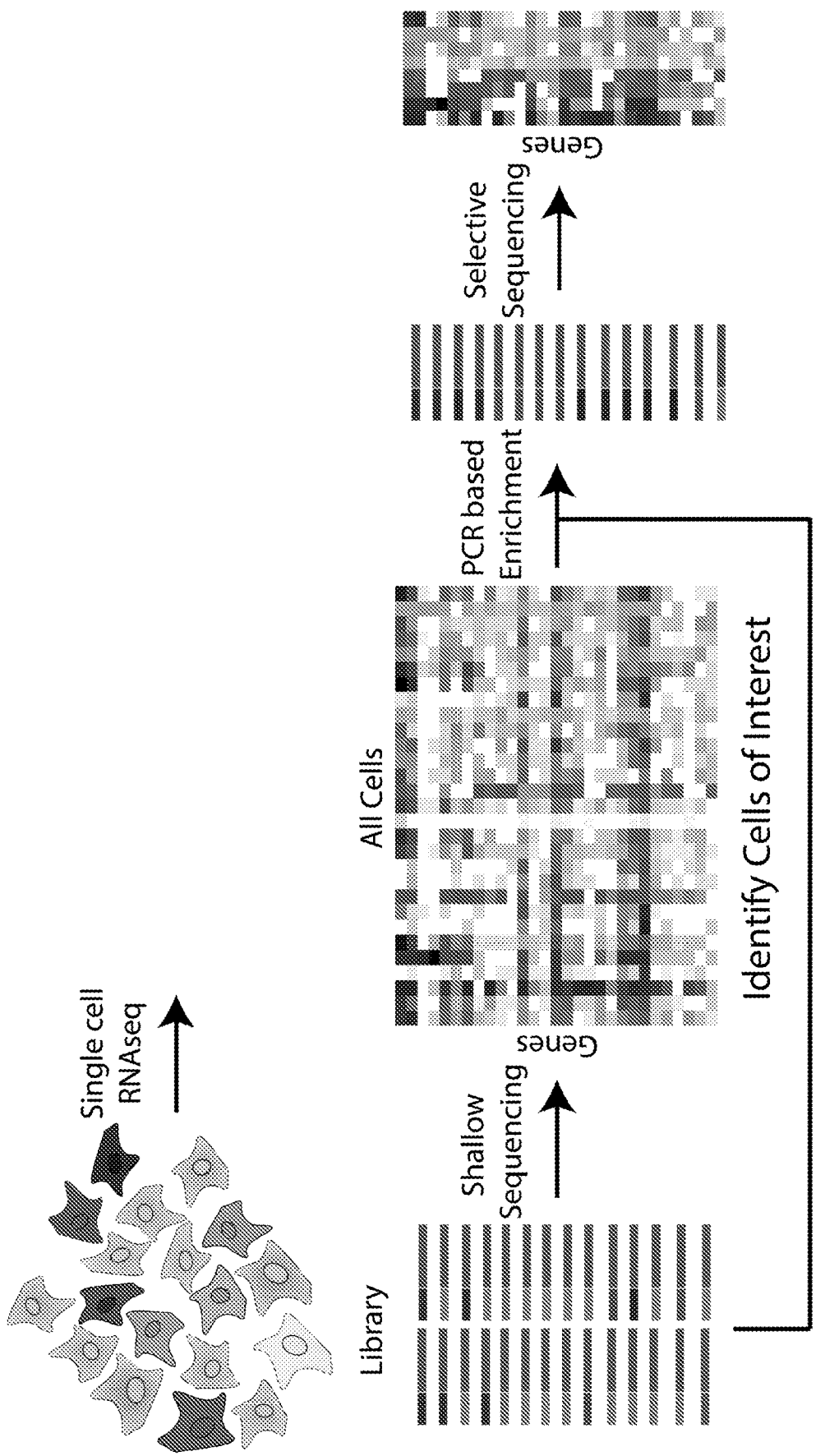

gene enrichment to identify target cell barcodes characterized by low-expression genes (1000 reads per cell) (LBA. Woodruff, et al., Nucleic Acids Research, 45(3):1553-1565, 2017). Lower primer synthesis cost corresponds to hypothetical future cases where 1) individual primers are pre-ordered and inventoried by a commercial provider or research organization such that primer costs can be amortized across multiple enrichment runs and 2) small custom primer pools are available as a service.

FIG. 27—Summary table for CD19$^+$ cell barcode targets. Barcodes identified in red either had low sequencing reads associated after enrichment or low number in genes identified in the original library and were removed from further analysis. (SEQ ID NOs. 11-38)

FIG. 28—Summary table for HLA-DR$^+$ cell barcode targets. Barcodes identified in red either had low sequencing reads associated after enrichment or low number in genes identified in the original library and were removed from further analysis. (SEQ ID NOs. 39-94)

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, 2$^{nd}$ edition (1989) (Sambrook, Fritsch, and Maniatis); Molecular Cloning: A Laboratory Manual, 4$^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, 2$^{nd}$ edition 2013 (E. A. Greenfield ed.); Animal Cell Culture (1987) (R.I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, 2nd edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

"Oligonucleotides", in the context of the invention, refers to multiple linked nucleotides (i.e., molecules comprising a sugar (e.g., ribose or deoxyribose) linked to an exchangeable organic base, which is either a pyrimidine (e.g., cytosine (C), thymidine (T) or uracil (U)) or a purine (e.g., adenine (A) or guanine (G)). Oligonucleotides include DNA such as D-form DNA and L-form DNA and RNA, as well as various modifications thereof. Modifications include base modifications, sugar modifications, and backbone modifications. Non-limiting examples of these are provided below.

Non-limiting examples of DNA variants that may be used in the invention are L-DNA (the backbone enantiomer of DNA, known in the literature), peptide nucleic acids (PNA) bisPNA clamp, a pseudocomplementary PNA, a locked nucleic acid (LNA), or co-nucleic acids of the above such as DNA-LNA co-nucleic acids. It is to be understood that the oligonucleotides used in products and methods of the invention may be homogeneous or heterogeneous in nature. As an example, they may be completely DNA in nature or they may be comprised of DNA and non-DNA (e.g., LNA) monomers or sequences. Thus, any combination of nucleic acid elements may be used. The oligonucleotide modification may render the oligonucleotide more stable and/or less susceptible to degradation under certain conditions. For example, in some instances, the oligonucleotides are nuclease-resistant.

The oligonucleotides may have a homogenous backbone (e.g., entirely phosphodiester or entirely phosphorothioate) or a heterogeneous (or chimeric) backbone. Phosphorothioate backbone modifications render an oligonucleotide less susceptible to nucleases and thus more stable (as compared to a native phosphodiester backbone nucleic acid) under certain conditions. Other linkages that may provide more stability to an oligonucleotide include without limitation phosphorodithioate linkages, methylphosphonate linkages, methylphosphorothioate linkages, boranophosphonate linkages, peptide linkages, alkyl linkages, dephospho type linkages, and the like. Thus, in some instances, the oligonucleotides have non-naturally occurring backbones.

Oligonucleotides may be synthesized in vitro. Methods for synthesizing nucleic acids, including automated nucleic acid synthesis, are also known in the art. Oligonucleotides having modified backbones, such as backbones comprising phosphorothioate linkages, and including those comprising chimeric modified backbones may be synthesized using automated techniques employing either phosphoramidate or H phosphonate chemistries. (F. E. Eckstein, "Oligonucleotides and Analogues—A Practical Approach" IRL Press, Oxford, U K, 1991, and M. D. Matteucci and M. H. Caruthers, Tetrahedron Lett. 21, 719 (1980)) Aryl and alkyl phosphonate linkages can be made, e.g., as described in U.S. Pat. No. 4,469,863; and alkylphosphotriester linkages (in which the charged oxygen moiety is alkylated), e.g., as described in U.S. Pat. No. 5,023,243 and European Patent No. 092,574, can be prepared by automated solid phase synthesis using commercially available reagents. Methods for making other DNA backbone modifications and substitutions have been described. Uhlmann E et al. (1990) Chem Rev 90:544; Goodchild J (1990) Bioconjugate Chem 1:165; Crooke ST et al. (1996) Annu Rev Pharmacol Toxicol 36:107-129; and Hunziker J et al. (1995) Mod Synth Methods 7:331-417.

The oligonucleotides may additionally or alternatively comprise modifications in their sugars. For example, a β-ribose unit or a β-D-2'-deoxyribose unit can be replaced by a modified sugar unit, wherein the modified sugar unit is for example selected from (3 D-ribose, α-D-2'-deoxyribose, L-2'-deoxyribose, 2'-F-2'-deoxyribose, arabinose, 2'-F-arabinose, 2'-O—(C1-C6)alkyl-ribose, preferably 2'-O—(C1-C6)alkyl-ribose is 2'-O-methylribose, 2'-O—(C2-C6)alkenyl-ribose, 2'40-(C1-C6)alkyl-O—(C1-C6)alkyl-ribose, 2'—NH2-2'-deoxyribose, (3 D xylo-furanose, a arabinofuranose, 2,4-dideoxy-β-D-erythro-hexo-pyranose, and carbocyclic (described, for example, in Froehler J (1992) Am Chem Soc 114:8320) and/or open-chain sugar analogs (described, for example, in Vandendriessche et al. (1993) Tetrahedron 49:7223) and/or bicyclosugar analogs (described, for example, in Tarkov M et al. (1993) Helv Chim Acta 76:481).

The oligonucleotides may comprise modifications in their bases. Modified bases include modified cytosines—such as 5-substituted cytosines (e.g., 5-methyl-cytosine, 5-fluoro-cytosine, 5-chloro-cytosine, 5-bromo-cytosine, 5-iodo-cytosine, 5-hydroxy-cytosine, 5-hydroxymethyl-cytosine, 5-difluoromethyl-cytosine, and unsubstituted or substituted 5-alkynyl-cytosine), 6-substituted cytosines, N4-substituted cytosines (e.g., N4-ethyl-cytosine), 5-aza-cytosine, 2-mercapto-cytosine, isocytosine, pseudo-isocytosine, cytosine analogs with condensed ring systems (e.g., N,N'-propylene cytosine or phenoxazine), and uracil and its derivatives (e.g., 5-fluoro-uracil, 5-bromo-uracil, 5-bromovinyl-uracil, 4-thio-uracil, 5-hydroxy-uracil, 5-propynyl-uracil), modified guanines such as 7-deazaguanine, 7 deaza 7 substituted guanine (such as 7 deaza 7 (C2-C6)alkynylguanine), 7 deaza 8 substituted guanine, hypoxanthine, N2-substituted guanines (e.g. N2-methyl-guanine), 5-amino-3-methyl-3H,6H-thiazolo[4,5-d]pyrimidine-2,7-dione, 2,6-diaminopurine, 2-aminopurine, purine, indole, adenine, substituted adenines (e.g. N6-methyl-adenine, 8-oxo-adenine) 8 substituted guanine (e.g. 8-hydroxyguanine and 8-bromoguanine), and 6-thioguanine. The nucleic acids may comprise universal bases (e.g. 3-nitropyrrole, P-base, 4-methyl-indole, 5-nitroindole, and K-base) and/or aromatic ring systems (e.g. fluorobenzene, difluorobenzene, benzimidazole or dichlorobenzimidazole, 1-methyl-1H-[1,2,4]triazole-3-carboxylic acid amide). A particular base pair that may be incorporated into the oligonucleotides of the invention is a dZ and dP non-standard nucleobase pair reported by Yang et al. NAR, 2006, 34(21):6095-6101. dZ, the pyrimidine analog, is 6-amino-5-nitro-3-(1'β-D-2'-deoxyribofuranosyl)-2(1H)-pyridone, and its Watson-Crick complement dP, the purine analog, is 2-amino-8-(1'β-D-1'-deoxyribofuranosyl)-imidazo[1,2-a]-1,3,5-triazin-4(8H)-one.

"Probes" and "Primers", as described herein, comprise oligonucleotides. They can be nucleic acids in whole or in part. They may comprise naturally occurring nucleotides and/or non-naturally occurring nucleotides. They may be or may comprise DNA, RNA, DNA analogs, RNA analogs, PNA, LNA and combinations thereof, provided it is able to hybridize in a sequence-specific manner to oligonucleotides and/or to be conjugated in some instances to a label.

In some embodiments, the probes or primers comprise adenine, thymine, guanine, and cytosine. In some embodiments, the probes or primers comprise uracil in place of thymine.

The probe or primer may form at least a Watson-Crick bond with the target. In other instances, the probe or primer such as the probe may form a Hoogsteen bond with the target, thereby forming a triplex. A probe or primer that binds by Hoogsteen binding enters the major groove of a nucleic acid and hybridizes with the bases located there. In some embodiments, the probes or primers can form both Watson-Crick and Hoogsteen bonds with the target. BisPNA probes, for instance, are capable of both Watson-Crick and Hoogsteen binding to a nucleic acid.

The probe or primer can be any length including but not limited to 8-100 nucleotides, 8-75 nucleotides, 8-50 nucleotides, 8-30 nucleotides, 18-30 nucleotides, and every integer therebetween as if explicitly recited herein.

The probes or primers are preferably single stranded, but they are not so limited. For example, when the probe or primer is a bisPNA it can adopt a secondary structure with the target resulting in a triple helix conformation, with one region of the bisPNA forming Hoogsteen bonds with the backbone of the identifier sequence and another region of the bisPNA forming Watson-Crick bonds with the bases of the target.

Hybridization: The binding of the probe or primer to the target via hybridization can be manipulated based on the hybridization conditions. For example, salt concentration and temperature can be modulated. Those of ordinary skill in the art will be able to determine optimum conditions for a desired specificity. In some embodiments, the hybridization conditions are stringent so that only completely complementary probes or primers will bind to the target. In other embodiments, less than stringent conditions are used.

Sequence-dependent binding when used in the context of a nucleic acid hybridization means recognition and binding to a particular linear arrangement of nucleotides in the nucleic acid. In the case of probes and primers, the linear arrangement includes contiguous nucleotides that each binds to a corresponding complementary nucleotide in the probes and primers.

The probes and primers described herein hybridize to their target nucleic acids, typically under stringent conditions. The term "stringent conditions" as used herein refers to parameters with which the art is familiar. Nucleic acid hybridization parameters may be found in references which compile such methods, e.g. Molecular Cloning: A Laboratory Manual, J. Sambrook, et al., eds., Fourth Edition, Cold Spring Harbor Laboratory Press, Cold Spring Harbor, N.Y., 2012, or Current Protocols in Molecular Biology, F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM NaH2PO4

(pH7), 0.5% SDS, 2 mM EDTA). SSC is 0.15M sodium chloride/0.015M sodium citrate, pH 7; SDS is sodium dodecyl sulphate; and EDTA is ethylenediaminetetraacetic acid. After hybridization, the membrane upon which the DNA is transferred is washed, for example, in 2×SSC at room temperature and then at 0.1-0.5×SSC/0.1×SDS at temperatures up to 68° C.

There are other conditions, reagents, and so forth which can be used, which result in a similar degree of stringency. The skilled artisan will be familiar with such conditions, and thus they are not given here. It will be understood, however, that the skilled artisan will be able to manipulate the conditions in a manner to permit specific and selective hybridization of probes and/or primers to the nucleic acids of the invention (e.g., by using lower stringency conditions).

Reference throughout this specification to "transcripts", "cDNAs", "library molecules", "library of transcripts", "sequencing library" or "DNA constructs" refers to barcoded molecules associated with a single-cell sequencing library. The terms may refer to single stranded cDNA resulting from RT-PCR of RNA transcripts, double stranded cDNA resulting from RT-PCR of RNA transcripts followed by second strand synthesis, or PCR, or paired end cDNA library molecules resulting from RT PCR of RNA transcripts followed by any method of library construction as described herein (e.g., Illumina). When the terms are recited in the context of a library of transcripts, it is meant to encompass barcoded single strand cDNA, barcoded double strand cDNA, or barcoded paired end cDNA library constructs. In some embodiments, a transcriptome refers to a set of cDNA molecules. In some embodiments, a transcriptome refers to one or more of mRNA molecules, siRNA molecules, tRNA molecules, rRNA molecules, in a sample, for example, a single cell or a population of cells. In some embodiments, a transcriptome refers to cDNA generated from one or more of mRNA molecules, siRNA molecules, tRNA molecules, rRNA molecules, in a sample, for example, a single cell or a population of cells.

All publications, published patent documents, and patent applications cited in this application are indicative of the level of skill in the art(s) to which the application pertains. All publications, published patent documents, and patent applications cited herein are hereby incorporated by reference to the same extent as though each individual publication, published patent document, or patent application was specifically and individually indicated as being incorporated by reference.

Overview

Transcriptional profiling of thousands of single cells in parallel by RNA-seq is now routine. However, due to reliance on pooled library preparation, targeting analysis to particular cells of interest is difficult. Provided herein are improved methods for identifying single-cell transcriptomes. Current methods for identifying transcriptomes of a single cell comprise single-cell RNA-seq (scRNA-seq). Single-cell RNA-seq can have limitations when it comes to detection of rare cell types. Some scRNA-seq methods are only able to profile ~2,000 cells/sequencing run so cells that are rare in the population will have very few representatives. scRNA-seq is also low pass sequencing, capturing only ~1% of the transcripts from a given cell. scRNA-seq is also extremely wasteful in terms of sequencing costs if there is a particular cell type of interest as the majority of the reads will be used on cells of lower interest.

It is an objective of the present invention to provide for methods of analyzing interesting cells or components that previously would be expensive or otherwise difficult to study. Embodiments disclosed herein provide methods for obtaining high resolution single-cell gene expression data from subpopulations of rare and/or interesting cells. The present invention relates to the analysis of complex single-cell sequencing libraries. Disclosed are methods for enrichment of library members based on the presence of cell-of origin barcodes to identify and concentrate DNA that is relevant to interesting cells or components that would be expensive or difficult to study otherwise. Also, disclosed are methods of capturing cDNA library molecules by use of CRISPR systems, hybridization or PCR. The present invention allows for identifying the properties of rare cells in single-cell RNA-seq data and accurately profile them through clustering approaches. Further, information on transcript abundances from subpopulations of single cells can be analyzed at a lower sequencing effort. The methods also allow for linking TCR alpha and beta chains at the single cell level.

Provided herein are improved methods to extract full single-cell transcriptomes from the complex RNA-seq libraries for targeted sequencing. In one embodiment, the approach described herein converts the barcodes themselves into primer sites by adding sequence from the universal sequencing primer site just upstream of the barcode and generating PCR primer sites of standard melting temperatures. Synthesized, complementary primers can then be used to amplify individual single-cell transcriptome libraries out of the complex tagmented RNA-seq library. The added primer sequence can also add enough sequence of the universal sequencing site to act as a handle for a secondary PCR reactions that adds the sequences required for standard Illumina sequencing. After the second PCR, the individual libraries can be re-pooled for sequencing. In certain embodiments, the approach described herein is able to convert a complex RNA-seq library into individual single-cell transcriptome libraries through only two PCR reactions.

Further, Applicants present a multiplexed PCR method for targeted sequencing of select cells from pooled single-cell sequence libraries. Applicants demonstrate this molecular enrichment method on multiple cell types within pooled single-cell RNA-seq libraries produced from primary human blood cells. Applicants describe a method that combines molecular enrichment with FACS to efficiently target ultra-rare cell types, such as the recently identified AXL$^+$SI-GLEC6$^+$ dendritic cell (AS DC) subset, in order to reduce the required sequencing effort to profile single cells by 100-fold. The results demonstrate that DNA barcodes identifying cells within pooled sequencing libraries can be used as targets to enrich for specific molecules of interest, for example reads from a set of target cells.

The present invention advantageously provides for high quality sequencing data that can be obtained with low sequencing depth. The high quality sequencing data further allows for clustering of rare cells. The methods leverage single-cell sequencing libraries prepared through various methods that incorporate a cell barcode (Indrop, Drop-seq, 10X genomics, Seq-Well, split-pool methods). The libraries are further processed after initial sequencing to identify promising cells. Further information on transcript abundances from these promising single cells can be analyzed at a lower sequencing effort (1/100×). Previous low throughput methods of identifying TCRs required sorting of individual T cells into microwells (Arnold et al., Nature Biotechnology 32, 684-692 (2014) doi:10.1038/nbt.2938). The methods of the present invention may be used to link TCR alpha and beta chains at the single-cell level by taking advantage of the cellular barcodes and known conserved regions of the gene. The use of conserved regions to TCR genes and cell barcodes allow for TCRs to be profiled at high throughput.

Figure 9:
FIG. 9—Schematic diagram showing a target transcript being contacted with a labeled oligonucleotide.

This approach has many advantages over traditional approaches. In contrast to methods such as FACS, no expensive equipment is needed to isolate the cells and cells can be processed in any basic lab or immediately in the clinic for eventual single-cell analysis. Since the selection occurs after creation of the stable cDNA library, any or various selection criteria can be decided on after the fact. This means that interesting phenotypes found in the low pass sequencing run can be selected for high depth sequencing. This also means clinical samples archived as RNA-seq libraries can be pulled out at any time to enrich for any new cell phenotype that may have been described for a given disease, making RNA-seq libraries similar to paraffin tissue blocks. Any combination of transcripts can be used to select cells for single-cell transcriptome sequencing, greatly expanding the number of markers, e.g., target transcripts, that can be used beyond surface expressed proteins, e.g., used in FACS. Cell barcodes used for enrichment can be selected directly on the barcode of the 2000 cells in the low pass sequencing data. However, as is shown in FIG. 9, if cells with rarer phenotypes are desired, biotinylated DNA probes complementary to the target transcripts of interest can be used to enrich the target transcripts from RNA-seq libraries generated from much larger numbers of cells. These enriched libraries are then sequenced to acquire the cell barcodes of cells expressing the desired transcripts in the much more complex RNA-seq library. Since the technique only requires two PCR reactions and a primer, it is also cheaper than prior techniques.

Thus, provided herein are methods for (i) identifying a barcode associated with transcripts from a single cell, (ii) counting the number of cells associated with a target gene by determining the number of unique barcodes, and (iii) obtaining or isolating the transcriptome of single cell, or cell type, or group of cells based on their unique barcode.

Single-Cell Libraries

The methods provided herein utilize libraries. In certain embodiments, any single-cell library type may be used for the present invention (e.g., any library wherein the cell of origin can be identified by a barcode). The library may be from RNA-seq, ATAC-seq, ChIP-seq, DNase-seq, ChIA-pet, RiCh-pet, CITE-seq (see, e.g., Stoeckius et al., Simultaneous epitope and transcriptome measurement in single cells, Nat Methods. 2017 Sep.;14(9):865-868), chromosome conformation capture (3C), HiC (see, e.g., Suhas et al., A 3D Map of the Human Genome at Kilobase Resolution Reveals Principles of Chromatin Looping, Cell 159 2015), genomic libraries (e.g., for genome seq and copy number variation analysis), or any footprinting method. The library may be composed of DNA molecules, or RNA molecules. In certain embodiments, the barcodes identify different samples, different samples where the samples are individual cells, different treatments, different locations, or different time points. The library may contain more than one type of barcode. In some embodiments, the libraries are RNA sequencing, e.g., RNA-seq, libraries. In some embodiments, the libraries are generated by single-cell RNA sequencing. In some embodiments, the RNA sequencing library comprises cDNA transcripts from a plurality of cells, wherein transcripts of each cell are identified with a unique barcode.

In certain embodiments, a sequencing library is provided that is configured for sequencing by using next generation technologies. Methods for constructing sequencing libraries are known in the art (see, e.g., Head et al., Library construction for next-generation sequencing: Overviews and challenges. Biotechniques. 2014; 56(2): 61-77). in certain embodiments, the library members (e.g., cDNA) may include sequencing adaptors that are compatible with use in, e.g., illumina's reversible terminator method, Roche's pyrosequencing method (454), Life Technologies' sequencing by ligation (the SOLiD platform) or Life Technologies' Ion Torrent platform. Examples of such methods are described in the following references: Margulies et al (Nature 2005 437: 376-80); Ronaghi et al (Analytical Biochemistry 19% 242: 84-9); Shendure et al (Science 2005 309: 1728-32); Imelfort et al (Brief Bioinform. 2009 10:609-18); Fox et al (Methods Mol. Biol. 2009; 553:79-108); Appleby et al (Methods Mol. Biol. 2009; 513:19-39); and Morozova et al (Genomics. 2008 92:255-64), which are incorporated by reference for the general descriptions of the methods and the particular steps of the methods, including all starting products, reagents, and final products for each of the steps. In certain embodiments, isolated product may contain sequences that are compatible with use in, e.g., Illumina's reversible terminator method, Roche's pyrosequencing method (454), Life Technologies' sequencing by ligation (the SOLiD platform) or Life Technologies' ion Torrent platform, as described above. The methods described herein are compatible with all of these platforms in that any adaptor sequence may be upstream or outside of a cell-identifying barcode sequence, thus allowing identification of barcode sequences by any sequencing platform. The isolated library members may be sequenced directly or, in some embodiments, may be amplified (e.g., PCR) to produce amplification products that are sequenced.

In some embodiments, the RNA sequencing library comprises 3' digital gene expression (DGE). DGE allows preparation of RNA-seq libraries from limited amounts of RNA template (e.g., single cells) across a large population of samples. DGE converts poly(A)+ mRNA to cDNA decorated with molecular barcodes. This method enables very high levels of sample multiplexing. The process can mark transcripts of a single cell with the same barcode and also uniquely marks each individual transcript molecule with Unique Molecular Indices (UMIs), which essentially barcode each input transcript. UMIs can overcome the effects of bias from library construction or amplification steps that affect other approaches. This method allows for the identification and quantification of transcripts. Methods for DGE include, but are not limited to, DropSeq, InDrop, 10X Genomics, and SeqWell. In certain embodiments, the present invention includes high-throughput single-cell RNA-seq nucleic acid profiling where the RNAs from different cells are tagged individually, allowing a single library to be created while retaining the cell identity of each read.

In certain embodiments, the invention involves single-cell RNA sequencing (see, e.g., Kalisky, T., Blainey, P. & Quake, S. R. Genomic Analysis at the Single-Cell Level. Annual review of genetics 45, 431-445, (2011); Kalisky, T. & Quake, S. R. Single-cell genomics. Nature Methods 8, 311-314 (2011); Islam, S. et al. Characterization of the single-cell transcriptional landscape by highly multiplex RNA-seq. Genome Research, (2011); Tang, F. et al. RNA-Seq analysis to capture the transcriptome landscape of a single cell. Nature Protocols 5, 516-535, (2010); Tang, F. et al. mRNA-Seq whole-transcriptome analysis of a single cell. Nature Methods 6, 377-382, (2009); Ramskold, D. et al. Full-length mRNA-Seq from single-cell levels of RNA and individual circulating tumor cells. Nature Biotechnology 30, 777-782, (2012); and Hashimshony, T., Wagner, F., Sher, N. & Yanai, I. CEL-Seq: Single-Cell RNA-Seq by Multiplexed Linear Amplification. Cell Reports, Cell Reports, Volume 2, Issue 3, p666-6'73, 2012).

In certain embodiments, the invention involves plate based single-cell RNA sequencing (see, e.g., Picelli, S. et al., 2014, "Full-length RNA-seq from single cells using Smart-seq2" Nature protocols 9, 171-181, doi: 10.1038/nprot.2014. 006).

In certain embodiments, the invention involves high-throughput single-cell RNA-seq. In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO2014210353A2; Zilionis, et al., 2017, "Single-cell barcoding and sequencing using droplet microfluidics" Nat Protoc. Jan;12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Vitak, et al., "Sequencing thousands of single-cell genomes with combinatorial indexing" Nature Methods, 14(3):302-308, 2017; Cao, et al., Comprehensive single-cell transcriptional profiling of a multicellular organism. Science, 357(6352):661-667, 2017; and Gierahn et al., "Seq-Well: portable, low-cost RNA sequencing of single cells at high throughput" Nature Methods 14, 395-398 (2017), all the contents and disclosure of each of which are herein incorporated by reference in their entirety.

In certain embodiments, the invention involves single nucleus RNA sequencing. In this regard reference is made to Swiech et al., 2014, "In vivo interrogation of gene function in the mammalian brain using CRISPR-Cas9" Nature Biotechnology Vol. 33, pp. 102-106; Habib et al., 2016, "Div-Seq: Single-nucleus RNA-Seq reveals dynamics of rare adult newborn neurons" Science, Vol. 353, Issue 6302, pp. 925-928; Habib et al., 2017, "Massively parallel single-nucleus RNA-seq with DroNc-seq" Nat Methods. 2017 Oct.;14(10):955-958; and International patent application number PCT/US2016/059239, published as WO2017164936 on Sep. 28, 2017, which are herein incorporated by reference in their entirety.

In SeqWell, an array of >80,000 sub-picoliter wells are used to isolate single cells and a barcoded transcript capture bead. A semi-porous membrane is used to seal the wells, preventing escape of macromolecules, such as mRNA, while allowing passage of small molecules and lysis buffers. This enables robust cell lysis within the sealed compartments and capture of the mRNA molecules on the beads. After capture, a barcode that is unique to each bead (and therefore, each well) is fused to each transcript captured in a well during reverse transcription. The barcoded cDNA libraries undergo whole transcriptome amplification (WTA) and are sequenced. In some embodiments, single-cell transcriptomes are recovered in silico by aggregating all the transcripts with the same bead barcode.

In some embodiments, the library comprises transcripts from a plurality of cells. In some embodiments, a plurality of cells comprises about 100, 500, 1,000, 10,000, 20,000. 30,000, 40,000, 50,000, 60,000, 70,000, 80,000, 90,000, 100,000, 200,000, 300,000, 400,000, 500,000, 600,000, 700, 000, 800,000, 900,000 or 1,000,000 or more cells. In some embodiments, the library is prepared using any method described herein, e.g., the SeqWell, InDrop, DropSeq, or 10× Genomics methods and a plurality of cells comprises between 10,000 and 1,000,000 cells, e.g., 20,000-100,000 cells.

In some embodiments, the plurality of cells comprises prokaryotic or eukaryotic cells. In some embodiments, the plurality of cells comprises mammalian cells. In some embodiments, the plurality of cells comprises a tissue sample. In some embodiments, the plurality of cells comprises some or all of a tumor, (e.g., a portion or all of a biopsy). In some embodiments, the plurality of cells comprises a bone marrow sample or a blood sample.

Figure 11:
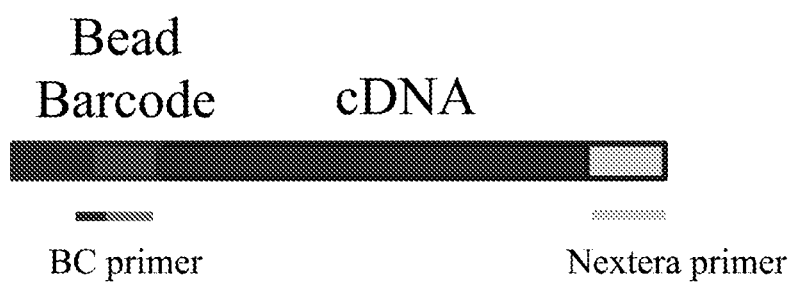
FIG. 11—Schematic diagram showing a configuration for amplifying a single cell transcriptome using primers with complementarity to barcode sequence.

In some embodiments, the transcripts in the library have a barcode. In some embodiments, the transcripts in the library have a barcode and further comprise universal primer sites at the 5' and 3' ends, as is shown in FIG. 11.

In some embodiments, in the library, every transcript from a single cell (i.e., the same single cell) has the same barcode and transcripts from different cells have different barcodes. In some embodiments, transcripts from each cell have a unique barcode. In some embodiments, transcripts from several (e.g., 2, 3, 4, 5, or 6) cells share the same barcode. In some embodiments, cells are separated into individual wells of a plate, dish, array, or slide (e.g., a SeqWell array) and transcripts from the cells of each well are labeled with a unique barcode.

In some embodiments, the barcode is 5' to a cDNA transcript. In some embodiments, the barcode is 3' to a cDNA transcript. In some embodiments, a barcode is 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides long, e.g., is from 10 to 20 nucleotides long.

In some embodiments, the cDNA transcripts of the single-cell library comprise a UMI 5' to the barcode. In some embodiments, the cDNA transcripts of the single-cell library comprise a UMI 3' to the barcode. In some embodiments, the UMI is a sequence that is unique to each transcript. In some embodiments, a UMI is 3, 4, 5, 6, 7, 8, 9, 10, 11, 12, 13, 14, or 15 nucleotides long, e.g., is from 4 to 10 nucleotides long.

In some embodiments, cDNA transcripts of the single-cell library comprise universal primer sites at the 5' terminus and/or at the 3' terminus. As used herein, a "universal primer site" is an exogenous primer binding site introduced into the nucleic acid molecule for the purpose of primer binding. Examples of universal primer sites include p5 and Nextera.

In some embodiments, the cDNA transcripts of the single-cell library comprise adenine, thymine, guanine, and cytosine. In some embodiments, the cDNA transcripts comprise uracil in place of thymine.

In some embodiments, the library is tagmented. In tagmented libraries, transposase can be used to randomly insert transposons into the transcript. The term "tagmentation" refers to a step in the Assay for Transposase Accessible Chromatin using sequencing (ATAC-seq) as described. (See, Buenrostro, J. D., Giresi, P. G., Zaba, L. C., Chang, H. Y., Greenleaf, W. J., Transposition of native chromatin for fast and sensitive epigenomic profiling of open chromatin, DNA-binding proteins and nucleosome position. Nature methods 2013; 10 (12): 1213-1218). Specifically, a hyperactive Tn5 transposase loaded in vitro with adapters for high-throughput DNA sequencing, can simultaneously fragment and tag a genome with sequencing adapters. In one embodiment, the adapters are compatible with the methods described herein.

In certain embodiments, tagmentation is used to introduce adaptor sequences to genomic DNA in regions of accessible chromatin (e.g., between individual nucleosomes) (see, e.g., US20160208323A1; US20160060691A1; WO2017156336A1; J. D. Buenrostro et al., Single-cell chromatin accessibility reveals principles of regulatory variation. Nature 523, 486-490 (2015); and Cusanovich, D. A., Daza, R., Adey, A., Pliner, H., Christiansen, L., Gunderson, K. L., Steemers, F. J., Trapnell, C. & Shendure, J. Multiplex single-cell profiling of chromatin accessibility by combinatorial cellular indexing. Science. 2015 May 22;348 (6237):910-4. doi: 10.1126/science.aab1601. Epub 2015 May 7).

In certain embodiments, barcoded library members from specific samples may be enriched. For example, cells from specific samples may be barcoded (see, e.g., Stoeckius et al., Cell "hashing" with barcoded antibodies enables multiplexing and doublet detection for single cell genomics, bioRxiv 237693; doi: doi.org/10.1101/237693).

Nucleic Acid Barcode, Barcode, and Unique Molecular Identifier (UMI)

The term "barcode" as used herein refers to a short sequence of nucleotides (for example, DNA or RNA) that is used as an identifier for an associated molecule, such as a target molecule and/or target nucleic acid, or as an identifier of the source of an associated molecule, such as a cell-of-origin.

The term "barcode" as used herein, also refers to any unique, non-naturally occurring, nucleic acid sequence that may be used to identify the originating source of a nucleic acid fragment. Such barcodes may be sequences including but not limited to about 20 base pair sequences. Although it is not necessary to understand the mechanism of an invention, it is believed that the barcode sequence provides a high-quality individual read of a barcode associated with a single cell, a viral vector, shRNA, sgRNA or cDNA such that multiple species can be sequenced together.

Barcoding may be performed based on any of the compositions or methods disclosed in patent publication WO 2014047561 A1, Compositions and methods for labeling of agents, incorporated herein in its entirety. In certain embodiments barcoding uses an error correcting scheme (T. K. Moon, Error Correction Coding: Mathematical Methods and Algorithms (Wiley, New York, ed. 1, 2005)). Not being bound by a theory, amplified sequences from single cells can be sequenced together and resolved based on the barcode associated with each cell.

In certain embodiments, where the sequencing library comprises amplified cDNA or PCR amplification is used for enriching barcoded cDNA molecules, sequencing is performed using unique molecular identifiers (UMI). The term "unique molecular identifiers" (UMI) as used herein refers to a sequencing linker or a subtype of nucleic acid barcode used in a method that uses molecular tags to detect and quantify unique amplified products. A UMI is used to distinguish effects through a single clone from multiple clones. The term "clone" as used herein may refer to a single mRNA or target nucleic acid to be sequenced. The UMI may also be used to determine the number of transcripts that gave rise to an amplified product. In preferred embodiments, the amplification is by PCR or multiple displacement amplification (MDA).

In certain embodiments, an UMI with a random sequence of between 4 and 20 base pairs is added to a template, which is amplified and sequenced. In preferred embodiments, the UMI is added to the 5' end of the template. Sequencing allows for high resolution reads, enabling accurate detection of true variants. As used herein, a "true variant" will be present in every amplified product originating from the original clone as identified by aligning all products with a UMI. Each clone amplified will have a different random UMI that will indicate that the amplified product originated from that clone. Background caused by the fidelity of the amplification process can be eliminated because true variants will be present in all amplified products and background representing random error will only be present in single amplification products (See e.g., Islam S. et al., 2014. Nature Methods No:11, 163-166). Not being bound by a theory, the UMI's are designed such that assignment to the original can take place despite up to 4-7 errors during amplification or sequencing.

Unique molecular identifiers can be used, for example, to normalize samples for variable amplification efficiency. For example, in various embodiments, featuring a solid or semisolid support (for example a hydrogel bead), to which nucleic acid barcodes (for example a plurality of barcodes sharing the same sequence) are attached, each of the barcodes may be further coupled to a unique molecular identifier, such that every barcode on the particular solid or semisolid support receives a distinct unique molecule identifier. A unique molecular identifier can then be, for example, transferred to a target molecule with the associated barcode, such that the target molecule receives not only a nucleic acid barcode, but also an identifier unique among the identifiers originating from that solid or semisolid support.

A nucleic acid barcode or UMI can have a length of at least, for example, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or 100 nucleotides, and can be in single- or double-stranded form. Target molecule and/or target nucleic acids can be labeled with multiple nucleic acid barcodes in combinatorial fashion, such as a nucleic acid barcode concatemer. Typically, a nucleic acid barcode is used to identify a target molecule and/or target nucleic acid as being from a particular discrete volume (e.g., cell), having a particular physical property (for example, affinity, length, sequence, etc.), or having been subject to certain treatment conditions. Target molecule and/or target nucleic acid can be associated with multiple nucleic acid barcodes to provide information about all of these features (and more). Each member of a given population of UMIs, on the other hand, is typically associated with (for example, covalently bound to or a component of the same molecule as) individual members of a particular set of identical, specific (for example, discreet volume-, physical property-, or treatment condition-specific) nucleic acid barcodes. Thus, for example, each member of a set of origin-specific nucleic acid barcodes, or other nucleic acid identifier or connector oligonucleotide, having identical or matched barcode sequences, may be associated with (for example, covalently bound to or a component of the same molecule as) a distinct or different UMI.

As disclosed herein, unique nucleic acid identifiers are used to label the target molecules and/or target nucleic acids, for example origin-specific barcodes and the like. The nucleic acid identifiers, nucleic acid barcodes, can include a short sequence of nucleotides that can be used as an identifier for an associated molecule, location, or condition. In certain embodiments, the nucleic acid identifier further includes one or more unique molecular identifiers and/or barcode receiving adapters. A nucleic acid identifier can have a length of about, for example, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or 100 base pairs (bp) or nucleotides (nt). In certain embodiments, a nucleic acid identifier can be constructed in combinatorial fashion by combining randomly selected indices (for example, about 1, 2, 3, 4, 5, 6, 7, 8, 9, or 10 indexes). Each such index is a short sequence of nucleotides (for example, DNA, RNA, or a combination thereof) having a distinct sequence. An index can have a length of about, for example, 4, 5, 6, 7, 8, 9, 10, 11, 12, 13, 14, 15, 16, 17, 18, 19, 20, 21, 22, 23, 24, or 25 bp or nt. Nucleic acid identifiers can be generated, for example, by split-pool synthesis methods, such as those described, for example, in International Patent Publication Nos. WO 2014/047556 and WO 2014/143158, each of which is incorporated by reference herein in its entirety.

One or more nucleic acid identifiers (for example a nucleic acid barcode) can be attached, or "tagged," to a target molecule. This attachment can be direct (for example, covalent or noncovalent binding of the nucleic acid identifier to the target molecule) or indirect (for example, via an additional molecule). Such indirect attachments may, for example, include a barcode bound to a specific-binding agent that recognizes a target molecule. In certain embodiments, a barcode is attached to protein G and the target molecule is an antibody or antibody fragment. Attachment of a barcode to target molecules (for example, proteins and other biomolecules) can be performed using standard methods well known in the art. For example, barcodes can be linked via cysteine residues (for example, C-terminal cysteine residues). In other examples, barcodes can be chemically introduced into polypeptides (for example, antibodies) via a variety of functional groups on the polypeptide using appropriate group-specific reagents (see for example www-.drmr.com/abcon). In certain embodiments, barcode tagging can occur via a barcode receiving adapter associate with (for example, attached to) a target molecule, as described herein.

Target molecules can be optionally labeled with multiple barcodes in combinatorial fashion (for example, using multiple barcodes bound to one or more specific binding agents that specifically recognizing the target molecule), thus greatly expanding the number of unique identifiers possible within a particular barcode pool. In certain embodiments, barcodes are added to a growing barcode concatemer attached to a target molecule, for example, one at a time. In other embodiments, multiple barcodes are assembled prior to attachment to a target molecule. Compositions and methods for concatemerization of multiple barcodes are described, for example, in International Patent Publication No. WO 2014/047561, which is incorporated herein by reference in its entirety.

In some embodiments, a nucleic acid identifier (for example, a nucleic acid barcode) may be attached to sequences that allow for amplification and sequencing (for example, SBS3 and P5 elements for Illumina sequencing). In certain embodiments, a nucleic acid barcode can further include a hybridization site for a primer (for example, a single-stranded DNA primer) attached to the end of the barcode. For example, an origin-specific barcode may be a nucleic acid including a barcode and a hybridization site for a specific primer. In particular embodiments, a set of origin-specific barcodes includes a unique primer specific barcode made, for example, using a randomized oligo type A nucleic acid identifier can further include a unique molecular identifier and/or additional barcodes specific to, for example, a common support to which one or more of the nucleic acid identifiers are attached. Thus, a pool of target molecules can be added, for example, to a discrete volume containing multiple solid or semisolid supports (for example, beads) representing distinct treatment conditions (and/or, for example, one or more additional solid or semisolid support can be added to the discreet volume sequentially after introduction of the target molecule pool), such that the precise combination of conditions to which a given target molecule was exposed can be subsequently determined by sequencing the unique molecular identifiers associated with it.

Labeled target molecules and/or target nucleic acids associated origin-specific nucleic acid barcodes (optionally in combination with other nucleic acid barcodes as described herein) can be amplified by methods known in the art, such as polymerase chain reaction (PCR). For example, the nucleic acid barcode can contain universal primer recognition sequences that can be bound by a PCR primer for PCR amplification and subsequent high-throughput sequencing. In certain embodiments, the nucleic acid barcode includes or is linked to sequencing adapters (for example, universal primer recognition sequences) such that the barcode and sequencing adapter elements are both coupled to the target molecule. In particular examples, the sequence of the origin specific barcode is amplified, for example using PCR. In some embodiments, an origin-specific barcode further comprises a sequencing adaptor. In some embodiments, an origin-specific barcode further comprises universal priming sites. A nucleic acid barcode (or a concatemer thereof), a target nucleic acid molecule (for example, a DNA or RNA molecule), a nucleic acid encoding a target peptide or polypeptide, and/or a nucleic acid encoding a specific binding agent may be optionally sequenced by any method known in the art, for example, methods of high-throughput sequencing, also known as next generation sequencing. A nucleic acid target molecule labeled with a barcode (for example, an origin-specific barcode) can be sequenced with the barcode to produce a single read and/or contig containing the sequence, or portions thereof, of both the target molecule and the barcode.

A nucleic acid barcode can be sequenced, for example, after cleavage, to determine the presence, quantity, or other feature of the target molecule. In certain embodiments, a nucleic acid barcode can be further attached to a further nucleic acid barcode. For example, a nucleic acid barcode can be cleaved from a specific-binding agent after the specific-binding agent binds to a target molecule or a tag (for example, an encoded polypeptide identifier element cleaved from a target molecule), and then the nucleic acid barcode can be ligated to an origin-specific barcode. The resultant nucleic acid barcode concatemer can be pooled with other such concatemers and sequenced. The sequencing reads can be used to identify which target molecules were originally present in which discrete volumes.

Barcodes Reversibly Coupled to Solid Substrate

In some embodiments, the origin-specific barcodes are reversibly coupled to a solid or semisolid substrate. In some embodiments, the origin-specific barcodes further comprise a nucleic acid capture sequence that specifically binds to the target nucleic acids and/or a specific binding agent that specifically binds to the target molecules. In specific embodiments, the origin-specific barcodes include two or more populations of origin-specific barcodes, wherein a first population comprises the nucleic acid capture sequence and a second population comprises the specific binding agent that specifically binds to the target molecules. In some examples, the first population of origin-specific barcodes further comprises a target nucleic acid barcode, wherein the target nucleic acid barcode identifies the population as one that labels nucleic acids. In some examples, the second population of origin-specific barcodes further comprises a target molecule barcode, wherein the target molecule barcode identifies the population as one that labels target molecules.

Barcode with Cleavage Sites

A nucleic acid barcode may be cleavable from a specific binding agent, for example, after the specific binding agent has bound to a target molecule. In some embodiments, the origin-specific barcode further comprises one or more cleavage sites. In some examples, at least one cleavage site is oriented such that cleavage at that site releases the origin-specific barcode from a substrate, such as a bead, for example a hydrogel bead, to which it is coupled. In some examples, at least one cleavage site is oriented such that the cleavage at the site releases the origin-specific barcode from the target molecule specific binding agent. In some examples, a cleavage site is an enzymatic cleavage site, such as an endonuclease site present in a specific nucleic acid sequence. In other embodiments, a cleavage site is a peptide cleavage site, such that a particular enzyme can cleave the amino acid sequence. In still other embodiments, a cleavage site is a site of chemical cleavage. In still other embodiments, a cleavage site is a site of photocleavage.

Barcode Adapters

In some embodiments, the target molecule is attached to an origin-specific barcode receiving adapter, such as a nucleic acid. In some examples, the origin-specific barcode receiving adapter comprises an overhang and the origin-specific barcode comprises a sequence capable of hybridizing to the overhang. A barcode receiving adapter is a molecule configured to accept or receive a nucleic acid barcode, such as an origin-specific nucleic acid barcode. For example, a barcode receiving adapter can include a single-stranded nucleic acid sequence (for example, an overhang) capable of hybridizing to a given barcode (for example, an origin-specific barcode), for example, via a sequence complementary to a portion or the entirety of the nucleic acid barcode. In certain embodiments, this portion of the barcode is a standard sequence held constant between individual barcodes. The hybridization couples the barcode receiving adapter to the barcode. In some embodiments, the barcode receiving adapter may be associated with (for example, attached to) a target molecule. As such, the barcode receiving adapter may serve as the means through which an origin-specific barcode is attached to a target molecule. A barcode receiving adapter can be attached to a target molecule according to methods known in the art. For example, a barcode receiving adapter can be attached to a polypeptide target molecule at a cysteine residue (for example, a C-terminal cysteine residue). A barcode receiving adapter can be used to identify a particular condition related to one or more target molecules, such as a cell of origin or a discreet volume of origin. For example, a target molecule can be a cell surface protein expressed by a cell, which receives a cell-specific barcode receiving adapter. The barcode receiving adapter can be conjugated to one or more barcodes as the cell is exposed to one or more conditions, such that the original cell of origin for the target molecule, as well as each condition to which the cell was exposed, can be subsequently determined by identifying the sequence of the barcode receiving adapter/barcode concatemer.

Barcode with Capture Moiety

In some embodiments, an origin-specific barcode further includes a capture moiety, covalently or non-covalently linked. Thus, in some embodiments the origin-specific barcode, and anything bound or attached thereto, that include a capture moiety are captured with a specific binding agent that specifically binds the capture moiety. In some embodiments, the capture moiety is adsorbed or otherwise captured on a surface. In specific embodiments, a targeting probe is labeled with biotin, for instance by incorporation of biotin-16-UTP during in vitro transcription, allowing later capture by streptavidin. Other means for labeling, capturing, and detecting an origin-specific barcode include: incorporation of aminoallyl-labeled nucleotides, incorporation of sulfhydryl-labeled nucleotides, incorporation of allyl- or azide-containing nucleotides, and many other methods described in Bioconjugate Techniques (2nd Ed), Greg T. Hermanson, Elsevier (2008), which is specifically incorporated herein by reference. In some embodiments, the targeting probes are covalently coupled to a solid support or other capture device prior to contacting the sample, using methods such as incorporation of aminoallyl-labeled nucleotides followed by 1-Ethyl-3-(3-dimethylaminopropyl)carbodiimide (EDC) coupling to a carboxy-activated solid support, or other methods described in Bioconjugate Techniques. In some embodiments, the specific binding agent has been immobilized for example on a solid support, thereby isolating the origin-specific barcode.

DNA barcoding is also a taxonomic method that uses a short genetic marker in an organism's DNA to identify it as belonging to a particular species. It differs from molecular phylogeny in that the main goal is not to determine classification but to identify an unknown sample in terms of a known classification. Kress et al., "Use of DNA barcodes to identify flowering plants" Proc. Natl. Acad. Sci. U.S.A. 102(23):8369-8374 (2005). Barcodes are sometimes used in an effort to identify unknown species or assess whether species should be combined or separated. Koch H., "Combining morphology and DNA barcoding resolves the taxonomy of Western Malagasy Liotrigona Moure, 1961" African Invertebrates 51(2): 413-421 (2010); and Seberg et al., "How many loci does it take to DNA barcode a crocus?" PLoS One 4(2):e4598 (2009). Barcoding has been used, for example, for identifying plant leaves even when flowers or fruit are not available, identifying the diet of an animal based on stomach contents or feces, and/or identifying products in commerce (for example, herbal supplements or wood). Soininen et al., "Analysing diet of small herbivores: the efficiency of DNA barcoding coupled with high-throughput pyrosequencing for deciphering the composition of complex plant mixtures" Frontiers in Zoology 6:16 (2009).

It has been suggested that a desirable locus for DNA barcoding should be standardized so that large databases of sequences for that locus can be developed. Most of the taxa of interest have loci that are sequenceable without species-specific PCR primers. CBOL Plant Working Group, "A DNA barcode for land plants" PNAS 106(31):12794-12797 (2009). Further, these putative barcode loci are believed short enough to be easily sequenced with current technology. Kress et al., "DNA barcodes: Genes, genomics, and bioinformatics" PNAS 105(8):2761-2762 (2008). Consequently, these loci would provide a large variation between species in combination with a relatively small amount of variation within a species. Lahaye et al., "DNA barcoding the floras of biodiversity hotspots" Proc Natl Acad Sci USA 105(8): 2923-2928 (2008).

DNA barcoding is based on a relatively simple concept. For example, most eukaryote cells contain mitochondria, and mitochondrial DNA (mtDNA) has a relatively fast mutation rate, which results in significant variation in mtDNA sequences between species and, in principle, a comparatively small variance within species. A 648-bp region of the mitochondrial cytochrome c oxidase subunit 1 (CO1) gene was proposed as a potential 'barcode'. As of 2009, databases of CO1 sequences included at least 620,000 specimens from over 58,000 species of animals, larger than databases available for any other gene. Ausubel, J., "A botanical macroscope" Proceedings of the National Academy of Sciences 106(31):12569 (2009).

Software for DNA barcoding requires integration of a field information management system (FIMS), laboratory information management system (LIMS), sequence analysis tools, workflow tracking to connect field data and laboratory data, database submission tools and pipeline automation for scaling up to eco-system scale projects. Geneious Pro can be used for the sequence analysis components, and the two plugins made freely available through the Moorea Biocode Project, the Biocode LIMS and Genbank Submission plugins handle integration with the FIMS, the LIMS, workflow tracking and database submission.

Additionally, other barcoding designs and tools have been described (see e.g., Birrell et al., (2001) Proc. Natl Acad. Sci. USA 98, 12608-12613; Giaever, et al., (2002) Nature 418, 387-391; Winzeler et al., (1999) Science 285, 901-906; and Xu et al., (2009) Proc Natl Acad Sci USA. Feb 17;106(7): 2289-94).

Sequencing

The invention also includes methods of sequencing or resequencing nucleic acids (e.g., a sequencing library). In these methods, subgroup(s) (e.g., based on barcode) of nucleic acids are isolated by selection using the methods described herein (e.g., using hybridization, PCR, CRISPR) and then the isolated subgroup of nucleic acids is subjected to nucleic acid sequencing. Any method of sequencing known in the art can be used before and after isolation. In certain embodiments, a sequencing library is generated and sequenced. The sequenced library is then enriched for specific barcoded cDNA molecules and resequenced.

The terms "depth" or "coverage" as used herein refers to the number of times a nucleotide is read during the sequencing process. In regards to single-cell RNA sequencing, "depth" or "coverage" as used herein refers to the number of mapped reads per cell. Depth in regards to genome sequencing may be calculated from the length of the original genome (G), the number of reads(N), and the average read length(L) as N×L/G. For example, a hypothetical genome with 2,000 base pairs reconstructed from 8 reads with an average length of 500 nucleotides will have 2× redundancy.

The terms "low-pass sequencing" or "shallow sequencing" as used herein refers to a wide range of depths greater than or equal to 0.1× up to 1×. Shallow sequencing may also refer to about 5000 reads per cell (e.g., 1,000 to 10,000 reads per cell).

The term "deep sequencing" as used herein indicates that the total number of reads is many times larger than the length of the sequence under study. The term "deep" as used herein refers to a wide range of depths greater than 1× up to 100×. Deep sequencing may also refer to 100× coverage as compared to shallow sequencing (e.g., 100,000 to 1,000,000 reads per cell).

The term "ultra-deep" as used herein refers to higher coverage (>100-fold), which allows for detection of sequence variants in mixed populations.

Identifying Cell Type

The methods described herein provide for isolating a transcriptome of a single cell from a library of transcripts, e.g., a RNA-seq library. In some embodiments, the barcode sequence of the single cell is identified so that the transcriptome can be isolated.

In some embodiments, the barcode sequence of the single cell is obtained by hybridizing a labeled oligonucleotide complementary to a target transcript with a target transcript that is known to be expressed by the single cell. In some embodiments, the barcode sequence of the single cell is obtained by PCR amplifying a target transcript that is known to be expressed by the single cell and sequencing the amplified PCR product as described herein. In some embodiments, the barcode sequence of the single cell is obtained by targeting a transcript that is known to be expressed by the single cell using a CRISPR system, as described herein. In some embodiments, the single cell expresses a single target transcript and the barcode is identified by sequencing the barcode of the cDNA comprising the target transcript. In some embodiments, the single cell expresses a plurality of target transcripts, e.g., 2, 3, 4, 5, 6, 7, 8, 9, or 10 or more target transcripts, e.g., a panel of target transcripts, and the barcode sequence of the single cell is obtained by hybridizing labeled oligonucleotides complementary to the panel of target transcripts with the panel of target transcript, or PCR amplifying the transcripts, or targeting the transcripts with a CRISPR system, either simultaneously or sequentially. In some embodiments, the single cell expresses a plurality of target transcripts and the barcode is identified by sequencing the barcode of the cDNA comprising the target transcripts and identifying the barcode as being associated with all of the target transcripts.

In some embodiments, the oligonucleotide is hybridized to the target transcript at 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., or 70° C. In some embodiments, the oligonucleotide is hybridized to the target transcript at 50° C.-70° C., e.g., 55° C.-65° C., e.g., 60° C. In some embodiments, the oligonucleotide is hybridized to the target transcript for 20, 21, 22, 23, 24, 25, 26, 27, 28, 29, 30, 31, 32, 33, 34, 35, 36, 37, 38, 39, or 40 minutes. In some embodiments, the oligonucleotide is hybridized to the target transcript for 20-40 minutes, e.g., 25-35 minutes, e.g., 30 minutes.

In some embodiments, the target transcript encodes a cytokine (e.g., IL-1α, IL1-β, IL-2, IL-3, IL-4, IL-5, IL-6, IL-8, IL-9, IL-10, IL-11, IL-12, IL-13, IL-16, IL-18, B4GALT7, IFN gamma, IFN omega, IFN-alpha, IFNA10, IFNA4, IFNA5/IFNaG, IFNA7, IFNB1/IFN-beta, IFNE, IFNZ, IL-28B/IFN-lambda-3, IL-29, IFNA8, LOC100425319, MEMO1, BLyS/TNFSF138, CD70/CD27L/TNFSF7, LTB, TL1A/TNFSF15, TNFSF10/TRAIL/APO-2L(CD253), CD40L/CD154/TNFSF5, Fas Ligand/FASLG/CD95L, RANKL/OPGL/TNFSF11 (CD254), TNF-beta/TNFSF1/Lymphotoxin alpha, TNFSF14/LIGHT/CD258, CD153/CD30L/TNFSF8, EDA-A1, OX-40L/TNFSF4/CD252, TNF-alpha/TNFA, TNFSF13, G-CSF, GM-CSF/CSF2, or M-CSF/CSF-1), a T cell receptor, a B cell receptor, a pathogen transcript (e.g., mRNA from a viral, bacterial, or fungal pathogen), a chemokine (e.g., ARMCX2, BCA-1/CXCL13, CCL11, CCL12/MCP-5, CCL13/MCP-4, CCL15/MIP-5/MIP-1 delta, CCL16/HCC-4/NCC4, CCL17/TARC, CCL18/PARC/MIP- 4, CCL19/MIP-3b, CCL2/MCP-1, CCL20/MIP-3 alpha/ MIP3A, CCL21/6Ckine, CCL22/1 VDC, CCL23/MIP 3, CCL24/Eotaxin-2/MPIF-2, CCL25/TECK, CCL26/Eotaxin-3, CCL27/CTACK, CCL28, CCL3/Mipla, CCL4/ MIP1B, CCL4L1/LAG-1, CCL5/RANTES, CCL6/C10, CCL8/MCP-2, CCL9, CMLS, CXCL1, CXCL10/Crg-2, CXCL12/SDF-1 beta, CXCL14/BRAK, CXCL15/Lungkine, CXCL16/SR-PSOX, CXCL17, CXCL2/MIP-2, CXCL3/GRO gamma, CXCL4/PF4, CXCL5, CXCL6/GCP-2, CXCL9/MIG, FAM19A1, FAM19A2, FAM19A3, FAM19A4/TAFA4, FAM19A5, Fractalkine/CX3CL1, I-309/CCL1/TCA-3, IL-8/CXCL8, MCP-3/CCL7, NAP-2/ PPBP/CXCL7, or XCL2), a circulating tumor cell marker (e.g., EpCAM, EphB4, EGFR, CEA, HER2, or MUC-1), or a cell activation marker (e.g., CD3, CD4, CD8, CD25, CD26, CD40L, CD69, CD127, CD154, CD137, CD134, CD196 or CD278). Mutations associated across the spectrum of human cancer types have been identified (e.g., Hodis E. et al., Cell. (2012) Jul 20;150(2):251-63; and Vogelstein, et al., Science (2013) Mar 29: Vol. 339, Issue 6127, pp. 1546-1558). A directory of cancer mutations, including gene specific mutations may be found at cancer.sanger.ac.uk/ cosmic, the Catalogue of Somatic Mutations in Cancer (COSMIC) (Forbes, et al.; COSMIC: somatic cancer genetics at high-resolution. Nucleic Acids Res 2017; 45 (D1): D777-D783. doi: 10.1093/nar/gkw1121) and www.mycancergenome.org. In certain embodiments, transcripts including any of these known mutations may be enriched. In certain embodiments, the oncogene may be selected from tp53, MUC16, KRAS, EGFR, VEGF, CDKN2A or any mutation found in a database herein.

In some embodiments, the single cell comprises any cell that comprises mRNA. In some embodiments, the single cell comprises a prokaryotic or eukaryotic cell. In some embodiments, the single cell comprises a mammalian cell. In some embodiments, the single cell is a T cell. Types of T cells include, but are not limited to, CD4+ T cells, CD8+ T cells, helper T cells, memory T cells (e.g., central memory T cells, effector memory T cells, tissue resident memory T cells, or virtual memory T cells), regulatory T cells, NKT cells, and gamma delta T cells. In some embodiments, the single cell is a B cell. Types of B cells include, but are not limited to plasmablasts, plasma cells, memory B cells, follicular B cells, marginal zone B cells, B-1 cells, B-1 cells and regulatory B cells. In some embodiments, the single cell is an immune cell other than a T cell or a B cell (e.g., a macrophage, a neutrophil, a dendritic cell, an innate lymphoid cell, a mast cell, an eosinophil, a basophil, a megakaryocyte, or a natural killer cell). In some embodiments, the cell is a cytokine secreting cell. Cytokines are produced by a range of cells, including immune cells, endothelial cells, fibroblasts, and various stromal cells. In some embodiments, the cell is a cancer cell. In some embodiments, the cancer cell is a blood cancer cell. In some embodiments, the cancer cell is a tumor cell. In some embodiments, the cell is a pathogen infected cell, e.g., a cell infected with a virus, bacterium, or fungi.

In some embodiments, the single cell is a cell that occurs at a frequency of less than 50%, 25%, 10%, 5%, 2%, 1.5%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, 0.0001% in the plurality of cells from which the single cell library is generated.

In some embodiments, the oligonucleotide is hybridized to the target transcript and the complex of the oligonucleotide hybridized to the target transcript is then separated from the library of transcripts. In some embodiments, oligonucleotide hybridized to the target transcript is separated from the library of transcripts by binding between the label on the oligonucleotide and a binding partner.

In some embodiments, the binding partner is conjugated to a bead. A "labeled" oligonucleotide or probe typically intends that the oligonucleotide or probe is conjugated, covalently or non-covalently, to one member of an affinity pair or of a binding pair. The members of a binding pair may be referred to as binding partners.

The binding partners may include without limitation antibodies including but not limited to single chain antibodies, antigen-binding antibody fragments, antigens (to be used to bind to their antibodies, for example), receptors, ligands, aptamers, aptamer receptors, small molecules, and the like, provided they are a member of a binding pair, with the understanding that the other member of the binding pair is present on the bead used for extraction or physical separation. Examples of binding pairs include biotin and avidin or streptavidin, antibody (or antibody fragment) and antigen, receptor and receptor ligand, aptamer and aptamer ligand, and the like.

The linkage between the oligonucleotide and the binding partner may be covalent or non-covalent depending on the strength of binding required for a particular application. Labeled oligonucleotides may be purchased commercially or they may be synthesized, for example, by first incorporating a reactive group (or moiety) into the oligonucleotide, including at or near one of its ends, and then reacting this group (or moiety) with the binding partner of interest which may or may not be modified itself. Suitable reactive groups are known in the art. Examples of reactive groups that can covalently conjugate to other reactive groups (leading to an irreversible conjugation) include but are not limited to amine groups (which react to, for example, esters to produce amides), carboxylic acids, amides, carbonyls (such as aldehydes, ketones, acyl chlorides, carboxylic acids, esters and amides) and alcohols. Those of ordinary skill in the art will be familiar with other "covalent" reactive groups. Virtually any reactive group may be used, provided it participates in an interaction of sufficient affinity to prevent dissociation of the binding partner from its oligonucleotide.

In some embodiments, the oligonucleotide is labeled with biotin and the affinity binding partner is streptavidin. In some embodiments, the oligonucleotide is labeled with streptavidin and the affinity binding partner is biotin.

In some embodiments, the oligonucleotide is 30, 40, 50, 60, 70, 80, 90, 100, 110, or 120 nucleotides in length.

In some embodiments, the oligonucleotide has 100% complementarity to the target transcript sequence. In some embodiments, the oligonucleotide has less than 100% complementarity to the target transcript sequence. In some embodiments, the oligonucleotide has 95%, 90%, 85%, or 80% or less complementarity to the target transcript sequence.

In some embodiments, once the target transcript is separated from the library of transcripts, the barcode on the target transcript is sequenced. The type of sequencing performed can be, for example, pyrosequencing, single-molecule real-time sequencing, ion torrent sequencing, sequencing by synthesis, sequencing by ligation (SOLiD™), and chain termination sequencing (e.g., Sanger sequencing). Sequencing methods are known in the art and commercially available (see, e.g., Ronaghi et al.; Uhlén, M; Nyrén, P (1998). "A sequencing method based on real-time pyrophosphate". Science 281 (5375): 363; and Ronaghi et al.; Karamohamed, S; Pettersson, B; Uhlén, M; Nyrén, P (1996). "Real-time DNA sequencing using detection of pyrophosphate release". Analytical Biochemistry 242 (1): 84-9.; and services and products available from Roche (454 platform), Illumina (HiSeq and MiSeq systems), Pacific Biosciences (PACBIO RS II), Life Technologies (Ion Proton™ systems and SOLiD™ systems)).

In some embodiments, more than one cell expresses the target transcript and the number of cells expressing the target transcript can be counted. In some embodiments, the unique barcodes associated with a target transcript are sequenced and each unique barcode corresponds to approximately one cell that expresses the target transcript, such that the number of barcodes identified corresponds to the number of cells expressing the target transcript. In some embodiments, the number of cells expressing a plurality, or a panel, of target transcripts can be identified by sequencing the unique barcodes that are associated with the target transcripts and counting the number of barcodes that are associated with each of the target transcripts in the panel.

Isolating a Transcriptome of a Single Cell

Provided herein are methods of isolating a transcriptome of a single cell from a RNA-seq library. Said methods employ the use of barcode specific primers. As such, said methods can be used in conjunction with the methods described herein for identifying barcodes, or can be used independently when the sequence of the barcode is otherwise available.

As used herein the term "transcriptome" refers to the set of transcripts molecules. In some embodiments, transcript refers to RNA molecules, e.g., messenger RNA (mRNA) molecules, small interfering RNA (siRNA) molecules, transfer RNA (tRNA) molecules, ribosomal RNA (rRNA) molecules, and complimentary sequences, e.g., cDNA molecules. In some embodiments, a transcriptome refers to a set of mRNA molecules. In some embodiments, a transcriptome refers to a set of cDNA molecules. In some embodiments, a transcriptome refers to one or more of mRNA molecules, siRNA molecules, tRNA molecules, rRNA molecules, in a sample, for example, a single cell or a population of cells. In some embodiments, a transcriptome refers to cDNA generated from one or more of mRNA molecules, siRNA molecules, tRNA molecules, rRNA molecules, in a sample, for example, a single cell or a population of cells. In some embodiments, a transcriptome refers to 50%, 55, 60, 65, 70, 75, 80, 85, 90, 91, 92, 93, 94, 95, 96, 97, 98, 99, 99.9, or 100% of transcripts from a single cell or a population of cells. In some embodiments, transcriptome not only refers to the species of transcripts, such as mRNA species, but also the amount of each species in the sample. In some embodiments, a transcriptome includes each mRNA molecule in the sample, such as all the mRNA molecules in a single cell.

The transcriptome for a single cell can be isolated from a single-cell library by amplification with barcode specific primers. In some embodiments, the barcode specific primers comprise 5' primer and a 3' primer, wherein the 5' primer or the 3' primer comprises a nucleotide sequence that is complementary to the unique barcode of the single cell. In some embodiments, the 5' primer or the 3' primer is complementary to 5, 6, 7, 8, 9, 10, 11, 12, 13, 14, 15 or all of the barcode sequence.

In some embodiments, the 5' primer comprises a nucleotide sequence that is complementary to a 5' universal primer site contained in each transcript of the library of transcripts and a nucleotide sequence that is complementary to the unique barcode and the 3' primer comprises a nucleotide sequence that is complementary to a 3' universal primer site contained in each transcript of the library of transcripts. In some embodiments, the 5' primer comprises a nucleotide sequence that is complementary to a 5' universal primer site contained in each transcript of the library of transcripts and the 3' primer comprises a nucleotide sequence that is complementary to a 3' universal primer site contained in each transcript of the library of transcripts and a nucleotide sequence that is complementary to the unique barcode. In some embodiments, the 5' primer comprises a nucleotide sequence that is complementary to a 5' universal primer site different from the 5' universal primer site contained in each transcript of the library of transcripts and a nucleotide sequence that is complementary to the unique barcode and the 3' primer comprises a nucleotide sequence that is complementary to a 3' universal primer site contained in each transcript of the library of transcripts. In some embodiments, the 5' primer comprises a nucleotide sequence that is complementary to a 5' universal primer site contained in each transcript of the library of transcripts and the 3' primer comprises a nucleotide sequence that is complementary to a 3' universal primer site different from the 3' universal primer site contained in each transcript of the library of transcripts and a nucleotide sequence that is complementary to the unique barcode.

In some embodiments, the primer comprising the barcode sequence comprises 10, 11, 12, 13, 14, 15, 16, 17, 18, 19, 20, 21, 22, 23, 24, 25, 26, 27, 28, 29, or 30 nucleotides of universal primer sequence. In some embodiments, the 5' primer and/or the 3' primer are 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length.

In some embodiments, the melting temperature of the 5' primer and/or the 3' primer is 60° C., 61° C., 62° C., 63° C., 64° C., 65° C., 66° C., 67° C., 68° C., 69° C., or 70° C.

In some embodiments, the melting temperature of the primer containing the barcode sequence is optimized by shortening the barcode and/or universal primer sequence. In some embodiments, the melting temperature is optimized by removing a single nucleotide from the 5' end of the primer (e.g., from the universal primer sequence) and measuring the melting temperature. In some embodiments, this is repeated until a melting temperature near 60° C., 61° C., 62° C., 63° C., 64° C., 65° C., 66° C., 67° C., 68° C., 69° C., or 70° C. is obtained. In some embodiments, a series of 5' end truncations of the barcode containing the primer are made, the melting temperature of each primer is measured, and the primer having the melting temperature closest to 60° C., 61° C., 62° C., 63° C., 64° C., 65° C., 66° C., 67° C., 68° C., 69° C., or 70° C. is selected.

In some embodiments, the transcriptome is amplified using the barcode specific primers. Amplification can be performed in a multiplexed manner, wherein multiple target nucleic acid sequences are amplified simultaneously.

In some embodiments, amplification can be performed using a polymerase chain reaction (PCR). As used herein, PCR can refer to a reaction for the in vitro amplification of specific DNA sequences by the simultaneous primer extension of complementary strands of DNA. As used herein, PCR can encompass derivative forms of the reaction, including but not limited to, RT-PCR, real-time PCR, nested PCR, quantitative PCR, multiplexed PCR, digital PCR, and assembly PCR.

Amplification can be performed in one or more rounds. In some instances there are multiple rounds of amplification. Amplification can comprise two or more rounds of amplification.

In some embodiments, amplification comprises a first amplification and a second amplification, with the first amplification being performed with barcode specific primers. In some embodiments, amplification comprises a first amplification and a second amplification, with the first amplification being performed with barcode specific primers and the second amplification being performed with universal primers.

In some embodiments, the amplification reaction is performed on a RNA-seq library that comprises uracil in place of thymine. In some embodiments, a first amplification reaction is performed with a polymerase that does not recognize uracil, e.g., Pfu-Pol, Taq, Kappa HiFi, or Uracil+. In some embodiments, the first amplification reaction is performed with barcode specific primers. In some embodiments, the universal primer of the barcode specific primer pair comprises uracil in place of thymine. In some embodiments, after the first amplification reaction, the amplification product is treated with exonuclease, e.g., exonuclease I, and uracil DNA glycosylase (UDG) which degrade any unutilized primers and removes any deoxyuracil bases in the DNA including those in the universal primer, eliminating this site as a priming site for future PCR rounds and thereby leaving only DNA strands primed with barcode-specific primer with universal primer sites on both sides of the DNA strand intact, making only these strands available for exponential amplification in future PCR rounds. In some embodiments, a second amplification reaction is then performed with universal primers.

In some embodiments, the products of the amplification reaction are purified. By way of example, but not by way of limitation, in some embodiments, a method for purifying the amplification product includes the reversible binding or absorption of the amplicon onto glass or silica fibers or particles in combination with chaotropic salts followed by their washing and elution. In some embodiments, purification methods include, but is not limited to, precipitation in an alcohol based solutions (e.g., such as ethanol or isopropanol), contacting with anion exchange resins, or size exclusion filters. In some embodiments, the amplification products are purified using AmPure beads. In some embodiments, the cleaning-up of the amplification product removes excess primers, dNTPs, salts and other components that may interfere with downstream processes.

In some embodiments, 90%, 95%, 99%, 99.9%, 99.99%, or more of the amplification product will be derived from cDNA having the unique barcode of the single cell.

In some embodiments, the amplification products are sequenced using the methods described herein.

In some embodiments, transcripts that occur at a frequency of less than $1:10^5$, $1:10^6$, $1:10^7$, $1:10^8$, $1:10^9$, $1:10^{10}$, or $1:10^{11}$ are identified. In some embodiments, transcripts that occur at a frequency of less than $1:10^8$ to $1:10^9$ are identified.

Additional Embodiments for Enriching Barcoded Library Molecules

In certain embodiments, specific cDNA molecules (i.e. transcripts, transcriptomes) are enriched from barcoded cDNA sequencing libraries (e.g., single-cell RNA-seq libraries). Methods of enriching nucleic acids from a pool of nucleic acids are known in the art and may be used in the present invention. Barcoded cDNAs 9 e.g., first or second strand cDNA) are directly selected (e.g., captured, enriched) using the methods described herein.

In certain embodiments, cDNA molecules associated with a specific cell or subset of cells are enriched. Barcodes associated with a specific cell or subset of cells may be determined by sequencing the library first. After determining barcodes the method is followed by enrichment and resequencing. Capturing cDNAs using such methods will boost cDNAs derived from rare cells to levels that can be detected and re-sequenced with fewer reads (coverage, depth) than without selection. Selection will also reduce the representation of cDNAs from extremely abundant cells, thus helping to normalize the representation of transcripts in the cDNA library.

In certain embodiments, cDNA molecules corresponding to a specific gene are enriched. Barcodes associated with the selected cDNA molecules can be identified by sequencing of the enriched cDNA molecules. The barcodes may then be used to enrich for cDNAs originating from cells expressing specific genes (e.g., TCRs) or cells expressing a specific level of a gene.

In certain embodiments, enriched cDNA molecules from T cells may be used to identify TCR pairs in single cells. In further embodiments, barcodes associated with cells of a specific immune state (e.g., activated, dysfunctional, cytolytic) are enriched. Not being bound by a theory, antigen specific TCRs may be identified in cells of a specific immune state. The enriched cDNA molecules can be related or unrelated as desired. For example, selected target sequences may be obtained from a group of nucleic acids that are genes involved in a disease, such as a group of genes implicated in one or more diseases such as cancers, etc.

The enriched cDNA molecules, while ideally containing 100% of the target sequences (i.e., when the selection method selects all of the target sequences from the sequencing library) and no additional non-targeted sequences, typically contains less than all of the target sequences and contains some amount of background of unwanted sequences. For example, more typically the subgroup of enriched cDNA molecules is at least about 20%, 30%, 40%, 50%, 60%, 70%, 75%, 80%, 85%, 90%, 95%, 98%, 99% or more of the target sequences. The purity of the subgroup (percentage of reads that align to the targets) is typically at least about 20%, 30%, 40%, 50%, 60%, 70%, 75%, 80%, 85%, 90%, 95%, 98%, 99% or more.

In some embodiments, it may be advantageous to repeat the selection process on the selected barcoded cDNA molecules in order to increase the enrichment. Not being bound by a theory, after one round of selection (e.g., hybridization), a several thousand-fold enrichment can be achieved. After a second round, the enrichment can rise dramatically (e.g., 15,000-fold average enrichment; see US20100029498), which can provide hundreds-fold coverage of the target in a single sequencer run. Thus, for experiments that require enrichment factors not achievable in a single round of selection, the methods preferentially include subjecting the isolated barcoded cDNA molecules (i.e., a portion or all of the target sequences) to one or more additional rounds of enrichment (e.g., solution hybridization with the set of bait sequences).

In certain embodiments, methods used in targeted sequencing may be advantageously adapted for use in enriching barcoded cDNAs from a sequencing library (see, e.g., Mamanova et al., Target-enrichment strategies for next-generation sequencing. Nat Methods. 2010; 7:111-118). Targeted sequencing refers to methods of enrichment and sequencing of a selected set of genes or specific genomic elements (e.g., exome, CpG islands and promoter/enhancer regions).

Enriching Library Molecules Using PCR

Methods of enrichment include highly multiplexed PCR (e.g., amplicon sequencing). In certain embodiments, PCR based methods of enrichment may be used to enrich for barcoded cDNA molecules. PCR enrichment typically involves multiple primer pairs in a mixture that are combined with DNA of interest in a multiplex approach to preserve precious DNA (e.g., AmpliSeq technology, ThermoFisher Scientific).

In one embodiment, enrichment of barcoded cDNA molecules may utilize novel PCR primers specific for both paired end cDNA adaptors and cell-of-origin barcodes that are present in the cDNA constructs of the present invention. In another embodiment, enrichment of barcoded cDNA molecules in the present invention may utilize novel PCR primers specific for both paired end cDNA adaptors and gene specific sequences that are also present in the cDNA constructs of the present invention. In exemplary embodiments, a PCR primer pair includes a constant primer specific to one end of a paired end sequencing library (e.g., forward or reverse primer) and a second primer (e.g., forward or reverse primer) that is complementary to the other end plus the barcode or gene specific sequence.

In certain embodiments, modifications to the barcode and UMI sequences would enable noise sources to be further suppressed. In certain embodiments, the cell barcode targeting primer has complementarity to the full 16 base pair sequence allowing for the greatest specificity for the targeted cell. In certain embodiments, lengthening the barcode sequence to add downstream bases that extend beyond the 3' terminus of the enrichment primer (or alternatively, shortening the enrichment primer) would allow the extension reaction to pick up a portion of the target cell barcode from the library molecule independent of primer hybridization. Extending the length of the UMI sequence, hence its complexity, would increase the average distances between UMI sequences in the final read set and enable more stringent sequence filtering procedures to exclude erroneous reads.

Another targeted PCR based sequencing method, developed by Raindance (Billerica, Mass.) uses microdroplet PCR and custom-designed droplet libraries (Tewhey, et al. Microdroplet-based PCR enrichment for large-scale targeted sequencing. Nat Biotechnol. 2009; 27:1025-1031). The nature of micro-droplet emulsion PCR significantly decreases PCR amplification bias (Hori et al., Uniform amplification of multiple DNAs by emulsion PCR. Biochem Biophys Res Commun. 2007; 352:323-328). Microdroplet PCR allows the user to set up $1.5 \times 10^6$ micro-droplet amplifications in a single tube in under an hour. The droplet libraries are designed based on 500 bp amplicons, and a single custom library can target from 2000 to 10,000 different amplicons covering up to $5 \times 10^6$ bases. In certain embodiments, barcoded cDNAs are enriched by Microdroplet-based PCR enrichment. Micro-droplet emulsion PCR may advantageously be used in the present invention to eliminate amplification bias caused by primer interactions in the case where multiple barcode sequences are enriched. Not being bound by a theory, the PCR primers of the present invention differ only in the barcode sequence and certain amplicons may be amplified disproportionately in a multiplexed reaction. The discrete encapsulation of microdroplet PCR reactions prevents possible primer pair interactions allowing for highly efficient simultaneous amplification of up to 4,000 targeted sequences (e.g., 4,000 different barcodes) and greatly reduces the amount of reagents required.

In certain embodiments, amplifying target sequences (e.g., barcodes, transcripts) may include other PCR methods (e.g., Cold-PCR).

Targets may also be enriched using NaME-PrO technology (see, e.g., Song et al., Nucleic Acids Res. 2016 Nov 2;44(19):e146. Epub 2016 Jul 18). NaME-PrO employs a double-strand-DNA-specific nuclease and overlapping oligonucleotide-probes interrogating WI-DNA targets and guiding nuclease digestion to these sites. Mutation-containing DNA creates probe-DNA mismatches that inhibit digestion, thus subsequent DNA-amplification magnifies DNA-alterations at ail selected targets. In certain embodiments, probes may be used to remove wild type transcripts from a cDNA library by hybridizing probes for wild type targets. The wild targets will be cut and the mutant transcripts will remain.

In certain embodiments, PCR primer pairs specific for amplifying sequences comprising barcodes may use a primer that hybridizes to a barcode or may use a gene specific primer. In one embodiment, PCR using primers specific for library adaptors and barcode sequence are used to enrich for barcoded cDNAs. Thus, using a barcode specific primer allows for enriching all cDNAs having specific barcodes (e.g., all cDNA molecules originating from a specific cell). Using primers specific for a gene of interest allows for enriching cDNAs generated from specific genes and the barcodes associated with the cDNAs may be identified.

In certain embodiments, amplification products are labeled with biotin. Biotin labeled amplicons may be isolated using an affinity agent (e.g., streptavidin beads), such that only amplified products are recovered.

Enriching Library Molecules Using Hybridization

Other methods of enrichment for targeted sequencing include hybridization capture methods, such as in exome sequencing. High quality kits are commercially available; SureSelect (Agilent Technologies), SeqCap (Roche NimbleGen, Madison, Wis.) and TruSeq Exome Enrichment Kit (Illumina). All three capture methods are based on probe hybridization with olingonucleotide bait sequences to generate enriched sequencing libraries from whole genome samples (see, e.g., Gnirke, et al. Solution hybrid selection with ultra-long oligonucleotides for massively parallel targeted sequencing. Nat Biotechnol. 2009; 27:182-189; and Hodges, et al. Genome-wide in situ exon capture for selective resequencing. Nat Genet. 2007; 39:1522-1527). In certain embodiments, hybridization capture is adapted for enriching barcoded cDNA molecules from a sequencing library. In exemplary embodiments, enrichment is performed by solution phase capture (Gnirke A, et al. 2009; and US patent application 20100029498) or microarray capture (e.g. modified NimbleGen platform). Methods for isolating target single stranded DNA with biotinylated RNA probes are also known in the art (e.g., SureSelect Target Enrichment, Agilent Technologies). In certain embodiments, biotinylated RNA probes may be used to enrich cDNA molecules.

In certain embodiments, cDNA sequences from a barcoded sequencing library may be enriched using hybridization bait sequences (hybridization probes). The hybridization bait sequences may be specific for the barcodes of interest (i.e., the barcoded cDNAs to be enriched). Previously, cDNAs were specifically selected for using long bait sequences specific to cellular RNAs. The present invention may utilize novel short oligonucleotides specific for cell-oforigin barcode sequences (e.g., 10 to 50 nucleotides). The hybridization probes may include a hybridization sequence complementary to individual barcode sequences, as well as sequences complementary to sequencing adaptors. For enriching cDNA molecules for specific genes long oligonucleotide probes as described herein may be used. As described further herein, following identification of barcodes associated with specific genes, the barcodes may then be enriched. In certain embodiments, the present invention utilizes short bait sequences specific to unique barcode sequences to selectively enrich cDNA molecules originating from rare cells or cell types of interest.

Solution hybridization provides favorable binding kinetics, higher sensitivity, and smaller reaction volumes. In certain embodiments, selection is carried out by hybridization in solution, i.e., neither the oligonucleotide bait sequences nor the barcoded cDNA molecules being selected from are attached to a solid surface. Performing the selection method by hybridization in solution minimizes the reaction volume and therefore the amount of target nucleic acid necessary to achieve the concentration necessary to drive the hybridization reaction. Performing the selection method described herein using hybridization in solution also means that amplification of the cDNA is not required. The ability to select without amplification eliminates amplification bias.

In certain embodiments, the bait sequences include an affinity tag and more preferably there is an affinity tag on each bait sequence in a set of bait sequences. Affinity tags include biotin molecules, magnetic particles, haptens, or other tag molecules that permit isolation of molecules tagged with the tag molecule. Such molecules and methods of attaching them to nucleic acids (e.g., the bait sequences used in the methods disclosed herein) are well known in the art.

Also known in the art are molecules, particles or devices that bind to or are capable of separating the set of tagged bait sequences from the hybridization mixture. In some embodiments of the methods, the molecules, particles or devices bind to the affinity tag. The molecules, particles or devices in some preferred embodiments is an avidin molecule, a magnet, or an antibody or antigen-binding fragment thereof.

In some embodiments, the bait sequences in the set of bait sequences are RNA molecules. A RNA-DNA duplex is more stable than a DNA-DNA duplex, and therefore provides for potentially better capture of nucleic acids. RNA bait sequences can be synthesized using any method known in the art, including de novo chemical synthesis and transcription of DNA molecules using a DNA-dependent RNA polymerase. The RNA molecules can be RNase-resistant RNA molecules, which can be made, for example, by using modified nucleotides during transcription to produce RNA molecules that resist RNase degradation. In certain embodiments, RNase-resistant RNA molecules are synthesized. In preferred embodiments, RNA bait sequences include an affinity tag. In some embodiments, RNA bait sequences are made by in vitro transcription, for example, using biotinylated UTP. In other embodiments, RNA bait sequences are produced without biotin and then biotin is crosslinked to the RNA molecules using methods well known in the art, such as psoralen crosslinking.

In some embodiments, in vitro transcription is used, for example based on adding RNA polymerase promoter sequences to one end of oligonucleotides. As is well known in the art, RNA promoter sequences can also be introduced during PCR amplification of bait sequences out of genomic DNA by tailing one primer of each target-specific primer pairs with an RNA-promoter sequence. if RNA is synthesized using biotinylated UTP, single stranded biotin-labeled. RNA bait molecules are produced. In preferred embodiments, the RNA baits correspond to only one strand of the double-stranded DNA target. As those skilled in the art will appreciate; such RNA baits are not self-complementary and are therefore more effective as hybridization drivers.

In certain embodiments, bait sequences are used to select for cDNA molecules corresponding to a specific gene. Barcodes associated with the selected cDNA molecules can be identified by sequencing of the enriched cDNA molecules. The barcodes may then be used to enrich for cDNAs originating from cells expressing specific genes (e.g., T cell receptors) or cells expressing a specific level of a gene.

The bait sequences for enriching cDNA molecules specific to a gene or genes may be synthetic long oligonucleotides or may be derived from (e.g., produced using) synthetic long oligonucleotides. In certain embodiments, the set of gene specific bait sequences is derived from oligonucleotides synthesized in a microarray and cleaved and eluted from the microarray. In other embodiments, the gene specific bait sequences are produced by nucleic acid amplification methods, e.g., using human DNA or pooled human DNA samples as the template.

Long bait sequences preferably are oligonucleotides between about 70 nucleotides and 1000 nucleotides in length, more preferably between about 100 nucleotides and 300 nucleotides in length, more preferably between about 130 nucleotides and 230 nucleotides in length and more preferably still are between about 150 nucleotides and 200 nucleotides in length. Intermediate lengths in addition to those mentioned above also can be used in the methods of the invention, such as oligonucleotides of about 70, 80, 90, 100, 110, 120, 130, 150, 160, 180, 190, 210, 220, 230, 240, 250, 300, 400, 500, 600, 700, 800, and 900 nucleotides in length, as well as oligonucleotides of lengths between the above-mentioned lengths. For selection of exons and other short targets, preferred bait sequence lengths are oligonucleotides of about 100 to about 300 nucleotides, more preferably about 130 to about 230 nucleotides, and still more preferably about 150 to about 200 nucleotides. The target-specific sequences in the oligonucleotides for selection of exons and other short targets are between about 40 and 1000 nucleotides in length, more preferably between about 70 and 300 nucleotides, more preferably between about 100 and 200 nucleotides, and more preferably still between about 120 and 170 nucleotides in length.

Minor Groove Binders

In certain embodiments, hybridization capture and PCR using short oligonucleotides specific to barcode sequences may utilize minor groove binders (MGB) to increase the melting temperature ($T_m$: the temperature at which half of the base pairs have become unpaired) of the capture probes or PCR primers. Minor groove binder oligonucleotide conjugates (or "probes") are described in, e.g., U.S. Pat. No. 6,312,894. The selection of minor groove binders and available minor groove binders have been disclosed in U.S. Pat. Nos. 5,801,155, 6,312,894 and 7,582,739. Although a general chemical formula for all known minor groove binding compounds cannot be provided because such compounds have widely varying chemical structures, compounds which are capable of binding in the minor groove of DNA, generally speaking, have a crescent shape three dimensional structure. Most minor groove binding compounds of the prior art have a strong preference for A-T (adenine and thymine) rich regions of the B form of double stranded DNA. A variety of suitable minor groove binders have been described in the literature (see, e.g., Wemmer et al., Curr.

Opin. Struct. BioL, 7:355-361 (1997); Walker et al, Biopolymers 14:323-334 (1997); Zimmer et al., Prog. Biophys. Molec. Bio., 47:31-1112 (1986); and Reddy et al., Pharmacol. Therap., 84:1-111 (1999)).

Conjugation of a minor groove binder (MGB) to an oligonucleotide (ODN) dramatically increases the stability of the hybrid formed between the oligonucleotide and its target. Increased stability (i.e., increased degree of hybridization) is manifested in a higher melting temperature ($T_m$) of hybrid duplexes formed by such MGB-oligonucleotide conjugates, compared to those formed by an unconjugated oligonucleotide of identical length and sequence. This effect is particularly pronounced for short oligonucleotides (e.g., less than about 21 nucleotides in length) and makes possible, for the use of short oligonucleotides as probes and primers, under high stringency conditions. Conjugation of an oligonucleotide with a MGB, with its attendant increase in hybrid stability, does not adversely affect the ability of the conjugated oligonucleotide to serve as a primer. Therefore, it is possible to use shorter oligonucleotides than previously required in for example, hybridization. In addition to increased duplex stabilization, MGB-oligonucleotide conjugates retain the heightened sensitivity to sequence mismatch that is characteristic of unconjugated short oligonucleotides with low melting temperatures. Thus, conjugation to a MGB endows very short oligonucleotides (e.g., oligonucleotides containing less than about 21 nucleotides) with greater specificity, by endowing them with the potential to form hybrids having a stability characteristic of much longer oligonucleotides, while retaining the ability to discriminate between sequences differing by a single nucleotide.

Enriching Library Molecules Using CRISPR

In certain embodiments, barcoded cDNAs are enriched using a CRISPR system. Methods of enriching genomic DNA fragments using Cas9/CRISPR have been described. In this regard, reference is made to US patent application US20140356867A1 assigned to Agilent Technologies.

CRISPR guide RNA (sgRNA, gRNA) complexes can be programmed to bind to any sequence, provided that the sequence has a PAM motif. Not being bound by a theory, enriching cDNA molecules using a CRISPR system may allow for more specific targeting of cDNA molecules distinguished by a short barcode sequence (e.g., 10 to 50 nucleotides) than for example hybridization. A CRISPR system can use an RNA guide to specifically target a barcode sequence in a library of barcoded cDNA molecules. In certain embodiments, each barcode is designed to be upstream of a PAM sequence specific for the CRISPR enzyme. In exemplary embodiments, the guide RNAs may be designed so that they direct binding of the CRISPR-gRNA complexes to a specific set of barcodes or gene(s) of interest. Designing guide RNAs for use in the present method are within the skill of one skilled in the art.

The CRISPR system may utilize any CRISPR enzyme capable of targeting DNA (e.g., Cas9, Cpf1). In certain embodiments, an enzymatically inactive CRISPR enzyme can be used to target different barcoded cDNA molecules. In certain embodiments, the CRISPR enzyme is mutated, such that it is enzymatically inactive. Not being bound by a theory, the mutant CRISPR enzyme is inactivated in the sense that it can bind, but it cannot cleave, the sequence to which it has been programmed to bind by the gRNA complexed to it. In certain embodiments, the Cas9 protein has amino acid substitutions at D10 and H840, or sites corresponding thereto. In particular embodiments, the Cas9 protein may have D 10A and H840A substitutions (or equivalent substitutions at positions corresponding to D10 and H840 in the *Streptococcus* Cas9 protein). In certain embodiments, a wild type Cas9 may be used, though it may have the additional effect of cleaving the target DNA sequence. However, if the Cas9 enzyme remains bound to the target DNA after cleavage, the target DNA may still be captured via Cas9 protein or the gRNA.

Conditions for binding Cas9-guide RNA complexes to target sequences in vitro are known and include, e.g., incubation in 10 mM Tris HCl (pH 7.5), 10 mM NaCl, 0.1 mg/mL BSA, and 10 mM $MgCl_2$ at 37° C.

After the CRISPR-gRNA complex has bound to the cDNA, the isolating step of the method can be done in any convenient way. The CRISPR cDNA bound complexes can be captured by using an antibody against the CRISPR protein (e.g., Cas9) or by using other means, e.g., an affinity tagged guide RNA or CRISPR protein. In certain embodiments, the isolating is done using a capture agent (e.g., an antibody) that specifically binds to the Cas9 protein. In other embodiments, the CRISPR protein (e.g., Cas9) may itself be a fusion protein, where the CRISPR protein is fused to a proteinaceous affinity tag such as avidin, streptavidin, protein A, maltose-binding protein, poly-histidine, HA-tag, c-myc tag, FLAG-tag, SNAP-tag, S-tag and glutathione-S-transferase (GST) or the like. Alternatively, the CRISPR protein can be conjugated to a non-proteinaceous affinity tag such as a biotin moiety (e.g., biotin). In these embodiments, the isolating can be done by binding the affinity tag to an affinity support (e.g., beads, column, array) that contains a capture agent that specifically binds to the affinity tag.

In alternative embodiments, the CRISPR-associated guide RNA may comprise an affinity tag, and the isolating may be done using a capture agent for the affinity tag. In these embodiments, the CRISPR-associated guide RNA may comprises a biotin moiety, and the isolating may be done using an affinity support that contains streptavidin or the like. Biotinylated RNA can be produced synthetically (e.g., using biotinylated ribonucleotides) or using any suitable enzymatic method (see, e.g., Moritz et al. RNA March 2014 20: 421-427). The affinity tag may be linked to the guide RNA at any position, including, but not limited to, the 5' end, the 3' end or any position in the interior of the oligonucleotide, e.g., in the middle of the oligonucleotide. In certain embodiments, the affinity tag may be cleavably linked to the guide RNAs such that the CRISPR-cDNA complexes can be cleaved from the support after the separation step.

In certain embodiments, a sample comprising cDNA from a sequencing library may be combined with a Cas9-gRNA complex that contains a mutant Cas9 protein that has inactivated nuclease activity and a Cas9-associated guide RNA that is complementary to a site in the cDNA (e.g., barcode, gene specific sequence), and the resultant mixture may be combined with a support that contains a suitable capture agent (e.g., beads, column, array). The capture agent may be immobilized on a support. The cDNA molecules that are not bound by the Cas9-gRNA complex do not bind to the support and are washed away, whereas the cDNA molecules that are bound by the Cas9-gRNA complex are retained on the support. The Cas9-gRNA complexes (or the cDNA bound to the Cas9-gRNA complexes) can be released from the support by any suitable method. Such conditions are known. After the complexes are contacted with the capture agent, the resultant composition may be washed to remove unbound products from the solid support. The separation step thereby produces two fractions, one containing the selected cDNA molecules (i.e., a cDNA molecule that is bound by the Cas9-gRNA complex) and the other that does not contain the selected cDNA molecules.

The isolated cDNA molecules may be released from the isolated Cas9 complexes. This may be done by subjecting the isolated complexes to moderately denaturing conditions, thereby releasing the cDNA molecules from the Cas-9 complex, or in fully denaturing conditions to yield single stranded DNA molecules.

In certain embodiments, a plurality of CRISPR complexes that contain a plurality (i.e., at least 2, at least 5, at least 10, at least 50, at least 100, at least 500 or more) of gRNAs in a multiplex reaction can be used to isolate a plurality of different barcoded cDNA molecules. The plurality of CRISPR complexes may all contain the same affinity tag.

In certain embodiments, the efficiency of target DNA capture may also be enhanced by forming chemical cross-links between the target DNA and the CRISPR protein. Alternatively, Cas9 could be programmed with a synthetic RNA that contains modified nucleotides or bases, such as nucleosides modified with thioethyl groups at the 2' position, or modified bases such as 4-thiouridine, 5-bromouridine, 5-iodouridine, and 6-thioguanosine. Modified synthetic RNAs could enable intra-strand crosslinking to the DNA target, allowing a chemical bond that would persist after denaturation or Cas9 protein removal.

In certain embodiments, inhibitors of DNases can be used to reduce degradation of DNA. DNase inhibitors that are compatible with Cas9 include, but are not limited to, 2-mercaptoethanol and actin.

With respect to general information on CRISPR-Cas Systems, components thereof, and delivery of such components, including methods, materials, delivery vehicles, vectors, particles, AAV, and making and using thereof, including as to amounts and formulations, all useful in the practice of the instant invention, reference is made to: U.S. Pat. Nos. 8,999,641, 8,993,233, 8,945,839, 8,932,814, 8,906,616, 8,895,308, 8,889,418, 8,889,356, 8,871,445, 8,865,406, 8,795,965, 8,771,945 and 8,697,359; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); European Patents EP 2 784 162 B1 and EP 2 771 468 B 1; European Patent Applications EP 2 771 468 (EP13818570.7), EP 2 764 103 (EP13824232.6), and EP 2 784 162 (EP14170383.5); and PCT Patent Publications PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO2014/093701 (PCT/US2013/074800), WO2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809). Reference is also made to U.S. provisional patent applications 61/758,468; 61/802,174; 61/806,375; 61/814,263; 61/819,803 and 61/828,130, filed on Jan. 30, 2013; Mar. 15, 2013; Mar. 28, 2013; Apr. 20, 2013; May 6, 2013 and May 28, 2013 respectively. Reference is also made to U.S. provisional patent application 61/836,123, filed on Jun. 17, 2013. Reference is additionally made to U.S. provisional patent applications 61/835,931, 61/835,936, 61/836,127, 61/836,101, 61/836,080 and 61/835,973, each filed Jun. 17, 2013. Further reference is made to U.S. provisional patent applications 61/862,468 and 61/862,355 filed on Aug. 5, 2013; 61/871,301 filed on Aug. 28, 2013; 61/960,777 filed on Sep. 25, 2013 and 61/961,980 filed on Oct. 28, 2013. Reference is yet further made to: PCT Patent applications Nos: PCT/US2014/041803, PCT/US2014/041800, PCT/US2014/041809, PCT/US2014/041804 and PCT/US2014/041806, each filed Jun. 10, 2014 6/10/14; PCT/US2014/041808 filed Jun. 11, 2014; and PCT/US2014/62558 filed Oct. 28, 2014, and U.S. Provisional Patent Applications Ser. Nos. 61/915,150, 61/915,301, 61/915,267 and 61/915,260, each filed Dec. 12, 2013; 61/757,972 and 61/768,959, filed on Jan. 29, 2013 and Feb. 25, 2013; 61/835,936, 61/836,127, 61/836,101, 61/836,080, 61/835,973, and 61/835,931, filed Jun. 17, 2013; 62/010,888 and 62/010,879, both filed Jun. 11, 2014; 62/010,329 and 62/010,441, each filed Jun. 10, 2014; 61/939,228 and 61/939,242, each filed Feb. 12, 2014; 61/980,012, filed Apr. 15,2014; 62/038,358, filed Aug. 17, 2014; 62/054,490, 62/055,484, 62/055,460 and 62/055,487, each filed Sep. 25, 2014; and 62/069,243, filed Oct. 27, 2014. Reference is also made to U.S. provisional patent applications Nos. 62/055,484, 62/055,460, and 62/055,487, filed Sep. 25, 2014; U.S. provisional patent application 61/980,012, filed Apr. 15, 2014; and U.S. provisional patent application 61/939,242 filed Feb. 12, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013. Reference is made to US provisional patent application USSN 61/980,012 filed Apr. 15, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013.

Mention is also made of U.S. application 62/091,455, filed, 12-Dec-14, PROTECTED GUIDE RNAS (PGRNAS); U.S. application 62/096,708, 24-Dec-14, PROTECTED GUIDE RNAS (PGRNAS); U.S. application 62/091,462, 12-Dec-14, DEAD GUIDES FOR CRISPR TRANSCRIPTION FACTORS; U.S. application 62/096,324, 23-Dec-14, DEAD GUIDES FOR CRISPR TRANSCRIPTION FACTORS; U.S. application 62/091,456, 12-Dec-14, ESCORTED AND FUNCTIONALIZED GUIDES FOR CRISPR-CAS SYSTEMS; U.S. application 62/091,461, 12-Dec-14, DELIVERY, USE AND THERAPEUTIC APPLICATIONS OF THE CRISPR-CAS SYSTEMS AND COMPOSITIONS FOR GENOME EDITING AS TO HEMATOPOIETIC STEM CELLS (HSCs); U.S. application 62/094,903, 19-Dec-14, UNBIASED IDENTIFICATION OF DOUBLE-STRAND BREAKS AND GENOMIC REARRANGEMENT BY GENOME-WIDE INSERT CAPTURE SEQUENCING; U.S. application 62/096,761, 24-Dec-14, ENGINEERING OF SYSTEMS, METHODS AND OPTIMIZED ENZYME AND GUIDE SCAFFOLDS FOR SEQUENCE MANIPULATION; U.S. application 62/098,059, 30-Dec-14, RNA-TARGETING SYSTEM; U.S. application 62/096,656, 24-Dec-14, CRISPR HAVING OR ASSOCIATED WITH DESTABILIZATION DOMAINS; U.S. application 62/096,697, 24-Dec-14, CRISPR HAVING OR ASSOCIATED WITH AAV; U.S. application 62/098,158, 30-Dec-14, ENGINEERED CRISPR COMPLEX INSERTIONAL TARGETING SYSTEMS; U.S. application 62/151,052, 22-Apr-15, CELLULAR TARGETING FOR EXTRACELLULAR EXOSOMAL REPORTING; U.S. application 62/054,490, 24-Sep-14, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 62/055,484, 25-Sep-14, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4-Dec-14, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24-Sep-14, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23-Oct-14, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/054,675, 24-Sep-14, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24-Sep-14, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25-Sep-14, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25-Sep-14, MULTIFUNCTIONAL-CRISPR COMPLEXES AND/OR OPTIMIZED ENZYME LINKED FUNCTIONAL-CRISPR COMPLEXES; U.S. application 62/087,475, 4-Dec-14, FUNCTIONAL SCREENING WITH OPTIMIZED FUNCTIONAL CRISPR-CAS SYSTEMS; U.S. application 62/055,487, 25-Sep-14, FUNCTIONAL SCREENING WITH OPTIMIZED FUNCTIONAL CRISPR-CAS SYSTEMS; U.S. application 62/087,546, 4-Dec-14, MULTIFUNCTIONAL CRISPR COMPLEXES AND/OR OPTIMIZED ENZYME LINKED FUNCTIONAL-CRISPR COMPLEXES; and U.S. application 62/098,285, 30-Dec-14, CRISPR MEDIATED IN VIVO MODELING AND GENETIC SCREENING OF TUMOR GROWTH AND METASTASIS.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Also with respect to general information on CRISPR-Cas Systems, mention is made of the following (also hereby incorporated herein by reference):

Multiplex genome engineering using CRISPR/Cas systems. Cong, L., Ran, F. A., Cox, D., Lin, S., Barretto, R., Habib, N., Hsu, P. D., Wu, X., Jiang, W., Marraffini, L.A., & Zhang, F. Science Feb 15;339(6121):819-23 (2013);

RNA-guided editing of bacterial genomes using CRISPR-Cas systems. Jiang W., Bikard D., Cox D., Zhang F, Marraffini L A. Nat Biotechnol Mar;31(3):233-9 (2013);

One-Step Generation of Mice Carrying Mutations in Multiple Genes by CRISPR/Cas-Mediated Genome Engineering. Wang H., Yang H., Shivalila C S., Dawlaty M M., Cheng A W., Zhang F., Jaenisch R. Cell May 9; 153(4):910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. Aug 22;500(7463):472-6. doi: 10.1038/Nature12466. Epub 2013 Aug 23 (2013);

Double Nicking by RNA-Guided CRISPR Cas9 for Enhanced Genome Editing Specificity. Ran, FA., Hsu, PD., Lin, CY., Gootenberg, J S., Konermann, S., Trevino, AE., Scott, DA., Inoue, A., Matoba, S., Zhang, Y., & Zhang, F. Cell Aug 28. pii: S0092-8674(13) 01015-5 (2013-A);

DNA targeting specificity of RNA-guided Cas9 nucleases. Hsu, P., Scott, D., Weinstein, J., Ran, FA., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);

Genome engineering using the CRISPR-Cas9 system. Ran, FA., Hsu, PD., Wright, J., Agarwala, V., Scott, DA., Zhang, F. Nature Protocols Nov;8(11):2281-308 (2013-B);

Genome-Scale CRISPR-Cas9 Knockout Screening in Human Cells. Shalem, O., Sanjana, N E., Hartenian, E., Shi, X., Scott, DA., Mikkelson, T., Heckl, D., Ebert, BL., Root, D E., Doench, JG., Zhang, F. Science Dec 12. (2013). [Epub ahead of print];

Crystal structure of cas9 in complex with guide RNA and target DNA. Nishimasu, H., Ran, FA., Hsu, PD., Konermann, S., Shehata, SI., Dohmae, N., Ishitani, R., Zhang, F., Nureki, O. Cell Feb 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. Apr 20. doi: 10.1038/ nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014(2014);

Development and Applications of CRISPR-Cas9 for Genome Engineering, Hsu P D, Lander E S, Zhang F., Cell. Jun 5;157(6):1262-78 (2014);

Genetic screens in human cells using the CRISPR/Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. Dec; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. Jan;33(1):102-6 (2015);

Genome-scale transcriptional activation by an engineered CRISPR-Cas9 complex, Konermann S, Brigham M D, Trevino A E, Joung J, Abudayyeh 00, Barcena C, Hsu P D, Habib N, Gootenberg J S, Nishimasu H, Nureki 0, Zhang F., Nature. Jan 29;517(7536):583-8 (2015);

A split-Cas9 architecture for inducible genome editing and transcription modulation, Zetsche B, Volz S E, Zhang F., (published online 2 Feb. 2015) Nat Biotechnol. Feb;33(2):139-42 (2015);

Genome-wide CRISPR Screen in a Mouse Model of Tumor Growth and Metastasis, Chen S, Sanjana N E, Zheng K, Shalem 0, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using *Staphylococcus aureus* Cas9, Ran F A, Cong L, Yan W X, Scott D A, Gootenberg J S, Kriz A J, Zetsche B, Shalem 0, Wu X, Makarova K S, Koonin EV, Sharp P A, Zhang F., (published online 1 Apr. 2015), Nature. Apr 9;520 (7546):186-91 (2015).

Shalem et al., "High-throughput functional genomics using CRISPR-Cas9," Nature Reviews Genetics 16, 299-311 (May 2015).

Xu et al., "Sequence determinants of improved CRISPR sgRNA design," Genome Research 25, 1147-1157 (August 2015).

Parnas et al., "A Genome-wide CRISPR Screen in Primary Immune Cells to Dissect Regulatory Networks," Cell 162, 675-686 (Jul. 30, 2015).

Ramanan et al., CRISPR/Cas9 cleavage of viral DNA efficiently suppresses hepatitis B virus," Scientific Reports 5:10833. doi: 10.1038/srep10833 (Jun. 2, 2015).

Nishimasu et al., Crystal Structure of *Staphylococcus aureus* Cas9," Cell 162, 1113-1126 (Aug. 27, 2015).

BCL11A enhancer dissection by Cas9-mediated in situ saturating mutagenesis, Canver et al., Nature 527 (7577):192-7 (Nov. 12, 2015) doi: 10.1038/nature15521. Epub 2015 Sep 16.

Cpf1 is a Single RNA-Guided Endonuclease of a Class 2 CRISPR-Cas System, Zetsche et al., Cell 163, 759-71 (Sep. 25, 2015).

Discovery and Functional Characterization of Diverse Class 2 CRISPR-Cas Systems, Shmakov et al., Molecular Cell, 60(3), 385-397 doi: 10.1016/j.molce1.2015.10.008 Epub Oct. 22, 2015.

Rationally engineered Cas9 nucleases with improved specificity, Slaymaker et al., Science 2016 Jan 1 351 (6268): 84-88 doi: 10.1126/science.aad5227. Epub 2015 Dec 1.

Gao et al, "Engineered Cpf1 Enzymes with Altered PAM Specificities," bioRxiv 091611; doi: dx.doi.org/10.1101/091611 (Dec. 4, 2016).

Cox et al., "RNA editing with CRISPR-Cas13," Science. 2017 Nov 24;358(6366):1019-1027. doi: 10.1126/science.aaq0180. Epub 2017 Oct 25.

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR/Cas system for the one-step generation of mice carrying mutations in multiple genes which were traditionally generated in multiple steps by sequential recombination in embryonic stem cells and/or time-consuming intercrossing of mice with a single mutation. The CRISPR/Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors.

Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry.

The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays. Shalem et al. (2015) described ways in which catalytically inactive Cas9 (dCas9) fusions are used to synthetically repress (CRISPRi) or activate (CRISPRa) expression, showing advances using Cas9 for genome-scale screens, including arrayed and pooled screens, knockout approaches that inactivate genomic loci and strategies that modulate transcriptional activity.

Shalem et al. (2015) described ways in which catalytically inactive Cas9 (dCas9) fusions are used to synthetically repress (CRISPRi) or activate (CRISPRa) expression, showing advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR/Cas9 knockout and nucleotide preference at the cleavage site. The authors also found that the sequence preference for CRISPRi/a is substantially different from that for CRISPR/Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Canver et al. (2015) demonstrated a CRISPR-Cas9-based functional investigation of non-coding genomic elements. The authors we developed pooled CRISPR-Cas9 guide RNA libraries to perform in situ saturating mutagenesis of the human and mouse BCL11A enhancers which revealed critical features of the enhancers.

Zetsche et al. (2015) reported characterization of Cpf1, a class 2 CRISPR nuclease from Francisella novicida U112 having features distinct from Cas9. Cpf1 is a single RNA-guided endonuclease lacking tracrRNA, utilizes a T-rich protospacer-adjacent motif, and cleaves DNA via a staggered DNA double-stranded break.

Shmakov et al. (2015) reported three distinct Class 2 CRISPR-Cas systems. Two system CRISPR enzymes (C2c1 and C2c3) contain RuvC-like endonuclease domains distantly related to Cpf1. Unlike Cpf1, C2c1 depends on both crRNA and tracrRNA for DNA cleavage. The third enzyme (C2c2) contains two predicted HEPN RNase domains and is tracrRNA independent.

Slaymaker et al (2016) reported the use of structure-guided protein engineering to improve the specificity of Streptococcus pyogenes Cas9 (SpCas9). The authors developed "enhanced specificity" SpCas9 (eSpCas9) variants which maintained robust on-target cleavage with reduced off-target effects.

Cox et al., (2017) reported the use of catalytically inactive Cas13 (dCas13) to direct adenosine-to-inosine deaminase activity by ADAR2 (adenosine deaminase acting on RNA type 2) to transcripts in mammalian cells. The system, referred to as RNA Editing for Programmable A to I Replacement (REPAIR), has no strict sequence constraints and can be used to edit full-length transcripts. The authors further engineered the system to create a high-specificity variant and minimized the system to facilitate viral delivery.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

Perturb-Seq

In certain embodiments, a population of single cells are screened by perturbation of target genes and analyzed by single-cell sequencing, thus generating single-cell barcoded libraries applicable for further analysis by the present invention. Methods and tools for genome-scale screening of perturbations in single cells using CRISPR-Cas9 have been described, herein referred to as perturb-seq (see e.g., Dixit et al., "Perturb-Seq: Dissecting Molecular Circuits with Scalable Single-Cell RNA Profiling of Pooled Genetic Screens" 2016, Cell 167, 1853-1866; Adamson et al., "A Multiplexed Single-Cell CRISPR Screening Platform Enables Systematic Dissection of the Unfolded Protein Response" 2016, Cell 167, 1867-1882; and International publication serial number WO/2017/075294). In certain embodiments, a set of signature genes may be perturbed in single cells and gene expression analyzed. Not being bound by a theory, networks of genes that are disrupted due to perturbation of a signature gene may be determined. Understanding the network of genes effected by a perturbation may allow for a gene to be linked to a specific pathway that may be targeted to modulate the signature and treat disease (e.g., cancer). Not being bound by a theory, sequencing of single perturbed cells may be able to identify interesting cells, but not be able to identify full transcriptomes for the cells (i.e., not every gene in a single cell may be detected). Enrichment of cDNA from the interesting cells followed by sequencing can allow for improved transcriptome analysis in these cells.

In one embodiment, the method comprises (1) introducing single-order or combinatorial perturbations to a population of cells, (2) measuring genomic, genetic, proteomic, epigenetic and/or phenotypic differences in single cells and (3) assigning a perturbation(s) to the single cells. Not being bound by a theory, a perturbation may be linked to a phenotypic change, preferably changes in gene or protein expression. In preferred embodiments, measured differences that are relevant to the perturbations are determined by applying a model accounting for co-variates to the measured differences. The model may include the capture rate of measured signals, whether the perturbation actually perturbed the cell (phenotypic impact), the presence of subpopulations of either different cells or cell states, and/or analysis of matched cells without any perturbation. In certain embodiments, the measuring of phenotypic differences and assigning a perturbation to a single cell is determined by performing single-cell RNA sequencing (RNA-seq). In preferred embodiments, the single-cell RNA-seq is performed by any method as described herein (e.g., Drop-seq, InDrop, 10X genomics, split-pool methods). In certain embodiments, unique barcodes are used to perform Perturb-seq. In certain embodiments, a guide RNA is detected by RNA-seq using a transcript expressed from a vector encoding the guide RNA. The transcript may include a unique barcode specific to the guide RNA. Not being bound by a theory, a guide RNA and guide RNA barcode is expressed from the same vector and the barcode may be detected by RNA-seq. Not being bound by a theory, detection of a guide RNA barcode is more reliable than detecting a guide RNA sequence, reduces the chance of false guide RNA assignment and reduces the sequencing cost associated with executing these screens. Thus, a perturbation may be assigned to a single cell by detection of a guide RNA barcode in the cell. In certain embodiments, a cell barcode is added to the RNA in single cells, such that the RNA may be assigned to a single cell. Generating cell barcodes is described herein for single-cell sequencing methods. In certain embodiments, a Unique Molecular Identifier (UMI) is added to each individual transcript and protein capture oligonucleotide. Not being bound by a theory, the UMI allows for determining the capture rate of measured signals, or preferably the number of transcripts captured. Not being bound by a theory, the data is more significant if the signal observed is derived from more than one transcript. In preferred embodiments, Perturb-seq is performed using a guide RNA barcode expressed as a polyadenylated transcript, a cell barcode, and a UMI.

Perturb-seq combines emerging technologies in the field of genome engineering and single-cell analysis, in particular the CRISPR-Cas9 system and droplet single-cell sequencing analysis. In certain embodiments, a CRISPR system is used to create an INDEL at a target gene. In other embodiments, epigenetic screening is performed by applying CRISPRa/i/x technology (see, e.g., Konermann et al. "Genome-scale transcriptional activation by an engineered CRISPR-Cas9 complex" Nature. 2014 Dec 10. doi: 10.1038/nature14136; Qi, L. S., et al. (2013). "Repurposing CRISPR as an RNA-guided platform for sequence-specific control of gene expression". Cell. 152 (5): 1173-83; Gilbert, L. A., et al., (2013). "CRISPR-mediated modular RNA-guided regulation of transcription in eukaryotes". Cell. 154 (2): 442-51; Komor et al., 2016, Programmable editing of a target base in genomic DNA without double-stranded DNA cleavage, Nature 533, 420-424; Nishida et al., 2016, Targeted nucleotide editing using hybrid prokaryotic and vertebrate adaptive immune systems, Science 353(6305); Yang et al., 2016, Engineering and optimizing deaminase fusions for genome editing, Nat Commun. 7:13330; Hess et al., 2016, Directed evolution using dCas9-targeted somatic hypermutation in mammalian cells, Nature Methods 13, 1036-1042; and Ma et al., 2016, Targeted AID-mediated mutagenesis (TAM) enables efficient genomic diversification in mammalian cells, Nature Methods 13, 1029-1035).

Automation

The methods of the invention are adaptable to standard liquid handling methods and devices. Thus, in some embodiments, the method is carried out using automated liquid handling technology as is known in the art, such as devices that handle multiwell plates. This can include automated library construction, hybridization, solution hybridization, PCR, CRISPR enrichment.

As those skilled in the art of laboratory automation will appreciate, other steps in preferred methods disclosed here including but not limited to setting up and incubating the reaction mixes, cleaning up the enriched cDNA molecules, amplification steps (e.g., by PCR), size-selection or size exclusion steps whether they are carried out by electrophoresis, chromatography, size-sensitive adsorption or elution methods can also be performed on commercially available or custom devices designed to specifications that are well known to those skilled in the art. In other preferred embodiments, robotic arms, plate hotel and other equipment well known to those in the art can be used to automate longer series of reaction steps, replenish reagents and labware and allow unsupervised processing of multiple sets of samples.

TCRs for use in Adoptive Cell Transfer (ACT)

In certain embodiments, identified T cell receptor (TCR) pairs are used in constructing cells for adoptive cell transfer. In certain embodiments, TCRs that are clonal or specific to an antigen are identified. As used herein, "ACT", "adoptive cell therapy" and "adoptive cell transfer" may be used interchangeably. In certain embodiments, Adoptive cell therapy (ACT) can refer to the transfer of cells to a patient with the goal of transferring the functionality and characteristics into the new host by engraftment of the cells (see, e.g., Mettananda et al., Editing an α-globin enhancer in primary human hematopoietic stem cells as a treatment for β-thalassemia, Nat Commun. 2017 Sep 4;8(1):424). As used herein, the term "engraft" or "engraftment" refers to the process of cell incorporation into a tissue of interest in vivo through contact with existing cells of the tissue. Adoptive cell therapy (ACT) can refer to the transfer of cells, most commonly immune-derived cells, back into the same patient or into a new recipient host with the goal of transferring the immunologic functionality and characteristics into the new host. If possible, use of autologous cells helps the recipient by minimizing GVHD issues. The adoptive transfer of autologous tumor infiltrating lymphocytes (TIL) (Besser et al., (2010) Clin. Cancer Res 16 (9) 2646-55; Dudley et al., (2002) Science 298 (5594): 850-4; and Dudley et al., (2005) Journal of Clinical Oncology 23 (10): 2346-57.) or genetically re-directed peripheral blood mononuclear cells (Johnson et al., (2009) Blood 114 (3): 535-46; and Morgan et al., (2006) Science 314(5796) 126-9) has been used to successfully treat patients with advanced solid tumors, including melanoma and colorectal carcinoma, as well as patients with CD19-expressing hematologic malignancies (Kalos et al., (2011) Science Translational Medicine 3 (95): 95ra73). In certain embodiments, allogenic cells immune cells are transferred (see, e.g., Ren et al., (2017) Clin Cancer Res 23 (9) 2255-2266). As described further herein, allogenic cells can be edited to reduce alloreactivity and prevent graft-versus-host disease. Thus, use of allogenic cells allows for cells to be obtained from healthy donors and prepared for use in patients as opposed to preparing autologous cells from a patient after diagnosis.

Aspects of the invention involve the adoptive transfer of immune system cells, such as T cells, specific for selected antigens, such as tumor associated antigens or tumor specific neoantigens (see, e.g., Maus et al., 2014, Adoptive Immunotherapy for Cancer or Viruses, Annual Review of Immunology, Vol. 32: 189-225; Rosenberg and Restifo, 2015, Adoptive cell transfer as personalized immunotherapy for human cancer, Science Vol. 348 no. 6230 pp. 62-68; Restifo et al., 2015, Adoptive immunotherapy for cancer: harnessing the T cell response. Nat. Rev. Immunol. 12(4): 269-281; and Jenson and Riddell, 2014, Design and implementation of adoptive therapy with chimeric antigen receptor-modified T cells. Immunol Rev. 257(1): 127-144; and Rajasagi et al., 2014, Systematic identification of personal tumor-specific neoantigens in chronic lymphocytic leukemia. Blood. 2014 Jul. 17;124(3):453-62).

Various strategies may for example be employed to genetically modify T cells by altering the specificity of the T cell receptor (TCR) for example by introducing new TCR α and β chains with selected peptide specificity (see U.S. Pat. No. 8,697,854; PCT Patent Publications: WO2003020763, WO2004033685, WO2004044004, WO2005114215, WO2006000830, WO2008038002, WO2008039818, WO2004074322, WO2005113595, WO2006125962, WO2013166321, WO2013039889, WO2014018863, WO2014083173; U.S. Pat. No. 8,088,379).

Chimeric Antigen Receptors (CARs)

As an alternative to, or addition to, TCR modifications, chimeric antigen receptors (CARs) may be used in order to generate immunoresponsive cells, such as T cells, specific for selected targets, such as malignant cells, with a wide variety of receptor chimera constructs having been described (see U.S. Pat. Nos. 5,843,728; 5,851,828; 5,912,170; 6,004,811; 6,284,240; 6,392,013; 6,410,031; 6,753,162; 8,211,422; and, PCT Publication WO9215322).

In general, CARs are comprised of an extracellular domain, a transmembrane domain, and an intracellular domain, wherein the extracellular domain comprises an antigen-binding domain that is specific for a predetermined target. While the antigen-binding domain of a CAR is often an antibody or antibody fragment (e.g., a single chain variable fragment, scFv), the binding domain is not particularly limited so long as it results in specific recognition of a target. For example, in some embodiments, the antigen-binding domain may comprise a receptor, such that the CAR is capable of binding to the ligand of the receptor. Alternatively, the antigen-binding domain may comprise a ligand, such that the CAR is capable of binding the endogenous receptor of that ligand. The antigen binding domain can include the CDRs from an identified TCR. Complementarity-determining regions (CDRs) are part of the variable chains in immunoglobulins (antibodies) and T cell receptors, generated by B-cells and T cells respectively, where these molecules bind to their specific antigen.

The antigen-binding domain of a CAR is generally separated from the transmembrane domain by a hinge or spacer. The spacer is also not particularly limited, and it is designed to provide the CAR with flexibility. For example, a spacer domain may comprise a portion of a human Fc domain, including a portion of the CH3 domain, or the hinge region of any immunoglobulin, such as IgA, IgD, IgE, IgG, or IgM, or variants thereof. Furthermore, the hinge region may be modified so as to prevent off-target binding by FcRs or other potential interfering objects. For example, the hinge may comprise an IgG4 Fc domain with or without a S228P, L235E, and/or N297Q mutation (according to Kabat numbering) in order to decrease binding to FcRs. Additional spacers/hinges include, but are not limited to, CD4, CD8, and CD28 hinge regions.

The transmembrane domain of a CAR may be derived either from a natural or from a synthetic source. Where the source is natural, the domain may be derived from any membrane bound or transmembrane protein. Transmembrane regions of particular use in this disclosure may be derived from CD8, CD28, CD3, CD45, CD4, CD5, CDS, CD9, CD16, CD22, CD33, CD37, CD64, CD80, CD86, CD134, CD137, CD154, TCR. Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Alternative CAR constructs may be characterized as belonging to successive generations. First-generation CARs typically consist of a single-chain variable fragment of an antibody specific for an antigen, for example comprising a VL linked to a VH of a specific antibody, linked by a flexible linker, for example by a CD8a hinge domain and a CD8a transmembrane domain, to the transmembrane and intracellular signaling domains of either CD3t or FcRγ (scFv-CD3t or scFv-FcRγ; see U.S. Pat. Nos. 7,741,465; 5,912,172; 5,906,936). Second-generation CARs incorporate the intracellular domains of one or more costimulatory molecules, such as CD28, OX40 (CD134), or 4-1BB (CD137) within the endodomain (for example scFv-CD28/OX40/4-1BB-CD3; see U.S. Pat. Nos. 8,911,993; 8,916,381; 8,975,071; 9,101,584; 9,102,760; 9,102,761). Third-generation CARs include a combination of costimulatory endodomains, such a CD3-chain, CD97, GDI 1a-CD18, CD2, ICOS, CD27, CD154, CDS, 0X40, 4-1BB, CD2, CD7, LIGHT, LFA-1, NKG2C, B7-H3, CD30, CD40, PD-1, or CD28 signaling domains (for example scFv-CD28-4-1BB-CD3ξ or scFv-CD28-OX40-CD3ξ; see U.S. Pat. Nos. 8,906,682; 8,399,645; 5,686,281; PCT Publication No. WO2014134165; PCT Publication No. WO2012079000). In certain embodiments, the primary signaling domain comprises a functional signaling domain of a protein selected from the group consisting of CD3 zeta, CD3 gamma, CD3 delta, CD3 epsilon, common FcR gamma (FCERIG), FcR beta (Fc Epsilon Rib), CD79a, CD79b, Fc gamma RIIa, DAP10, and DAP12. In certain preferred embodiments, the primary signaling domain comprises a functional signaling domain of CD3t or FcRγ. In certain embodiments, the one or more costimulatory signaling domains comprise a functional signaling domain of a protein selected, each independently, from the group consisting of: CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8 alpha, CD8 beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D. In certain embodiments, the one or more costimulatory signaling domains comprise a functional signaling domain of a protein selected, each independently, from the group consisting of: 4-1BB, CD27, and CD28. In certain embodiments, a chimeric antigen receptor may have the design as described in U.S. Pat. No. 7,446,190, comprising an intracellular domain of CD3 chain (such as amino acid residues 52-163 of the human CD3 zeta chain, as shown in SEQ ID NO: 14 of U.S. Pat. No. 7,446,190), a signaling region from CD28 and an antigen-binding element (or portion or domain; such as scFv). The CD28 portion, when between the zeta chain portion and the antigen-binding element, may suitably include the transmembrane and signaling domains of CD28 (such as amino acid residues 114-220 of SEQ ID NO: 10, full sequence shown in SEQ ID NO: 6 of U.S. Pat. No. 7,446,190; these can include the following portion of CD28 as set forth in Genbank identifier NM 006139 (sequence version 1, 2 or 3):

IEVMYPPPYLDNEKSNGTIIHVKGKHLCPSPLFPGPSKPFWVLVVVGGVL

ACYSLLVTVAFIIFWVRSKRSRLLHSDYMNMTPRRPGPTRKHYQPYAPPR

DFAAYRS).

Alternatively, when the zeta sequence lies between the CD28 sequence and the antigen-binding element, intracellular domain of CD28 can be used alone (such as amino sequence set forth in SEQ ID NO: 9 of U.S. Pat. No. 7,446,190). Hence, certain embodiments employ a CAR comprising (a) a zeta chain portion comprising the intracellular domain of human CD3t chain, (b) a costimulatory signaling region, and (c) an antigen-binding element (or portion or domain), wherein the costimulatory signaling region comprises the amino acid sequence encoded by SEQ ID NO: 6 of U.S. Pat. No. 7,446,190.

Alternatively, costimulation may be orchestrated by expressing CARs in antigen-specific T cells, chosen so as to be activated and expanded following engagement of their native αβTCR, for example by antigen on professional antigen-presenting cells, with attendant costimulation. In addition, additional engineered receptors may be provided on the immunoresponsive cells, for example to improve targeting of a T cell attack and/or minimize side effects.

By means of an example and without limitation, Kochenderfer et al., (2009) J Immunother. 32 (7): 689-702 described anti-CD19 chimeric antigen receptors (CAR). FMC63-28Z CAR contained a single chain variable region moiety (scFv) recognizing CD19 derived from the FMC63 mouse hybridoma (described in Nicholson et al., (1997) Molecular Immunology 34: 1157-1165), a portion of the human CD28 molecule, and the intracellular component of the human TCR-ξ molecule. FMC63-CD828BBZ CAR contained the FMC63 scFv, the hinge and transmembrane regions of the CD8 molecule, the cytoplasmic portions of CD28 and 4-1BB, and the cytoplasmic component of the TCR-ξ molecule. The exact sequence of the CD28 molecule included in the FMC63-28Z CAR corresponded to Genbank identifier NM_006139; the sequence included all amino acids starting with the amino acid sequence IEVMYPPPY and continuing all the way to the carboxy-terminus of the protein. To encode the anti-CD19 scFv component of the vector, the authors designed a DNA sequence which was based on a portion of a previously published CAR (Cooper et al., (2003) Blood 101: 1637-1644). This sequence encoded the following components in frame from the 5' end to the 3' end: an XhoI site, the human granulocyte-macrophage colony-stimulating factor (GM-CSF) receptor α-chain signal sequence, the FMC63 light chain variable region (as in Nicholson et al., supra), a linker peptide (as in Cooper et al., supra), the FMC63 heavy chain variable region (as in Nicholson et al., supra), and a NotI site. A plasmid encoding this sequence was digested with XhoI and NotI. To form the MSGV-FMC63-28Z retroviral vector, the XhoI and NotI-digested fragment encoding the FMC63 scFv was ligated into a second XhoI and NotI-digested fragment that encoded the MSGV retroviral backbone (as in Hughes et al., (2005) Human Gene Therapy 16: 457-472) as well as part of the extracellular portion of human CD28, the entire transmembrane and cytoplasmic portion of human CD28, and the cytoplasmic portion of the human TCR-molecule (as in Maher et al., 2002, Nature Biotechnology 20: 70-75). The FMC63-28Z CAR is included in the KTE-C19 (axicabtagene ciloleucel) anti-CD19 CAR-T therapy product in development by Kite Pharma, Inc. for the treatment of inter alia patients with relapsed/refractory aggressive B-cell non-Hodgkin lymphoma (NHL). Accordingly, in certain embodiments, cells intended for adoptive cell therapies, more particularly immunoresponsive cells such as T cells, may express the FMC63-28Z CAR as described by Kochenderfer et al. (supra). Hence, in certain embodiments, cells intended for adoptive cell therapies, more particularly immunoresponsive cells such as T cells, may comprise a CAR comprising an extracellular antigen-binding element (or portion or domain; such as scFv) that specifically binds to an antigen, an intracellular signaling domain comprising an intracellular domain of a CD3t chain, and a costimulatory signaling region comprising a signaling domain of CD28. Preferably, the CD28 amino acid sequence is as set forth in Genbank identifier NM 006139 (sequence version 1,2 or 3) starting with the amino acid sequence IEVMYPPPY and continuing all the way to the carboxy-terminus of the protein. The sequence is reproduced herein:

IEVMYPPPYLDNEKSNGTIIHVKGKHLCPSPLFPGPSKPFWVLVVVGGVL

ACYSLLVTVAFIIFWVRSKRSRLLHSDYMNMTPRRPGPTRKHYQPYAPPR

DFAAYRS.

Various combinations of a signal sequence (human CD8-alpha or GM-CSF receptor), extracellular and transmembrane regions (human CD8-alpha) and intracellular T cell signaling domains (CD28-CD3ξ; 4-1BB-CD3ξ; CD27-CD3ξ; CD28-CD27-CD3ξ, 4-1BB-CD27-CD3ξ; CD27-4-1BB-CD3ξ; CD28-CD27-FcεRI gamma chain; or CD28-FcεRI gamma chain) were disclosed. Hence, in certain embodiments, cells intended for adoptive cell therapies, more particularly immunoresponsive cells such as T cells, may comprise a CAR comprising an extracellular antigen-binding element that specifically binds to an antigen, an extracellular and transmembrane region as set forth in Table 1 of WO2015187528 and an intracellular T cell signaling domain as set forth in Table 1 of WO2015187528.

In certain embodiments, the immune cell may, in addition to a CAR or exogenous TCR as described herein, further comprise a chimeric inhibitory receptor (inhibitory CAR) that specifically binds to a second target antigen and is capable of inducing an inhibitory or immunosuppressive or repressive signal to the cell upon recognition of the second target antigen. In certain embodiments, the chimeric inhibitory receptor comprises an extracellular antigen-binding element (or portion or domain) configured to specifically bind to a target antigen, a transmembrane domain, and an intracellular immunosuppressive or repressive signaling domain. In certain embodiments, the second target antigen is an antigen that is not expressed on the surface of a cancer cell or infected cell or the expression of which is downregulated on a cancer cell or an infected cell. In certain embodiments, the second target antigen is an MHC-class I molecule. In certain embodiments, the intracellular signaling domain comprises a functional signaling portion of an immune checkpoint molecule, such as for example PD-1 or CTLA4. Advantageously, the inclusion of such inhibitory CAR reduces the chance of the engineered immune cells attacking non-target (e.g., non-cancer) tissues.

Alternatively, T cells expressing CARs may be further modified to reduce or eliminate expression of endogenous TCRs in order to reduce off-target effects. Reduction or elimination of endogenous TCRs can reduce off-target effects and increase the effectiveness of the T cells (U.S. Pat. No. 9,181,527). T cells stably lacking expression of a functional TCR may be produced using a variety of approaches. T cells internalize, sort, and degrade the entire T cell receptor as a complex, with a half-life of about 10 hours in resting T cells and 3 hours in stimulated T cells (von Essen, M. et al. 2004. J. Immunol. 173:384-393). Proper functioning of the TCR complex requires the proper stoichiometric ratio of the proteins that compose the TCR complex. TCR function also requires two functioning TCR zeta proteins with ITAM motifs. The activation of the TCR upon engagement of its MHC-peptide ligand requires the engagement of several TCRs on the same T cell, which all must signal properly. Thus, if a TCR complex is destabilized with proteins that do not associate properly or cannot signal optimally, the T cell will not become activated sufficiently to begin a cellular response.

Accordingly, in some embodiments, TCR expression may eliminated using RNA interference (e.g., shRNA, siRNA, miRNA, etc.), CRISPR, or other methods that target the nucleic acids encoding specific TCRs (e.g., TCR-α and TCR-β) and/or CD3 chains in primary T cells. By blocking expression of one or more of these proteins, the T cell will no longer produce one or more of the key components of the TCR complex, thereby destabilizing the TCR complex and preventing cell surface expression of a functional TCR.

In some instances, CAR may also comprise a switch mechanism for controlling expression and/or activation of the CAR. For example, a CAR may comprise an extracellular, transmembrane, and intracellular domain, in which the extracellular domain comprises a target-specific binding element that comprises a label, binding domain, or tag that is specific for a molecule other than the target antigen that is expressed on or by a target cell. In such embodiments, the specificity of the CAR is provided by a second construct that comprises a target antigen binding domain (e.g., an scFv or a bispecific antibody that is specific for both the target antigen and the label or tag on the CAR) and a domain that is recognized by or binds to the label, binding domain, or tag on the CAR. See, e.g., WO 2013/044225, WO 2016/000304, WO 2015/057834, WO 2015/057852, WO 2016/070061, U.S. Pat. No. 9,233,125, US 2016/0129109. In this way, a T cell that expresses the CAR can be administered to a subject, but the CAR cannot bind its target antigen until the second composition comprising an antigen-specific binding domain is administered.

Alternative switch mechanisms include CARs that require multimerization in order to activate their signaling function (see, e.g., US 2015/0368342, US 2016/0175359, US 2015/0368360) and/or an exogenous signal, such as a small molecule drug (US 2016/0166613, Yung et al., Science, 2015), in order to elicit a T cell response. Some CARs may also comprise a "suicide switch" to induce cell death of the CAR T cells following treatment (Buddee et al., PLoS One, 2013) or to downregulate expression of the CAR following binding to the target antigen (WO 2016/011210).

Constructing Cells

Alternative techniques may be used to transform target immunoresponsive cells, such as protoplast fusion, lipofection, transfection or electroporation. A wide variety of vectors may be used, such as retroviral vectors, lentiviral vectors, adenoviral vectors, adeno-associated viral vectors, plasmids or transposons, such as a Sleeping Beauty transposon (see U.S. Pat. Nos. 6,489,458; 7,148,203; 7,160,682; 7,985,739; 8,227,432), may be used to introduce CARs, for example using 2nd generation antigen-specific CARs signaling through CD3t and either CD28 or CD137. Viral vectors may for example include vectors based on HIV, SV40, EBV, HSV or BPV.

Cells that are targeted for transformation may for example include T cells, Natural Killer (NK) cells, cytotoxic T lymphocytes (CTL), regulatory T cells, human embryonic stem cells, tumor-infiltrating lymphocytes (TIL) or a pluripotent stem cell from which lymphoid cells may be differentiated. T cells expressing a desired CAR may for example be selected through co-culture with γ-irradiated activating and propagating cells (AaPC), which co-express the cancer antigen and co-stimulatory molecules. The engineered CAR T cells may be expanded, for example by co-culture on AaPC in presence of soluble factors, such as IL-2 and IL-21. This expansion may for example be carried out so as to provide memory CAR+ T cells (which may for example be assayed by non-enzymatic digital array and/or multi-panel flow cytometry). In this way, CAR T cells may be provided that have specific cytotoxic activity against antigen-bearing tumors (optionally in conjunction with production of desired chemokines such as interferon-γ). CAR T cells of this kind may for example be used in animal models, for example to treat tumor xenografts.

In certain embodiments, ACT includes co-transferring CD4+ Th1 cells and CD8+ CTLs to induce a synergistic antitumour response (see, e.g., Li et al., Adoptive cell therapy with CD4+ T helper 1 cells and CD8+ cytotoxic T cells enhances complete rejection of an established tumour, leading to generation of endogenous memory responses to non-targeted tumour epitopes. Clin Transl Immunology. 2017 October; 6(10): e160).

In certain embodiments, Th17 cells are transferred to a subject in need thereof. Th17 cells have been reported to directly eradicate melanoma tumors in mice to a greater extent than Th1 cells (Muranski P, et al., Tumor-specific Th17-polarized cells eradicate large established melanoma. Blood. 2008 Jul 15; 112(2):362-73; and Martin-Orozco N, et al., T helper 17 cells promote cytotoxic T cell activation in tumor immunity. Immunity. 2009 Nov 20; 31(5):787-98).

Those studies involved an adoptive T cell transfer (ACT) therapy approach, which takes advantage of CD4+ T cells that express a TCR recognizing tyrosinase tumor antigen. Exploitation of the TCR leads to rapid expansion of Th17 populations to large numbers ex vivo for reinfusion into the autologous tumor-bearing hosts.

In certain embodiments, ACT may include autologous iPSC-based vaccines, such as irradiated iPSCs in autologous anti-tumor vaccines (see e.g., Kooreman, Nigel G. et al., Autologous iPSC-Based Vaccines Elicit Anti-tumor Responses In Vivo, Cell Stem Cell 22, 1-13, 2018, doi.org/10.1016/j.stem.2018.01.016).

To guard against possible adverse reactions, engineered immunoresponsive cells may be equipped with a transgenic safety switch, in the form of a transgene that renders the cells vulnerable to exposure to a specific signal. For example, the herpes simplex viral thymidine kinase (TK) gene may be used in this way, for example by introduction into allogeneic T lymphocytes used as donor lymphocyte infusions following stem cell transplantation (Greco, et al., Improving the safety of cell therapy with the TK-suicide gene. Front. Pharmacol. 2015; 6: 95). In such cells, administration of a nucleoside prodrug such as ganciclovir or acyclovir causes cell death. Alternative safety switch constructs include inducible caspase 9, for example triggered by administration of a small-molecule dimerizer that brings together two nonfunctional icasp9 molecules to form the active enzyme. A wide variety of alternative approaches to implementing cellular proliferation controls have been described (see U.S. Patent Publication No. 20130071414; PCT Patent Publication WO2011146862; PCT Patent Publication WO2014011987; PCT Patent Publication WO2013040371; Zhou et al. BLOOD, 2014, 123/25:3895-3905; Di Stasi et al., The New England Journal of Medicine 2011; 365:1673-1683; Sadelain M, The New England Journal of Medicine 2011; 365:1735-173; Ramos et al., Stem Cells 28(6):1107-15 (2010)).

In certain embodiments, T cells comprising a CAR or an exogenous TCR, may be manufactured as described in WO2015120096, by a method comprising: enriching a population of lymphocytes obtained from a donor subject; stimulating the population of lymphocytes with one or more T cell stimulating agents to produce a population of activated T cells, wherein the stimulation is performed in a closed system using serum-free culture medium; transducing the population of activated T cells with a viral vector comprising a nucleic acid molecule which encodes the CAR or TCR, using a single cycle transduction to produce a population of transduced T cells, wherein the transduction is performed in a closed system using serum-free culture medium; and expanding the population of transduced T cells for a predetermined time to produce a population of engineered T cells, wherein the expansion is performed in a closed system using serum-free culture medium. In certain embodiments, T cells comprising a CAR or an exogenous TCR, may be manufactured as described in WO2015120096, by a method comprising: obtaining a population of lymphocytes; stimulating the population of lymphocytes with one or more stimulating agents to produce a population of activated T cells, wherein the stimulation is performed in a closed system using serum-free culture medium; transducing the population of activated T cells with a viral vector comprising a nucleic acid molecule which encodes the CAR or TCR, using at least one cycle transduction to produce a population of transduced T cells, wherein the transduction is performed in a closed system using serum-free culture medium; and expanding the population of transduced T cells to produce a population of engineered T cells, wherein the expansion is performed in a closed system using serum-free culture medium. The predetermined time for expanding the population of transduced T cells may be 3 days. The time from enriching the population of lymphocytes to producing the engineered T cells may be 6 days. The closed system may be a closed bag system. Further provided is population of T cells comprising a CAR or an exogenous TCR obtainable or obtained by said method, and a pharmaceutical composition comprising such cells.

In certain embodiments, T cell maturation or differentiation in vitro may be delayed or inhibited by the method as described in WO2017070395, comprising contacting one or more T cells from a subject in need of a T cell therapy with an AKT inhibitor (such as, e.g., one or a combination of two or more AKT inhibitors disclosed in claim 8 of WO2017070395) and at least one of exogenous Interleukin-7 (IL-7) and exogenous Interleukin-15 (IL-15), wherein the resulting T cells exhibit delayed maturation or differentiation, and/or wherein the resulting T cells exhibit improved T cell function (such as, e.g., increased T cell proliferation; increased cytokine production; and/or increased cytolytic activity) relative to a T cell function of a T cell cultured in the absence of an AKT inhibitor.

Isolating T Cells

In certain embodiments, T cells are isolated from a subject. The T cell receptors may be identified according to the present invention. The TCRs may be present on any type of T cell, including, e.g., thymocytes, Th or Tc; Th1, Th2, Th17, Thαβ, CD4+, CD8+, effector Th, memory Th, regulatory Th, CD4+/CD8+ thymocytes, CD4—/CD8—thymocytes, γδ T cells, etc.

Immune cells may be obtained using any method known in the art. In one embodiment, allogenic T cells may be obtained from healthy subjects. In one embodiment T cells that have infiltrated a tumor are isolated. T cells may be removed during surgery. T cells may be isolated after removal of tumor tissue by biopsy. T cells may be isolated by any means known in the art. In one embodiment, T cells are obtained by apheresis. In one embodiment, the method may comprise obtaining a bulk population of T cells from a tumor sample by any suitable method known in the art. For example, a bulk population of T cells can be obtained from a tumor sample by dissociating the tumor sample into a cell suspension from which specific cell populations can be selected. Suitable methods of obtaining a bulk population of T cells may include, but are not limited to, any one or more of mechanically dissociating (e.g., mincing) the tumor, enzymatically dissociating (e.g., digesting) the tumor, and aspiration (e.g., as with a needle).

The bulk population of T cells obtained from a tumor sample may comprise any suitable type of T cell. Preferably, the bulk population of T cells obtained from a tumor sample comprises tumor infiltrating lymphocytes (TILs).

The tumor sample may be obtained from any mammal. Unless stated otherwise, as used herein, the term "mammal" refers to any mammal including, but not limited to, mammals of the order Lagomorpha, such as rabbits; the order Carnivora, including Felines (cats) and Canines (dogs); the order Artiodactyla, including Bovines (cows) and Swines (pigs); or of the order Perissodactyla, including Equines (horses). The mammals may be non-human primates, e.g., of the order Primates, Ceboids, or Simoids (monkeys) or of the order Anthropoids (humans and apes). In some embodiments, the mammal may be a mammal of the order Rodentia, such as mice and hamsters. Preferably, the mammal is a non-human primate or a human. An especially preferred mammal is the human.

T cells can be obtained from a number of sources, including peripheral blood mononuclear cells (PBMC), bone marrow, lymph node tissue, spleen tissue, and tumors. In certain embodiments of the present invention, T cells can be obtained from a unit of blood collected from a subject using any number of techniques known to the skilled artisan, such as Ficoll separation. In one preferred embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor) according to the manufacturer's instructions. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient. A specific subpopulation of T cells, such as CD28+, CD4+, CDC, CD45RA+, and CD45RO+ T cells, can be further isolated by positive or negative selection techniques. For example, in one preferred embodiment, T cells are isolated by incubation with anti-CD3/anti-CD28 (i.e., 3×28)-conjugated beads, such as DYNABEADS® M-450 CD3/CD28 T, or XCYTE DYNABEADS™ for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells.

Enrichment of a T cell population by negative selection can be accomplished with a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

Further, monocyte populations (i.e., CD14+ cells) may be depleted from blood preparations by a variety of methodologies, including anti-CD14 coated beads or columns, or utilization of the phagocytotic activity of these cells to facilitate removal. Accordingly, in one embodiment, the invention uses paramagnetic particles of a size sufficient to be engulfed by phagocytotic monocytes. In certain embodiments, the paramagnetic particles are commercially available beads, for example, those produced by Life Technologies under the trade name Dynabeads™. In one embodiment, other non-specific cells are removed by coating the paramagnetic particles with "irrelevant" proteins (e.g., serum proteins or antibodies). Irrelevant proteins and antibodies include those proteins and antibodies or fragments thereof that do not specifically target the T cells to be isolated. In certain embodiments, the irrelevant beads include beads coated with sheep anti-mouse antibodies, goat anti-mouse antibodies, and human serum albumin.

In brief, such depletion of monocytes is performed by preincubating T cells isolated from whole blood, apheresed peripheral blood, or tumors with one or more varieties of irrelevant or non-antibody coupled paramagnetic particles at any amount that allows for removal of monocytes (approximately a 20:1 bead:cell ratio) for about 30 minutes to 2 hours at 22 to 37 degrees C., followed by magnetic removal of cells which have attached to or engulfed the paramagnetic particles. Such separation can be performed using standard methods available in the art. For example, any magnetic separation methodology may be used including a variety of which are commercially available, (e.g., DYNAL® Magnetic Particle Concentrator (DYNAL MPC®)). Assurance of requisite depletion can be monitored by a variety of methodologies known to those of ordinary skill in the art, including flow cytometric analysis of CD14 positive cells, before and after depletion.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one embodiment, the concentration of cells used is $5 \times 10^6$/ml. In other embodiments, the concentration used can be from about $1 \times 10^5$/ml to $1 \times 10^6$/ml, and any integer value in between.

T cells can also be frozen. Wishing not to be bound by theory, the freeze and subsequent thaw step provides a more uniform product by removing granulocytes and to some extent monocytes in the cell population. After a washing step to remove plasma and platelets, the cells may be suspended in a freezing solution. While many freezing solutions and parameters are known in the art and will be useful in this context, one method involves using PBS containing 20% DMSO and 8% human serum albumin, or other suitable cell freezing media, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

T cells for use in the present invention may be antigen-specific T cells. For example, tumor-specific T cells can be used. In certain embodiments, antigen-specific T cells can be isolated from a patient of interest, such as a patient afflicted with a cancer or an infectious disease. In one embodiment, neoepitopes are determined for a subject and T cells specific to these antigens are isolated. Antigen-specific cells for use in expansion may also be generated in vitro using any number of methods known in the art, for example, as described in U.S. Patent Publication No. US 20040224402 entitled, Generation and Isolation of Antigen-Specific T Cells, or in U.S. Pat. Nos. 6,040,177. Antigen-specific cells for use in the present invention may also be generated using any number of methods known in the art, for example, as described in Current Protocols in Immunology, or Current Protocols in Cell Biology, both published by John Wiley & Sons, Inc., Boston, Mass.

In a related embodiment, it may be desirable to sort or otherwise positively select (e.g. via magnetic selection) the antigen specific cells prior to or following one or two rounds of expansion. Sorting or positively selecting antigen-specific cells can be carried out using peptide-WIC tetramers (Altman, et al., Science. 1996 Oct. 4; 274(5284):94-6). In another embodiment, the adaptable tetramer technology approach is used (Andersen et al., 2012 Nat Protoc. 7:891-902). Tetramers are limited by the need to utilize predicted binding peptides based on prior hypotheses, and the restriction to specific HLAs. Peptide-MHC tetramers can be generated using techniques known in the art and can be made with any MHC molecule of interest and any antigen of interest as described herein. Specific epitopes to be used in this context can be identified using numerous assays known in the art. For example, the ability of a polypeptide to bind to WIC class I may be evaluated indirectly by monitoring the ability to promote incorporation of $^{125}$I labeled β2-microglobulin (β2m) into WIC class I/β2m/peptide heterotrimeric complexes (see Parker et al., J. Immunol. 152:163, 1994).

In one embodiment cells are directly labeled with an epitope-specific reagent for isolation by flow cytometry followed by characterization of phenotype and TCRs. In one embodiment, T cells are isolated by contacting with T cell specific antibodies. Sorting of antigen-specific T cells, or generally any cells of the present invention, can be carried out using any of a variety of commercially available cell sorters, including, but not limited to, MoFlo sorter (DakoCytomation, Fort Collins, Colo.), FACSAria™, FACSArray™, FACSVantage™, BD™ LSR II, and FACSCalibur™ (BD Biosciences, San Jose, Calif.).

In a preferred embodiment, the method comprises selecting cells that also express CD3. The method may comprise specifically selecting the cells in any suitable manner. Preferably, the selecting is carried out using flow cytometry. The flow cytometry may be carried out using any suitable method known in the art. The flow cytometry may employ any suitable antibodies and stains. Preferably, the antibody is chosen such that it specifically recognizes and binds to the particular biomarker being selected. For example, the specific selection of CD3, CD8, TIM-3, LAG-3, 4-1BB, or PD-1 may be carried out using anti-CD3, anti-CD8, anti-TIM-3, anti-LAG-3, anti-4-1BB, or anti-PD-1 antibodies, respectively. The antibody or antibodies may be conjugated to a bead (e.g., a magnetic bead) or to a fluorochrome. Preferably, the flow cytometry is fluorescence-activated cell sorting (FACS). TCRs expressed on T cells can be selected based on reactivity to autologous tumors. Additionally, T cells that are reactive to tumors can be selected for based on markers using the methods described in patent publication Nos. WO2014133567 and WO2014133568, herein incorporated by reference in their entirety. Additionally, activated T cells can be selected for based on surface expression of CD107a.

In one embodiment of the invention, the method further comprises expanding the numbers of T cells in the enriched cell population. Such methods are described in U.S. Pat. No. 8,637,307 and is herein incorporated by reference in its entirety. The numbers of T cells may be increased at least about 3-fold (or 4-, 5-, 6-, 7-, 8-, or 9-fold), more preferably at least about 10-fold (or 20-, 30-, 40-, 50-, 60-, 70-, 80-, or 90-fold), more preferably at least about 100-fold, more preferably at least about 1,000 fold, or most preferably at least about 100,000-fold. The numbers of T cells may be expanded using any suitable method known in the art. Exemplary methods of expanding the numbers of cells are described in patent publication No. WO 2003057171, U.S. Pat. No. 8,034,334, and U.S. Patent Application Publication No. 2012/0244133, each of which is incorporated herein by reference.

In one embodiment, ex vivo T cell expansion can be performed by isolation of T cells and subsequent stimulation or activation followed by further expansion. In one embodiment of the invention, the T cells may be stimulated or activated by a single agent. In another embodiment, T cells are stimulated or activated with two agents, one that induces a primary signal and a second that is a co-stimulatory signal. Ligands useful for stimulating a single signal or stimulating a primary signal and an accessory molecule that stimulates a second signal may be used in soluble form. Ligands may be attached to the surface of a cell, to an Engineered Multivalent Signaling Platform (EMSP), or immobilized on a surface. In a preferred embodiment both primary and secondary agents are co-immobilized on a surface, for example a bead or a cell. In one embodiment, the molecule providing the primary activation signal may be a CD3 ligand, and the co-stimulatory molecule may be a CD28 ligand or 4-1BB ligand.

Antigen Specific TCRs

In certain embodiments, TCRs are identified from a subject. In certain embodiments, the subject may have a disease associated with a specific immune response. The subject may have cancer, an infection, an autoimmune disease, or an inflammatory disease. The disease may be associated with an immune response against specific antigens. Thus, TCRs associated with an immune response can be identified according to the present invention.

As used herein "immune response" refers to a response by a cell of the immune system, such as a B cell, T cell (CD4+ or CD8+), regulatory T cell, antigen-presenting cell, dendritic cell, monocyte, macrophage, NKT cell, NK cell, basophil, eosinophil, or neutrophil, to a stimulus. In some embodiments, the response is specific for a particular antigen (an "antigen-specific response"), and refers to a response by a CD4 T cell, CD8 T cell, or B cell via their antigen-specific receptor. In some embodiments, an immune response is a T cell response, such as a CD4+ response or a CD8+ response. Such responses by these cells can include, for example, cytotoxicity, proliferation, cytokine or chemokine production, trafficking, or phagocytosis, and can be dependent on the nature of the immune cell undergoing the response.

T cell response refers more specifically to an immune response in which T cells directly or indirectly mediate or otherwise contribute to an immune response in a subject. T cell-mediated response may be associated with cell mediated effects, cytokine mediated effects, and even effects associated with B cells if the B cells are stimulated, for example, by cytokines secreted by T cells. By means of an example but without limitation, effector functions of MHC class I restricted Cytotoxic T lymphocytes (CTLs), may include cytokine and/or cytolytic capabilities, such as lysis of target cells presenting an antigen peptide recognized by the T cell receptor (naturally-occurring TCR or genetically engineered TCR, e.g., chimeric antigen receptor, CAR), secretion of cytokines, preferably IFN gamma, TNF alpha and/or or more immunostimulatory cytokines, such as IL-2, and/or antigen peptide-induced secretion of cytotoxic effector molecules, such as granzymes, perforins or granulysin. By means of example but without limitation, for MHC class II restricted T helper (Th) cells, effector functions may be antigen peptide-induced secretion of cytokines, preferably, IFN gamma, TNF alpha, IL-4, IL5, IL-10, and/or IL-2. By means of example but without limitation, for T regulatory (Treg) cells, effector functions may be antigen peptide-induced secretion of cytokines, preferably, IL-10, IL-35, and/or TGF-beta. B cell response refers more specifically to an immune response in which B cells directly or indirectly mediate or otherwise contribute to an immune response in a subject. Effector functions of B cells may include in particular production and secretion of antigen-specific antibodies by B cells (e.g., polyclonal B cell response to a plurality of the epitopes of an antigen (antigen-specific antibody response)), antigen presentation, and/or cytokine secretion.

During persistent immune activation, such as during uncontrolled tumor growth or chronic infections, subpopulations of immune cells, particularly of CD8+ or CD4+ T cells, become compromised to different extents with respect to their cytokine and/or cytolytic capabilities. Such immune cells, particularly CD8+ or CD4+ T cells, are commonly referred to as "dysfunctional" or as "functionally exhausted" or "exhausted". As used herein, the term "dysfunctional" or "functional exhaustion" refer to a state of a cell where the cell does not perform its usual function or activity in response to normal input signals, and includes refractivity of immune cells to stimulation, such as stimulation via an activating receptor or a cytokine. Such a function or activity includes, but is not limited to, proliferation (e.g., in response to a cytokine, such as IFN-gamma) or cell division, entrance into the cell cycle, cytokine production, cytotoxicity, migration and trafficking, phagocytotic activity, or any combination thereof. Normal input signals can include, but are not limited to, stimulation via a receptor (e.g., T cell receptor, B cell receptor, co-stimulatory receptor). Unresponsive immune cells can have a reduction of at least 10%, 20%, 30%, 40%, 50%, 60%, 70%, 80%, 90%, 95%, or even 100% in cytotoxic activity, cytokine production, proliferation, trafficking, phagocytotic activity, or any combination thereof, relative to a corresponding control immune cell of the same type. In some particular embodiments of the aspects described herein, a cell that is dysfunctional is a CD8+ T cell that expresses the CD8+ cell surface marker. Such CD8+ cells normally proliferate and produce cell killing enzymes, e.g., they can release the cytotoxins perforin, granzymes, and granulysin. However, exhausted/dysfunctional T cells do not respond adequately to TCR stimulation, and display poor effector function, sustained expression of inhibitory receptors and a transcriptional state distinct from that of functional effector or memory T cells. Dysfunction/exhaustion of T cells thus prevents optimal control of infection and tumors. Exhausted/dysfunctional immune cells, such as T cells, such as CD8+ T cells, may produce reduced amounts of IFN-gamma, TNF-alpha and/or one or more immunostimulatory cytokines, such as IL-2, compared to functional immune cells. Exhausted/dysfunctional immune cells, such as T cells, such as CD8+ T cells, may further produce (increased amounts of) one or more immunosuppressive transcription factors or cytokines, such as IL-10 and/or Foxp3, compared to functional immune cells, thereby contributing to local immunosuppression. Dysfunctional CD8+ T cells can be both protective and detrimental against disease control.

CD8+ T cell function is associated with their cytokine profiles. It has been reported that effector CD8+ T cells with the ability to simultaneously produce multiple cytokines (polyfunctional CD8+ T cells) are associated with protective immunity in patients with controlled chronic viral infections as well as cancer patients responsive to immune therapy (Spranger et al., 2014, J. Immunother. Cancer, vol. 2, 3). In the presence of persistent antigen CD8+ T cells were found to have lost cytolytic activity completely over time (Moskophidis et al., 1993, Nature, vol. 362, 758-761). It was subsequently found that dysfunctional T cells can differentially produce IL-2, TNFa and IFNg in a hierarchical order (Wherry et al., 2003, J. Virol., vol. 77, 4911-4927). Decoupled dysfunctional and activated CD8+ cell states have also been described (see, e.g., Singer, et al. (2016). A Distinct Gene Module for Dysfunction Uncoupled from Activation in Tumor-Infiltrating T Cells. Cell 166, 1500-1511 e1509; and WO/2017/075478).

TCRs associated with T cell balance may be identified, such as the balance between T cell types, e.g., between Th17 and other T cell types, for example, regulatory T cells (Tregs). For example, the level of and/or balance between Th17 activity and inflammatory potential. As used herein, terms such as "Th17 cell" and/or "Th17 phenotype" and all grammatical variations thereof refer to a differentiated T helper cell that expresses one or more cytokines selected from the group the consisting of interleukin 17A (IL-17A), interleukin 17F (IL-17F), and interleukin 17A/F heterodimer (IL17-AF). As used herein, terms such as "Th1 cell" and/or "Th1 phenotype" and all grammatical variations thereof refer to a differentiated T helper cell that expresses interferon gamma (IFNγ). As used herein, terms such as "Th2 cell" and/or "Th2 phenotype" and all grammatical variations thereof refer to a differentiated T helper cell that expresses one or more cytokines selected from the group the consisting of interleukin 4 (IL-4), interleukin 5 (IL-5) and interleukin 13 (IL-13). As used herein, terms such as "Treg cell" and/or "Treg phenotype" and all grammatical variations thereof refer to a differentiated T cell that expresses Foxp3.

As used herein, terms such as "pathogenic Th17 cell" and/or "pathogenic Th17 phenotype" and all grammatical variations thereof refer to Th17 cells that, when induced in the presence of TGF-β3, express an elevated level of one or more genes selected from Cxcl3, IL22, IL3, Cc14, Gzmb, Lrmp, Cc15, Casp1, Csf2, Cc13, Tbx21, Icos, IL17r, Stat4, Lgals3 and Lag, as compared to the level of expression in a TGF-β3-induced Th17 cells. As used herein, terms such as "non-pathogenic Th17 cell" and/or "non-pathogenic Th17 phenotype" and all grammatical variations thereof refer to Th17 cells that, when induced in the presence of TGF-β3, express a decreased level of one or more genes selected from IL6st, IL1rn, Ikzf3, Maf, Ahr, IL9 and IL10, as compared to the level of expression in a TGF-β3-induced Th17 cells.

Depending on the cytokines used for differentiation, in vitro polarized Th17 cells can either cause severe autoimmune responses upon adoptive transfer (pathogenic Th17 cells') or have little or no effect in inducing autoimmune disease (non-pathogenic cells') (Ghoreschi et al., 2010; Lee et al., 2012). In vitro differentiation of naïve CD4 T cells in the presence of TGF-01+IL-6 induces an IL-17A and IL-10 producing population of Th17 cells, that are generally non-pathogenic, whereas activation of naïve T cells in the presence IL-10+IL-6+IL-23 induces a T cell population that produces IL-17A and IFN-γ, and are potent inducers of autoimmune disease induction (Ghoreschi et al., 2010).

A dynamic regulatory network controls Th17 differentiation (See e.g., Yosef et al., Dynamic regulatory network controlling Th17 cell differentiation, Nature, vol. 496: 461-468 (2013); Wang et al., CDSL/AIM Regulates Lipid Biosynthesis and Restrains Th17 Cell Pathogenicity, Cell Volume 163, Issue 6, p1413-142'7, 3 Dec. 2015; Gaublomme et al., Single-Cell Genomics Unveils Critical Regulators of Th17 Cell Pathogenicity, Cell Volume 163, Issue 6, p1400-1412, 3 Dec. 2015; and International publication numbers WO2016138488A2, WO2015130968, WO/2012/048265, WO/2014/145631 and WO/2014/134351, the contents of which are hereby incorporated by reference in their entirety).

The CD8+ T cell response within the tumor microenvironment (TME) is functionally (Sakuishi et al., 2010; Williams et al., 2017; Woo et al., 2012; Xu et al., 2015) and transcriptionally (Singer et al., 2016; Tirosh et al., 2016; Zheng et al., 2017) heterogeneous. At one end of the functional spectrum are CD8$^+$ tumor-infiltrating lymphocytes (TILs) that lack the expression of co-inhibitory or immune checkpoint receptors (e.g. CTLA-4 and PD-1) and exhibit effector potential, while at the opposite end are CD8+ TILs that co-express multiple checkpoint receptors and exhibit an "exhausted" or dysfunctional phenotype.

In certain embodiments, the presence of antigen specific immune cells may be used to detect an immune state. The term "antigen" as used throughout this specification refers to a molecule or a portion of a molecule capable of being bound by an antibody, or by a T cell receptor (TCR) when presented by MHC molecules. At the molecular level, an antigen is characterized by its ability to be bound at the antigen-binding site of an antibody. The specific binding denotes that the antigen will be bound in a highly selective manner by its cognate antibody and not by the multitude of other antibodies which may be evoked by other antigens. An antigen is additionally capable of being recognized by the immune system. In some instances, an antigen is capable of eliciting a humoral immune response in a subject. In some instances, an antigen is capable of eliciting a cellular immune response in a subject, leading to the activation of B- and/or T-lymphocytes. In some instances, an antigen is capable of eliciting a humoral and cellular immune response in a subject. Hence, an antigen may be preferably antigenic and immunogenic. Alternatively, an antigen may be antigenic and not immunogenic. Typically, an antigen may be a peptide, polypeptide, protein, nucleic acid, an oligo- or polysaccharide, or a lipid, or any combination thereof, a glycoprotein, proteoglycan, glycolipid, etc. In certain embodiments, an antigen may be a peptide, polypeptide, or protein. An antigen may have one or more than one epitope. The terms "antigenic determinant" or "epitope" generally refer to the region or part of an antigen that specifically reacts with or is recognized by the immune system, specifically by antibodies, B cells, or T cells.

In certain embodiments, TCRs are identified that recognize a tumor antigen. The term "tumor antigen" as used throughout this specification refers to an antigen that is uniquely or differentially expressed by a tumor cell, whether intracellular or on the tumor cell surface (preferably on the tumor cell surface), compared to a normal or non-neoplastic cell. By means of example, a tumor antigen may be present in or on a tumor cell and not typically in or on normal cells or non-neoplastic cells (e.g., only expressed by a restricted number of normal tissues, such as testis and/or placenta), or a tumor antigen may be present in or on a tumor cell in greater amounts than in or on normal or non-neoplastic cells, or a tumor antigen may be present in or on tumor cells in a different form than that found in or on normal or non-neoplastic cells. The term thus includes tumor-specific antigens (TSA), including tumor-specific membrane antigens, tumor-associated antigens (TAA), including tumor-associated membrane antigens, embryonic antigens on tumors, growth factor receptors, growth factor ligands, etc. Examples of tumor antigens include, without limitation, B cell maturation antigen (BCMA) (see, e.g., Friedman et al., Effective Targeting of Multiple BCMA-Expressing Hematological Malignancies by Anti-BCMA CAR T Cells, Hum Gene Ther. 2018 Mar 8; Berdeja JG, et al. Durable clinical responses in heavily pretreated patients with relapsed/refractory multiple myeloma: updated results from a multicenter study of bb2121 anti-Bcma CAR T cell therapy. Blood. 2017; 130:740; and Mouhieddine and Ghobrial, Immunotherapy in Multiple Myeloma: The Era of CAR T Cell Therapy, Hematologist, May-June 2018, Volume 15, issue 3); PSA (prostate-specific antigen); prostate-specific membrane antigen (PSMA); PSCA (Prostate stem cell antigen); Tyrosine-protein kinase transmembrane receptor ROR1; fibroblast activation protein (FAP); Tumor-associated glycoprotein 72 (TAG72); Carcinoembryonic antigen (CEA); Epithelial cell adhesion molecule (EPCAM); Mesothelin; Human Epidermal growth factor Receptor 2 (ERBB2 (Her2/neu)); Prostate; Prostatic acid phosphatase (PAP); elongation factor 2 mutant (ELF2M); Insulin-like growth factor 1 receptor (IGF-1R); gp1OO; BCR-ABL (breakpoint cluster region-Abelson); tyrosinase; New York esophageal squamous cell carcinoma 1 (NY-ESO-1); κ-light chain, LAGE (L antigen); MAGE (melanoma antigen); Melanoma-associated antigen 1 (MAGE-A1); MAGE A3; MAGE A6; legumain; Human papillomavirus (HPV) E6; HPV E7; prostein; survivin; PCTA1 (Galectin 8); Melan-A/MART-1; Ras mutant; TRP-1 (tyrosinase related protein 1, or gp75); Tyrosinase-related Protein 2 (TRP2); TRP-2/INT2 (TRP-2/intron 2); RAGE (renal antigen); receptor for advanced glycation end products 1 (RAGE1); Renal ubiquitous 1, 2 (RU1, RU2); intestinal carboxyl esterase (iCE); Heat shock protein 70-2 (HSP70-2) mutant; thyroid stimulating hormone receptor (TSHR); CD123; CD171; CD19; CD20; CD22; CD26; CD30; CD33; CD44v7/8 (cluster of differentiation 44, exons 7/8); CD53; CD92; CD100; CD148; CD150; CD200; CD261; CD262; CD362; CS-1 (CD2 subset 1, CRACC, SLAMF7, CD319, and 19A24); C-type lectin-like molecule-1 (CLL-1); ganglioside GD3 (aNeu5Ac (2-8)aNeu5Ac(2-3)bDGalp(1-4)bDG1cp(1-1)Cer); Tn antigen (Tn Ag); Fms-Like Tyrosine Kinase 3 (FLT3); CD38; CD138; CD44v6; B7H3 (CD276); KIT (CD117); Interleukin-13 receptor subunit alpha-2 (IL-13Ra2); Interleukin 11 receptor alpha (IL-11Ra); prostate stem cell antigen (PSCA); Protease Serine 21 (PRSS21); vascular endothelial growth factor receptor 2 (VEGFR2); Lewis(Y) antigen; CD24; Platelet-derived growth factor receptor beta (PDGFR-beta); stage-specific embryonic antigen-4 (SSEA-4); Mucin 1, cell surface associated (MUC1); mucin 16 (MUC16); epidermal growth factor receptor (EGFR); epidermal growth factor receptor variant III (EGFRvIII); neural cell adhesion molecule (NCAM); carbonic anhydrase IX (CAIX); Proteasome (Prosome, Macropain) Subunit, Beta Type, 9 (LMP2); ephrin type-A receptor 2 (EphA2); Ephrin B2; Fucosyl GM1; sialyl Lewis adhesion molecule (sLe); ganglioside GM3 (aNeu5Ac(2-3)bDGalp(1-4)bDG1cp(1-1) Cer); TGS5; high molecular weight-melanoma-associated antigen (HMWMAA); o-acetyl-GD2 ganglioside (OAcGD2); Folate receptor alpha; Folate receptor beta; tumor endothelial marker 1 (TEM1/CD248); tumor endothelial marker 7-related (TEM7R); claudin 6 (CLDN6); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); CT (cancer/testis (antigen)); melanoma cancer testis antigen-1 (MAD-CT-1); melanoma cancer testis antigen-2 (MAD-CT-2); Fos-related antigen 1; p53; p53 mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetylglucosaminyl-transferase V (NA17); paired box protein Pax-3 (PAX3); Androgen receptor; Cyclin B1; Cyclin D1; v-myc avian myelocytomatosis viral oncogene neuroblastoma derived homolog (MYCN); Ras Homolog Family Member C (RhoC); Cytochrome P450 1B1 (CYP1B1); CCCTC-Binding Factor (Zinc Finger Protein)-Like (BORIS); Squamous Cell Carcinoma Antigen Recognized By T Cells-1 or 3 (SART1, SART3); Paired box protein Pax-5 (PAXS); proacrosin binding protein sp32 (OY-TES1); lymphocyte-specific protein tyrosine kinase (LCK); A kinase anchor protein 4 (AKAP-4); synovial sarcoma, X breakpoint-1, -2, -3 or -4 (SSX1, SSX2, SSX3, SSX4); CD79a; CD79b; CD72; Leukocyte-associated immunoglobulin-like receptor 1 (LAIR1); Fc fragment of IgA receptor (FCAR); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRLS); mouse double minute 2 homolog (MDM2); livin; alphafetoprotein (AFP); transmembrane activator and CAML Interactor (TACI); B-cell activating factor receptor (BAFF-R); V-Ki-ras2 Kirsten rat sarcoma viral oncogene homolog (KRAS); immunoglobulin lambda-like polypeptide 1 (IGLL1); 707-AP (707 alanine proline); ART-4 (adenocarcinoma antigen recognized by T4 cells); BAGE (B antigen; b-catenin/m, b-catenin/mutated); CAMEL (CTL-recognized antigen on melanoma); CAP1 (carcinoembryonic antigen peptide 1); CASP-8 (caspase-8); CDC27m (cell-division cycle 27 mutated); CDK4/m (cycline-dependent kinase 4 mutated); Cyp-B (cyclophilin B); DAM (differentiation antigen melanoma); EGP-2 (epithelial glycoprotein 2); EGP-40 (epithelial glycoprotein 40); Erbb2, 3, 4 (erythroblastic leukemia viral oncogene homolog-2, -3, 4); FBP (folate binding protein); fAchR (Fetal acetylcholine receptor); G250 (glycoprotein 250); GAGE (G antigen); GnT-V (N-acetylglucosaminyltransferase V); HAGE (helicase antigen); ULA-A (human leukocyte antigen-A); HST2 (human signet ring tumor 2); KIAA0205; KDR (kinase insert domain receptor); LDLR/FUT (low density lipid receptor/GDP L-fucose: b-D-galactosidase 2-a-L fucosyl-transferase); L1CAM (L1 cell adhesion molecule); MC1R (melanocortin 1 receptor); Myosin/m (myosin mutated); MUM-1, -2, -3 (melanoma ubiquitous mutated 1, 2, 3); NA88-A (NA cDNA clone of patient M88); NKG2D (Natural killer group 2, member D) ligands; oncofetal antigen (h5T4); p190 minor bcr-abl (protein of 190KD bcr-abl); Pml/RARa (promyelocytic leukaemia/retinoic acid receptor a); PRAME (preferentially expressed antigen of melanoma); SAGE (sarcoma antigen); TEL/AML1 (translocation Ets-family leukemia/acute myeloid leukemia 1); TPI/m (triose-phosphate isomerase mutated); and CD70.

In certain embodiments, a TCR is identified for a antigen to be targeted in adoptive cell therapy (such as particularly CAR or TCR T cell therapy) of an universal tumor antigen. In certain preferred embodiments, the universal tumor antigen is selected from the group consisting of: a human telomerase reverse transcriptase (hTERT), survivin, mouse double minute 2 homolog (MDM2), cytochrome P450 1B1 (CYP1B1), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53, cyclin (D1), and any combinations thereof.

Administration of Cells

The administration of cells or population of cells, such as immune system cells expressing an endogenous TCR or CAR, as disclosed herein may be carried out in any convenient manner, including by aerosol inhalation, injection, ingestion, transfusion, implantation or transplantation. The cells or population of cells may be administered to a patient subcutaneously, intradermally, intratumorally, intranodally, intramedullary, intramuscularly, intrathecally, by intravenous or intralymphatic injection, or intraperitoneally. In some embodiments, the disclosed CARs may be delivered or administered into a cavity formed by the resection of tumor tissue (i.e. intracavity delivery) or directly into a tumor prior to resection (i.e. intratumoral delivery). In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. Dosing in CART cell therapies may for example involve administration of from $10^6$ to $10^9$ cells/kg, with or without a course of lymphodepletion, for example with cyclophosphamide. The cells or population of cells can be administrated in one or more doses. In another embodiment, the effective amount of cells are administrated as a single dose. In another embodiment, the effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions are within the skill of one in the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, the effective amount of cells or composition comprising those cells are administrated parenterally. The administration can be an intravenous administration. The administration can be directly done by injection within a tumor.

In certain embodiments, a patient in need of a T cell therapy may be conditioned by a method as described in WO2016191756 comprising administering to the patient a dose of cyclophosphamide between 200 mg/m2/day and 2000 mg/m2/day and a dose of fludarabine between 20 mg/m2/day and 900 mg/m$^2$/day.

The invention is further described in the following examples, which do not limit the scope of the invention described in the claims.

EXAMPLES

Example 1—PCR Enrichment of Single-Cell Library Members

Applicants provide for a PCR-based approach to enrich pooled single-cell sequence libraries for reads from individual cells of interest. This approach enables investigators to selectively access relevant information out of such libraries with reduced sequencing effort. For example, cells that initially lack sequence coverage can be targeted for deeper follow-up sequencing and rare cell populations too small in quantity or too sensitive to perturbation for pre-selection by FACS can be enriched from the original pooled sequence library. Alternatively, the PCR enrichment approach can be combined with complementary enrichment approaches like FACS to target ultra-rare cell types.

Figure 1C:
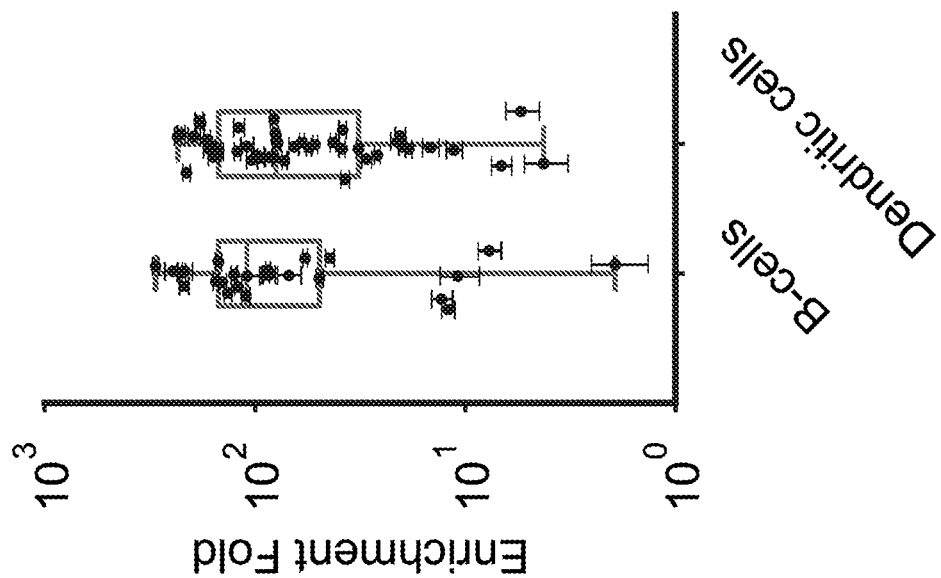
Figure 1B:
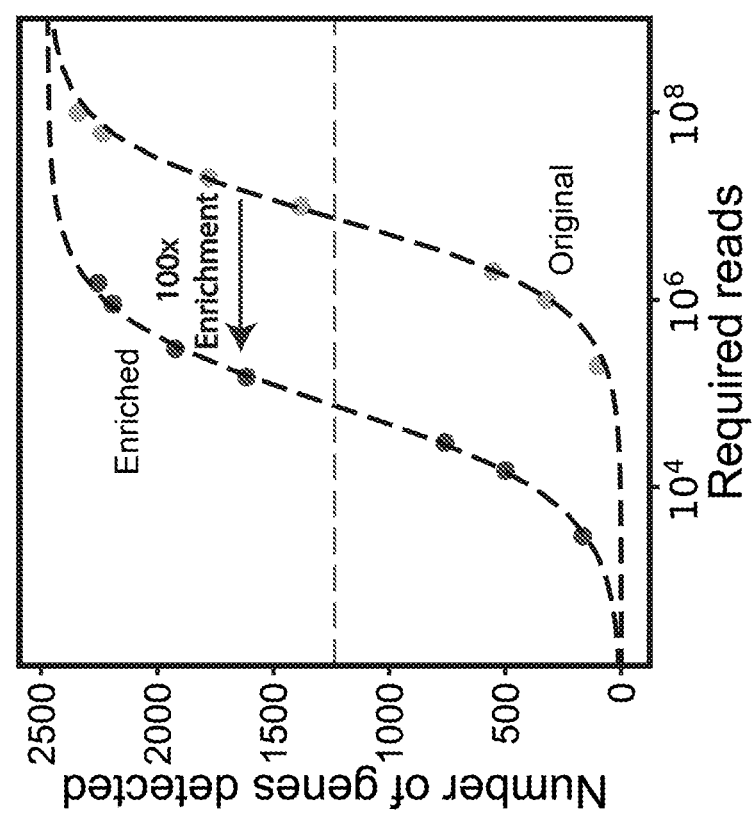
Figures 2A, 2B:
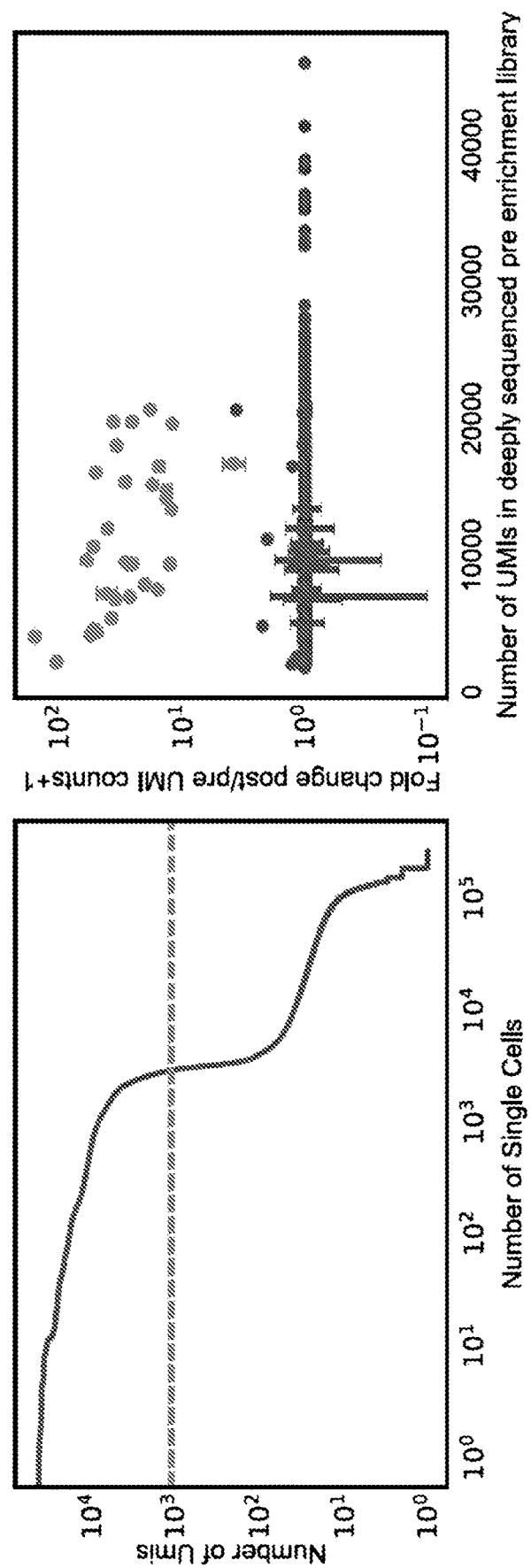
FIG. 2A-FIG. 2B—UMI distribution across 2000 single-cell libraries.
Figure 3A:
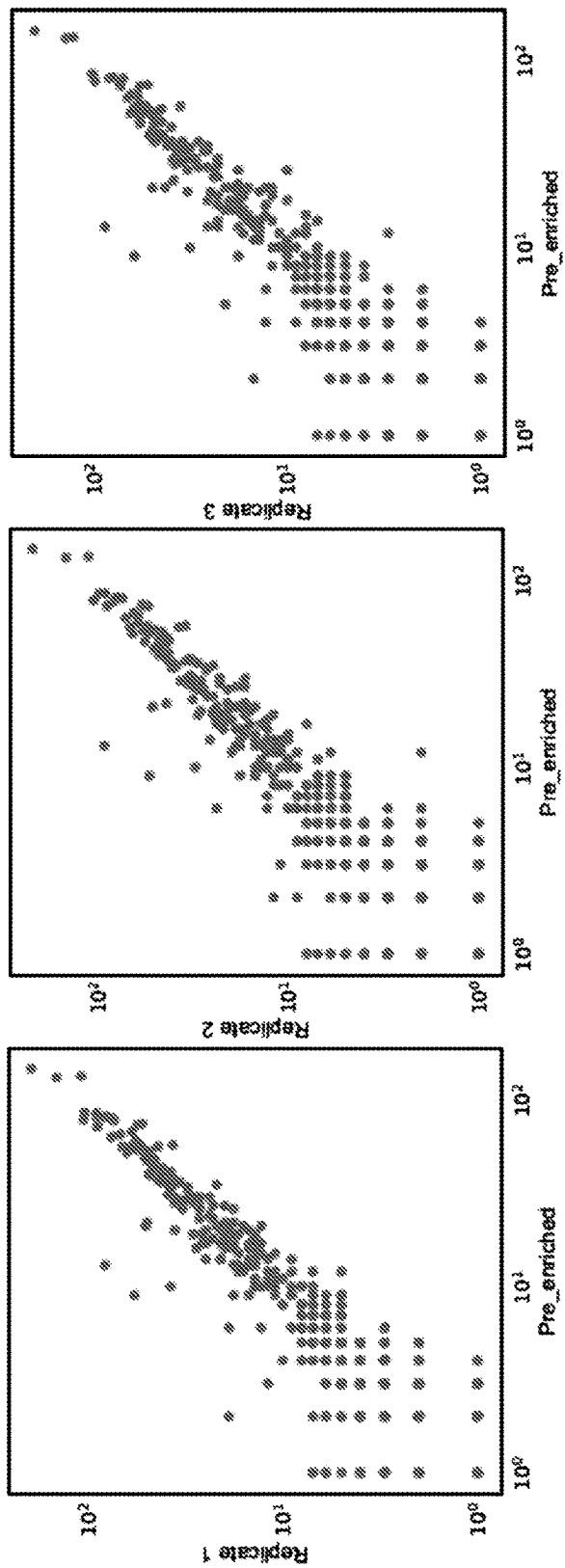
FIG. 3A-FIG. 3B—Correlation of pre and post enriched single cells.
Figure 3B:
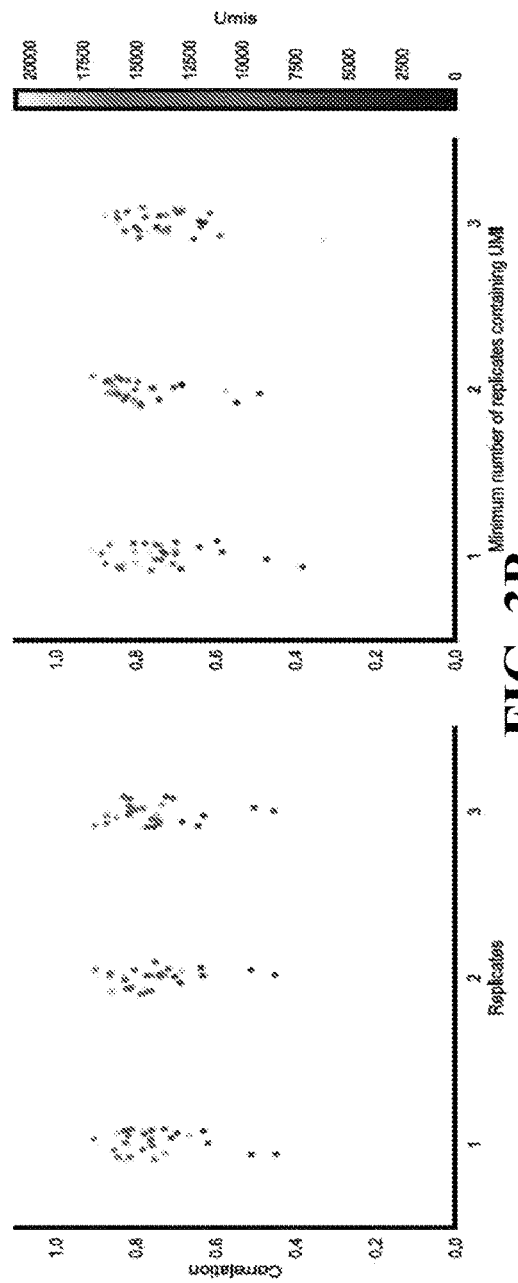
Figure 4:
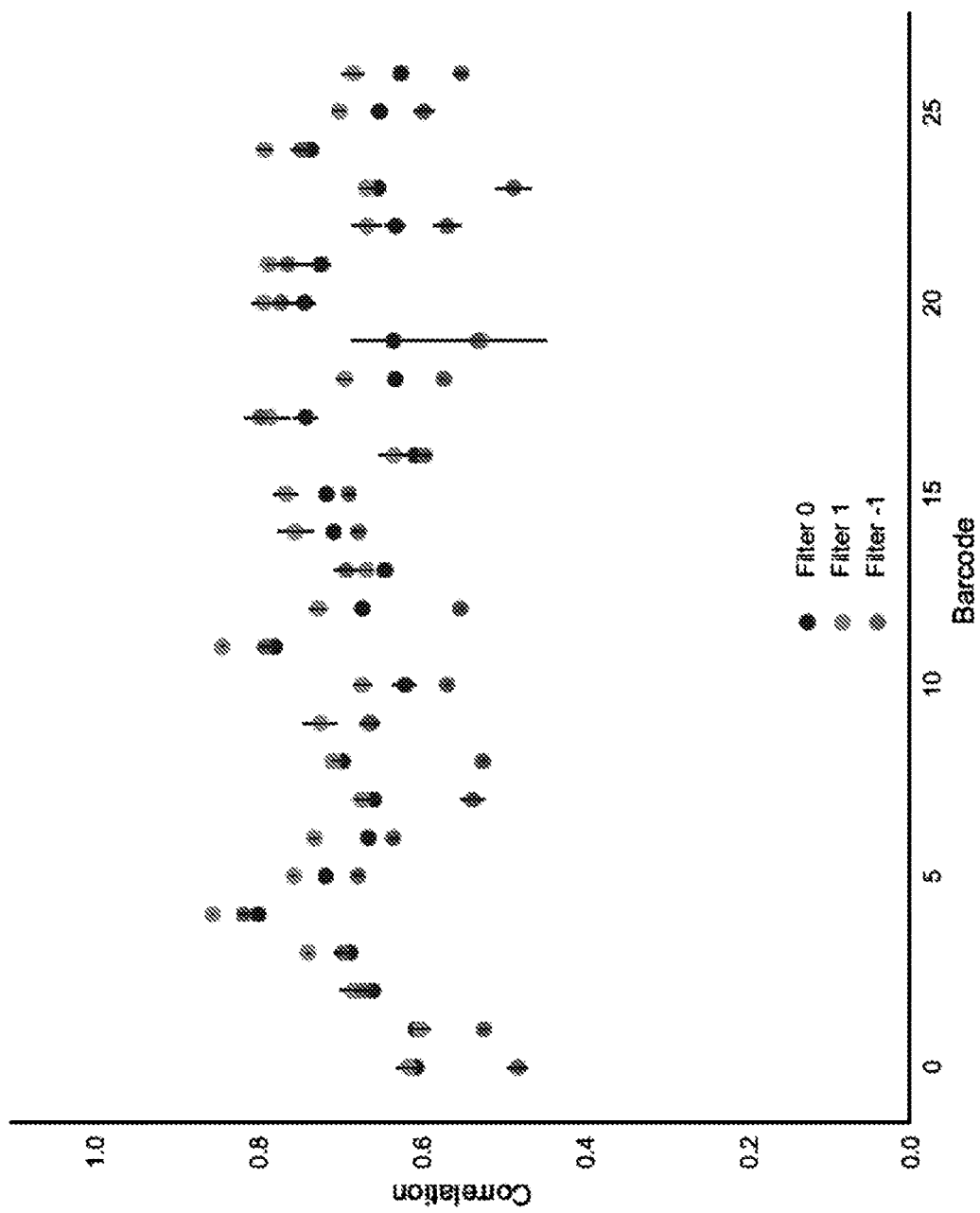
FIG. 4—Correlation thresholded on expression levels of genes. The number of UMIs per gene was thresholded. The blue represents all the data without any threshold. The black included all expressed genes (number of UMIs per gene greater than 0) in the original pre enriched library. The red included all genes that had an expression level greater than one.
Figure 5:
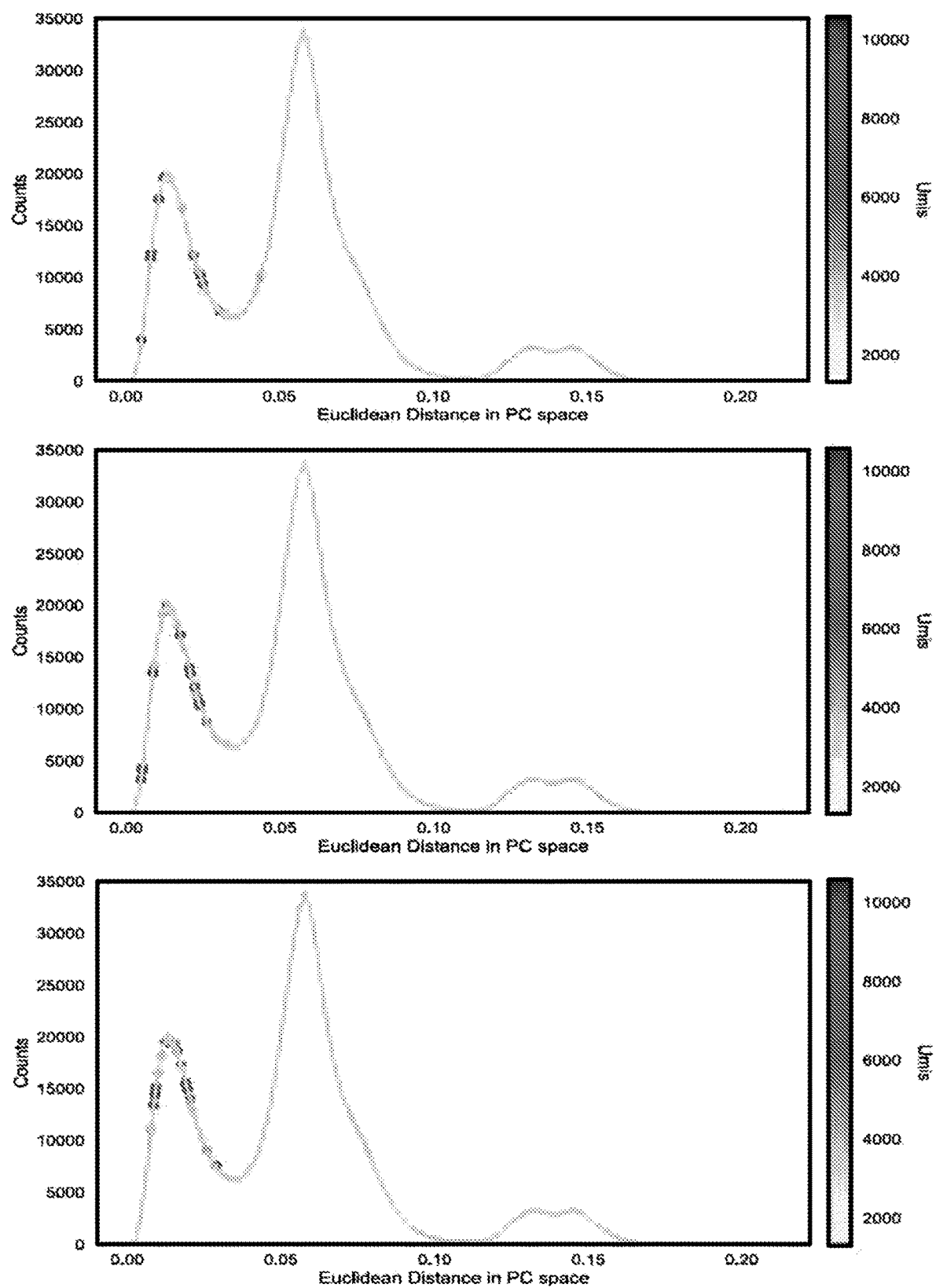
FIG. 5—Pairwise euclidean distance of all single cells in PC space. UMIs are present in at least (Top) 1, (Middle) 2, or (Bottom) 3 replicates. The histogram represents the distance between all single cells that were not enriched. The data points on the histogram are all barcodes enriched colored by the UMI counts in the control library.
Figure 6:
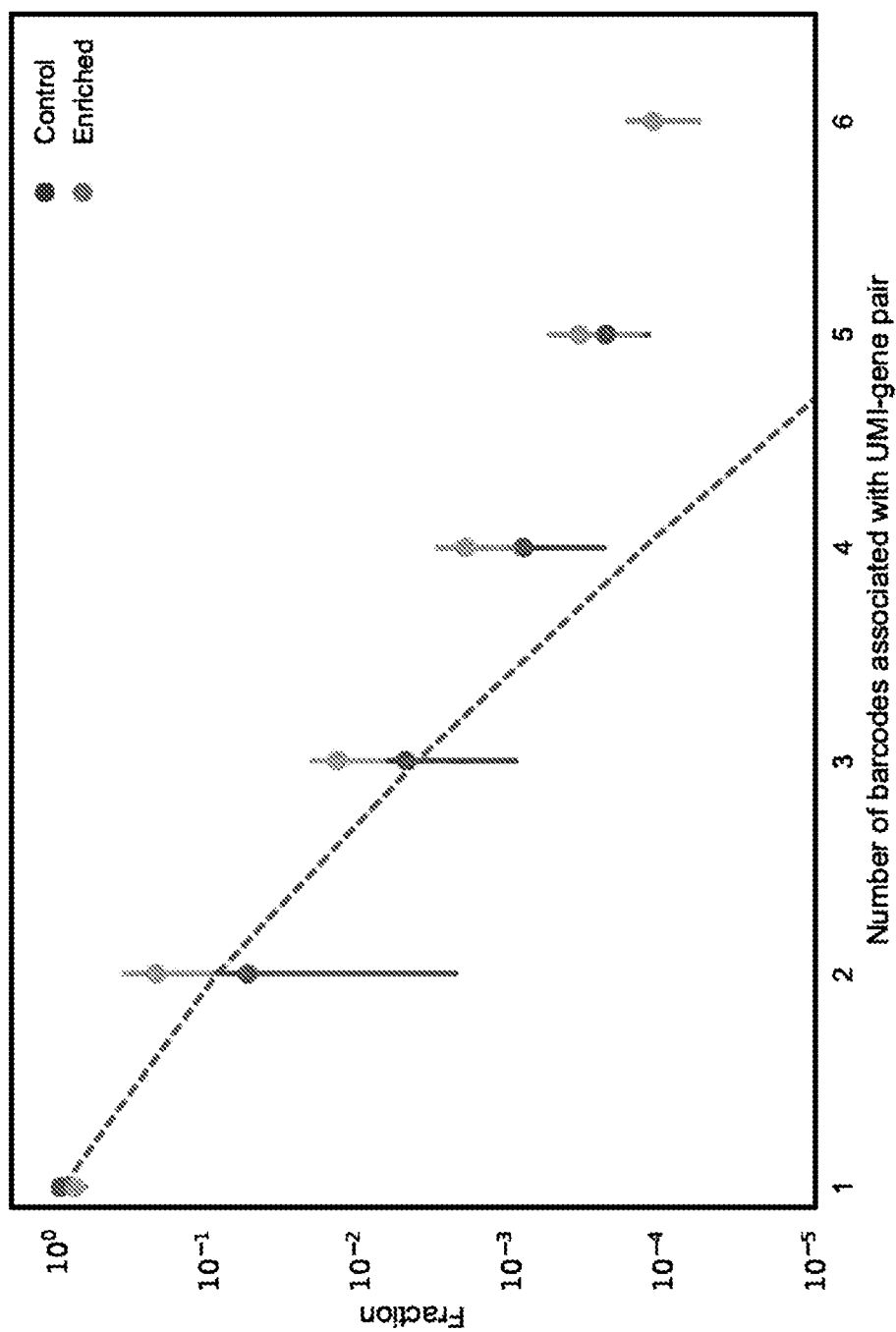
FIG. 6—Distribution of non-unique UMI-gene pairs. The frequency of collisions in UMI-genes across all targeted barcodes. The dotted line represents the expected poisson distribution of UMI clashes. The blue represents barcodes in the control library and the green represents the enriched samples.
Figure 7:
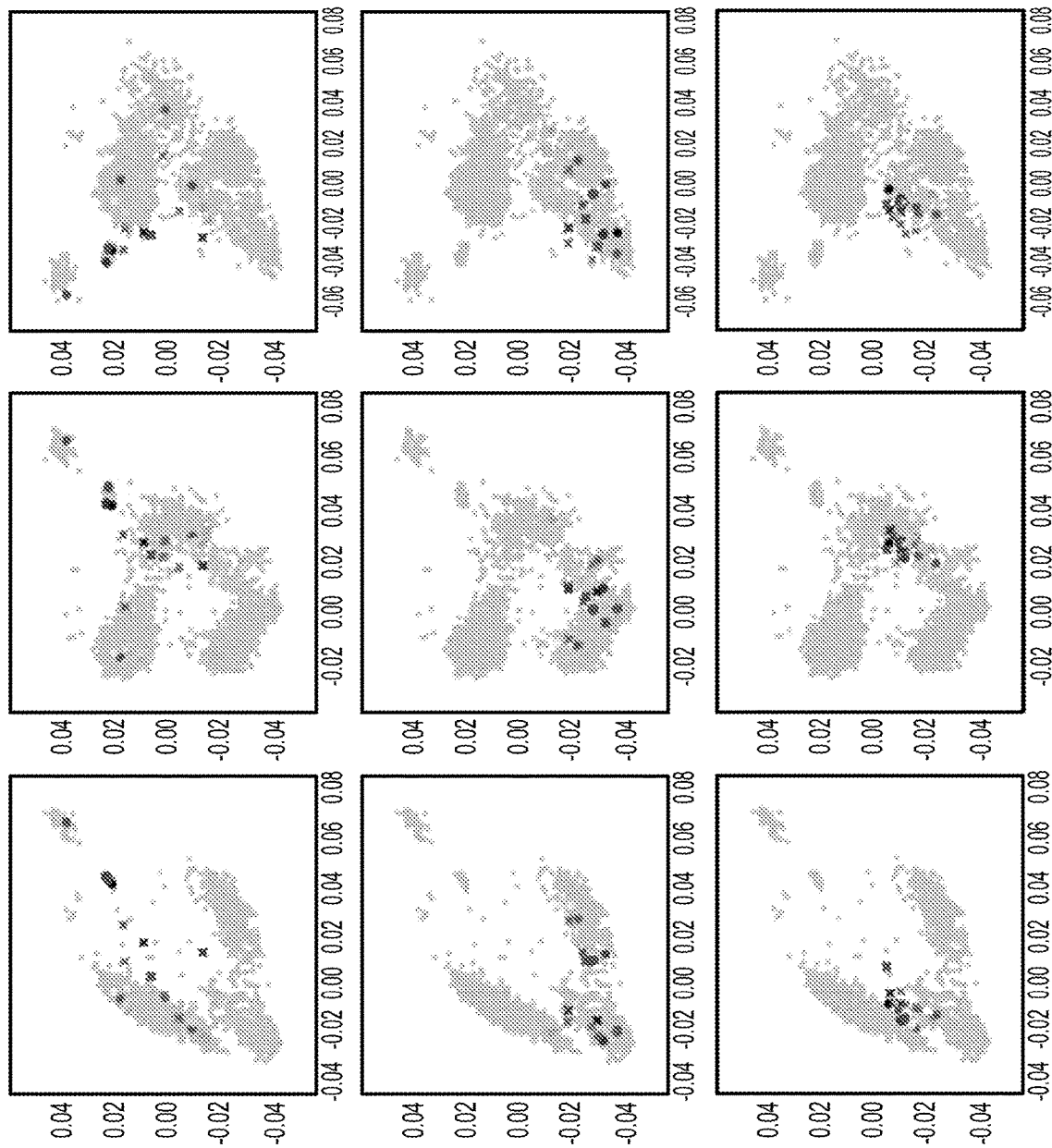
FIG. 7—All barcodes in the 2000 cell enrichment. Each row plots 10 barcodes that were enriched. Circles and crosses refer to pre and post enrichment positions with each color representing a cell barcode. Plots show PC1 vs PC2, PC3, and PC4 in the columns.
Figure 8:
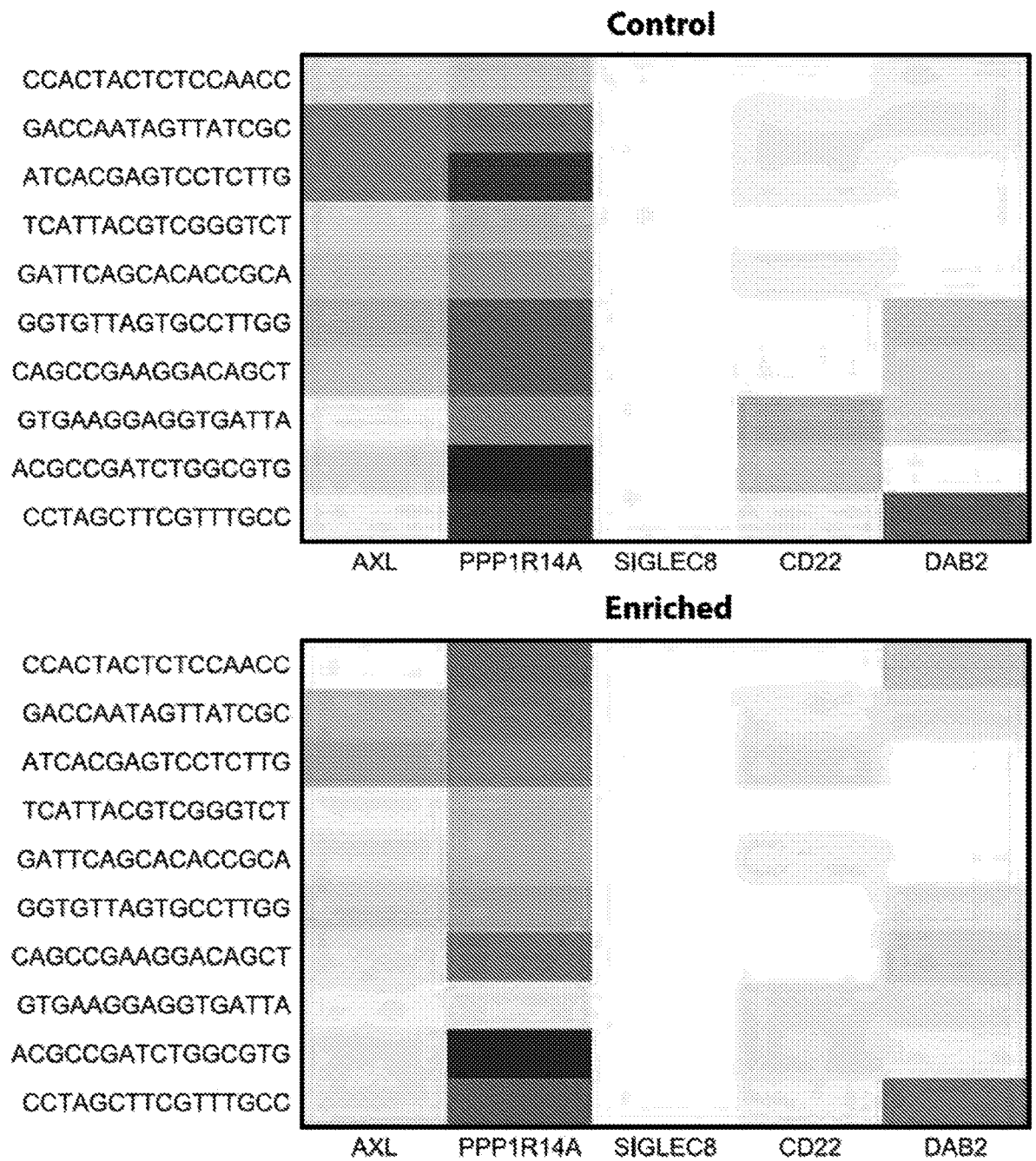
FIG. 8—Gene expression profile of potential AS cells. A comparison of gene expression profiles for marker genes signifying AS cells in the deeply sequenced control library to the enriched samples. None of these genes were detectable in the original library when sequenced at the same depth as the enriched libraries. (SEQ ID NOs. 1-10)

In an example embodiment, Applicants perform a PCR-based approach to enrich a pooled single-cell library for specific cells of interest based on an initial analysis of a shallow sequence dataset (e.g. 5000 reads per cell). Applicants then enrich the library to focus sequencing effort on high-quality examples of the cell types of interest in the study. The method works by using PCR primers specific to the barcodes of target cells to preferentially amplify these from the pooled sequence library in multiplex PCR reactions (10-plex; FIG. 1A, Table 1). The resulting 100-fold enriched libraries are then sequenced efficiently to achieve deep coverage of high-quality target cells at far lower overall sequencing effort than would previously be required (FIG. 1B, FIG. 1E, FIG. 2). To test the method, Applicants targeted 25 single cells (representing low and high quality cells) within a HLADR+ population of primary human immune cells from a library of 2000 cells. RNA abundances determined by sequencing the enriched libraries quantitatively recapitulated RNA abundances from the deeply sequenced original library (FIG. 1F, FIG. 2, FIG. 8). Data from the enriched library also resulted in congruent cluster assignments in reduced-dimensional data representations (FIG. 1G, FIG. 5 and FIG. 7).

In another example, Applicants apply PCR enrichment to populations of primary human B-cells, monocytes, and dendritic cells from blood, which represent 15-35%, 10-15%, and 1-2% of total peripheral blood mononuclear cells (PBMCs), respectively. Applicants pre-enriched these populations by FACS using the following cell surface markers: B cells, CD19$^+$ subset, from here on referred to as CD19$^+$ cells; monocytes and dendritic cells, Lineage$^-$(Lin$^-$) HLA-DR$^+$ cell subset, from here on referred to as HLA-DR$^+$ cells. Applicants demonstrate how FACS pre-enrichment can be combined with PCR enrichment from large pooled sequence libraries to focus sequencing effort on an ultra-rare cell type of interest such as the AS DCs within the HLA-DR$^+$ subset, which represents only 1-3% of human blood DCs and 0.01-0.06% of total PBMCs.

Figure 16:
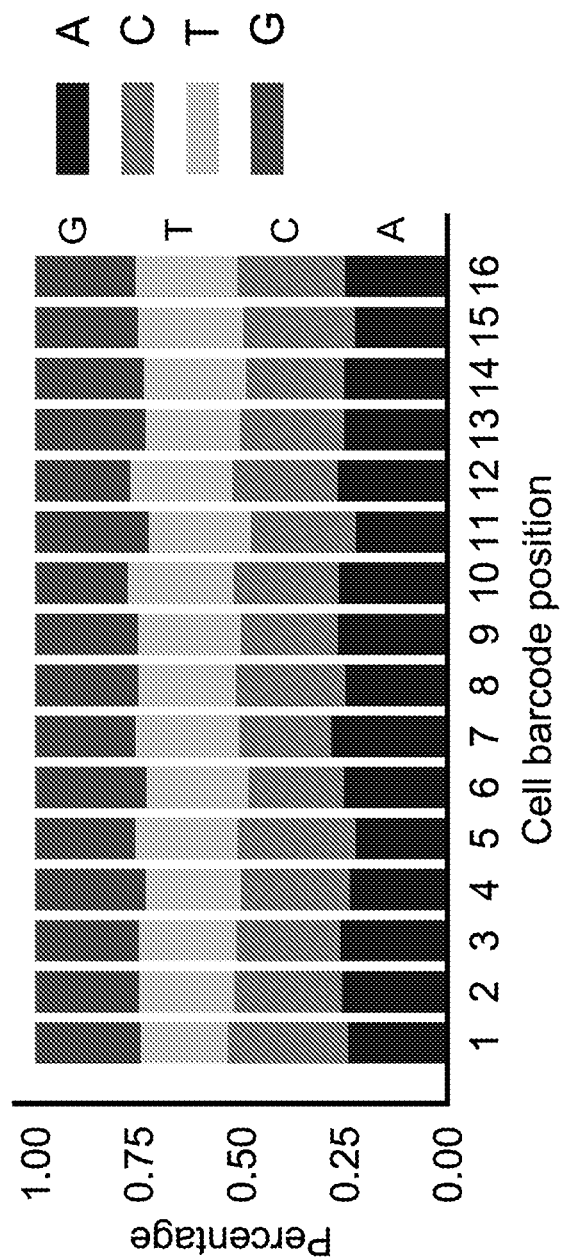
FIG. 16—Cell barcode structure. The base composition of each position of the 16 bp 10X cell barcodes in the original HLA-DR library. The GC content per barcode ranges from 31% to 69%.
Figure 17:
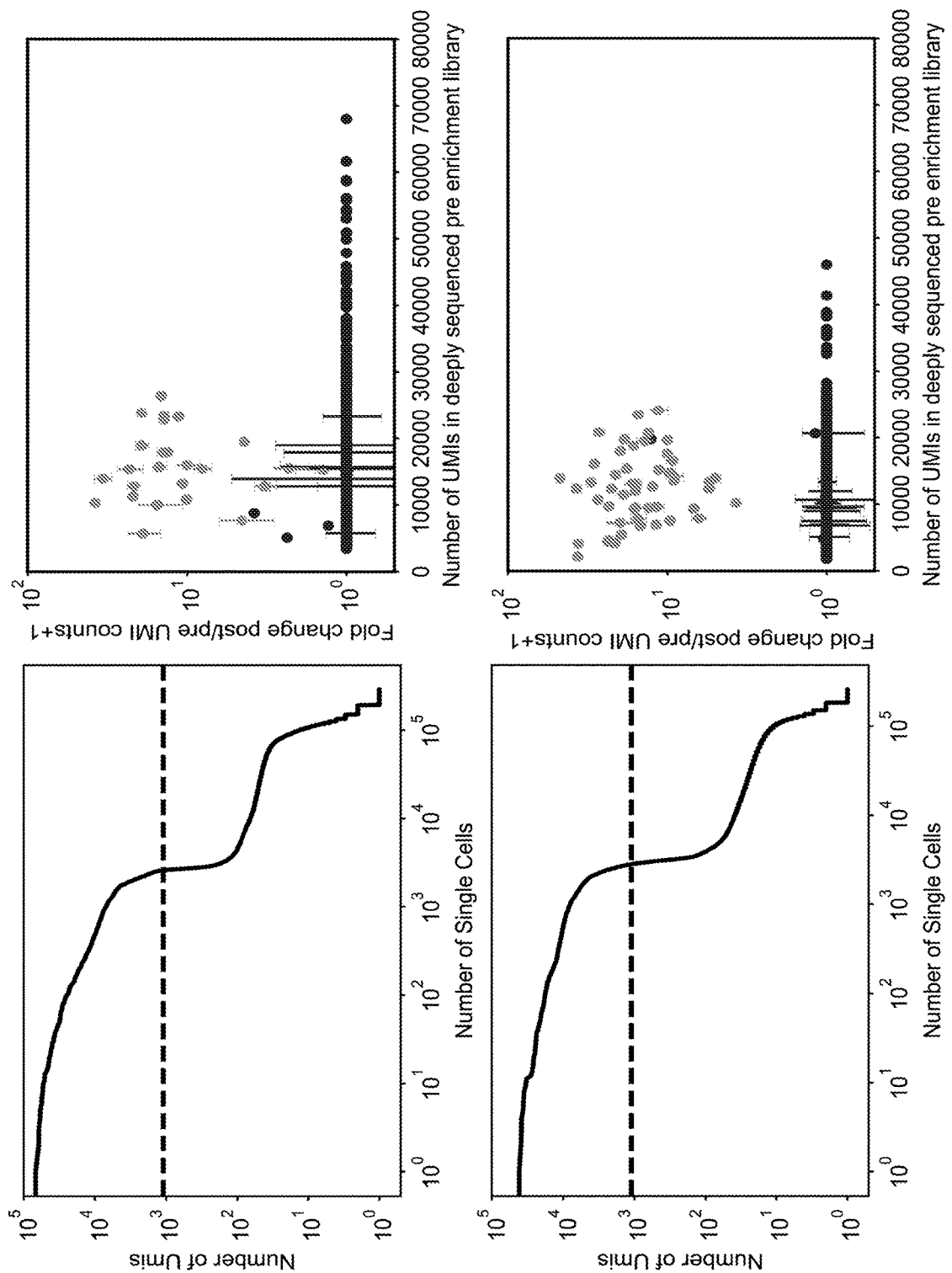
FIG. 17—UMI count distribution and fold changes in single-cell RNA-seq sequence library of CD19$^+$ cells (top) and HLA-DR$^+$ cells (bottom). UMI distribution (left). The dashed line (threshold of approximately 1000 UMIs) represents the cutoff used when selecting cells/barcodes for analysis (the cutoff was set using 10X Genomics' Cell-Ranger pipeline). UMI enrichment (right). The number of UMIs detected in the targeted group of cells (red) was increased 10-100 fold in the targeted cells/barcodes after multiplexed enrichment. The total sequencing effort for the control and enriched libraries were normalized. The few non-target barcodes seen above are similar in structure on the 5' end to the barcodes that were targeted.
Figure 18:
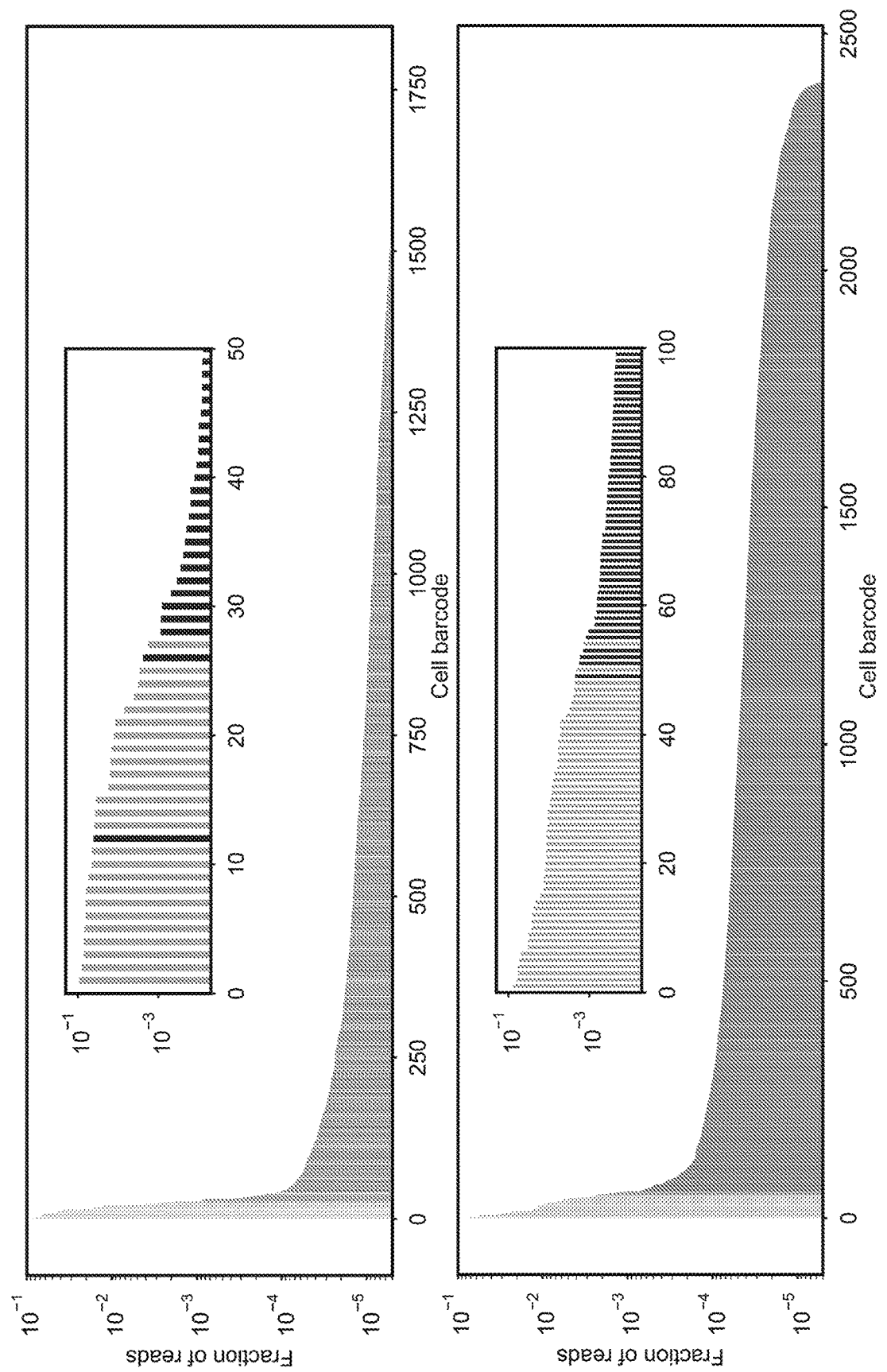
FIG. 18—Analysis of on-target and off-target sequencing reads. Read abundance (data fraction) by cell barcode in the post enrichment dataset for the CD19$^+$ (top) and HLA-DR$^+$ (bottom) libraries. The data highlighted in red represent on-target amplification whereas the data in blue correspond to other non-target barcodes (originating from the pre enrichment libraries).

Example 2—Target Cell Enrichment by Multiplexed Hemi-Specific PCR Enables a 100-Fold Decrease in Sequencing Effort To preferentially amplify molecules representing target cells in the pooled sequence library, Applicants carried out multiplexed hemi-specific PCR with forward PCR primers cognate to the barcodes of target cells (up to 15-plex tested; FIG. 1A, FIG. 27 and FIG. 28) and a common reverse P7 primer. To test the method, Applicants targeted 19 cells in a sequence library representing 1760 CD19$^+$ cells, and 46 cells within a sequence library representing 2397 HLA-DR$^+$ cells. The forward PCR primers were designed to target the 16 base pair (bp) cell barcode appended to each cDNA 3' tag sequence in the pooled RNA-seq libraries (FIG. 16). Target barcodes were selected to represent cells with higher (25, 000) and lower (1000) counts of unique transcript molecules (FIG. 17, FIG. 27 and FIG. 28). In this embodiment, Applicants define target cell enrichment as the ratio in sequencing effort needed to access a specific level of information from a particular cell, here quantified as the number of detected genes. The libraries produced by the PCR protocol were enriched approximately 100-fold for the group of targeted cells (FIG. 1B, FIG. 1C, and FIG. 17). This enriched pooled library can be further sequenced to achieve deep coverage of high-quality target cells at far lower overall sequencing effort than would have been required in sequencing the original library. Applicants found that the majority of reads in the enriched libraries corresponded to the targeted cells (FIG. 18, medians across replicates were 70%-90%).

Example 3—Gene Expression Profiles of Target Cells are Faithfully Recapitulated after PCR Enrichment To evaluate the reliability of the method, Applicants compared the expression profiles of cells targeted in the enriched libraries to each cell in the original library. RNA abundances in the enriched libraries quantitatively recapitulated RNA abundances from the original libraries, which were deeply sequenced and computationally resampled to provide matched control datasets for statistical comparison.

Figure 1D:
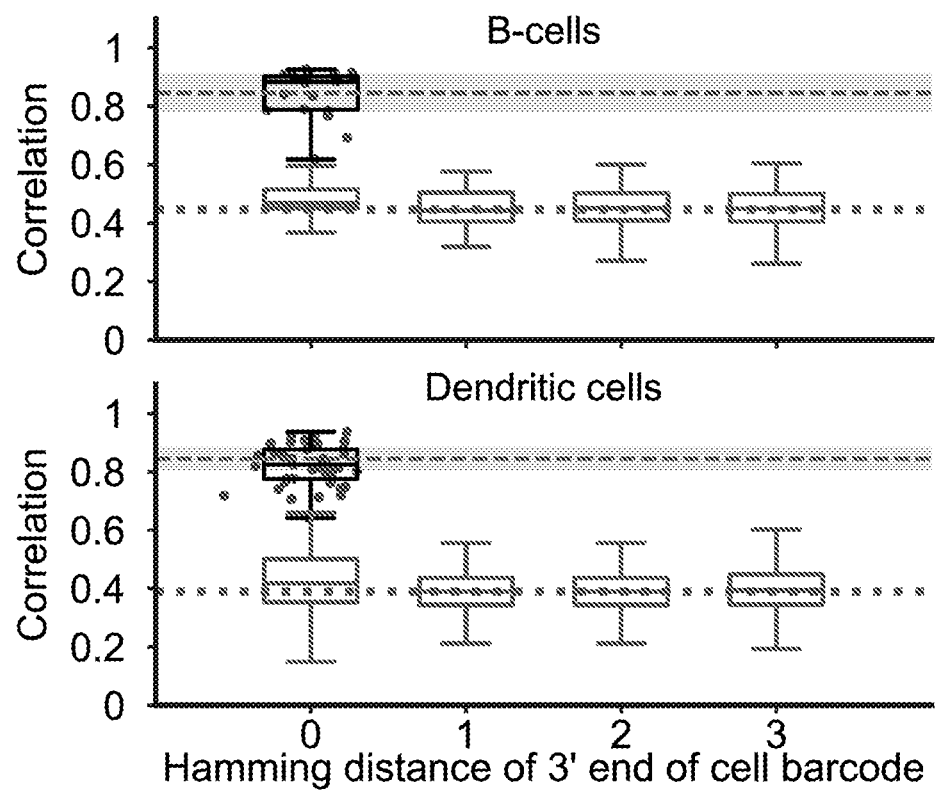
Figure 19:
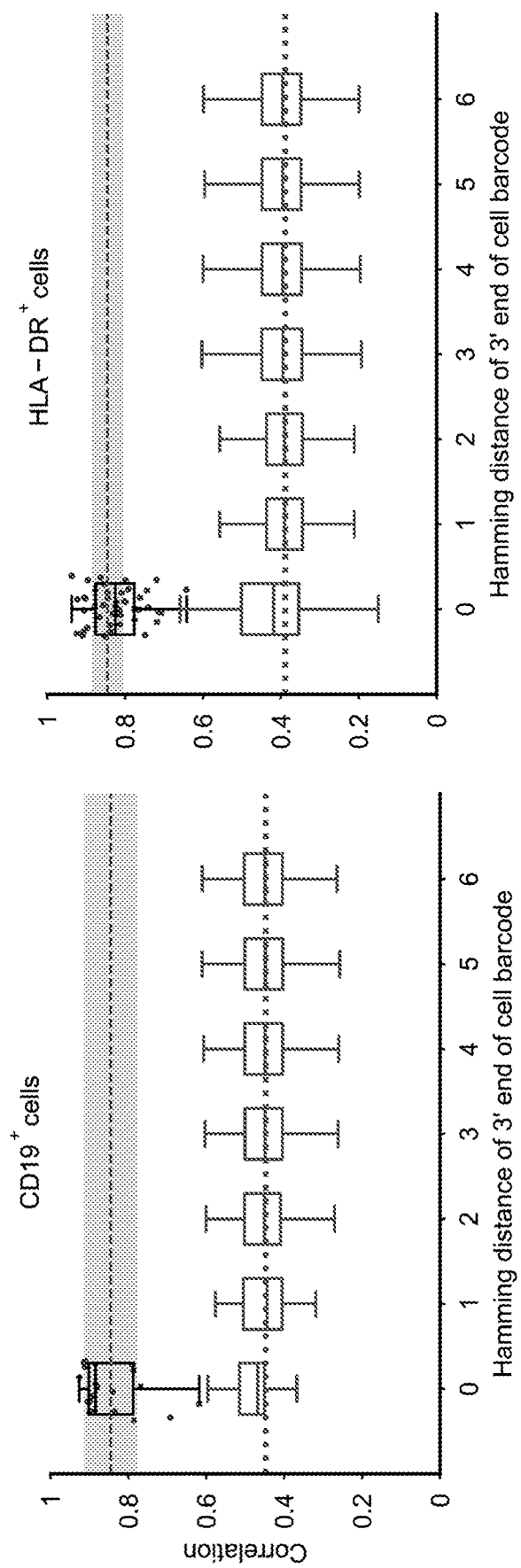
FIG. 19—Correlation of single-cell gene expression profiles before and after enrichment. The pairwise correlation of gene expression profiles before and after PCR enrichment all libraries. The upper dashed line and shaded region in each plot represent the mean +/− two standard deviation of bootstrap replicates of the original gene expression profiles against themselves (which represents the best correlation achievable given the read sampling, UMI sampling, and distribution of expression levels across genes in these specific cells). Red points show the correlation for targeted cells (post-enrichment profiles versus pre-enrichment profiles for the same cell). Gray box plots show distribution of correlation coefficients for control (non target) cells existing in the library (post-enrichment profiles of the subject control cell versus pre-enrichment profiles of all cells). The dotted line shows the mean correlation for the cell barcodes that had at least 6 mismatches at the 3' end. Control comparisons are shown as a function of the number of mismatches (Hamming distance) between the six most 3' base pairs of the 16 base pair subject control cell barcode and the six most 3' base pairs of the 16 base pair barcode of compared targeted cells.
Figure 20:
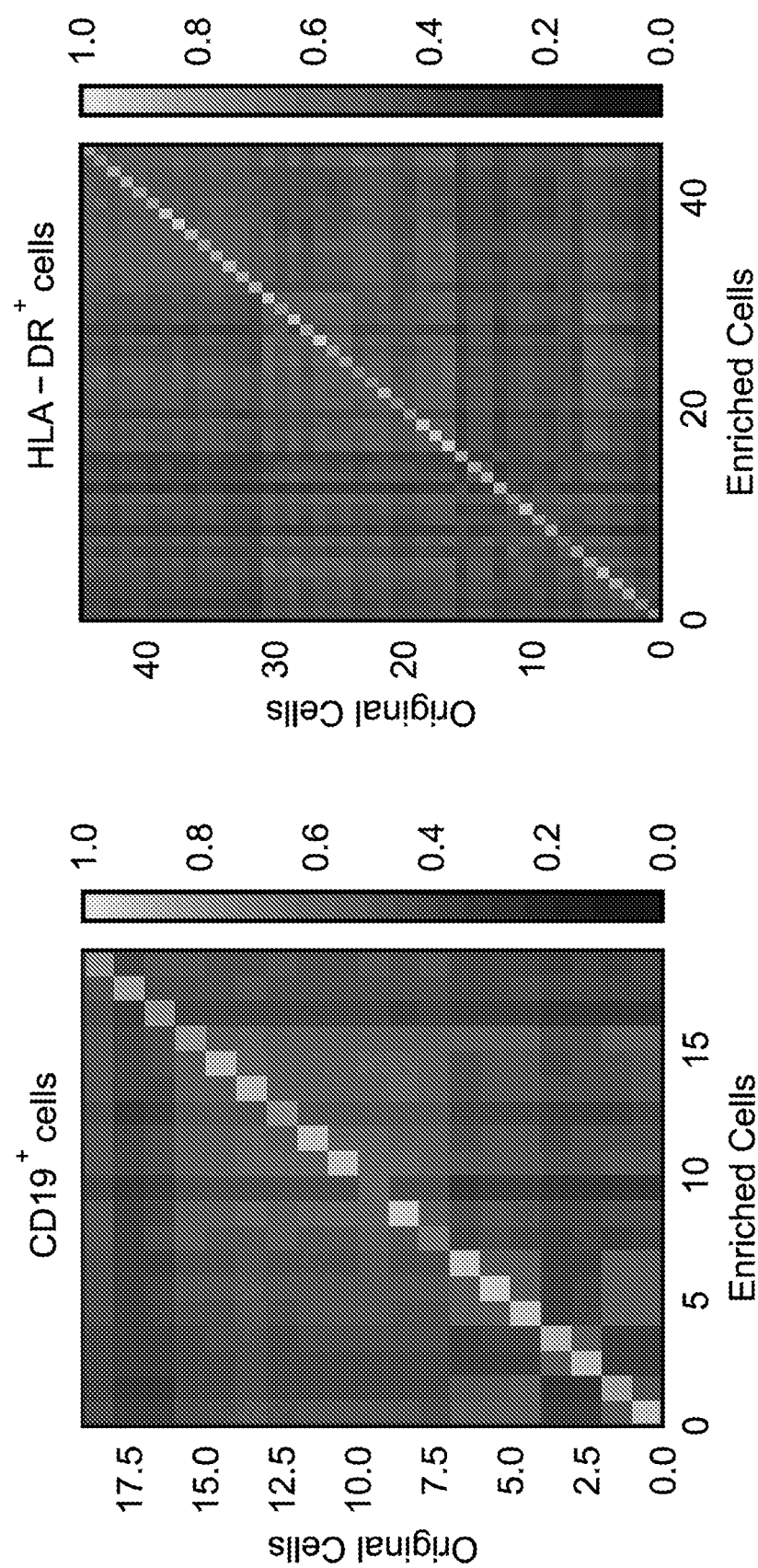
FIG. 20—Pairwise correlation of all enriched libraries. The heatmap shows a comparison of the targeted barcode in the control versus the enriched for all libraries. The diagonal represents correlations for targeted cell pre/post PCR enrichment.
Figure 21:
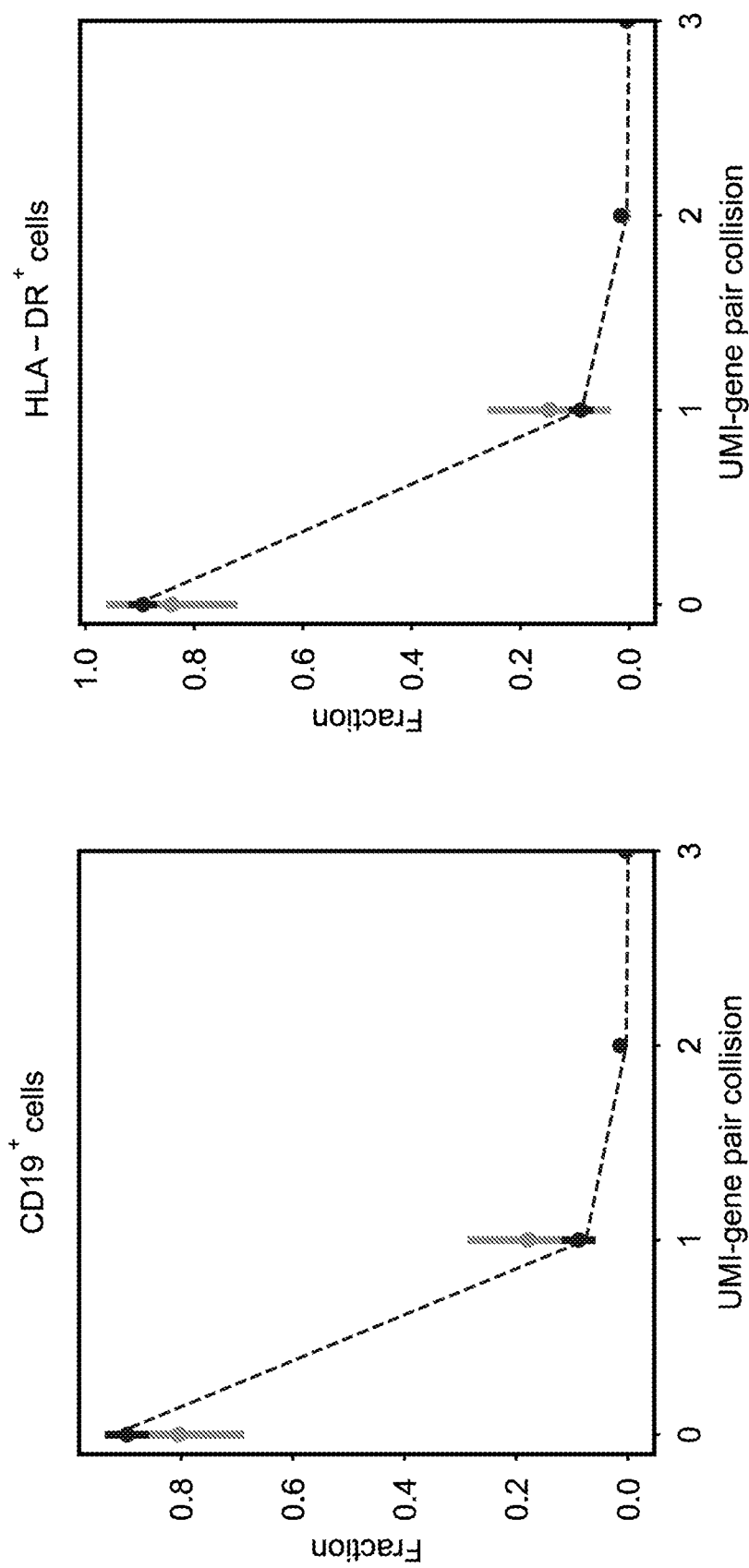
FIG. 21—Distribution of duplicate UMI-gene pairs. The frequency of duplicate UMI-gene pairs across all targeted cells/barcodes. The dotted line represents the expected distribution of UMI-gene duplicates across cells/barcodes. The black points represent the observed fractions of UMI-genes in the pre-enriched sample and the blue points represent the corresponding fractions of all cells in the post-enriched sample. The error bars represent +/−1 SD across all cells.
Figure 22:
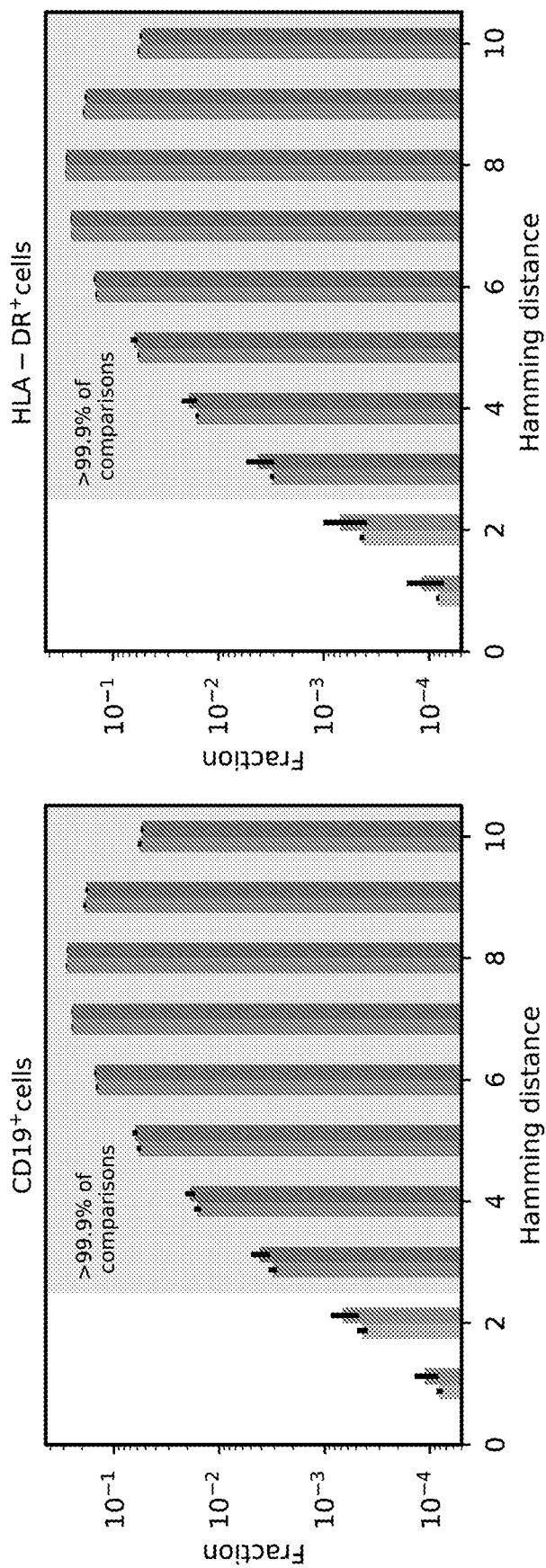
FIG. 22—Analysis of pre and post enrichment inter-UMI distances. The histogram of the pairwise hamming distance between all UMI families identified for each cell barcode. The data show the mean and standard deviation of hamming distances across all cell barcodes for CD19$^+$ (left) and HLA-DR$^+$ (right) libraries. The distribution of hamming distance is shown for both the pre (gray) and post (red) enrichment datasets.

Applicants hypothesized that the base sequence at the 3' end of the barcode PCR primer would be critical for maintaining specificity during amplification. Although 0.1% of cell barcodes share the same 6 base sequence at the 3' end and are at risk for mis-priming events, Applicants find that data from cells enriched in the CD19$^+$ and HLA-DR$^+$ libraries show expression profiles that are well-correlated with the corresponding pre-enrichment profiles (mean correlation of approximately 0.82; as good as resampled replicates of the pre-enrichment profiles compared with themselves) (FIG. 1D, FIG. 19). Further, the pairwise comparison of correlations across all targeted barcodes show the highest correlation for the intended target cell (FIG. 20). Applicants observed a slight increase (statistically significant for the CD19 and HLA-DR subset) in the correlation to non-targeted cells when the 3' end of the barcode has perfect complementary (hamming distance of 0). This effect is presumably caused by cross-priming, but does not significantly affect the final results as the filtering procedure (Material and Methods) is designed to remove spurious UMI counts. In addition to barcode mis-priming, PCR chimeras have the potential to add noise to the measured gene expression profiles (BioRxiv: doi.org/10.1101/093237). Applicants estimated that PCR-driven chimeras increase the UMI+ gene collision rate by only a few percent above the statistically expected collision rate (FIG. 21). An additional source of noise can arise due to polymerase error during PCR amplification of UMI sequences, which might lead to inflated UMI counts. Although Applicants did observe an increase in the number of UMIs at small Hamming distances (1-2) that could be explained by polymerase errors, more than 99.9% of inter-UMI distance counts were at Hamming distances of 3 or more (FIG. 22), indicating that UMI inflation has only a minor potential effect on the data and that the filtering procedures likely exclude an effect. Applicants note here that noise from all four sources: shared 3' barcode sequence, statistical UMI+ gene collisions, PCR-driven chimerism, and UMI sequence errors can likely be reduced by increasing the barcode/UMI complexity and redesigning the primers used for enrichment.

Figures 15A, 15B:
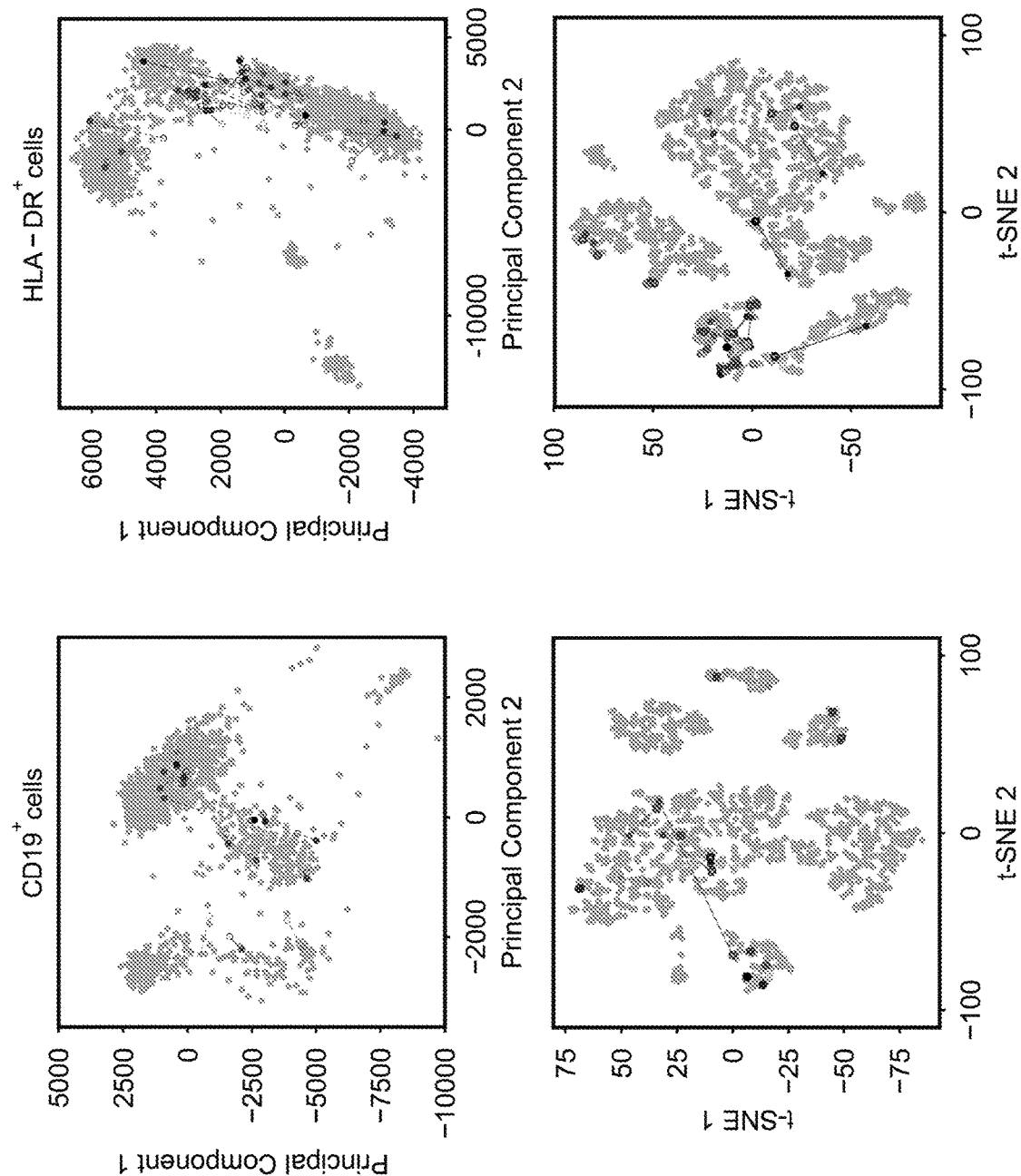
FIG. 15A-FIG. 15C—Single-cell expression profile before and after enrichment.
Figure 23:
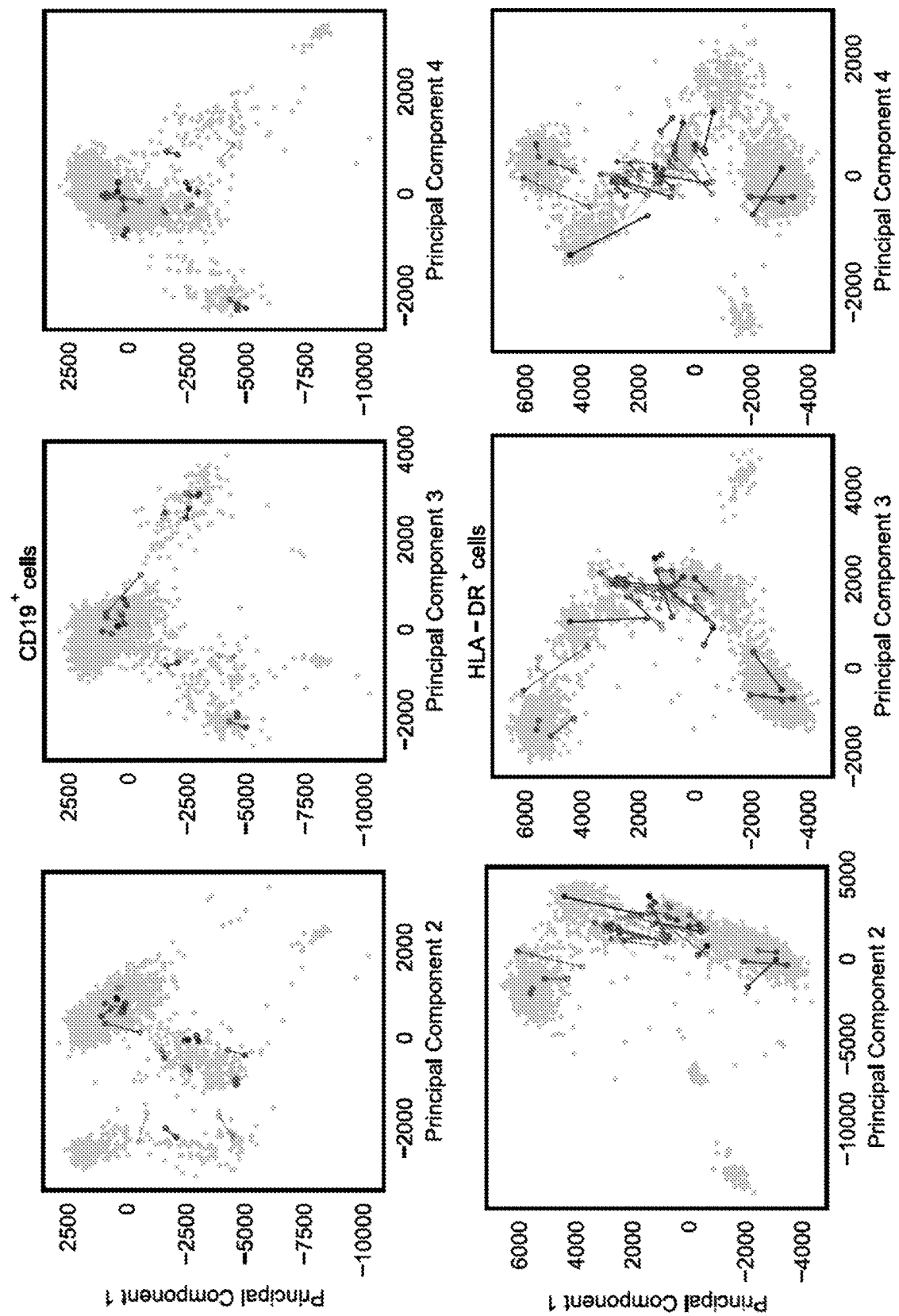
FIG. 23—Principal components analysis (PCA) of each multiplex target enrichment set from RNA-Seq sequence libraries of CD19$^+$ cells and HLA-DR$^+$ cells. Each row plots a sample library that was enriched (PC1 versus PC2, PC3, and PC4 in the columns). Closed circles and open circles refer to pre- and post-enrichment positions respectively, with each color representing a single cell.
Figure 24:
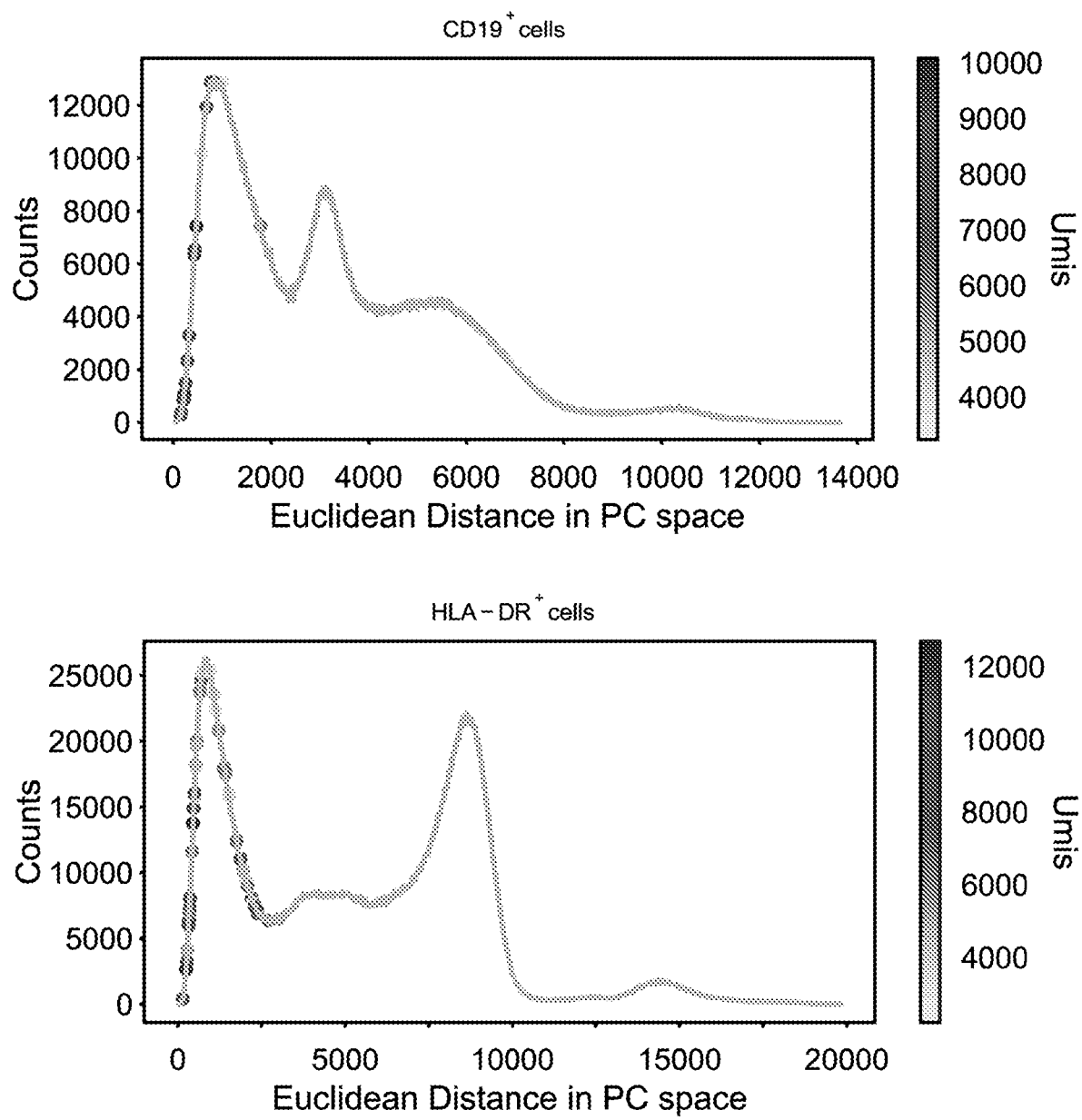
FIG. 24—Pairwise Euclidean distance of all targeted barcodes pre/post enrichment in principal components (PC) space. CD19$^+$ cells (top) HLA-DR$^+$ cells (bottom). The histogram represents the distance between all single cells in the original, pre-enriched library (deeply sequenced). The colored points on the histogram represent each of the cells/barcodes enriched, which are shaded according to the number of UMI counts detected in the original, pre-enriched library.

Example 4—Principal Components Analysis Results in Congruent Cluster Assignments Next, Applicants sought to quantify differences in gene expression profiles before and after enrichment with principal components analysis (PCA). Post-enrichment expression profiles localized cells to similar locations as found in the original libraries in principal components space when Applicants projected post-enrichment data onto the principal components defined using the original dataset (FIG. 15A-B and FIG. 23). Applicants used Euclidean distance as a metric to quantify how much the position of cells shifted relative to the underlying distribution of cell locations (FIG. 24). Data clustering by k-means resulted in the same cluster assignments for most cells before and after enrichment (16/19 for CD19$^+$, adjusted mutual information score (AMI)=0.81; and 43/46 for HLA-DR$^+$, AMI=0.75, where AMI=0 indicates the expected score for random re-clustering, and AMI=1 indicates identical re-clustering).

Example 5—Marker Gene Expression Profiles for AS DCs are Reproduced with Good Fidelity A dendritic cell (DC) subset, characterized by the expression of AXL, SIGLEC1 and SIGLEC6 antigens, named AS DCs has been previously described (see, e.g., Villani et al., Single-cell RNA-seq reveals new types of human blood dendritic cells, monocytes, and progenitors. Science 21 Apr. 2017: Vol. 356, Issue 6335). Here, cell targeting enabled analysis of putative AS DC cells, which exist in only 2-3% abundance within the HLADR+ populations (combining FACS enrichment and PCR-based molecular enrichment to target the AS DCs, which occur at low abundance in this human PBMC sample). AS DC cells are of interest because they are implicated in potently activating T cells.

Figure 15C:
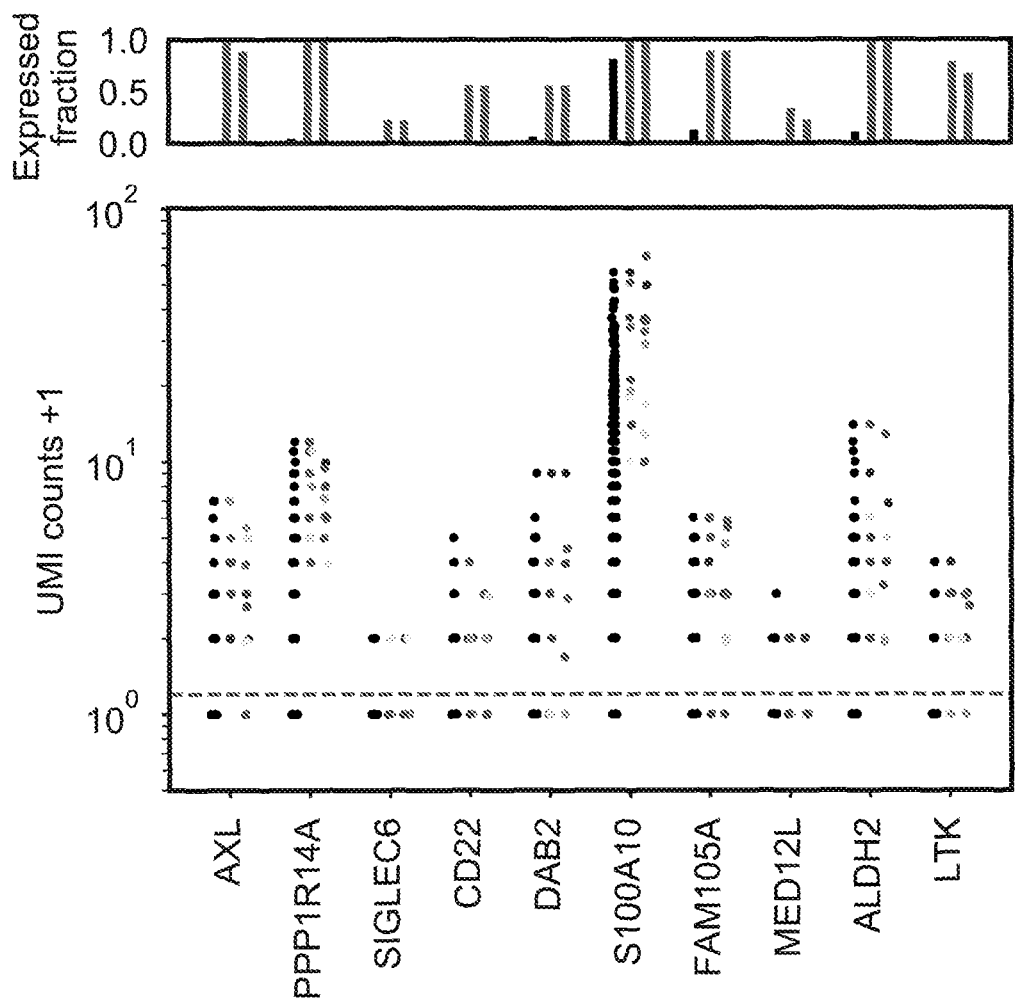
Figure 25:
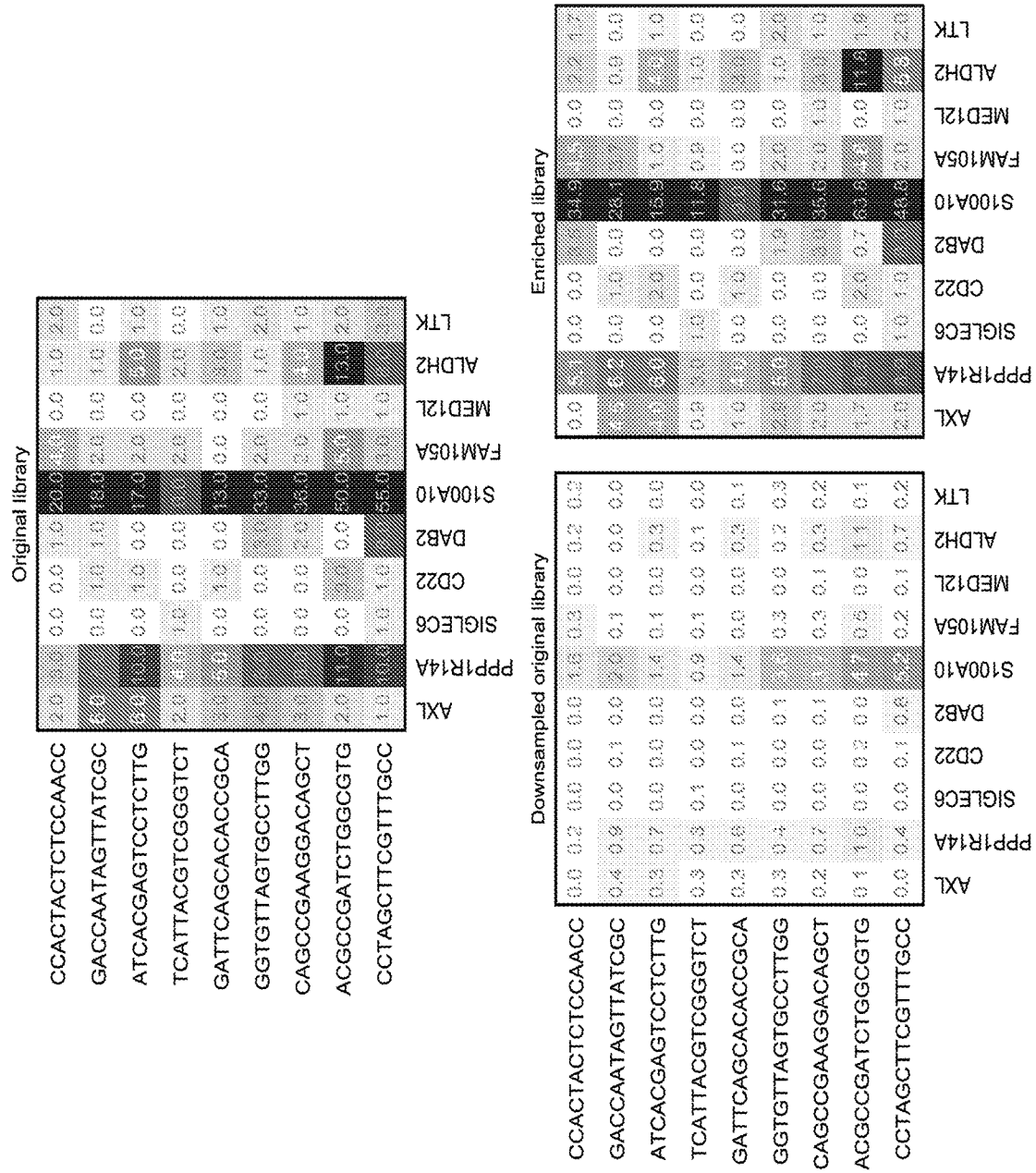
FIG. 25—Gene expression profile of the previously described 10 best classifier genes for AXL$^+$SIGLEC6$^+$ (AS) DCs. The UMI counts used to generate FIG. 2C. A comparison of gene expression profiles for marker genes defining AS DCs between the deeply sequenced control library (top) and the enriched samples (bottom right). Sequencing the original library at equal depth to the enriched libraries shows only low level expression (bottom left). (SEQ ID NOs. 1-7 and 9 and 10)

Applicants applied the framework described herein to target putative AS DCs by combining enrichment of HLA-DR$^+$ cells by FACS with PCR-based multiplexed molecular enrichment from a pooled RNA-seq sequence library to target the extremely rare AS DCs. In the enriched library, only 1 million reads were needed to reliably identify key discriminating genes (Villani, 2017) expressed in the nine putative AS DCs captured in the enriched HLA-DR$^+$ library (FIG. 15C). Expression of these AS DC-discriminating genes were either not detectable or showed in extremely low counts at the same level of sequencing effort in the original library, which was enriched only by FACS (FIG. 25). While the biological role of AS DCs remains to be fully elucidated, the discovery study (Villani, 2017) reported several properties relevant to the design of new therapeutic and vaccination modalities, highlighting the need to develop new strategies to enrich and profile rare cell populations like the AS DCs from many different samples to further decipher their unique properties.

Example 6—PCR Enrichment Discussion

These results demonstrate that individual cells can be enriched from single-cell libraries and that the enriched libraries faithfully represent the original expression profile. Only 1.1 million total reads were needed to identify key features in the expression profile of 10 targeted putative AS DC cells in the enriched library that were not detectable at the same level of sequencing effort in the original library (FIG. 8). Selective enrichment of target cells from large pooled single-cell sequencing libraries promises to reduce the required sequencing effort by one to two orders of magnitude while simultaneously enabling deep sequencing of high-information-content cells.

Further, the results demonstrate that individual cells can be enriched at the molecular level from complex pooled single-cell libraries and that the enriched libraries faithfully represent the targeted cells' original expression profiles. The PCR approach for targeted enrichment requires a single-cell sequencing library where cell origin is identified by a short barcode sequence, a list of barcode sequences that corresponds to cells of interest, and a set of PCR primers that complement the listed barcodes. Currently, investigators can select cells to target based on initial analysis of a shallow sequence dataset. For many cases, as few as 1000-5000 RNA-seq reads per cell are sufficient to identify cell types of interest (G. Heimberg, et al., Cell Systems, 2:239-250, 2016; DA. Jaitin, et al., Science, 343:776-779, 2014; DJ. Kliebenstein, Front. Plant Sci., 3, 2012; and AA. Pollen, et al., Nat Biotech, 32(10):239-250, 2014). In other cases, where target cells can only be identified by signatures reliant on detecting the expression of low-abundance transcripts, desirable target cells can be enriched by depleting cells identifiable as other, non-target cell types and low-quality cells (e.g. those with fewer detected UMIs). To positively identify target cells in populations defined by the expression of low-abundance transcripts, approaches that target signature genes specifically would be highly efficient (LBA. Woodruff, et al., Nucleic Acids Research, 45(3):1553-1565, 2017; SJ. Spencer, et al., ISME, 10:427-436, 2016; and B. Howie, et al., Science, 7(301), 2015).

Although the noise sources in aggregate do not have a significant effect on the precision of the expression profiles obtained from the enriched libraries (FIG. 1D, FIG. 19), modifications to the barcode and UMI sequences would enable these noise sources to be further suppressed. In this work, the cell barcode targeting primer had complementarity to the full 16 base pair sequence allowing for the greatest specificity for the targeted cell. Lengthening the barcode sequence to add downstream bases that extend beyond the 3' terminus of the enrichment primer (or alternatively, shortening the enrichment primer) would allow the extension reaction to pick up a portion of the target cell barcode from the library molecule independent of primer hybridization. Extending the length of the UMI sequence, hence its complexity, would increase the average distances between UMI sequences in the final read set and enable more stringent sequence filtering procedures to exclude erroneous reads. Primer modifications, such as 3' phosphorothioate linkages, could help maintain barcode fidelity and be combined with other design changes. Lastly, while Applicants recommend 25 cycles of PCR in the enrichment PCR, optimization to fewer PCR cycles could potentially improve the quality of enriched sequence libraries when the input library is of high quality and contains a sufficient fraction of on-target content.

Figure 26:
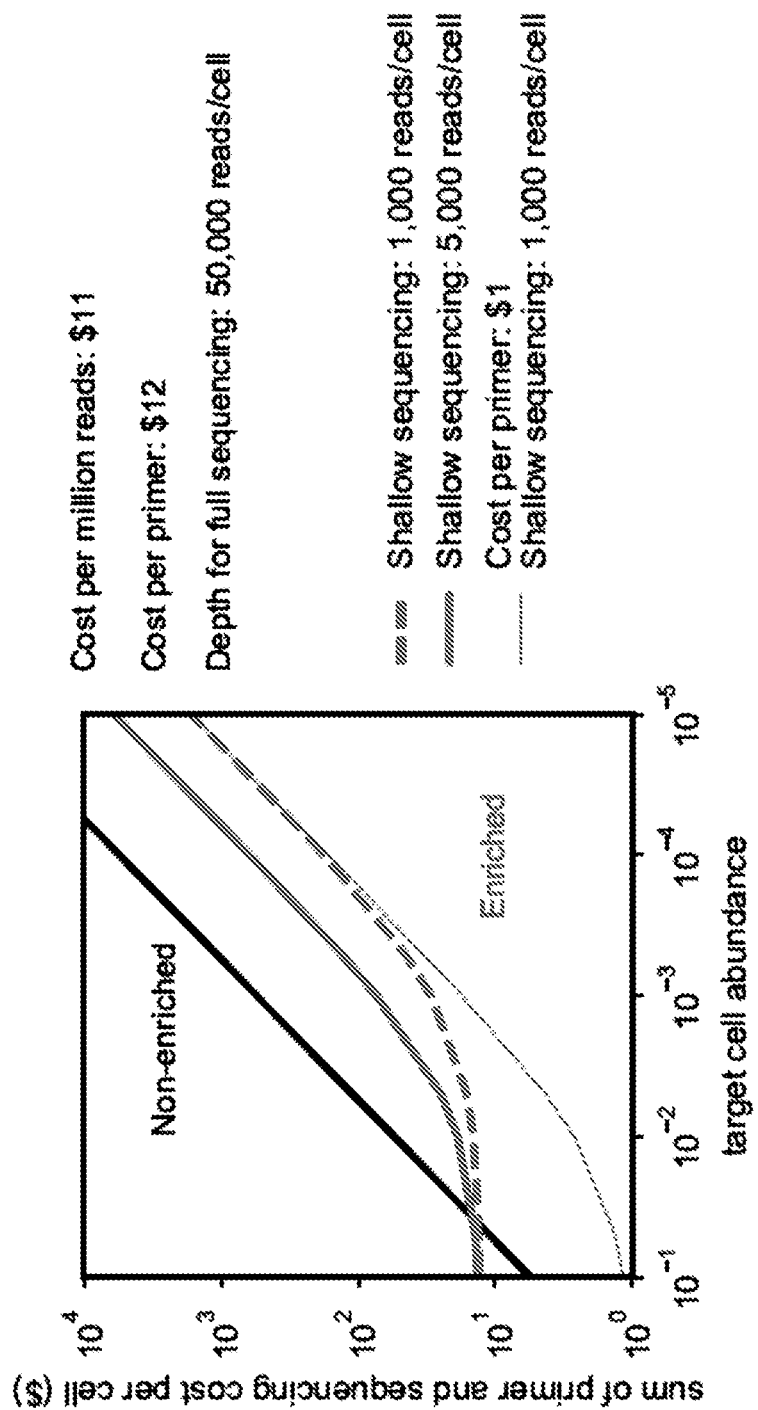
FIG. 26—Analysis of sequencing/primer synthesis trade off at different target cell abundances. The sequencing cost per cell is plotted for enriched libraries (red) and the original library (black) with target cell abundances ranging from 10% to 0.001% and the assumptions as listed. Lower read counts per cell in the initial shallow sequencing step for target identification correspond to 1) whole transcriptome profiling to identify target cell types characterized by profiling high-expression genes (1,000 reads per cell) and 2)

Target enrichment is most advantageous when targeting rare populations and the potential enrichment-fold achievable by targeting is large. In this work, Applicants utilized individual oligonucleotide primers to enrich the target cells, which is convenient for targeting small numbers of cells as would be needed for rare population studies. To explore the tradeoff in sequencing effort and the need for primer synthesis, Applicants plotted results from a simple model representing a typical current use case as a function of the abundance of the target cell population (FIG. 26). Within the assumptions of the model, targeting is favorable for target cell abundances as high as 5%. Emerging advances such as widely available small custom oligonucleotide primer pools are likely to accelerate PCR enrichment workflows and make PCR enrichment practical for target populations at abundances >5% by reducing the cost per custom primer (S. Palluk, et al., Nat. Biotech. 2018). In addition, technologies and approaches for pooled single-cell library construction are improving rapidly (HM. Kang, et al., Nat Biotech, 36(1):89-94, 2018) which promise to make sequencing, rather than pooled sample preparation, the overall workflow bottleneck, and bring attention to the need for cell targeting approaches. The enrichment protocol depends primarily on the presence of cell-specific barcodes and is readily extensible to a wide variety of pooled single-cell applications beyond expression profiling that are read out using DNA sequencing and encode cell of origin using a compact sequence barcode (GXY. Zheng, et al., Nat Biotech, 34(3): 303-311, 2016; SA. Vitak, et al., Nat. Meth., 14(3):302-308, 2017; and DA. Cusanovich, et al., Science, 348(6237):910-914, 2015). Compatible scRNA-seq approaches include 10X Genomics, Drop-seq, and Seq-well. Further development of the protocol described here or alternative approaches would be required for applications that distribute the cell identity information more sparsely across the library molecules, for example those that use dual end barcoding or long barcodes.

Importantly, target cell enrichment may have future biomedical applications. For example, the enrichment method may allow comparison of rare cell types across cellular mixtures from many subjects, such as tracking rare malignant cell states, non-malignant cell states in tumor samples, and circulating tumor cells (CTCs) in blood. In-depth analyses of particular cells of interest may enable access to more precise single-cell expression profiles and enable diagnostic, prognostic, or theranostic tests informed by quantitative (rather than binary) gene expression states that are invisible to current analytics like flow cytometry or imaging. Selective molecular enrichment of target cells from large pooled single-cell sequence libraries promises to reduce the sequencing effort required to profile rare cells by one to two orders of magnitude while simultaneously enabling selective deep sequencing of high-information-content cells.

Table 1 depicts an example primer design for targeted barcodes. The conserved portion of the primer consisted of the P5 flowcell attachment motif and the read 1 sequencing primer sequence. There was no index barcode on the forward primer. Sample de-multiplexing was carried out through use of the reverse index 2 designed as a TruSeq adapter. (SEQ ID NO. 127 and SEQ ID NOs. 39-69)

TABLE 1

| P5 and Read 1 | Single cell Barcode |
|---|---|
| AATGATACGGCGACCACCGAGATCTACACACACTCTTTCCCTACACGACGCTCTTCCGATCT | GCACTCTGTGCCTGCA |
| AATGATACGGCGACCACCGAGATCTACACACACTCTTTCCCTACACGACGCTCTTCCGATCT | CGTCAGGAGATGCCTT |
| AATGATACGGCGACCACCGAGATCTACACACACTCTTTCCCTACACGACGCTCTTCCGATCT | GGCCGATGTCGTCTTC |
| AATGATACGGCGACCACCGAGATCTACACACACTCTTTCCCTACACGACGCTCTTCCGATCT | TTAGGCAAGCACGCCT |
| AATGATACGGCGACCACCGAGATCTACACACACTCTTTCCCTACACGACGCTCTTCCGATCT | GTTACAGGTACGACCC |
| AATGATACGGCGACCACCGAGATCTACACACACTCTTTCCCTACACGACGCTCTTCCGATCT | CAGCTAATCCAAAGTC |
| AATGATACGGCGACCACCGAGATCTACACACACTCTTTCCCTACACGACGCTCTTCCGATCT | TATCAGGCAGGGATTG |
| AATGATACGGCGACCACCGAGATCTACACACACTCTTTCCCTACACGACGCTCTTCCGATCT | ATCACGAGTGACCAAG |
| AATGATACGGCGACCACCGAGATCTACACACACTCTTTCCCTACACGACGCTCTTCCGATCT | GGGTCTGGTAGCTCCG |
| AATGATACGGCGACCACCGAGATCTACACACACTCTTTCCCTACACGACGCTCTTCCGATCT | GCTCCTACAGACTCGC |
| AATGATACGGCGACCACCGAGATCTACACACACTCTTTCCCTACACGACGCTCTTCCGATCT | ACGCCGATCTGGCGTG |
| AATGATACGGCGACCACCGAGATCTACACACACTCTTTCCCTACACGACGCTCTTCCGATCT | AACACGTTCCACGCAG |

TABLE 1-continued

| P5 and Read 1 | Single cell Barcode |
|---|---|
| AATGATACGGCGACCACCGAGATCTACACACACTCTTTCCCTACACGACGCTCTTCCGATCT | TTCTCAAAGGGCACTA |
| AATGATACGGCGACCACCGAGATCTACACACACTCTTTCCCTACACGACGCTCTTCCGATCT | ACGTCAAAGTACGATA |
| AATGATACGGCGACCACCGAGATCTACACACACTCTTTCCCTACACGACGCTCTTCCGATCT | GAGTCCGCAATCACAC |
| AATGATACGGCGACCACCGAGATCTACACACACTCTTTCCCTACACGACGCTCTTCCGATCT | ACAGCCGAGTGAACGC |
| AATGATACGGCGACCACCGAGATCTACACACACTCTTTCCCTACACGACGCTCTTCCGATCT | GGTATTGCAATGTTGC |
| AATGATACGGCGACCACCGAGATCTACACACACTCTTTCCCTACACGACGCTCTTCCGATCT | TTCTCCTCACGACGAA |
| AATGATACGGCGACCACCGAGATCTACACACACTCTTTCCCTACACGACGCTCTTCCGATCT | TGCCAAATCGCACTCT |
| AATGATACGGCGACCACCGAGATCTACACACACTCTTTCCCTACACGACGCTCTTCCGATCT | TCAGATGCAGACAGGT |
| AATGATACGGCGACCACCGAGATCTACACACACTCTTTCCCTACACGACGCTCTTCCGATCT | TTCCCAGCACACAGAG |
| AATGATACGGCGACCACCGAGATCTACACACACTCTTTCCCTACACGACGCTCTTCCGATCT | CCTAGCTTCGTTTGCC |
| AATGATACGGCGACCACCGAGATCTACACACACTCTTTCCCTACACGACGCTCTTCCGATCT | ACGCCGATCTGGCGTG |
| AATGATACGGCGACCACCGAGATCTACACACACTCTTTCCCTACACGACGCTCTTCCGATCT | GTGAAGGAGGTGATTA |
| AATGATACGGCGACCACCGAGATCTACACACACTCTTTCCCTACACGACGCTCTTCCGATCT | CAGCCGAAGGACAGCT |
| AATGATACGGCGACCACCGAGATCTACACACACTCTTTCCCTACACGACGCTCTTCCGATCT | GGTGTTAGTGCCTTGG |
| AATGATACGGCGACCACCGAGATCTACACACACTCTTTCCCTACACGACGCTCTTCCGATCT | GATTCAGCACACCGCA |
| AATGATACGGCGACCACCGAGATCTACACACACTCTTTCCCTACACGACGCTCTTCCGATCT | TCATTACGTCGGGTCT |
| AATGATACGGCGACCACCGAGATCTACACACACTCTTTCCCTACACGACGCTCTTCCGATCT | ATCACGAGTCCTCTTG |
| AATGATACGGCGACCACCGAGATCTACACACACTCTTTCCCTACACGACGCTCTTCCGATCT | GACCAATAGTTATCGC |
| AATGATACGGCGACCACCGAGATCTACACACACTCTTTCCCTACACGACGCTCTTCCGATCT | CCACTACTCTCCAACC |

Example 7—Methods

Sample sourcing and FACS. This study was performed in accordance with protocols approved by the institutional review board at Partners (Brigham and Women's Hospital) and the Broad Institute. Healthy donors were recruited from the Boston-based PhenoGenetic project, a resource of healthy subjects that are re-contactable by genotype (Xia, 2012). The donors had no family history of cancer, allergies, inflammatory disease, autoimmune disease, chronic metabolic disorders, or infectious disorders. Each donor provided written informed consent for the genetic research studies and molecular testing.

For profiling HLA-DR$^+$ and the CD19$^+$ cells, PBMCs were first isolated from fresh blood within 2 hours of collection using Ficoll-Paque density gradient centrifugation as described previously (Lee, 2014). PBMC suspensions were immunostained with an antibody panel according to the manufacturer's protocol (Suppliers listed in Supplementary Table 3) designed to target live HLA-DR$^+$ cells and deplete other blood lineages (CD235a, CD3, CD4, CD8, CD19, CD56) or to target live CD19$^+$ cells and deplete other blood lineages (CD235a, CD3, CD4, CD8, HLA-DR, CD56) (Supplementary Table 3). Cells were sorted in a solution of 1×PBS and 0.04% of BSA and resuspended at a concentration of 1000 cells per μl.

10X library prep. Single-cell RNA library preparation was performed with 10X's single-cell kit according to the manufacturer's protocol. Single-cell RNA-seq library preparation was performed with the Chromium Single Cell 3' method (10X Genomics) according to the manufacturer's protocol.

Single-cell barcode enrichment. Pooled single-cell RNA-seq libraries were diluted and combined in equal volume with KAPA 2× high fidelity hot start PCR master mix. The final DNA template and total primer concentrations were 0.1 nM and 0.1 uM, respectively. For multiplex (10-15-plex) barcode amplification, forward primers consisted of sequencing adapters (62 base pairs) and cell barcode specific sequence (16 base pairs) whereas reverse primers were complimentary to the fixed truseq adaptor sequence. Hemi-specific PCR was performed with an initial hot start at 95° C. for 5 min, followed by 25 cycles of (95° C.-0.5 min, 68° C.-1 min, 72° C.-1 min), and ended with a final 4 min extension at 72° C. The reaction products were confirmed on an agarose gel. As few as 15 cycles of PCR and lower annealing temperatures were also tested and produced good results, although care should be taken when reducing cycle number to ensure that sufficient product quantity is obtained to enable purification and any desired quality control steps prior to sequencing. Each PCR was performed in triplicate to assess replicability. The PCR products were then purified by SPRI (Agentcourt, 1:1 sample:reagent ratio) and quantified with the Qubit fluorescence assay (Qubit dsDNA HS Assay Kit, ThermoFisher Scientific).

In another example, 10X libraries were diluted and added to a KAPA 2× high fidelity hot start PCR master mix at a final concentration of 0.1 nM. The 20,000 cell library was created by mixing at equal molar ratio 6 lanes of a 10X single-cell chip. For single barcode amplification, PCR primers were added at final concentration of 0.5 uM whereas for multiplex (10) barcode amplification, primers were at a final concentration of 0.1 uM. PCR was performed for 25 cycles and the final product was confirmed on an agarose gel. Each PCR was performed in triplicate to reduce noise in downstream analysis. The PCR product was then cleaned with 1:1 SPRI clean up and then quantified through a Qubit assay.

Sequencing and primary data processing. Target-enriched single-cell RNA-seq libraries were loaded at 1.8 pM on a DNA sequencer (Illumina Miniseq) where read 1 (26 bp) sequenced bases in the cell barcode and UMI and read 2 (124 bp) sequenced bases in the transcript. Primary processing of the raw data was conducted using the CellRanger pipeline (10X Genomics). Secondary analyses were carried out using custom Python scripts. The custom scripts used for secondary analysis can be found at (github.com/nranu/SC_enrichment). Replicate sequence reads were aggregated by unique molecular identifier (UMI) with secondary analysis operating on UMI counts. Any UMI that received 2 or fewer reads was removed prior to secondary analysis.

Enrichment definition. To determine enrichment level, Applicants evaluated the information content on genes identified for the enriched libraries compared to the deeply sequenced original library (control). The deeply sequenced control represented 100% in the definition of genes identified. The enriched and control libraries were down sampled to identify the fraction of total genes identified at various read depths compared to the number of genes identified in the fully sequenced control. The enrichment fold was defined as the fractional number of reads required to identify 50% of genes from the original library.

Aggregating replicates. The gene expression profiles were used to identify UMI-gene-cell barcode tuples that were high versus low confidence based on whether the UMI-gene-cell barcode appeared in three, two, or only one replicate.

Correlation analysis and Bootstrapplng. Gene expression profiles of a given cell were compared before and after enrichment by computing Pearson correlation coefficients. Correlation coefficients were calculated using the expression profiles of targeted single cells in the enriched libraries and the corresponding expression profiles within the original library. 1000 Bootstrap read samples were then generated from each dataset to enable comparing pre-enriched single-cell datasets against themselves. Bootstrap samples of both pre- and post-enrichment data matched the read depth present in the pre-enrichment library for each cell. To determine the highest expected correlation coefficient values given the statistical noise from read and UMI counting, correlations were computed among Bootstrap replicates from the pre-enrichment data derived from the same cells.

In an example, the Pearson correlation of single-cell gene expression profiles was determined for the deeply sequenced pre-enrichment vs targeted enriched samples. The correlation was calculated for equal number of UMIs per cell detected across the pre and post enriched samples. The UMIs for a given cell barcode were then bootstrapped 1000 times for the correlation comparison of enriched vs pre-enriched and for resampled pre-enriched vs pre-enriched.

Principal Components Analysis (PCA) and clustering. Feature selection was performed by excluding genes detected in fewer than three cells and removing genes that had low coefficients of variation with a nonparametric Loess regression using a window of 33%. This selection identified approximately 1000 highly variable genes that were well-represented in the dataset. Next, the UMI counts per cell were normalized by the median of UMI counts across all cells and loge transformed with a pseudocount of 1 and finally, Z-transformed. PCA was performed with the original deeply sequenced library as a training set with the enriched data subsequently projected onto the components defined in analysis of the original library.

In an example, the unexpressed genes across all cells were removed, the UMI counts per cell were normalized by the median of UMI counts across all cells, genes with high variation in relation to their expression levels were selected (650 genes), loge transformed with a pseudocount of 1 and then were Z-transformed. The Z-transformed expression data was then used in PCA with each of the enriched barcodes sequentially. The data were then clustered by k means which correctly predicted the clustering of pre and post enriched single-cell barcodes 24 out of 25 times.

Poisson Modeling of non-unique UMI-gene pairs. The theoretical distribution of repeats in unique UMIs is represented by a Poisson distribution with a mean of the ratio between the unique number of UMI in the original library and the total number of UMIs observed. The control and enriched distribution was then plotted for all barcodes amplified for the frequency at which each UMI within those barcodes clashed with barcodes from a different library.

Targeting putative $AXL^+$ $SIGLEC6^+$ DC (AS DC) cells. To identify AS DC 'purity scores', Applicants used a previously described signature scoring system (Villani, 2017). Briefly, Applicants assigned a quantitative score to each cell based on the overall expression of a pre-defined signature gene set after correcting for 'drop-out' effects that commonly characterize single-cell data (Shalek, 2015). The reported AS DC population purity score was based on the top 10 most discriminative genes previously reported: AXL, PPP1R14A, SIGLEC6, CD22, DAB2, S100A10, FAM105A, MED12L, ALDH2, and LTK. This 'purity score' was used to identify the most likely AS DC candidate cells in the $HLA-DR^+$ 10X library. Note that not all of the 10 classifier-genes were expressed across the putative AS DC candidates in the 10X library, which could be explained by different dropout rates characterizing the 10X library and Smart-Seq2 libraries, the latter having been used in the original AS DC discovery and characterization study (Villani, 2017).

Target cell enrichment calculation. In FIG. 1B, the enriched and control datasets were down sampled to identify the number of total genes identified at various read depths. Reported enrichment fold values were calculated by determining the fold-difference in overall sequencing effort required to identify expression of 50% of the "detectable genes" for the target cell out of the maximum number of "detectable genes" for a particular cell, defined operationally here as the total number of genes detected in the deeply sequenced original library. Applicants also performed a similar analysis for low abundance UMIs (UMIs with 3 reads in the deeply sequenced pre-library) and found that the enrichment values for low abundance UMIs was slightly lower but similar (also about 100-fold) than found in the analysis for all UMIs, indicating good sensitivity of the method for detecting low-abundance UMIs.

UMI-gene pair uniqueness analysis. To determine the frequency of cases in which UMI sequences "collide" on a given gene and how this was affected by the PCR enrichment procedure, Applicants modeled the expected frequency of UMI collisions and compared these results to experimental data. Applicants detect "collisions" as observations of an identical UMI-gene pair associated with more than one cell. The theoretical distribution of such events is modeled as a Poisson distribution with a mean equal to the ratio of the unique number of UMIs in the original library to the total number of UMIs observed. The UMI-gene pairs that were identified in the enriched cells was then compared to all existing UMI-gene pairs in the deeply sequenced original samples. The sequencing effort was normalized on a per cell basis.

Sequencing cost model:

$$\text{Total Cost} = \frac{(\text{Cost}_{read}) \times (\text{Reads}_{cell})}{\text{Abundance}} \quad \text{Non-enriched}$$

$$\text{Total Cost} = \text{Cost}_{primer} + \underbrace{\frac{(\text{Cost}_{read}) \times (\text{Reads}_{cell})}{(\text{Abundance}) \times (\text{Enrich}_{fold})}}_{\substack{\text{Enriched} \\ \text{sequencing}}} + \underbrace{\frac{(\text{Cost}_{read}) \times (\text{Reads}_{cell})}{\text{Abundance}}}_{\substack{\text{Shallow} \\ \text{seqeuencing}}} \quad \text{Enriched}$$

TABLE 2

List of antibodies used to enriched for the LIN⁻HLA-DR⁺ cell fraction

| Antigen | Fluorochrome | Clone | Catalogue | Manufacturer |
| --- | --- | --- | --- | --- |
| CD19 | FITC | HIB19 | 302206 | Biolegend |
| CD3 | PerCP Cy5.5 | HIT3a | 300327 | BD |
| CD235a | PE/Cy7 | HI264 | 349111 | Biolegend |
| CD4 | PE | RPA-T4 | 300508 | Biolegend |
| CD8 | APC | SK1 | 344722 | Biolegend |
| CD14 | APC-Cy ™ 7 | MφP9 | 557831 | BD |
| HLA-DR | BV605 | L243 | 307640 | Biolegend |
| CD56 | BV711 | HCD56 | 318336 | Biolegend |
| DAPI | | | 422801 | Biolegend |

Example 8—Pilot Experiment for PCR Enrichment

Primers designed to 14 base pair barcode sequences leads to non-specific amplifiable sequences. Designing a primer 4 bp short allows ~400 more amplifiable sequences if assuming ideal specificity.

```
                                        (SEQ ID NO. 95)
Barcode 1      CTATTGTGATGGTC (maps to 282 genes)

(SEQ ID NO. 96)
Barcode 2      GAGGATCTTGCTTT (maps to 298 genes)

(SEQ ID NO. 97)
Barcode 3      GGCCGAACTCGTAG (maps to 339 genes)
```

Specificity of amplification can be tested using 3 primer sets per barcode (trimmed from 3' end above) (10 bp barcode; 12 bp barcode; and 14 bp barcode) and including a sequence complementary to the P7 Illumina adaptor sequence. The combination of barcode and adaptor should result in high specificity (forward primer: (P7)—(barcode); reverse primer: (P5)—Read 1 sequence). PCR amplification includes testing 5, 10, and 15 cycles of amplification at ~65 C annealing temperature. The amplification is then analyzed by quantifying crosstalk in primer sets vs # of cycles and the number of times that the unique barcode-combination gene pair defined above is incorrect in sequencing. The enrichment factor is also quantified and compared to the number of cycles. The number of reads correctly mapped to the gene of interest before and after enrichment is calculated.

```
                                        (SEQ ID NO. 98)
(P7 sequence: CAAGCAGAAGACGGCATACGAGAT).
```

Applicants also test PCR enrichment with a known sequencing library. The library includes the following barcode sequences (BC) that can be tested for enrichment (Table 3). Forward primers are designed to enrich each barcode sequence from the library.

Specificity of amplification can be tested using 3 primer sets per barcode (trimmed from 3' end above) (10 bp barcode; 12 bp barcode; and 14 bp barcode) as previously performed. (SEQ ID NOs. 99-125)

TABLE 3

| Index | BC | Counts | Primer |
| --- | --- | --- | --- |
| 105 | AGAATGGACGACAT | 95 | CAAGCAGAAGACGGCATACGAGAT ATGTCGTCCATTCT |
| 401 | GGCGACACAGAGTA | 91 | CAAGCAGAAGACGGCATACGAGAT TACTCTGTGTCGCC |
| 403 | GGCTAATGGATGAA | 29 | CAAGCAGAAGACGGCATACGAGAT TTCATCCATTAGCC |
| 413 | GTACAGTGTCGACA | 30 | CAAGCAGAAGACGGCATACGAGAT TGTCGACACTGTAC |
| 72 | ACGGAGGAACCTGA | 382 | CAAGCAGAAGACGGCATACGAGAT TCAGGTTCCTCCGT |
| 558 | TGTAGGTGGTTACG | 400 | CAAGCAGAAGACGGCATACGAGAT CGTAACCACCTACA |
| 22 | AAGCCATGGCCTTC | 790 | CAAGCAGAAGACGGCATACGAGAT GAAGGCCATGGCTT |
| 307 | GAAATACTCCCTAC | 787 | CAAGCAGAAGACGGCATACGAGAT GTAGGGAGTATTTC |
| 265 | CGTAGCCTTAGTCG | 1585 | CAAGCAGAAGACGGCATACGAGAT CGACTAAGGCTACG |

Example 9—Extracting Single-Cell Transcriptomes from SeqWell Libraries Reagents Tagmented SeqWell library—It is essential that the library is already tagmented
List of barcodes to be isolated
Kapa HiFi mix P7 primer
(SEQ ID NO. 124)
CAAGCAGAAGACGGCATACGAGAT P5-TSO_Hybrid
(SEQ ID NO. 126)
AATGATACGGCGACCACCGAGATCTACACGCCTGTCCGCGGAAGCAGTGG
TATCAACGCAGAGT*A*C Equipment
  Thermal cycler
  96 well magnet
Designing transcriptome-specific primer (Automated design implemented in scRNASeqPrimers_BC.m Matlab script)
  1. Each selected barcode is fused to 20 nucleotides of the universal primer sequence directly upstream from the barcode in the SeqWell library
  2. A series of iterative single base 5' truncations are made from the original fusion.
  3. The melting temperature of each construct is calculated.
  4. The primer with a melting temperature closest to 65° C. is chosen for each barcode
  5. Order primers in 96 well plate pre-dissolved at 10 uM.
Amplifying single-cell libraries
  1. A PCR reactions for each barcode is created according to:
    >1pg tagmented SeqWell library
    25 uL Kap HiFi 2× mix
    1 uL 10 uM barcode-specific primer
    1 uL 10 uM P7 primer
    water to a total of 50 uL
  2. Amplify PCR reactions according to:
    95° C. 3 minutes
    25 cycles of:
      98° C. 20 s
      67° C. 20 s
      72° C. 30 s
    Then:
    4° C. forever
  3. Create 2nd PCR reaction mix according to/barcode:
    25 uL Kap HiFi 2× mix
    1 uL 10 uM barcode-specific primer
    1 uL 10 uM P7 primer
    22 uL water
  4. Aliquot 49 uL of mix out into 96 well PCR plate
  5. Transfer 1 uL of first PCR reaction to 2nd reaction
  6. Amplify reaction according to:
    95° C. 3 minutes
    15 cycles of:
      98° C. 20 s
      67° C. 20 s
      72° C. 30 s
    Then:
    4° C. forever
  7. Purify reactions using AmPure beads
  8. Analyze a sample of 12 reactions by BioA
  9. Depending on the complexity of the library, you may need more or less amplification
    a. If libraries are over-amplified, dilute Reaction 1 prior to adding to reaction 2.
    b. If libraries are under-amplified, increase cycles in 2nd reaction
  10. Once appropriate conditions are found, quantitate all libraries and pool at equal concentrations
  11. Sequence library like a normal SeqWell library.

Example 10—Isolating Single-Cell Transcriptomes

Figure 10:
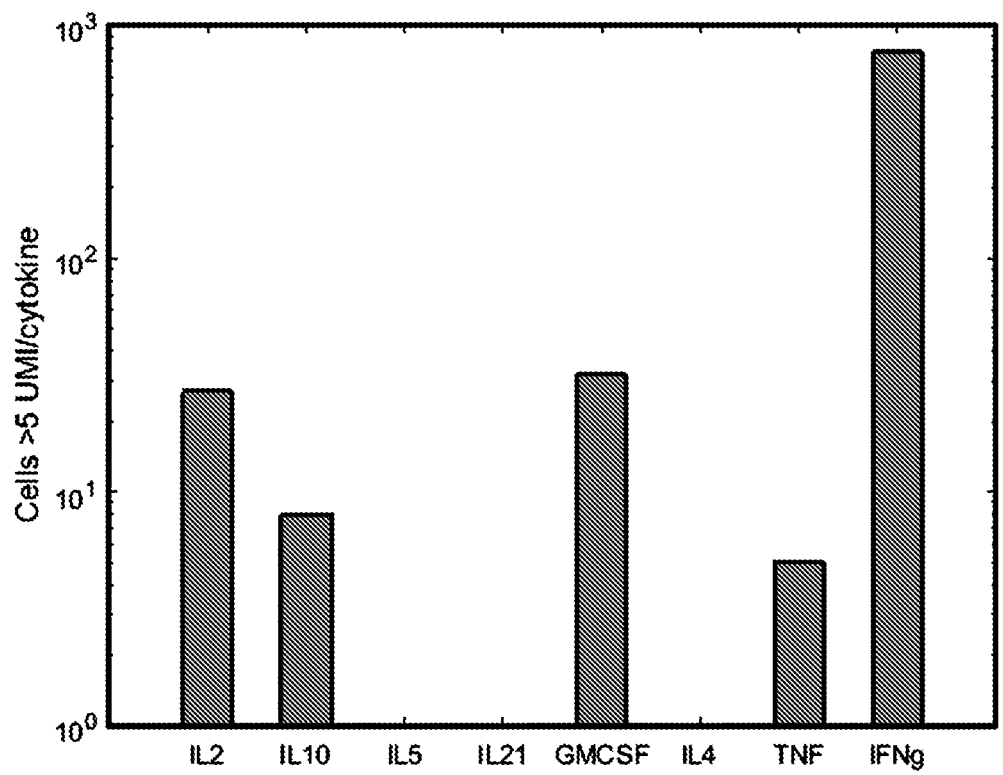
FIG. 10—Graph showing the number of cells expressing IL2, IL10, IL5, IL21, GM-CSF, IL4, TNF, and IFNg. A RNA sequencing library was prepared from a population of cells, transcripts expressing each cytokine were isolated, and the transcripts were sequenced to count the number of cells as determined by the number of unique barcodes.

Single-cell transcriptomes can be isolated by first identifying the barcode in the cell type of interest from a single-cell RNA sequencing library, e.g., a SeqWell or a DropSeq library. FIG. 9 shows a schematic diagram of how the barcode is identified. A labeled oligo can be designed that will hybridize to a transcript that is found in the cell type of interest. The oligo-transcript complex can then be isolated using the label on the oligo and the transcript can be sequenced to identify the sequence of the barcode of the cell type of interest. In FIG. 10, oligos for the genes shown were used to quantitate the number of cells expressing the cytokines shown. The transcripts expressing a particular cytokine were isolated and sequenced using the methods described, with each unique barcode identified representing an individual cell.

Figure 12:
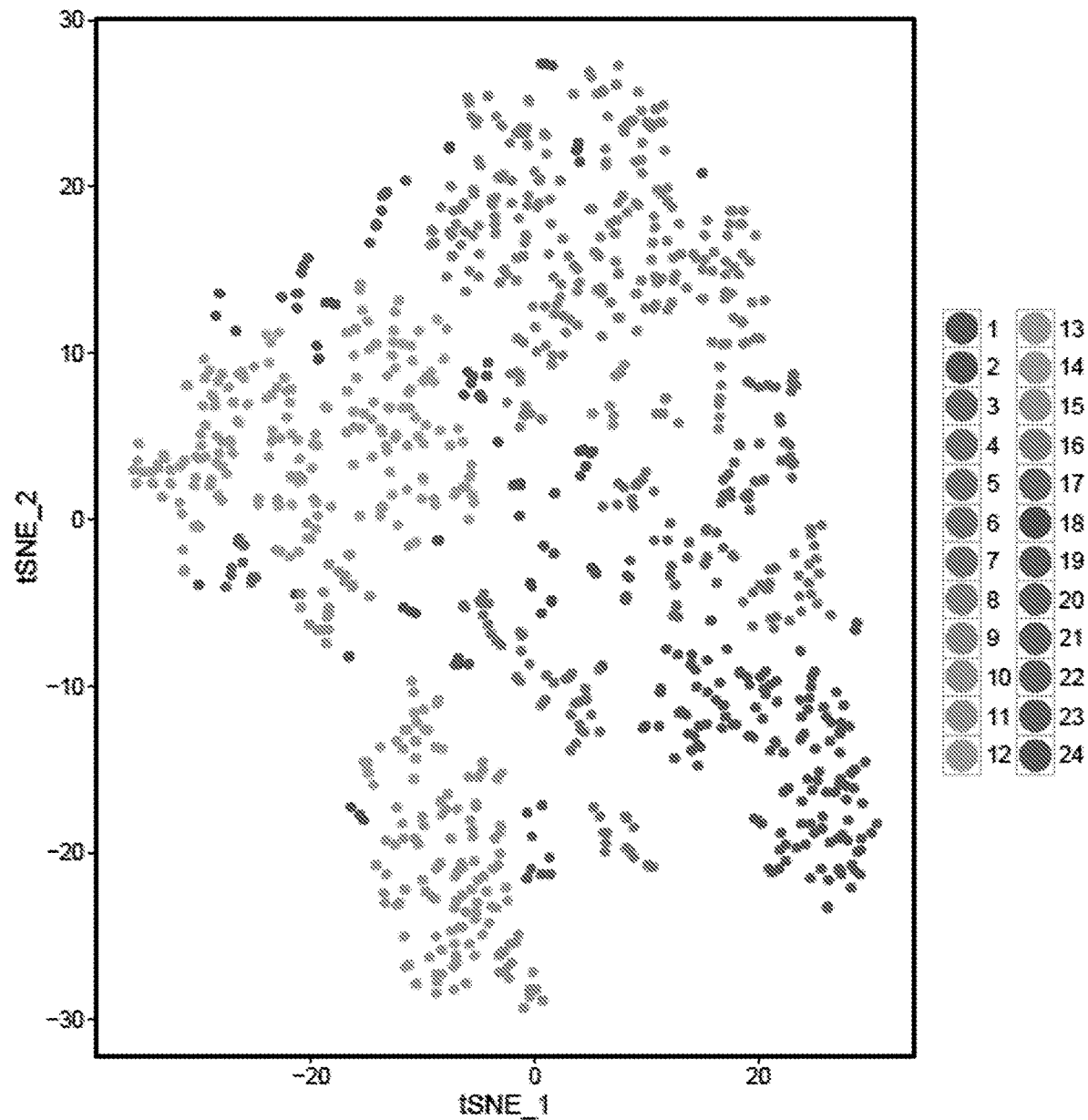
FIG. 12—tSNE plot of single-cell transcriptomes generated using the methods described herein.
Figure 13:
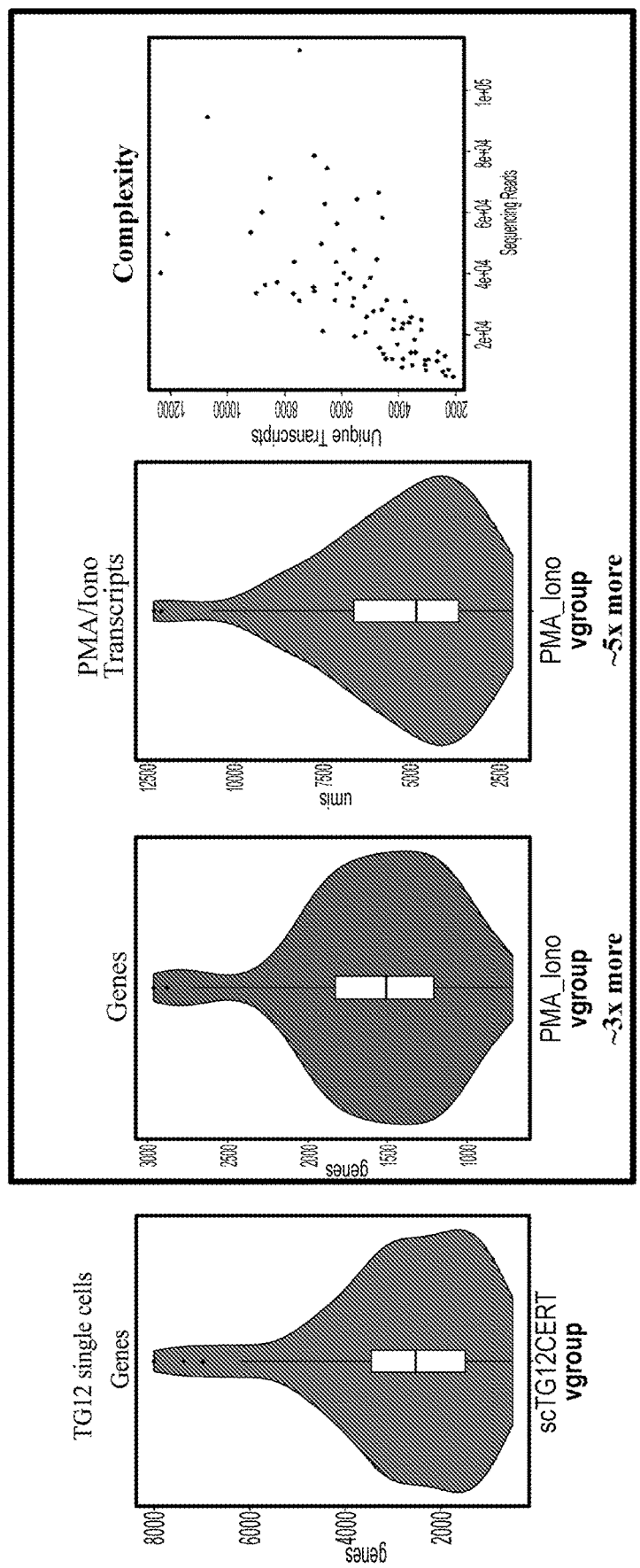
FIG. 13—Series of graphs showing, from right to left, the number of genes detected in TG12 cells from a RNA sequencing library, the number of genes detected in TG12 cells using the library of a single-cell transcriptome described herein, the number of transcripts in PMA/iono stimulated cells using the single-cell transcriptome library described herein, and complexity—the number of unique transcripts as a function of the number of sequencing reads.
Figure 14:
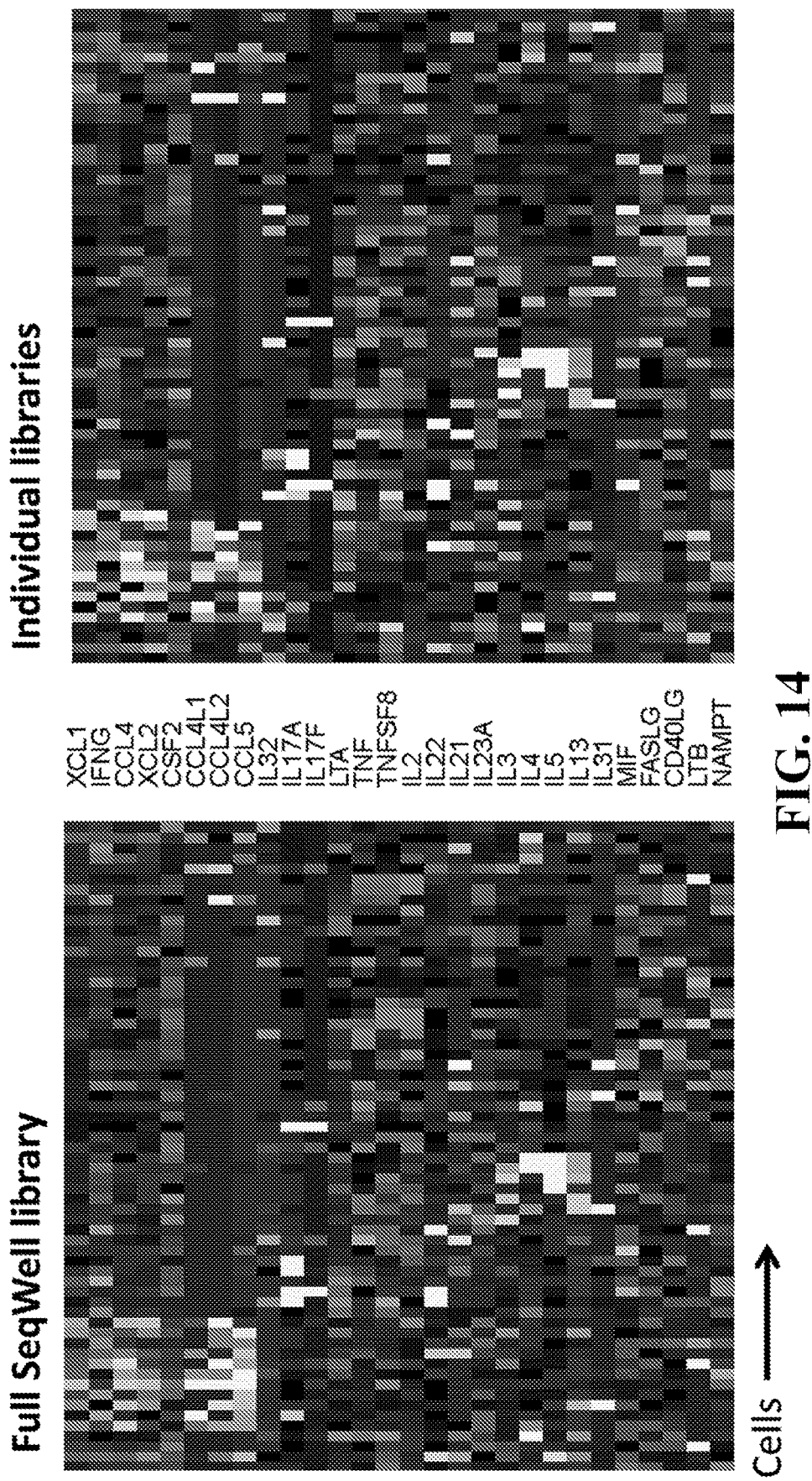
FIG. 14—Series of graphs showing a heatmap of gene expression in individual cells using the RNA sequencing library (left) or the library of a single-cell transcriptome described herein (right).

Once the barcode of the cell type of interest is identified, the transcriptome of the cell can be isolated by amplifying the transcriptome of cells having the unique barcode. FIG. 11 shows a schematic of the amplification reaction. Each transcript will have universal primers at the 5' end and 3' end with the barcode between the universal primer and the cDNA at the 5' end. The transcripts of only those cells having the barcode can be amplified by using primers which contain universal primer sequence (15 bp) and barcode sequence (12 bp) on the 5' end. On the 3' end, universal primers are used. FIG. 12 shows tSNE plots of single-cell transcriptomes of PMA/iono stimulated cells generated using the methods described. PMA/iono stimulates cytokine production. FIG. 13 shows the number of genes detected for each single-cell transcriptome using the methods described for TG12 cells. 3× more genes were identified in libraries generated for single cells than when assaying the transcriptome from a full RNA sequencing library (in this case a SeqWell library). For PMA/iono stimulated cells, the number of transcripts from libraries of single-cell transcriptomes are also shown. For 66/76 single-cell transcriptomes, there were >500 genes or 1000 transcripts identified without sequencing to saturation. A large number of T cell receptor genes were identified. A comparison was done of transcription levels in single cells assayed from the full RNA sequencing library (in this case a SeqWell library) or from the libraries of a single-cell transcriptome. FIG. 14 shows a heatmap comparison of expression levels in selected cells for selected target genes. The results demonstrate that similar results are obtained using both techniques. This suggests there is no PCR effect due to the additional amplification reactions associated with creating the library for the individual cell.

REFERENCES

M. Enge, H E. Arda, M. Mignardi, J. Beausang, R. Bottino, S K. Kim, and S R. Quake. Single-cell analysis of human pancreas reveals transcriptional signatures of aging and somatic mutation patterns. Cell, 171(2):321-330, 2017.

T M. Gierahn, M R. Wadsworth, TK. Hughes, BD. Bryson, A. Butler, R. Satija, S. Fortune, J C. Love, and AK.

Shalek. Seq-well: portable, low-cost RNA sequencing of single cells at high throughput. Nat Meth, 14(4):395-398, 2017.

X. Han, R. Wang, Y. Zhou, L. Fei, H. Sun, S. Lai, A. Saadatpour, Z. Zhou, H. Chen, F. Ye, D. Huang, Y. Xu, W. Huang, M. Jiang, X. Jiang, J. Mao, Y. Chen, C. Lu, J. Xie, Q. Fang, Y. Wang, R. Yue, T. Li, H. Huang, SH. Orkin, GC. Yuan, M. Chen, and G. Guo. Mapping the mouse cell atlas by Microwell-seq. Cell, 172:1091-1107, 2018.

A M. Klein, L. Mazutis, I. Akartuna, N. Tallapragada, A. Veres, V. Li, L. Peshkin, D A. Weitz, and Kirschner M W. Droplet barcoding for single-cell transcriptomics applied to embryonic stem cells. Cell, 161(5):1187-1201, 2015.

E Z. Macosko, A. Basu, R. Satija, J. Nemesh, K. Shekhar, M. Goldman, I. Tirosh, A R. Bialas, N. Kamitaki, E M. Martersteck, J J. Trombetta, D A. Weitz, J R. Sanes, A K. Shalek, A. Regev, and S A. McCarroll. Highly parallel genome-wide expression profiling of individual cells using nanoliter droplets. Cell, 161(5):1202-1211, 2015.

G L. Manno, D. Gyllborg, S. Codeluppi, K. Nishimura, C. Salto, A. Zeisel, L E. Borm, SRW. Stott, E M. Toledo, J C. Villaescusa, P. Lonnerberg, J. Ryge, R A. Barker, E. Arenas, and S Linnarsson. Molecular diversity of midbrain development in mouse, human, and stem cells. Cell, 167(2):566-580, 2016.

CC. Ooi, GL. Mantalas, W. Koh, NF. Neff, T. Fuchigami, D J. Wong, R J. Wilson, S. Park, S S. Gambhir, S R. Quake, and S X. Wang. High-throughput full-length single-cell mRNAseq of rare cells. PLoS ONE, 12(11), 2017.

MJT. Stubbington, B. Mahata, V. Svensson, A. Deonarine, J K. Nissen, A G. Betz, and S A. Teichmann. An atlas of mouse CD4+ T cell transcriptomes. Bio Direct, 10, 2015.

SC. Bendall and GP. Nolan. From single cells to deep phenotypes in cancer. Nat Biotech, 30(7):639-647, 2012.

A K. Shalek, R. Satija, Shuga J., J J. Trombetta, D. Gennert, D. Lu, P. Chen, R S. Gertner, J T. Gaublomme, N. Yosef, S. Schwartz, B. Fowler, S. Weaver, J. Wang, X. Wang, R. Ding, R. Raychowdhury, N. Friedman, N. Hacohen, H. Park, A P. May, and A. Regev. Single-cell RNA-seq reveals dynamic paracrine control of cellular variation. Nature, 510:363-369, 2014.

A C. Villani, R. Satija, G. Reynolds, S. Sarkizova, K. Shekhar, J. Fletcher, M. Griesbeck, A. Butler, S. Zheng, S. Lazo, E. Jardine, D. Dixon, E. Stephenson, E. Nilsson, I. Grundberg, D. McDonald, A. Filby, W. Li, P. Jager, 0. Rozenblatt-Rosen, A A. Lane, M. Haniffa, A. Regev, and N Hacohen. Single-cell RNA-seq reveals new types of human blood dendritic cells, monocytes, and progenitors. Science, 356(6335), 2017.

C. Benz, M R. Copley, D G. Kent, S. Wohrer, A. Cortes, N. Aghaeepour, E. Ma, H. Mader, K. Rowe, C. Day, D. Treloar, R R. Brinkman, and C J Eaves. Hematopoietic stem cell subtypes expand differentially during development and display distinct lymphopoietic programs. Cell Stem Cell, 10:273-283, 2012.

D. Grun, A. Lyubimova, L. Kester, K. Wiebrands, 0. Basak, N. Sasaki, H. Clevers, and A V. Oudenaarden. Single-cell messenger RNA sequencing reveals rare intestinal cell types. Nature, 525:251-255, 2015.

B. Mahata, X. Zhang, A A. Kolodziejczyk, V. Proserpio, L. Haim-Vilmovsky, A E. Taylor, D. Hebenstreit, F A. Dingler, V. Moignard, B. Gottgens, W. Arlt, ANJ. McKenzie, and S A. Teichmann. Single-cell RNA sequencing reveals T helper cells synthesizing steroids de novo to contribute to immune homeostasis. Cell Rep, 7:1130-1142, 2014.

A E. Saliba, A J. Westermann, S A. Gorski, and J. Vogel. Single-cell RNA-seq: advances and future challenges. Nuc. Acids Res., 42(14), 2014.

Z. Xia, Q. Liu, C T. Berger, B T. Keenan, A. Kaliszewska, PC. Cheney, GP. Srivastava, I W. Castillo, P L. De Jager, and G. Alter. A 17q12 allele is associated with altered NK cell subsets and function. J. Immunol., 188(7), 2012.

M N. Lee, C. Ye, A C. Villani, T. Raj, W. Li, T M. Eisenhaure, S H. Imboywa, P I. Chipendo, F A. Ran, K. Slowikowski, L D. Ward, K. Raddassi, C. McCabe, M R. Lee, I Y. Frohlich, D A. Hafler, M. Kellis, S. Raychaudhuri, F. Zhang, BE. Stranger, C O. Benoist, P L. De Jager, A. Regev, and N. Hacohen. Common genetic variants modulate pathogen-sensing responses in human dendritic cells. Science, 343(6975), 2014.

G. Heimberg, R. Bhatnagar, H. El-Samad, and M. Thomson. Low dimensionality in gene expression data enables the accurate extraction of transcriptional programs from shallow sequencing. Cell Systems, 2:239-250, 2016.

D A. Jaitin, E. Kenigsberg, H. Keren-Shaul, N. Elefant, F. Paul, I. Zaretsky, A. Mildner, N. Cohen, S. Jung, A. Tanay, and I. Amit. Massively parallel single cell RNA-seq for marker-free decomposition of tissues into cell types. Science, 343:776-779, 2014.

D J. Kliebenstein. Exploring the shallow end; estimating information content in transcriptomics studies. Front. Plant Sci., 3, 2012.

A A. Pollen, T J. Nowakowski, J. Shuga, X. Wang, A A. Leyrat, JSH. Lui, N. Li, L. Szpankowski, B. Fowler, N. Chen, P. and Ramalingam, G. Sun, M. Thu, M. Norris, R. Lebofsky, D. Toppani, D W. Kemp, M. Wong, B. Clerkson, BN. Jones, S. Wu, L. Knutsson, B. Alvarado, J. Wang, L S. Weaver, A P. May, R C. Jones, M A. Unger, A R. Kriegstein, and JAA. West. Low-coverage single-cell mRNA sequencing reveals cellular heterogeneity and activated signaling pathways in developing cerebral cortex. Nat Biotech, 32(10):239-250, 2014.

LBA. Woodruff, T E. Gorochowski, N Roehner, T S. Mikkelsen, D Densmore, DB. Gordon, R Nicol, and CA. Voigt. Registry in a tube: multiplexed pools of retrievable parts for genetic design space exploration. Nucleic Acids Research, 45(3):1553-1565, 2017.

S J. Spencer, M V. Tamminen, S P. Preheim, M T. Guo, A W. Briggs, I L. Brito, D A. Weitz, LK. Pitkanen, F. Vigneault, M P. Virta and E J. Alm. Massively parallel sequencing of single cells by epicPCR links functional genes with phylogenetic markers. ISME, 10:427-436, 2016.

B. Howie, A M. Sherwood, A D. Berkebile, J Berka, R O. Emerson, D W. Williamson, I. Kirsch, M Vignali, M J. Rieder, C S. Carlson, and H S. Robins. High-throughput pairing of T cell receptor α and β sequences. Science, 7(301), 2015.

S. Palluk, D H. Arlow, T. de Rond, S. Barthel, J S. Kang, R. Bector, H M. Baghdassarian, A N. Truong, P W. Kim, A K. Singh, N J. Hillson, and J D. Keasling. De novo DNA synthesis using polymerase-nucleotide conjugates. Nat. Biotech. 2018.

H M. Kang, M. Subramaniam, S. Targ, M. Nguyen, L. Maliskova, E. McCarthy, E. Wan, S. Wong, L. Byrnes, C M. Lanata, RE. Gate, S. Mostafavi, A. Marson, N. Zaitlen, L A. Criswell, and C J. Ye. Multiplexed droplet single-cell RNA sequencing using natural genetic variation. Nat Biotech, 36(1):89-94, 2018.

GXY. Zheng, B T. Lau, M. Schnall-Levin, M. Jarosz, J M. Bell, C M. Hindson, S. Kyriazopoulou-Panagiotopoulou, D A. Masquelier, L. Merrill, J M. Terry, P A. Mudivarti, P W. Wyatt, R. Bharadwaj, A J. Makarewicz, Y. Li, P.

Belgrader, A D. Price, A J. Lowe, P. Marks, G M. Vurens, P. Hardenbol, L. Montesclaros, M. Luo, L. Greenfield, A. Wong, D E. Birch, S W. Short, K P. Bjornson, P. Patel, E S. Hopmans, C. Wood, S. Kaur, GK. Lockwood, D. Stafford, J P. Delaney, I. Wu, H S. Ordonez, S M. Grimes, S. Greer, J Y. Lee, K. Belhocine, K M. Giorda, W H. Heaton, G P. McDermott, Z W. Bent, F. Meschi, N O. Kondov, R. Wilson, J A. Bernate, S. Gauby, A. Kindwall, C. Bermejo, A N. Fehr, A. Chan, S. Saxonov, Ness KSD., B J. Hindson, and H P. Ji. Haplotyping germline and cancer genomes with high-throughput linked-read sequencing. Nat Biotech, 34(3):303-311, 2016.

S A. Vitak, K A. Torkenczy, J L. Rosenkrantz, A J. Fields, L. Christiansen, M R. Wong, L. Carbone, F J. Steemers, and A. Adey. Sequencing thousands of single-cell genomes with combinatorial indexing. Nat. Meth., 14(3):302-308, 2017.

D A. Cusanovich, R. Daza, A. Adey, H A. Pliner, L. Christiansen, K L. Gunderson, F J. Steemers, C. Trapnell, and J. Shendure. Multiplex single-cell profiling of chromatin accessibility by combinatorial cellular indexing. Science, 348(6237):910-914, 2015.

LBA. Woodruff, T E. Gorochowski, N Roehner, T S. Mikkelsen, D Densmore, D B. Gordon, R Nicol, and C A. Voigt. Registry in a tube: multiplexed pools of retrievable parts for genetic design space exploration. Nucleic Acids Research, 45(3):1553-1565, 2017.

The invention is further described by the following numbered paragraphs:

1. A method for identifying a barcode associated with transcripts from a single cell in a library of transcripts comprising:

providing a library of transcripts from a plurality of cells, with transcripts from each cell comprising a unique barcode;

contacting the library of transcripts with a labeled oligonucleotide that is complementary to a target transcript encoding a specific T cell receptor or a specific B cell receptor under conditions sufficient for the labeled oligonucleotide to hybridize with the target transcript; and separating the labeled oligonucleotide hybridized to the target transcript from the library of transcripts;

thereby separating cell barcodes of cells expressing the T cell receptor or B cell receptor.

2. The method of paragraph 1, wherein the single cell is a T cell or a B cell.

3. A method for identifying a barcode associated with transcripts from a single cell in a library of transcripts comprising:

providing a library of transcripts from a plurality of cells, with transcripts from each cell comprising a unique barcode;

contacting the library of transcripts with a labeled oligonucleotide that is complementary to a target transcript under conditions sufficient for the labeled oligonucleotide to hybridize with the target transcript; and separating the labeled oligonucleotide hybridized to the target transcript from the library of transcripts;

thereby separating cell barcodes of cells expressing the target of interest.

4. The method of any of paragraphs 1-3, further comprising sequencing the barcode in the target transcript(s).

5. The method of paragraph 4, wherein the barcode is sequenced by pyrosequencing, single-molecule real-time sequencing, ion torrent sequencing, sequencing by synthesis, sequencing by ligation, or Sanger sequencing.

6. The method of paragraph 4 or 5, further comprising counting the unique barcodes that are identified as a measure of the number of cells that express the target transcript, wherein each unique barcode identifies a single cell.

7. The method of any of paragraphs 4-6, wherein the method is a method of identifying a transcriptome from a single cell and further comprises amplifying transcripts from the single cell based on the unique barcode.

8. The method of paragraph 7, further comprising sequencing the amplified transcripts.

9. The method of any of paragraphs 1-8, wherein the library of transcripts is a single cell RNA sequencing library.

10. The method of paragraph 9, wherein the single cell RNA sequencing library is generated by 3' digital gene expression (DGE), SeqWell, or DropSeq.

11. The method of any of paragraphs 1-10, wherein the library of transcripts is generated from 50,000 cells or more.

12. The method of any of paragraphs 7-11, wherein transcripts that occur at a frequency of less than $1:10^8$ to $1:10^9$ in the library of transcripts are identified.

13. The method of any of paragraphs 1-12, wherein the single cell is a cell type that is present at a frequency of less than 1%-0.001%.

14. The method of any of paragraphs 1-13, wherein the target transcript encodes a cytokine, a T cell receptor, a B cell receptor, a pathogen transcript, a chemokine, a circulating tumor cell marker, or a cell activation marker.

15. The method of paragraph 14, wherein the circulating tumor cell marker is selected from EpCAM, EphB4, EGFR, CEA, HER2, or MUC-1.

16. The method of paragraph 14, wherein the cell activation marker is selected from CD154, CD137, CD134, CD278, or CD69.

17. The method of any of paragraphs 1-16, wherein the single cell is a tumor cell, a T cell, a B cell, an NK cell, a cytokine-secreting cell, a dendritic cell, or a pathogen-infected cell.

18. The method of any of paragraphs 1-17, wherein the plurality of cells comprises cultured cells, some or all of a tumor, a tissue sample, a bone marrow sample, or a blood sample.

19. The method of any of paragraphs 1-18, wherein the labeled oligonucleotide comprises a biotin label.

20. The method of paragraph 19, wherein the separating the labeled oligonucleotide hybridized to the target transcript from the library of transcripts comprises contacting the biotin-labeled oligonucleotide hybridized to the target transcript with streptavidin.

21. The method of paragraph 20, wherein the streptavidin is conjugated to a bead.

22. The method of any of paragraphs 1-21, wherein the barcode is 10-15 nucleotides in length.

23. The method of paragraph 7, wherein amplifying the transcripts from the single cell comprises:

providing a library of transcripts from a plurality of cells, with transcripts from each cell comprising a unique barcode, and wherein the library comprises uracil;

amplifying the transcripts having the unique barcode by contacting the library of transcripts with a 5' primer and a 3' primer, wherein the 5' primer or the 3' primer comprises a nucleotide sequence that is complementary to the unique barcode of the single cell and a polymerase that does not recognize uracil;

treating the amplified transcripts with uracil DNA glycosylase (UDG) and exonuclease; and amplifying the transcripts treated with uracil DNA glycosylase (UDG) and exonuclease.

24. A method for isolating a transcriptome of a single cell from a library of transcripts comprising:

providing a library of transcripts from a plurality of cells, with transcripts from each cell comprising a unique barcode;

contacting the library of transcripts with a 5' primer and a 3' primer, wherein the 5' primer or the 3' primer comprises a nucleotide sequence that is complementary to the unique barcode of the single cell; and amplifying the transcripts comprising the unique barcode of the single cell;

thereby obtaining a plurality of transcripts from the single cell.

25. The method of paragraph 24, wherein:

(a) the 5' primer comprises a nucleotide sequence that is complementary to a 5' universal primer site contained in each transcript of the library of transcripts and a nucleotide sequence that is complementary to the unique barcode and the 3' primer comprises a nucleotide sequence that is complementary to a 3' universal primer site contained in each transcript of the library of transcripts;

(b) the 5' primer comprises a nucleotide sequence that is complementary to a 5' universal primer site contained in each transcript of the library of transcripts and the 3' primer comprises a nucleotide sequence that is complementary to a 3' universal primer site contained in each transcript of the library of transcripts and a nucleotide sequence that is complementary to the unique barcode;

(c) the 5' primer comprises a nucleotide sequence that is complementary to a 5' universal primer site different from the 5' universal primer site contained in each transcript of the library of transcripts and a nucleotide sequence that is complementary to the unique barcode and the 3' primer comprises a nucleotide sequence that is complementary to a 3' universal primer site contained in each transcript of the library of transcripts; or (d) the 5' primer comprises a nucleotide sequence that is complementary to a 5' universal primer site contained in each transcript of the library of transcripts and the 3' primer comprises a nucleotide sequence that is complementary to a 3' universal primer site different from the 3' universal primer site contained in each transcript of the library of transcripts and a nucleotide sequence that is complementary to the unique barcode.

26. The method of paragraph 24 or 25, further comprising sequencing the amplified transcripts.

27. The method of any of paragraphs 24-26, wherein the library of transcripts is a single cell RNA sequencing library.

28. The method of paragraph 27, wherein the single cell RNA sequencing library is generated by 3' digital gene expression (DGE), SeqWell, or DropSeq.

29. The method of any of paragraphs 24-28, wherein the library of transcripts is generated from 50,000 cells or more.

30. The method of any of paragraphs 24-29, wherein transcripts that occur at a frequency of less than $1:10^8$ to $1:10^9$ in the library of transcripts are identified.

31. The method of any of paragraphs 24-30, wherein the single cell is a cell type that is present at a frequency of less than 1%-0.001%.

32. The method of any of paragraphs 24-31, wherein the single cell is a tumor cell, a T cell, a B cell, an NK cell, a cytokine-secreting cell, a dendritic cell, or a pathogen-infected cell.

33. The method of any of paragraphs 24-32, wherein the plurality of cells comprises cultured cells, some or all of a tumor, a tissue sample, a bone marrow sample, or a blood sample.

34. The method of any of paragraphs 24-33, wherein the barcode is 10-15 nucleotides in length.

35. The method of any of paragraphs 24-34, wherein the library of transcripts comprises uracil.

36. The method of paragraph 35, further comprising:

treating the amplified transcripts with uracil DNA glycosylase (UDG) and exonuclease; and amplifying the transcripts a second time.

37. A method for isolating a transcriptome of a single cell from a library of transcripts comprising:

providing a library of transcripts from a plurality of cells, with transcripts from each cell comprising a unique barcode;

isolating a target transcript from the library of transcripts;

sequencing the barcode in the target transcript(s); and amplifying the transcripts comprising the unique barcode of the single cell;

thereby isolating the transcriptome of the single cell.

38. The method of paragraph 37, wherein isolating a target transcript from the library of transcripts comprises:

contacting the library of transcripts with a labeled oligonucleotide that is complementary to the target transcript under conditions sufficient for the labeled oligonucleotide to hybridize with the target transcript; and separating the labeled oligonucleotide hybridized to the target transcript from the library of transcripts.

39. The method of paragraph 38, wherein the labeled oligonucleotide comprises a biotin label.

40. The method of paragraph 39, wherein the separating the labeled oligonucleotide hybridized to the target transcript from the library of transcripts comprises contacting the biotin-labeled oligonucleotide hybridized to the target transcript with streptavidin.

41. The method of paragraph 40, wherein the streptavidin is conjugated to a bead.

42. The method of any of paragraphs 37-41, wherein amplifying the transcripts comprises contacting the library of transcripts with a 5' primer and a 3' primer, wherein the 5' primer or the 3' primer comprises a nucleotide sequence that is complementary to the sequenced unique barcode of the single cell.

43. The method of paragraph 42, wherein:

(a) the 5' primer comprises a nucleotide sequence that is complementary to a 5' universal primer site contained in each transcript of the library of transcripts and a nucleotide sequence that is complementary to the unique barcode and the 3' primer comprises a nucleotide sequence that is complementary to a 3' universal primer site contained in each transcript of the library of transcripts;

(b) the 5' primer comprises a nucleotide sequence that is complementary to a 5' universal primer site contained in each transcript of the library of transcripts and the 3' primer comprises a nucleotide sequence that is complementary to a 3' universal primer site contained in each transcript of the library of transcripts and a nucleotide sequence that is complementary to the unique barcode;

(c) the 5' primer comprises a nucleotide sequence that is complementary to a 5' universal primer site different from the 5' universal primer site contained in each transcript of the library of transcripts and a nucleotide sequence that is complementary to the unique barcode and the 3' primer comprises a nucleotide sequence that is complementary to a 3' universal primer site contained in each transcript of the library of transcripts; or (d) the 5' primer comprises a nucleotide sequence that is complementary to a 5' universal primer site contained in each transcript of the library of transcripts and the 3' primer comprises a nucleotide sequence that is complementary to a 3' universal primer site different from the 3' universal primer site contained in each transcript of the library of transcripts and a nucleotide sequence that is complementary to the unique barcode.

44. The method of any of paragraphs 37-43, wherein the barcode is sequenced by pyrosequencing, single-molecule real-time sequencing, ion torrent sequencing, sequencing by synthesis, sequencing by ligation, or Sanger sequencing.

45. The method of any of paragraphs 37-44, further comprising counting the unique barcodes that are identified as a measure of the number of cells that express the target transcript, wherein each unique barcode identifies a single cell.

46. The method of any of paragraphs 37-45, wherein the library of transcripts is a single cell RNA sequencing library.

47. The method of paragraph 46, wherein the single cell RNA sequencing library is generated by 3' digital gene expression (DGE), SeqWell, or DropSeq.

48. The method of any of paragraphs 37-47, wherein the library of transcripts is generated from 50,000 cells or more.

49. The method of any of paragraphs 37-48, wherein transcripts that occur at a frequency of less than $1:10^8$ to $1:10^9$ in the library of transcripts are identified.

50. The method of any of paragraphs 37-49, wherein the single cell is a cell type that is present at a frequency of less than 1%-0.001%.

51. The method of any of paragraphs 37-50, wherein the target transcript encodes a cytokine, a T cell receptor, a B cell receptor, a pathogen transcript, a chemokine, a circulating tumor cell marker, or a cell activation marker.

52. The method of paragraph 51, wherein the circulating tumor cell marker is selected from EpCAM, EphB4, EGFR, CEA, HER2, or MUC-1.

53. The method of paragraph 51, wherein the cell activation marker is selected from CD154, CD137, CD134, CD278, CD69.

54. The method of any of paragraphs 37-53, wherein the single cell is a tumor cell, a T cell, a B cell, an NK cell, a cytokine-secreting cell, a dendritic cell, or a pathogen-infected cell.

55. The method of any of paragraphs 37-54, wherein the plurality of cells comprises cultured cells, some or all of a tumor, a tissue sample, a bone marrow sample, or a blood sample.

56. The method of any of paragraphs 37-55, wherein the barcode is 10-15 nucleotides in length.

57. The method of paragraph 42, wherein the library of transcripts comprises uracil.

58. The method of paragraph 57, wherein amplifying the transcripts further comprising:
    treating the amplified transcripts with uracil DNA glycosylase (UDG) and exonuclease; and
    amplifying the transcripts a second time.

59. A method for isolating a transcriptome of a single cell from a library of transcripts comprising:
    providing a library of transcripts from a plurality of cells, with transcripts from each cell comprising a unique barcode;
    detecting and separating the transcripts comprising the unique barcode of the single cell; and
    sequencing the transcripts; wherein:
    (i) the library of transcripts is generated from 50,000 cells or more;
    (ii) transcripts that occur at a frequency of less than $1:10^8$ to $1:10^9$ in the library of transcripts are identified; or
    (iii) the single cell is a cell type that occur at a frequency of less than 1%-0.001% in the plurality of cells.

60. The method of paragraph 59, wherein detecting and separating the transcripts comprising the unique barcode of the single cell comprises:
    isolating a target transcript from the library of transcripts;
    sequencing the barcode in the target transcript(s); and
    amplifying the transcripts comprising the unique barcode of the single cell.

61. The method of paragraph 60, wherein isolating a target transcript from the library of transcripts comprises:
    contacting the library of transcripts with a labeled oligonucleotide that is complementary to the target transcript under conditions sufficient for the labeled oligonucleotide to hybridize with the target transcript; and separating the labeled oligonucleotide hybridized to the target transcript from the library of transcripts.

62. The method of paragraph 61, wherein the labeled oligonucleotide comprises a biotin label.

63. The method of paragraph 62, wherein the separating the labeled oligonucleotide hybridized to the target transcript from the library of transcripts comprises contacting the biotin-labeled oligonucleotide hybridized to the target transcript with streptavidin.

64. The method of paragraph 63, wherein the streptavidin is conjugated to a bead.

65. The method of any of paragraphs 60-64, wherein amplifying the transcripts comprises contacting the library of transcripts with a 5' primer and a 3' primer, wherein the 5' primer or the 3' primer comprises a nucleotide sequence that is complementary to the sequenced unique barcode of the single cell.

66. The method of paragraph 65, wherein:
    (a) the 5' primer comprises a nucleotide sequence that is complementary to a 5' universal primer site contained in each transcript of the library of transcripts and a nucleotide sequence that is complementary to the unique barcode and the 3' primer comprises a nucleotide sequence that is complementary to a 3' universal primer site contained in each transcript of the library of transcripts;
    (b) the 5' primer comprises a nucleotide sequence that is complementary to a 5' universal primer site contained in each transcript of the library of transcripts and the 3' primer comprises a nucleotide sequence that is complementary to a 3' universal primer site contained in each transcript of the library of transcripts and a nucleotide sequence that is complementary to the unique barcode;
    (c) the 5' primer comprises a nucleotide sequence that is complementary to a 5' universal primer site different from the 5' universal primer site contained in each transcript of the library of transcripts and a nucleotide sequence that is complementary to the unique barcode and the 3' primer comprises a nucleotide sequence that is complementary to a 3' universal primer site contained in each transcript of the library of transcripts; or
    (d) the 5' primer comprises a nucleotide sequence that is complementary to a 5' universal primer site contained in each transcript of the library of transcripts and the 3' primer comprises a nucleotide sequence that is complementary to a 3' universal primer site different from the 3' universal primer site contained in each transcript of the library of transcripts and a nucleotide sequence that is complementary to the unique barcode.

67. A set of primers for isolating a transcriptome of a single cell from a library of transcripts comprising:
    (a) the 5' primer comprises a nucleotide sequence that is complementary to a 5' universal primer site contained in each transcript of the library of transcripts and a nucleotide sequence that is complementary to a unique barcode that is present on the transcripts from the single cell and the 3' primer comprises a nucleotide sequence that is complementary to a 3' universal primer site contained in each transcript of the library of transcripts;

(b) the 5' primer comprises a nucleotide sequence that is complementary to a 5' universal primer site contained in each transcript of the library of transcripts and the 3' primer comprises a nucleotide sequence that is complementary to a 3' universal primer site contained in each transcript of the library of transcripts and a nucleotide sequence that is complementary to the unique barcode;

(c) the 5' primer comprises a nucleotide sequence that is complementary to a 5' universal primer site different from the 5' universal primer site contained in each transcript of the library of transcripts and a nucleotide sequence that is complementary to the unique barcode and the 3' primer comprises a nucleotide sequence that is complementary to a 3' universal primer site contained in each transcript of the library of transcripts; or (d) the 5' primer comprises a nucleotide sequence that is complementary to a 5' universal primer site contained in each transcript of the library of transcripts and the 3' primer comprises a nucleotide sequence that is complementary to a 3' universal primer site different from the 3' universal primer site contained in each transcript of the library of transcripts and a nucleotide sequence that is complementary to the unique barcode.

The invention is further described by the following numbered statements:

1. A method of enriching barcoded DNA constructs from a single cell sequence library comprising capture of DNA library molecules from the library by targeting cell-identifying barcodes and/or genome specific sequences.

2. The method according to statement 1, comprising:
   a) capture of DNA library molecules from the library by targeting genome specific sequences;
   b) sequencing the captured DNA constructs;
   c) identifying cell-identifying barcodes associated with the captured DNA constructs; and
   d) capturing DNA library molecules from the library by targeting the identified cell-identifying barcodes,
   whereby DNA constructs associated with single cells and genome specific sequences are enriched.

3. The method according to statement 1 or 2, wherein the targeted cell-identifying barcodes identify at least one sub-population of single cells represented within the sequencing library, whereby DNA constructs are enriched for at least one subpopulation of cells.

4. The method according to any of statements 1 to 3, wherein the sequencing library is generated from a tissue sample.

5. The method according to any of statements 1 to 4, wherein the genome specific sequences are exon sequences.

6. The method according to any of statements 1 to 5, wherein the DNA constructs are cDNA constructs.

7. The method according to any of statements 1 to 6, wherein capture comprises PCR amplification of DNA constructs with primer pairs comprising complementary sequences to the cell-identifying barcodes or genome specific sequences.

8. The method according to statement 7, wherein capture comprises PCR amplification of single cell barcoded constructs specific for at least one subpopulation of cells.

9. The method according to statement 7 or 8, wherein the single cell barcoded constructs are pair-end constructs comprising a first priming site upstream of a single cell barcode at one end and a second priming site at the other end, and wherein PCR amplification comprises a first primer specific for the first priming site and single cell barcode and a second primer specific for the second priming site.

10. The method according to any of statements 7 to 9, wherein at least one primer for amplification of DNA constructs comprises biotin, whereby amplification products may be separated from the library.

11. The method according to any of statements 1 to 6, wherein capture comprises hybridization of DNA library molecules to oligonucleotides specific for cell-identifying barcodes or genome specific sequences.

12. The method according to statement 11, wherein hybridization is performed in solution.

13. The method according to statement 11 or 12, further comprising PCR amplification of hybridized DNA library molecules.

14. The method according to any of statements 1 to 6, wherein capture comprises contacting the sequencing library with a CRISPR system, wherein the CRISPR system comprises CRISPR guide RNAs complementary to cell-identifying barcodes or genome specific sequences.

15. The method according to statement 14, wherein contacting the sequencing library with a CRISPR system is performed in solution.

16. The method according to statement 14 or 15, wherein the CRISPR system comprises an enzymatically inactive CRISPR enzyme.

17. The method according to statement 14 to 16, wherein the CRISPR system comprises an RNA guided DNA targeting CRISPR enzyme.

18. The method according to statement 17, wherein the CRISPR enzyme is Cas9 or Cpf1.

19. The method according to any of statements 14 to 18, wherein the captured DNA library molecules are isolated on a solid support and released from the solid support by treatment with RNase, proteinase, or denaturing conditions.

20. A sequencing method for determining single cell gene expression in a subpopulation of cells within a population of cells comprising:
   a) enriching single cell barcoded constructs for at least one subpopulation of cells from a single cell RNA-seq library, wherein the library comprises cDNA constructs comprising cell-identifying barcodes; and
   b) sequencing the enriched single cell barcoded constructs, whereby gene expression is determined for the subpopulation of cells.

21. The method according to statement 20, wherein enriching comprises any method according to statements 1 to 19 specific for enriching cell barcoded constructs.

22. The method according to statement 20 or 21, further comprising step (a') before step (a), wherein step (a') comprises performing single cell RNA sequencing on a population of cells, wherein a single cell barcoded RNA-seq library is constructed, the library is sequenced, and subpopulations of cells are determined by gene expression analysis of the single cells.

23. The method according to any of statements 20 to 22, wherein the sequencing of the enriched single cell barcoded constructs in step (b) comprises a sequencing depth greater than 10×.

24. The method according to any of statements 20 to 22, wherein the sequencing of the enriched single cell barcoded constructs in step (b) comprises a sequencing depth less than 10×.

25. The method according to any of statements 20 to 24, wherein the sequencing of the RNA-seq library in step (a') comprises deep sequencing.

26. The method according to any of statements 20 to 25, wherein the subpopulation of cells comprises rare cells.

27. The method according to statement 26, wherein the subpopulation of cells comprises 0.1% or less of the population of cells.

28. The method according to any of statements 20 to 27, wherein the subpopulation of cells comprises T cells and barcodes specific to T cell are enriched.

29. The method according to statement 28, wherein T cell receptor (TCR) alpha and beta pairs are determined in the T cells.

30. The method according to statements 28 or 29, wherein the single cell RNA-seq library is generated from a tumor sample and the T cells are tumor infiltrating lymphocytes (TIL).

31. A sequencing method for determining gene expression of a subset of genes comprising:
a) enriching cDNA constructs for a subset of genes from a sequencing library, wherein the subset of genes comprises at least one gene; and
b) sequencing the enriched cDNA constructs, whereby gene expression is determined for the subset of genes.

32. The method according to statement 31, wherein enriching comprises any method according to statements 1 to 19 specific for enriching constructs comprising genome specific sequences.

33. The method according to statement 31 or 32, wherein the sequencing of the enriched cDNA constructs in step (b) comprises a sequencing depth greater than 10×.

34. The method according to statement 31 or 32, wherein the sequencing of the enriched cDNA constructs in step (b) comprises a sequencing depth less than 10×.

35. The method according to any of statements 31 to 34, wherein the sequencing library is a single cell library, wherein the enriched cDNA constructs comprise cell-identifying barcodes, whereby upon sequencing gene expression may be assigned to single cells.

36. A sequencing method for determining gene expression in a subpopulation of cells within a population of cells, wherein the subpopulation of cells express a subset of genes of interest comprising:
a) determining gene expression of a subset of genes and identifying barcodes associated with expression of the subset genes in a single cell library;
b) enriching cDNA constructs comprising cell-identifying barcodes associated with expression of the subset of genes from the single cell library comprising the barcodes; and
c) sequencing the enriched cDNA constructs, whereby gene expression is determined for the subpopulation of cells expressing a subset of genes of interest.

37. The method according to statement 36, wherein enriching in step (b) comprises any method according to statements 1 to 19 specific for enriching cell barcoded constructs.

\* \* \*

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method of enriching barcoded constructs from a sequenced nucleic acid library generated from a plurality of cells comprising capturing nucleic acid library molecules from the sequenced nucleic acid library by targeting library transcripts comprising one or more cell-identifying barcodes
    wherein the method is a method of identifying a transcriptome from at least one single cell or a subpopulation of single cells, said method comprising enriching library molecules from the at least one single cell or subpopulation of single cells based on the one or more unique cell-identifying barcodes, wherein the targeted barcodes identify transcripts of single cells represented within the sequenced nucleic acid library,
    wherein targeting comprises introducing to the sequenced nucleic acid library an oligonucleotide, the oligonucleotide comprising a primer, a sequence for hybridizing to the one or more cell-identifying barcodes, and a label.

2. The method according to claim 1, comprising:
    a) capturing DNA library molecules from the library by targeting one or more target transcripts;
    b) sequencing the captured DNA library molecules;
    c) identifying cell-identifying barcodes associated with the captured DNA library molecules; and
    d) capturing DNA library molecules from the library by targeting the identified cell-identifying barcodes,
    whereby DNA constructs associated with single cells expressing one or more target transcripts are enriched.

3. The method according to claim 1, wherein capturing comprises PCR amplification of one or more DNA library molecules with primer pairs complementary to each of the one or more DNA library molecules, wherein the primer pairs comprise one primer comprising a complementary sequence to all or part of a cell-identifying barcode or a complementary sequence to a target transcript sequence for each of the one or more DNA library molecules.

4. The method according to claim 1, wherein capturing comprises PCR amplification of one or more DNA library molecules specific for at least one single cell or subpopulation of single cells,
    optionally, wherein PCR amplification comprises contacting the library with a 5' primer and a 3' primer, wherein the 5' primer or the 3' primer comprises a nucleotide sequence that is complementary to the unique barcode of a single cell from the at least one single cell or subpopulation of single cells; and
    amplifying the library molecules comprising the unique barcode of the single cell;
    thereby obtaining a plurality of transcripts from the single cell,
    optionally, wherein (a) the 5' primer comprises a nucleotide sequence that is complementary to a 5' universal primer site contained in each library molecule and a nucleotide sequence that is complementary to the unique barcode and the 3' primer comprises a nucleotide sequence that is complementary to a 3' universal primer site contained in each library molecule;
    (b) the 5' primer comprises a nucleotide sequence that is complementary to a 5' universal primer site contained in each library molecule and the 3' primer comprises a nucleotide sequence that is complementary to a 3' universal primer site contained in each library molecule and a nucleotide sequence that is complementary to the unique barcode;
    (c) the 5' primer comprises a nucleotide sequence that is complementary to a 5' universal primer site different from the 5' universal primer site contained in each library molecule and a nucleotide sequence that is complementary to the unique barcode and the 3' primer comprises a nucleotide sequence that is complementary to a 3' universal primer site contained in each library molecule; or
    (d) the 5' primer comprises a nucleotide sequence that is complementary to a 5' universal primer site contained in each library molecule and the 3' primer comprises a nucleotide sequence that is complementary to a 3' universal primer site different from the 3' universal primer site contained in each library molecule and a nucleotide sequence that is complementary to the unique barcode, or
    optionally, wherein the library molecules are pair-end DNA constructs comprising a first priming site outside of a single cell barcode at one end of the construct and a second priming site at the other end of the construct, and wherein PCR amplification comprises a first primer specific for the first priming site and single cell barcode and a second primer specific for the second priming site.

5. The method according to claim 3, wherein at least one primer for amplification of DNA library molecules comprises a label, wherein amplification products may be separated from the library by capturing amplification products comprising the label, optionally,
    wherein the label comprises biotin, optionally,
    wherein the separating of the labeled amplification product from the library comprises contacting the biotin-labeled amplification product with streptavidin, optionally,
    wherein the streptavidin is conjugated to a bead.

6. The method according to claim 3, wherein the library molecules comprise uracil, optionally,
    wherein the method further comprises treating the amplified library molecules with uracil DNA glycosylase (UDG) and exonuclease; and
    amplifying the library molecules a second time; or
    wherein amplifying the library molecules from the single cell comprises:
    providing a single cell library from a plurality of cells, with library molecules from each cell comprising a barcode, and wherein the library comprises uracil;
    amplifying the transcripts having the barcode by contacting the library of transcripts with a 5' primer and a 3' primer, wherein the 5' primer or the 3' primer comprises a nucleotide sequence that is complementary to the barcode of the single cell and a polymerase that does not recognize uracil;
    treating the amplified transcripts with uracil DNA glycosylase (UDG) and exonuclease; and
    amplifying the transcripts treated with uracil DNA glycosylase (UDG) and exonuclease.

7. The method according to claim 3, further comprising sequencing the amplified library molecules.

8. The method according to claim 1, wherein capturing comprises hybridization of DNA library molecules to oligonucleotides specific for target cell-identifying barcodes or target transcript sequences; and separating the oligonucleotides hybridized to the target cell-identifying barcodes or target transcript sequences from the library, optionally,
    wherein hybridization is performed in solution; and/or
    wherein the oligonucleotides comprise a label, wherein DNA library molecules may be separated from the library by capturing hybridized DNA library molecules comprising the label, more preferably, wherein the label comprises biotin, optionally, wherein the separating of the labeled oligonucleotide hybridized to the target library molecules comprises contacting the biotin-labeled oligonucleotide hybridized to the target library molecules with streptavidin, optionally, wherein the streptavidin is conjugated to a bead; and/or wherein the method further comprises PCR amplification of hybridized library molecules; and/or wherein the method further comprises sequencing the hybridized library molecules.

9. The method according to claim 1, wherein capturing comprises contacting the library with a CRISPR system, wherein the CRISPR system comprises CRISPR guide RNAs complementary to target cell-identifying barcodes or target transcript sequences, optionally, wherein contacting the library with a CRISPR system is performed in solution; and/or wherein the CRISPR system comprises an enzymatically inactive CRISPR enzyme; and/or wherein the CRISPR system comprises an RNA guided DNA targeting or RNA-targeting CRISPR enzyme, optionally, wherein the CRISPR enzyme is Cas9, Cpf1, or Cas13; and/or wherein the captured DNA library molecules are isolated on a solid support and released from the solid support by treatment with RNase, proteinase, or denaturing conditions; and/or wherein the method further comprises sequencing the captured library molecules.

10. The method of claim 1, wherein the method is a sequencing method for identifying a single cell transcriptome in at least one single cell or subpopulation of single cells within a population of cells comprising:
 a) enriching library molecules from a single cell RNA sequencing (scRNA-seq) library for at least one single cell or subpopulation of single cells, wherein the library molecules comprise cell-identifying barcodes; and
 b) sequencing the enriched library molecules, whereby gene expression is determined for the at least one single cell or subpopulation of single cells.

11. The method according to claim 10, further comprising step (a') before step (a), wherein step (a') comprises performing single cell RNA sequencing on a population of cells thereby generating a library of barcoded library molecules and a dataset comprising barcodes and natural sequences, wherein barcodes are identified for at least one single cell or subpopulation of single cells of interest from the population of cells, optionally preferably, wherein the single cell RNA sequencing in step (a') comprises deep sequencing of the library.

12. The method according to claim 10, wherein the at least one single cell or subpopulation of single cells comprises T cells, B cells, macrophages, neutrophils, dendritic cells, megakaryocytes, monocytes, basophils, or eosinophils and barcodes specific to T cells, B cells, macrophages, neutrophils, dendritic cells, megakaryocytes, monocytes, basophils, or eosinophils are enriched, optionally, wherein T cell receptor (TCR) or B cell receptor (BCR) pairs are determined; and/or wherein the single cell RNA-seq library is generated from a tumor sample comprising tumor infiltrating lymphocytes (TIL).

13. The method of claim 1, wherein the method is a sequencing method for identifying a single cell transcriptome in at least one single cell or subpopulation of single cells within a population of cells, wherein the at least one single cell or subpopulation of cells express or lack expression of a subset of transcripts of interest comprising:
 a) determining expression of the transcripts of interest in a single cell library from the population of cells, wherein the library molecules comprise cell-identifying barcodes;
 b) identifying barcodes associated with expression or lack of expression of the transcripts of interest in the single cell library;
 c) enriching library molecules comprising the cell-identifying barcodes associated with expression of the transcripts of interest from the single cell library; and
 d) sequencing the enriched library molecules, whereby a single cell transcriptome is identified for at least one single cell or subpopulation of single cells expressing a subset of transcripts of interest.

14. The method of claim 1, wherein the method is a method for identifying a barcode associated with transcripts from a single cell in a library of transcripts comprising:
 providing a library of transcripts from a plurality of cells, with transcripts from each cell comprising a barcode;
 contacting the library of transcripts with a labeled oligonucleotide that is complementary to a target transcript encoding a specific T cell receptor or a specific B cell receptor under conditions sufficient for the labeled oligonucleotide to hybridize with the target transcript; and
 separating the labeled oligonucleotide hybridized to the target transcript from the library of transcripts;
 thereby separating cell barcodes of cells expressing the T cell receptor or B cell receptor, optionally, wherein the single cell is a T cell or a B cell.

15. The method of claim 1, wherein the method is a method for isolating a transcriptome of a single cell from a library of transcripts comprising:
 providing a library of transcripts from a plurality of cells, with transcripts from each cell comprising a unique barcode;
 detecting and separating the transcripts comprising the unique barcode of the single cell; and
 sequencing the transcripts; wherein:
 (i) the library of transcripts is generated from 50,000 cells or more;
 (ii) transcripts that occur at a frequency of less than $1:10^8$ to $1:10^9$ in the library of transcripts are identified; or
 (iii) the single cell is a cell type that occur at a frequency of less than 1%-0.001% in the plurality of cells, optionally,
 wherein detecting and separating the transcripts comprising the unique barcode of the single cell comprises:
 isolating a target transcript from the library of transcripts;
 sequencing the barcode in the target transcript(s); and
 amplifying the transcripts comprising the barcode of the single cell.

16. The method according to claim 1, wherein the captured library molecules are sequenced by pyrosequencing, single-molecule real-time sequencing, ion torrent sequencing, sequencing by synthesis, sequencing by degradation, sequencing by ligation, sequencing by hybridization, Sanger sequencing or by the use of a biological or a solid state nanopore; and/or wherein the sequencing of the captured library molecules comprises a sequencing depth greater than about 5000 reads per cell; and/or wherein the sequencing of the captured library molecules comprises a sequencing depth less than about 5000 reads per cell; and/or wherein the method further comprises counting the unique barcodes that are identified from sequencing of a single cell library or enriched single cell library as a measure of the number of cells that express a target transcript or subset of transcripts, wherein each unique barcode identifies a single cell; and/or wherein the library is a single cell RNA sequencing (scRNA-seq) library, optionally, wherein the single cell RNA sequencing library is generated by 3' digital gene expression (DGE), SMART-seq2, SeqWell, droplet microfluidic barcoding, split and pool barcoding, or combinatorial indexing; and/or wherein the barcode is 10-20 nucleotides in length; and/or wherein the library is generated from 50,000 cells or more; and/or wherein transcripts that occur at a frequency of less than $1:10^8$ to $1:10^9$ in the library are identified; and/or wherein the single cell is a cell type that is present at a frequency of less than 1%-0.001%; and/or wherein the target transcript encodes a cytokine, a T cell receptor, a B cell receptor, a pathogen transcript, a chemokine, a circulating tumor cell marker, or a cell activation marker; and/or wherein the at least one single cell or subpopulation of single cells comprises a tumor cell, a T cell, a B cell, an NK cell, a cytokine-secreting cell, a dendritic cell, or a pathogen-infected cell; and/or wherein the library is generated from a population of cells comprising cultured cells, some or all of a tumor, a tissue sample, a bone marrow sample, or a blood sample.

17. The method of claim 16, wherein the circulating tumor cell marker is selected from EpCAM, EphB4, EGFR, CEA, HER2, or MUC-1.

18. The method of claim 16, wherein the cell activation marker is selected from CD154, CD137, CD134, CD278, or CD69.

* * * * *

UNITED STATES PATENT AND TRADEMARK OFFICE
CERTIFICATE OF CORRECTION

| | |
|---|---|
| PATENT NO. | : 11,702,649 B2 |
| APPLICATION NO. | : 16/758640 |
| DATED | : July 18, 2023 |
| INVENTOR(S) | : Paul Blainey et al. |

It is certified that error appears in the above-identified patent and that said Letters Patent is hereby corrected as shown below:

In the Specification

In Column 9, Line 7, delete "CD19+" and insert -- $CD19^+$ --.

In Column 13, Line 24, delete "(3 D-ribose," and insert -- β D-ribose, --.

In Column 13, Line 29, delete "(3 D xylo" and insert -- β D xylo --.

In Column 18, Line 12, delete "19%" and insert -- 1996 --.

In Column 18, Line 25, delete "ion" and insert -- Ion --.

In Column 19, Line 4, delete "p666-6'73," and insert -- p666-673, --.

In Column 29, Line 2, delete "CCL22/1 VDC," and insert -- CCL22/MDC, --.

In Column 29, Line 6, delete "CMLS," and insert -- CML5, --.

In Column 33, Line 67, delete "9 e.g.," and insert -- (e.g., --.

In Column 36, Line 9, delete "overlapplng" and insert -- overlapping --.

In Column 36, Line 10, delete "WI-DNA" and insert -- WT-DNA --.

In Column 36, Line 14, delete "ail" and insert -- all --.

In Column 37, Line 67, delete "if" and insert -- If --.

In Column 50, Line 40, delete "Fokl" and insert -- FokI --.

Signed and Sealed this
Nineteenth Day of March, 2024

Katherine Kelly Vidal
*Director of the United States Patent and Trademark Office*

CERTIFICATE OF CORRECTION (continued)
U.S. Pat. No. 11,702,649 B2

In Column 20, Line 45, delete "Fokl" and insert -- FokI --.

In Column 53, Line 30, delete "a and" and insert -- α and --.

In Column 54, Line 38, delete "CD3t" and insert -- CD3ζ --.

In Column 54, Line 38, delete "CD3t" and insert -- CD3ζ --.

In Column 54, Line 44, delete "CD3;" and insert -- CD3ζ; --.

In Column 54, Line 47, delete "CD3-chain," and insert -- CD3ζ-chain, --.

In Column 54, Line 60, delete "CD3t" and insert -- CD3ζ --.

In Column 55, Line 20, delete "CD3" and insert -- CD3ζ --.

In Column 55, Line 45, delete "CD3t" and insert -- CD3ζ --.

In Column 56, Line 27, delete "TCR-molecule" and insert -- TCR-ζ molecule --.

In Column 56, Line 43, delete "CD3t" and insert -- CD3ζ --.

In Column 58, Line 29, delete "CD3t" and insert -- CD3ζ --.

In Column 63, Line 45, delete "peptide-WIC" and insert -- peptide-MHC --.

In Column 63, Line 57, delete "WIC" and insert -- MHC --.

In Column 63, Line 59, delete "WIC" and insert -- MHC --.

In Column 67, Line 24, delete "TGF-01+IL-6" and insert -- TGF-β1+IL-6 --.

In Column 67, Line 27, delete "IL-10+IL-6+IL-23" and insert -- IL-1β+IL-6+IL-23 --.

In Column 67, Line 33, delete "CDSL/AIM" and insert -- CD5L/AIM --.

In Column 67, Line 35, delete "142'7," and insert -- 1427, --.

In Column 67, Line 42, delete "CD8+" and insert -- $CD8^+$ --.

In Column 67, Line 51, delete "CD8+" and insert -- $CD8^+$ --.

In Column 69, Line 58, delete "(PAXS);" and insert -- (PAX5); --.

In Column 70, Line 4, delete "(FCRLS);" and insert -- (FCRL5); --.

CERTIFICATE OF CORRECTION (continued)
U.S. Pat. No. 11,702,649 B2

In Column 71, Line 2, delete "CART" and insert -- CAR T --.

In Column 77, Line 35, delete "1xPBS" and insert -- 1x PBS --.

In Column 79, Line 35, delete "Bootstrapplng." and insert -- Bootstrapping. --.

In Column 79, Line 66, delete "loge" and insert -- $\log_2$ --.

In Column 80, Line 8, delete "loge" and insert -- $\log_2$ --.

In the Claims

In Column 137, Line 49, in Claim 11, delete "optionally preferably," and insert -- optionally, --.